United States Patent
Sivalingam et al.

(10) Patent No.: US 12,104,173 B2
(45) Date of Patent: Oct. 1, 2024

(54) METHOD FOR DIFFERENTIATION OF HUMAN PLURIPOTENT STEM CELL LINES IN SUSPENSION CULTURE

(71) Applicant: AGENCY FOR SCIENCE, TECHNOLOGY AND RESEARCH, Singapore (SG)

(72) Inventors: Jaichandran Sivalingam, Singapore (SG); Steve Oh, Singapore (SG); Shaul Reuveny, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 1042 days.

(21) Appl. No.: 16/962,973

(22) PCT Filed: Jan. 15, 2019

(86) PCT No.: PCT/SG2019/050023
§ 371 (c)(1),
(2) Date: Jul. 17, 2020

(87) PCT Pub. No.: WO2019/143292
PCT Pub. Date: Jul. 25, 2019

(65) Prior Publication Data
US 2020/0399602 A1 Dec. 24, 2020

(30) Foreign Application Priority Data
Jan. 18, 2018 (SG) .......................... 10201800488W

(51) Int. Cl.
*C12N 5/0789* (2010.01)
*C12N 5/078* (2010.01)

(52) U.S. Cl.
CPC .......... *C12N 5/0647* (2013.01); *C12N 5/0641* (2013.01); *C12N 2501/10* (2013.01); *C12N 2501/115* (2013.01); *C12N 2501/15* (2013.01); *C12N 2501/155* (2013.01); *C12N 2501/20* (2013.01); *C12N 2501/392* (2013.01); *C12N 2501/415* (2013.01); *C12N 2501/727* (2013.01); *C12N 2501/999* (2013.01); *C12N 2506/00* (2013.01); *C12N 2506/11* (2013.01); *C12N 2527/00* (2013.01)

(58) Field of Classification Search
CPC .................................................... C12N 5/0647
See application file for complete search history.

(56) References Cited

U.S. PATENT DOCUMENTS

| | | |
|---|---|---|
| 2007/0178586 A1 | 8/2007 | Yang et al. |
| 2014/0193903 A1 | 7/2014 | Oh et al. |
| 2014/0242693 A1 | 8/2014 | Fryer et al. |
| 2016/0186141 A1 | 6/2016 | Cao et al. |

FOREIGN PATENT DOCUMENTS

| | | |
|---|---|---|
| JP | 2011-514169 A | 5/2011 |
| JP | 2016-504037 A | 2/2016 |
| JP | 2016-534731 A | 11/2016 |
| WO | WO-2014/013255 A1 | 1/2014 |
| WO | WO-2014/200340 A1 | 12/2014 |
| WO | WO-2015/065524 A2 | 5/2015 |
| WO | WO-2016/114723 A1 | 7/2016 |
| WO | WO-2017/193177 A1 | 11/2017 |

OTHER PUBLICATIONS

Olivier et al. (2016, Stem Cells Translation Med. vol. 5, pp. 1-12, (Year: 2016).*
Katagiri et al., 2016, Cold Spring Harb. Perspect. Biol., vol. 8, pp. 1-27 (Year: 2016).*
Decision of Refusal in JP Application No. 2020-539279 dated May 15, 2023, 7 pages.
Orlova et al., "Generation, Expansion and Functional Analysis of Endothelial Cells and Pericytes Derived From Human Pluripotent Stem Cells", Nature Protocols, vol. 9, No. 6, 2014, pp. 1514-1531.
Olivier et al., "High-Efficiency Serum-Free Feeder-Free Erythroid Differentiation of Human Pluripotent Stem Cells Using Small Molecules", Stem Cells Translation Medicine, vol. 5, 2016, pp. 1394-1405.
Hosseinizand et al., "Agitation Increases Expansion of Cord Blood Hematopoietic Cells and Promotes Their Differentiation Into Myeloid Lineage", Cytotechnology, vol. 68, 2016, pp. 969-978.
Boehm et al., "The Effect of Mild Agitation on in vitro Erythroid Development", Journal of Immunological Methods, vol. 360, 2010, pp. 20-29.
Pearson et al., "The Stepwise Specification of Embryonic Stem Cells to Hematopoietic Fate is Driven by Sequential Exposure to Bmp4, Activin A, bFGF and VEGF", Development, vol. 135, No. 8, Mar. 13, 2008, pp. 1525-1535.
Pick et al., "Differentiation of Human Embryonic Stem Cells in Serum-Free Medium Reveals Distinct Roles for Bone Morphogenetic Protein 4, Vascular Endothelial Growth Factor, Stem Cell Factor, and Fibroblast Growth Factor 2 in Hematopoiesis", Stem Cells, vol. 25, No. 9, Jun. 7, 2007, pp. 2206-2214.
Onuma et al., "A Stable Chimeric Fibroblast Growth Factor (FGF) Can Successfully Replace Basic FGF in Human Pluripotent Stem Cell Culture", PLoS One, vol. 10, No. 4, Apr. 7, 2015, pp. 13 pages.
Lu et al., "3D Microcarrier System for Efficient Differentiation of Human Pluripotent Stem Cells Into Hematopoietic Cells Without Feeders and Serum", Regen Med., vol. 8, No. 4, Jul. 4, 2013, pp. 413-424.

(Continued)

*Primary Examiner* — Anoop K Singh
*Assistant Examiner* — David A Montanari
(74) *Attorney, Agent, or Firm* — MARSHALL, GERSTEIN & BORUN LLP

(57) ABSTRACT

Methods of differentiation of pluripotent stem cells into hematopoietic precursor cells, wherein the method is carried out under suspension agitation, and wherein a GSK-3-inhibitor or a Wnt pathway activator is added during a stage of mesoderm induction, and cell culture media for use in the methods, as well as kits for performing the same.

12 Claims, 75 Drawing Sheets

Specification includes a Sequence Listing.

(56) References Cited

OTHER PUBLICATIONS

Lodish et al., "From Stem Cell to Erythroblast: Regulation of Red Cell Production at Multiple Levels by Multiple Hormones", IUBMB Life, vol. 62, No. 7, Jul. 31, 2010, pp. 492-496.
Livak et al., "Analysis of Relative Gene Expression Data Using Real-Time Quantitative PCR and the $2^{-\Delta\Delta C_T}$ Method", Methods, vol. 25, 2001, pp. 402-408.
Olivier et al., "High-Efficiency Serum-Free Feeder-Free Erythroid Differentiation of Human Pluripotent Stem Cells Using Small Molecules", Stem Cells Transl Med, vol. 5, No. 10, Jul. 8, 2016, pp. 1394-1405.
Sivalingnam et al., "Superior Red Blood Cell Generation From Human Pluripotent Stem Cells Through a Novel Microcarrier-Based Embryoid Body Platform", Tissue Engineering: Part C, vol. 22, No. 8, 2016, pp. 765-780.
Tan et al., "Human Finger-Prick Induced Pluripotent Stem Cells Facilitate the Development of Stem Cell Banking", Stem Cells Transl Med,, vol. 3, 2014, pp. 586-598.
Search Report and Written Opinion in International Application No. PCT/SG2019/050023 dated Apr. 17, 2019, 19 pages.
Second Office Action in CN Application No. 2019800203280 dated Nov. 28, 2023, 10 pages.

\* cited by examiner

| | Static hPSC expansion | Agitated hPSC expansion | $p$-value |
|---|---|---|---|
| Total Hematopoietic precursors per well (Day 14) | $5.77 \times 10^6 \pm 6.30 \times 10^5$ | $1.39 \times 10^5 \pm 2.18 \times 10^4$ | 0.0009 |
| Total Erythroblast per well (Day 28) | $2.62 \times 10^7 \pm 4.72 \times 10^6$ | $4.11 \times 10^4 \pm 2.37 \times 10^4$ | 0.005 |
| CD235a+ cells (%)(Day 28) | $51.8\% \pm 2.0$ | $0.51\% \pm 0.1$ | <0.0001 |
| HbF+ cells (%)(Day 28) | $65.7\% \pm 2.3$ | $0.70\% \pm 0.05$ | <0.0001 |
| RBC pellet (Day 28) | | | |

| Condition | Dose and duration of factors evaluated | | | | Response outcome | |
|---|---|---|---|---|---|---|
| | Activin A (ng/ml) | CHIR$_{24hr}$ (µM) | CHIR$_{48hr}$ (µM) | BMP4 (ng/ml) | % KDR+ cells | Total number of Hematopoietic precursors |
| 1 | 0 | 0 | 0 | 50 | 0.44 | 136000 |
| 2 | 80 | 0 | 0 | 10 | 1.07 | 271500 |
| 3 | 0 | 15 | 0 | 10 | 9.19 | 401500 |
| 4 | 80 | 15 | 0 | 50 | 18.5 | 469000 |
| 5 | 0 | 0 | 15 | 10 | 1.18 | 271000 |
| 6 | 80 | 0 | 15 | 50 | 2.06 | 403000 |
| 7 | 0 | 15 | 15 | 50 | 30.7 | 185500 |
| 8 | 80 | 15 | 15 | 10 | 25.6 | 370500 |
| 9 | 0 | 0 | 0 | 10 | 0.6 | 96500 |
| 10 | 80 | 0 | 0 | 50 | 0.97 | 92500 |
| 11 | 0 | 15 | 0 | 50 | 17.7 | 655000 |
| 12 | 80 | 15 | 0 | 10 | 16.3 | 348000 |
| 13 | 0 | 0 | 15 | 50 | 4.57 | 75500 |
| 14 | 80 | 0 | 15 | 10 | 1.38 | 108500 |
| 15 | 0 | 15 | 15 | 10 | 38 | 60000 |
| 16 | 80 | 15 | 15 | 50 | 38.7 | 381000 |
| 17 | 0 | 7.5 | 7.5 | 30 | 5.61 | 498000 |
| 18 | 80 | 7.5 | 7.5 | 30 | 19.2 | 362000 |
| 19 | 40 | 0 | 7.5 | 30 | 2.42 | 304500 |
| 20 | 40 | 15 | 7.5 | 30 | 36.6 | 469500 |
| 21 | 40 | 7.5 | 0 | 30 | 9.25 | 344500 |
| 22 | 40 | 7.5 | 15 | 30 | 30.8 | 350500 |

| Condition | Activin A (ng/ml) | CHIR$_{24hr}$ (μM) | CHIR$_{48hr}$ (μM) | BMP4 (ng/ml) | % KDR+ cells | Total number of Hematopoietic precursors |
|---|---|---|---|---|---|---|
| 23 | 40 | 7.5 | 7.5 | 30 | 9.24 | 450500 |
| 24 | 40 | 7.5 | 7.5 | 30 | 11.4 | 388000 |
| 25 | 40 | 7.5 | 7.5 | 10 | 30.1 | 440500 |
| 26 | 40 | 7.5 | 7.5 | 50 | 28.3 | 491000 |
| 27 | 40 | 7.5 | 7.5 | 30 | 16.9 | 425000 |
| 28 | 40 | 7.5 | 7.5 | 30 | 26.7 | 385500 |
| 29 | 40 | 7.5 | 7.5 | 30 | 14 | 368500 |

B

B

| | Condition 7 | Condition 18 | p-value |
|---|---|---|---|
| Total cells per well (Day 34) | $9.77 \times 10^7 \pm 4.6 \times 10^6$ | $4.31 \times 10^7 \pm 5.9 \times 10^5$ | 0.0003 |
| CD235a+ cells (%) | 79.2 % ± 2.77 | 60.07 % ± 4.77 | 0.03 |
| CD235a+ CD71+ cells (%) | 63.5 % ± 1.82 | 34.8 % ± 7.28 | 0.019 |
| CD235a+ CD71- cells (%) | 15.7 % ± 1.30 | 25.27 % ± 2.74 | 0.03 |
| HbF+ cells (%) | 99.43 % ± 0.12 | 67.10 % ± 0.55 | <0.0001 |

Condition 7

Condition 18

FIG. 5 contiued
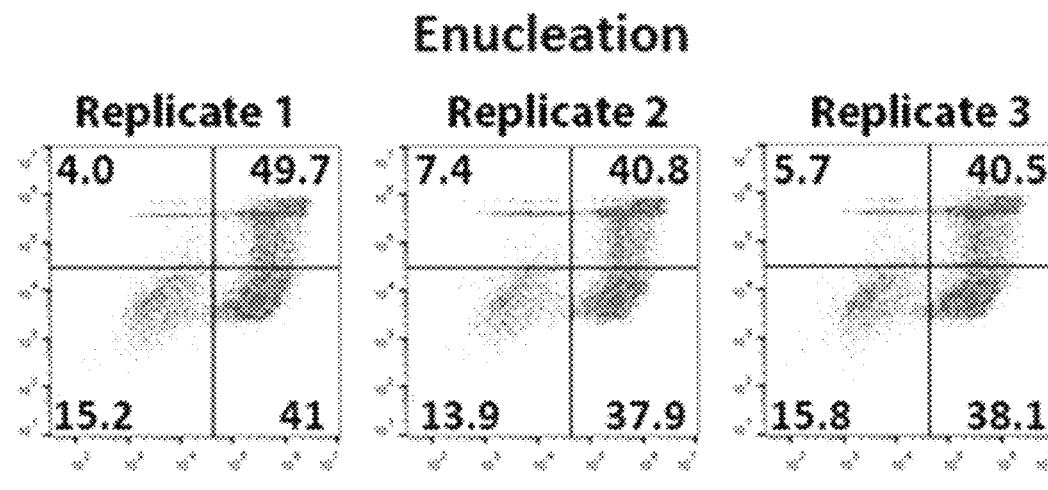
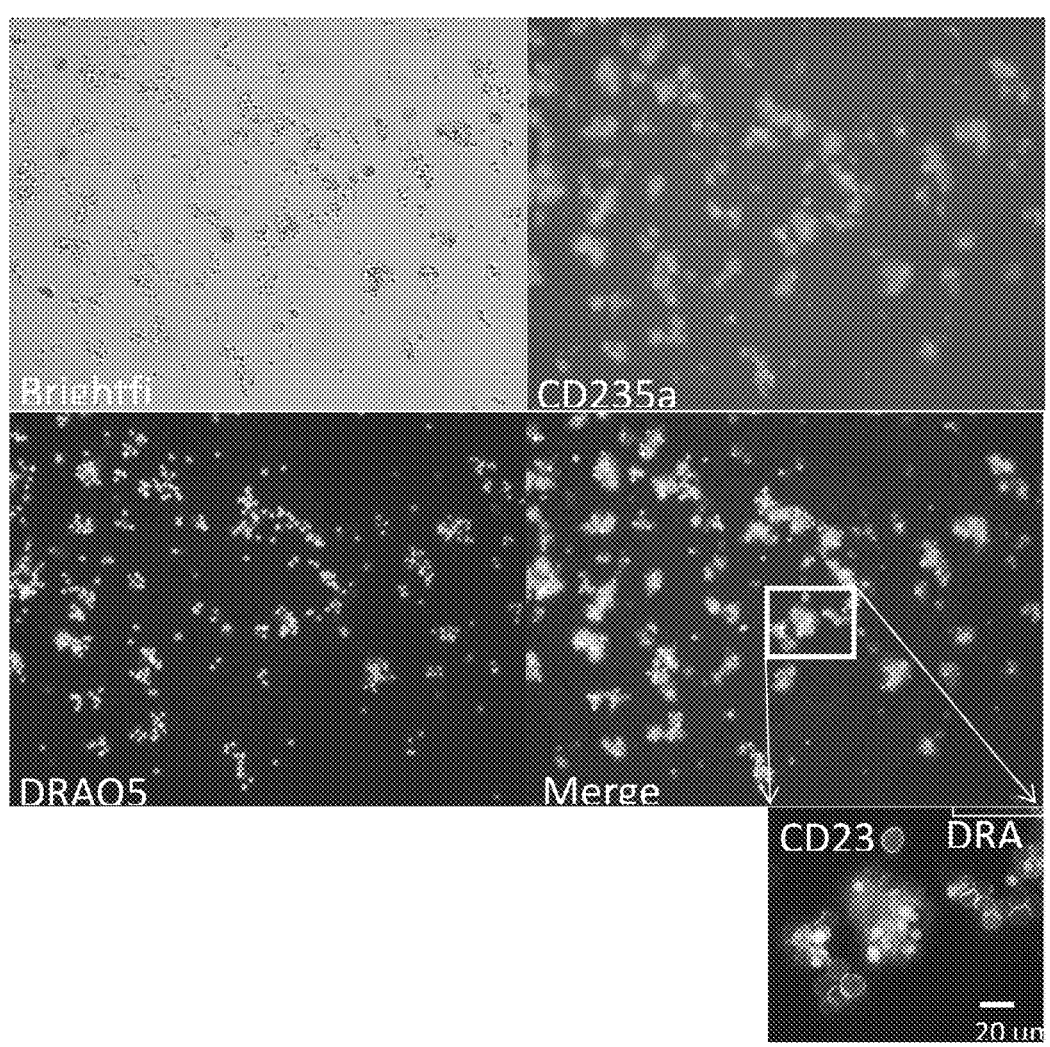

| Condition | Dose and duration of factors evaluated | | | | Response outcome |
|---|---|---|---|---|---|
| | Activin A (ng/ml) | CHIR$_{24hr}$ (µM) | CHIR$_{48hr}$ (µM) | BMP4 (ng/ml) | % KDR+ cells |
| 1 | 0 | 0 | 0 | 10 | 11.4 |
| 2 | 0 | 0 | 0 | 50 | 12.3 |
| 3 | 50 | 0 | 0 | 10 | 38.1 |
| 4 | 50 | 0 | 0 | 50 | 30 |
| 5 | 0 | 12 | 0 | 10 | 48.5 |
| 6 | 0 | 12 | 0 | 50 | 53.8 |
| 7 | 50 | 12 | 0 | 10 | 57.2 |
| 8 | 50 | 12 | 0 | 50 | 49 |
| 9 | 0 | 0 | 12 | 10 | 27.2 |
| 10 | 0 | 0 | 12 | 50 | 33.1 |
| 11 | 50 | 0 | 12 | 10 | 45.9 |
| 12 | 50 | 0 | 12 | 50 | 45.4 |
| 13 | 0 | 12 | 12 | 10 | 53.7 |
| 14 | 0 | 12 | 12 | 50 | 42.9 |
| 15 | 50 | 12 | 12 | 10 | 54.3 |
| 16 | 50 | 12 | 12 | 50 | 69.6 |
| 17 | 25 | 6 | 6 | 10 | 63.7 |
| 18 | 25 | 6 | 6 | 50 | 54.6 |
| 19 | 0 | 6 | 6 | 30 | 49.8 |
| 20 | 50 | 6 | 6 | 30 | 55.1 |
| 21 | 25 | 0 | 6 | 30 | 49.4 |
| 22 | 25 | 12 | 6 | 30 | 47.8 |
| 23 | 25 | 6 | 6 | 30 | 47 |

| Condition | Activin A (ng/ml) | CHIR$_{24hr}$ (μM) | CHIR$_{48hr}$ (μM) | BMP4 (ng/ml) | % KDR+ cells |
|---|---|---|---|---|---|
| 24 | 25 | 6 | 12 | 30 | 43.4 |
| 25 | 25 | 6 | 6 | 30 | 59.9 |
| 26 | 25 | 6 | 6 | 30 | 69.3 |
| 27 | 25 | 6 | 6 | 30 | 53.2 |
| 28 | 25 | 6 | 6 | 30 | 56.6 |
| 29 | 25 | 6 | 6 | 30 | 59.5 |

FIG. 9 contined
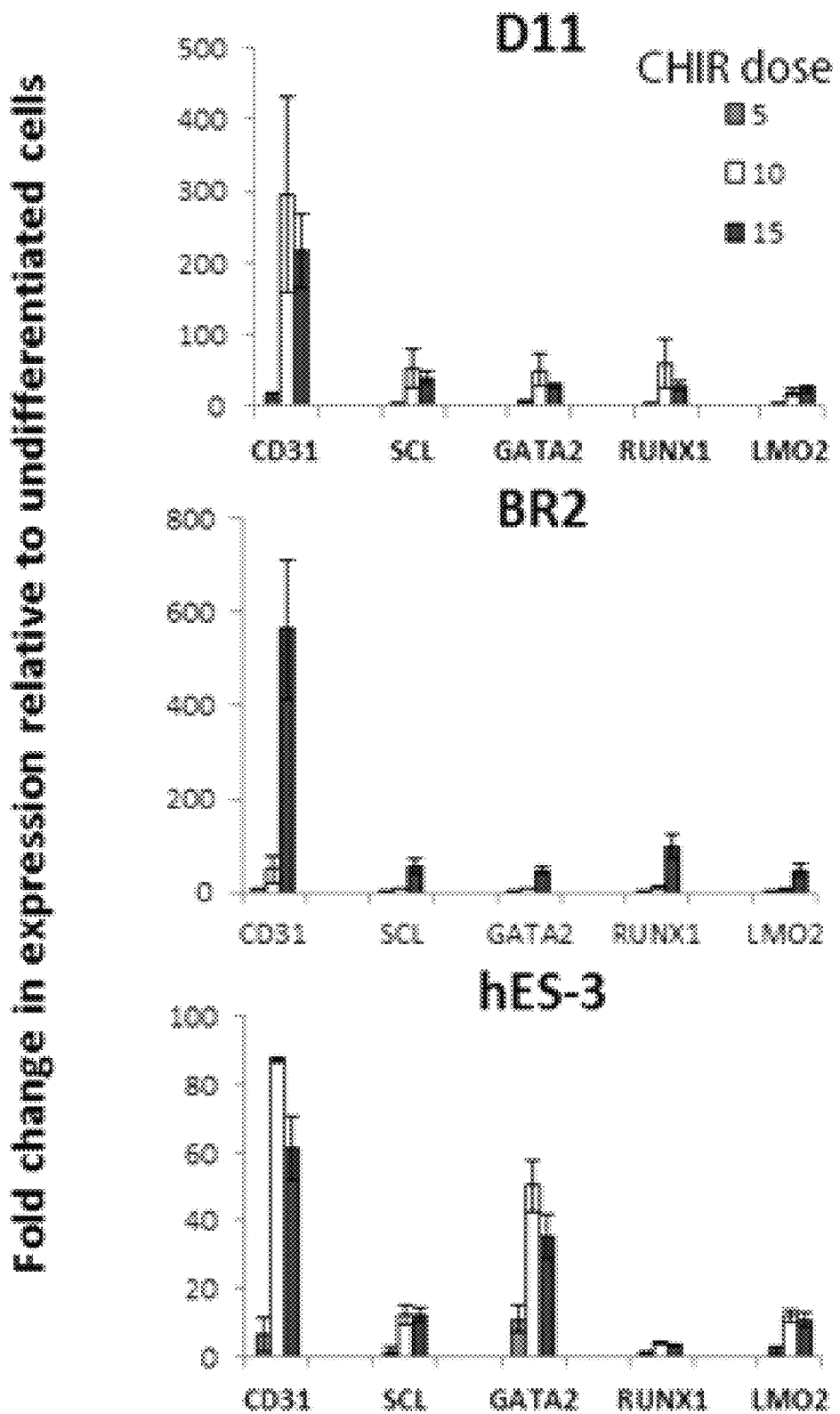

| Condition | Activin A (ng/ml) | CHIR$_{24hr}$ (μM) | CHIR$_{48hr}$ (μM) | SB (μM) | BMP4 (ng/ml) | KDR |
|---|---|---|---|---|---|---|
| 1 | 0 | 0 | 0 | 0 | 50 | 0.44 |
| 2 | 80 | 0 | 0 | 0 | 10 | 1.07 |
| 3 | 0 | 15 | 0 | 0 | 10 | 9.19 |
| 4 | 80 | 15 | 0 | 0 | 50 | 18.5 |
| 5 | 0 | 0 | 15 | 0 | 10 | 1.18 |
| 6 | 80 | 0 | 15 | 0 | 50 | 2.06 |
| 7 | 0 | 15 | 15 | 0 | 50 | 30.7 |
| 8 | 80 | 15 | 15 | 0 | 10 | 35.6 |
| 9 | 0 | 0 | 0 | 30 | 10 | 0.8 |
| 10 | 80 | 0 | 0 | 30 | 50 | 0.97 |
| 11 | 0 | 15 | 0 | 30 | 50 | 17.7 |
| 12 | 80 | 15 | 0 | 30 | 10 | 16.3 |
| 13 | 0 | 0 | 15 | 30 | 50 | 4.57 |
| 14 | 80 | 0 | 15 | 30 | 10 | 1.38 |
| 15 | 0 | 15 | 15 | 30 | 10 | 38 |
| 16 | 80 | 15 | 15 | 30 | 50 | 38.7 |
| 17 | 0 | 7.5 | 7.5 | 15 | 30 | 5.61 |
| 18 | 80 | 7.5 | 7.5 | 15 | 30 | 19.2 |
| 19 | 40 | 0 | 7.5 | 15 | 30 | 2.42 |
| 20 | 40 | 15 | 7.5 | 15 | 30 | 38.6 |
| 21 | 40 | 7.5 | 0 | 15 | 30 | 9.25 |
| 22 | 40 | 7.5 | 15 | 15 | 30 | 30.8 |
| 23 | 40 | 7.5 | 7.5 | 0 | 30 | 9.24 |
| 24 | 40 | 7.5 | 7.5 | 30 | 30 | 11.4 |
| 25 | 40 | 7.5 | 7.5 | 15 | 10 | 33.1 |
| 26 | 40 | 7.5 | 7.5 | 15 | 50 | 28.3 |
| 27 | 40 | 7.5 | 7.5 | 15 | 30 | 16.9 |
| 28 | 40 | 7.5 | 7.5 | 15 | 30 | 28.7 |
| 29 | 40 | 7.5 | 7.5 | 15 | 30 | 14 |

| | Dose and duration of factors evaluated | | | | Response outcome |
|---|---|---|---|---|---|
| Condition | Activin A (ng/ml) | CHIR$_{24hr}$ (µM) | CHIR$_{48hr}$ (µM) | BMP4 (ng/ml) | % KDR+ cells |
| 1 | 0 | 0 | 0 | 10 | 11.4 |
| 2 | 0 | 0 | 0 | 50 | 12.3 |
| 3 | 50 | 0 | 0 | 10 | 38.1 |
| 4 | 50 | 0 | 0 | 50 | 30 |
| 5 | 0 | 12 | 0 | 10 | 48.5 |
| 6 | 0 | 12 | 0 | 50 | 59.8 |
| 7 | 50 | 12 | 0 | 10 | 57.2 |
| 8 | 50 | 12 | 0 | 50 | 49 |
| 9 | 0 | 0 | 12 | 10 | 27.2 |
| 10 | 0 | 0 | 12 | 50 | 33.1 |
| 11 | 50 | 0 | 12 | 10 | 45.9 |
| 12 | 50 | 0 | 12 | 50 | 45.4 |
| 13 | 0 | 12 | 12 | 10 | 53.7 |
| 14 | 0 | 12 | 12 | 50 | 42.9 |
| 15 | 50 | 12 | 12 | 10 | 54.3 |
| 16 | 50 | 12 | 12 | 50 | 69.8 |
| 17 | 25 | 6 | 6 | 30 | 63.7 |
| 18 | 25 | 6 | 6 | 50 | 54.6 |
| 19 | 0 | 6 | 6 | 30 | 49.8 |
| 20 | 50 | 6 | 6 | 30 | 55.1 |
| 21 | 25 | 0 | 6 | 30 | 48.4 |
| 22 | 25 | 12 | 6 | 30 | 47.8 |
| 23 | 25 | 6 | 0 | 30 | 47 |
| 24 | 25 | 6 | 12 | 30 | 43.4 |
| 25 | 25 | 6 | 6 | 30 | 59.9 |
| 26 | 25 | 6 | 6 | 30 | 69.3 |
| 27 | 25 | 6 | 6 | 30 | 53.2 |
| 28 | 25 | 6 | 6 | 30 | 56.6 |
| 29 | 25 | 6 | 6 | 30 | 59.5 |

| Condition | | T-bra 24 hr | T-bra 48 hr | T-bra 96 hr |
|---|---|---|---|---|
| No treatment | | 2.00% | 1.93% | |
| Condition #1 | 10 ng/ml BMP4 | 4.00% | 7.75% | 5.36% |
| Condition #2 | 50 ng/ml BMP4 | 3.37% | 8.36% | 4.56% |
| Condition #4 | 50 ng/ml BMP4; 80 ng/ml Activin A | 2.38% | 6.66% | 2.11% |
| Condition #7 | 10 ng/ml BMP4; 80 ng/ml Activin A; 15 uM CHIR$_{24hr}$ | 14.0% | 52.6% | 1.45% |
| Condition #16 | 50 ng/ml BMP4; 80 ng/ml Activin A; 15 uM CHIR$_{24hr}$; 15 uM CHIR$_{48hr}$ | 24.3% | 44.9% | 2.63% |
| Condition #18 | 50 ng/ml BMP4; 40 ng/ml Activin A; 7.5 uM CHIR$_{24hr}$; 7.5 uM CHIR$_{48hr}$ | 51.3% | 89.6% | 1.19% |

| Test | Lines | hES-3 | IMR90 | BR2 | BR7 | D12 | D11 | D5 | D9 | X13 |
|---|---|---|---|---|---|---|---|---|---|---|
| Pluripotency (%) | Oct-4 | 94.6 ± 0.7 | 83.7 ± 0.3 | 92.5 ± 0.9 | 72.9 ± 2.1 | 94.3 ± 0.7 | 84.9 ± 1.4 | 83.4 ± 1.9 | 81.8 ± 1.1 | 80.6 ± 0.4 |
| | Tra1-60 | | | | | | | | | |
| | SSEA4 | 99.7 ± 0.1 | 99.9 ± 0.03 | 97.2 ± 0.7 | 99.4 ± 0.1 | 99.2 ± 0.2 | 99.1 ± 0.2 | 98.1 ± 0.2 | 98.9 ± 0.6 | 97.2 ± 0.4 |
| Survival | | | | | | | | | | |
| Fold-expansion | | 10.1 ± 1.1 | 12.5 ± 0.9 | 8.0 ± 0.7 | 9.6 ± 0.9 | 8.0 ± 0.8 | 7.8 ± 1.4 | 7.7 ± 0.9 | 8.0 ± 0.5 | 5.3 ± 0.8 |
| Homogeneity | | 1 | 1.3 ± 0.4 | 0.6 ± 0.2 | 0.7 ± 0.05 | 0.6 ± 0.1 | | | | |
| IGF-2 mRNA level (relative to hES-3) | | 1 | 1.3 ± 0.4 | 0.6 ± 0.2 | 0.7 ± 0.05 | 0.6 ± 0.1 | 0.71 ± 0.08 | 0.47 ± 0.03 | 0.36 ± 0.04 | 0.28 ± 0.07 |

A

C

|  | IMR90 | X13 |
|---|---|---|
| Percent erythroid cells (CD235a) | 86.8 % ± 1.8 | 78.3 % ± 2.4 |
| HbF | 98.9 % ± 0.5 | 98.2 % ± 0.9 |
| Cumulative fold expansion (Day 29) | 108 ± 54 | 185 ± 60 |

FIG. 24

| BMP4 (ng/ml) | 10 | 50 | 50 | 10 | 50 | 50 |
| Activin A (ng/ml) | - | - | 50 | 50 | 50 | 25 |
| CHIR99021 (uM) | - | - | - | 12 | 12 | 6 |
| CHIR98014 (uM) | - | - | - | - | 12 | 6 |
| SB431542 (uM) | 20 | - | 20 | 20 | 20 | 10 |

| | Erythroid cells (% CD235a) | HbF (%) | Cumulative fold expansion (Day 42) |
|---|---|---|---|
| D5 | 74.6 ± 6.8 | 99.2 ± 0.1 | 3712 ± 1651 |
| D9 | 57.5 ± 4.6 | 97.8 ± 0.3 | 121 ± 37 |
| D11^ | 33.9 ± 13.6 | 53.6 ± 14.4 | N.A |
| D12^ | 36.1 ± 4.2 | 58.5 ± 11.3 | N.A |
| X13 | 67.4 ± 3.8 | 96.9 ± 1.4 | 12605 ± 2125 |
| BR2^ | 37.1 ± 3.5 | 48.9 ± 8.0 | N.A |
| BR7 | 33.8 ± 3.6 | 95.5 ± 1.5 | 31 ± 7.7 |
| IMR90 | 75.9 ± 1.8 | 98.1 ± 0.5 | 913 ± 342 |
| hES-3 | 78.5 ± 3.0 | 99.3 ± 0.1 | 324 ± 84 |

FIG. 26 continued

| | D12 agitate | D5 agitate |
|---|---|---|
| CD235a+ CD71+ | 55.2 % ± 2.56 | 48.9 % ± 3.13 |
| CD235a+ CD71- | 8.18 % ± 0.83 | 6.39 % ± 0.30 |
| CD235a+ CD36+ | 57.1 % ± 2.33 | 50.1 % ± 3.27 |
| CD235a+CD36- | 9.86 % ± 0.86 | 4.81 % ± 0.07 |
| Total CD235a | 63.4 % ± 2.22 | 55.3 % ± 2.84 |
| HbF | 93.6 % ± 0.87 | 76.3 % ± 4.63 |
| HbA | 56.8 % ± 1.14 | 11.78 % ± 1.81 |
| CD14 | 0.02 % ± 0.004 | 0.007 % ± 0.017 |
| CD15 | 0.05 % ± 0.02 | 0.02 % ± 0.05 |
| CD133 | 0.05 % ± 0.03 | 0.89 % ± 0.087 |
| CXCR4 | 0.14 % ± 0.058 | 1.10 % ± 0.20 |
| Cumulative fold-expansion (Day 35) | 385 ± 152 | 835 ± 373 |

E

|  | Glucose (g/L) | Lactate (g/L) | Ammonia (mM) |
|---|---|---|---|
| Media | 3.61 ± 0.03 | 0.41 ± 0.02 | 0 |
| D9 | 1.85 ± 0.03 | 2.49 ± 0.02 | 4.65 ± 0.10 |
| D12 | 3.92 ± 0.01 | 0.97 ± 0.13 | 3.92 ± 0.01 |
| BM1 | 3.94 ± 0.19 | 1.18 ± 0.06 | 2.47 ± 0.15 |
| C86 | 3.6 ± 0.25 | 1.34 ± 0.14 | 3.28 ± 0.30 |
| BR7 | 3.98 ± 0.20 | 1.02 ± 0.09 | 2.97 ± 0.25 |
| X13 | 4.09 ± 0.10 | 0.96 ± 0.10 | 1.05 ± 0.12 |

A

| Day 27 | Spinner 1 | Spinner 2 | Spinner 3 |
|---|---|---|---|
| Concentration (cells/ml) | $1.7 \times 10^7$ ± $5.2 \times 10^5$ | $1.32 \times 10^7$ ± $3.2 \times 10^5$ | $1.38 \times 10^7$ ± $3.2 \times 10^5$ |
| Total cells/ 50 ml | $8.5 \times 10^8$ ± $1.5 \times 10^7$ | $6.6 \times 10^8$ ± $1.6 \times 10^7$ | $6.9 \times 10^8$ ± $1.6 \times 10^7$ |
| Total media used (ml) | 575 | 575 | 575 |
| Lactate production [g/L/per 24hr/8.5e8 cells] | 1.5 | 1.46 | 1.53 |
| Ammonia production [mM/per 24 hr/ 8.5e8 cells] | 1.32 | 1.17 | 1.53 |
| Glucose consumption [g/L/per 24hr/8.5e8 cells] | 1.47 | 0.94 | 1.072 |

C BMP4 signaling

FIG. 39 contined
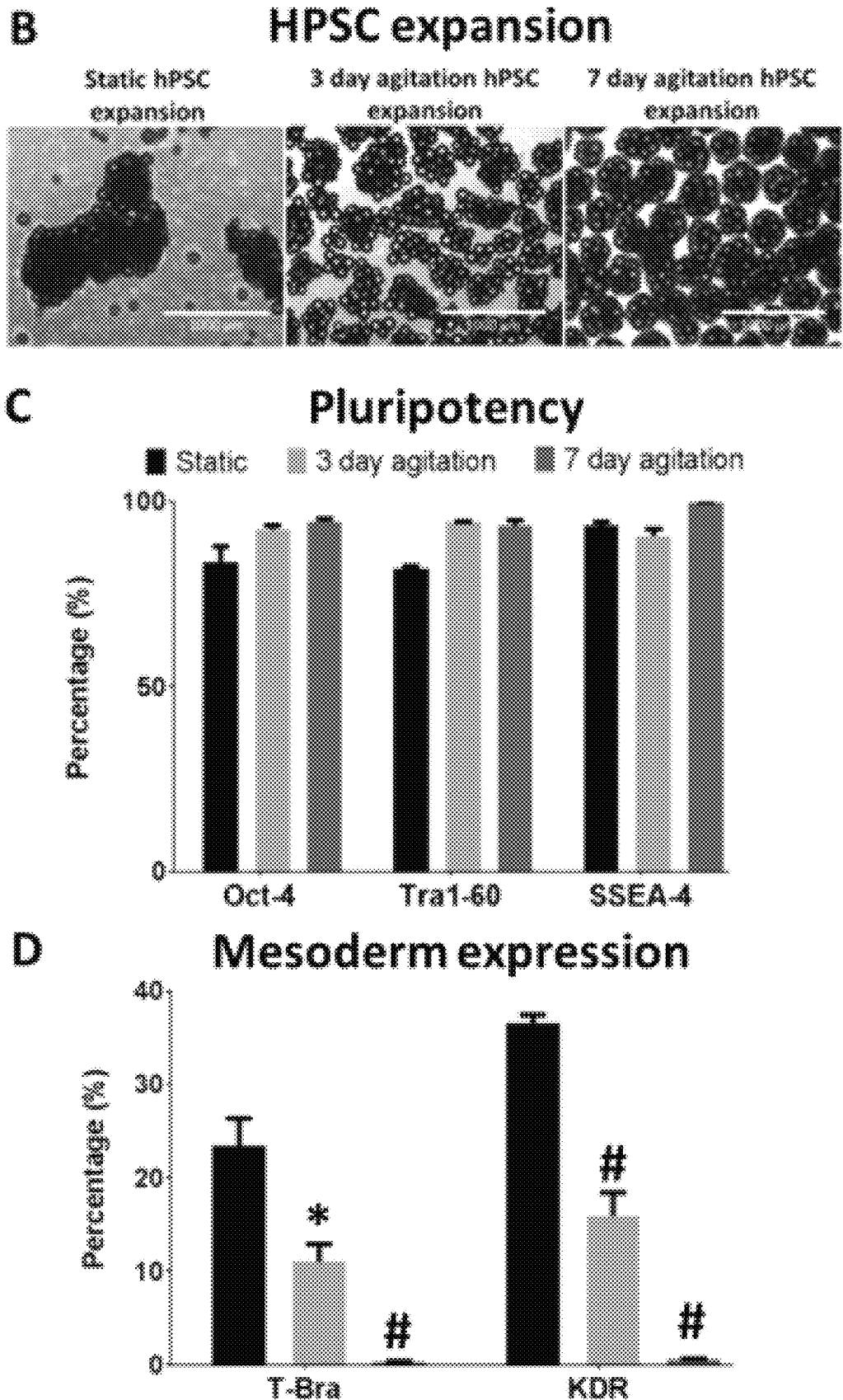

E Hematopoietic markers

F Hematopoietic precursor expansion

G Hematopoietic expansion

| | Static | 3 day agitation | 7 day agitation | Static vs 7 day p-value | Static vs 3 day p-value |
|---|---|---|---|---|---|
| CD235a+ CD71+ (%) | 27.5 % ± 1.2 | 21.6 % ± 1.8 | 0.23 % ± 0.04 | <0.0001 | 0.053 |
| Total CD235a+ (%) | 51.8 % ± 2.0 | 40.4 % ± 3.4 | 0.51 % ± 0.1 | <0.0001 | 0.045 |
| HbF (%) | 65.7 % ± 2.3 | 60.2 % ± 3.8 | 0.70 % ± 0.05 | <0.0001 | 0.28 |
| Total yield (Day 28) | $2.62 \times 10^7 \pm 4.7 \times 10^6$ | $1.26 \times 10^7 \pm 3.5 \times 10^6$ | $4.11 \times 10^6 \pm 2.4 \times 10^4$ | 0.0052 | 0.08 |
| RBC pellet (Day 28) | 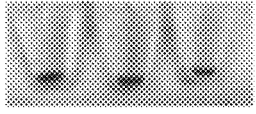 | 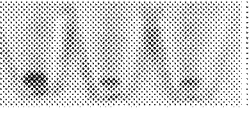 | 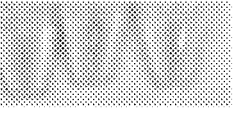 | | |

| | | D5 | X13 | D9 | BR7 | IMR90 | hES-3 |
|---|---|---|---|---|---|---|---|
| Hemox analysis ($P_{50}$ value) | | 12.9 ± 0.3 | 10.5 ± 0.4 | 12.6 ± 0.7 | NA | 10.1 ± 0.3 | 13.4 ± 0.1 |
| Hemoglobin (% of total hemoglobin) | Alpha | 21.8 ± 2.2 | 37.2 ± 1.0 | 54 ± 0.2 | 71.1 ± 1.3 | 74.7 ± 2.6 | 20.9 ± 1.5 |
| | Beta | 2.7 ± 0.7 | 10.6 ± 0.4 | NIL | 5.5 ± 1.0 | NIL | 1.3 ± 0.3 |
| | Gamma | 13.1 ± 0.7 | 15.7 ± 0.2 | 25.9 ± 2.9 | 19.6 ± 0.7 | 19.7 ± 2.1 | 15.3 ± 1.4 |
| | Epsilon | 66.7 ± 5.4 | 36.5 ± 0.8 | 20.1 ± 2.7 | 3.4 ± 1.1 | 5.6 ± 1.0 | 62.5 ± 2.4 |
| Enucleation (Percent CD235a+ DRAQ5-) | | 39 ± 1.0 | 32 ± 1.6 | 28 ± 1.2 | NA | 40.6 ± 1.4 | NA |

E Giemsa staining to identify enucleated RBCs

F Immunofluorescence staining for CD235a/DRAQ5

METHOD FOR DIFFERENTIATION OF HUMAN PLURIPOTENT STEM CELL LINES IN SUSPENSION CULTURE

CROSS-REFERENCE TO RELATED APPLICATIONS

This application claims the benefit of priority of SG provisional application No. 10201800488W, filed 18 Jan. 2018, the contents of it being hereby incorporated by reference in its entirety for all purposes.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "55747_Seqlisting.txt", which was created on Jul. 16, 2020 and is 4,757 bytes in size. The subject matter of the Sequence Listing is incorporated herein in its entirety by reference.

FIELD OF THE INVENTION

The present invention relates generally to the field of molecular biology. In particular, the present invention relates to a method of cell differentiation.

BACKGROUND OF THE INVENTION

Erythroid differentiation of human induced pluripotent stem cells (hiPSCs) has been proposed as a means for generating limitless supply of red blood cells (RBCs). For this to be a reality, scalable suspension culture differentiation methods have to be developed. The erythroid differentiation of human pluripotent stem cells (hPSCs) expanded in agitation microcarrier (MC) suspension culture using a bone morphogenetic protein-4 (BMP4)-based differentiation protocol had been previous shown, wherein mesoderm induction and erythroblast expansion were done in static condition. However, repeated attempts to implement this process to differentiate multiple hPSC lines demonstrated variability in erythroid differentiation.

Universal O-negative (neg) red blood cells (RBCs) can be derived from differentiation of human induced pluripotent stem cells (hiPSCs) generated from donors with O-negative blood type. Red blood cells generated from human induced pluripotent stem cells can potentially serve as a limitless source of cells to supplement the emergency transfusion needs of healthcare industry. Given that each unit of blood requires one trillion red blood cells, there is a need to develop efficient differentiation and bioprocesses that could allow for the generation of increased numbers of red blood cells. While many means to differentiate human induced pluripotent stem cells into erythroid cells have been described, these have not yet been demonstrated to be capable of up-scaling.

SUMMARY OF THE INVENTION

In one aspect, the present invention refers to a method of differentiation of pluripotent stem cells into hematopoietic precursor cells, wherein the method is carried out under suspension agitation, and wherein a GSK-3-inhibitor or a Wnt pathway activator is added during a stage of mesoderm induction.

In another aspect, the present invention refers to a cell culture media for differentiation of pluripotent stem cells into hematopoietic precursor cells, thereby generating hematopoietic precursor cells from pluripotent stem cells using microcarrier embryoid bodies (EB), the cell culture media comprising a bone morphogenic protein, a GSK-3 kinase inhibitor, wherein the inhibitor is selected from the group consisting of CHIR99021, (2'Z,3'E)-6-Bromoindirubin-3'-oxime (Bio; CAS 667463-62-9), Kenpaullone (CAS 142273-20-9), GSK-3beta Inhibitor XII (TWS119; CAS 601514-19-6), Bio-Acetoxime (CAS 667463-85-6), CHIR-98014, SB216763 (CAS 280744-09-4), GSK-3beta Inhibitor VIII (CAS 487021-52-3) and combinations thereof, or a Wnt pathway activator, Activin A, and a vascular endothelial growth factor.

In yet another aspect, the present invention refers to a cell culture media for differentiation of pluripotent stem cells into hematopoietic precursor cells, thereby generating hematopoietic precursor cells from pluripotent stem cells using microcarrier embryoid bodies (EB) or pluripotent stem cells, the cell culture media comprising a bone morphogenic protein, Activin A, and a vascular endothelial growth factor.

In a further aspect, the present invention refers to a cell culture media for differentiation of pluripotent stem cells into hematopoietic precursor cells, thereby generating hematopoietic precursor cells from pluripotent stem cells using microcarrier embryoid bodies (EB) or pluripotent stem cells, the cell culture media comprising a bone morphogenic protein, Activin A, bFGF (basic fibroblast growth factor) or variant thereof, a hormone, a cytokine, and a vascular endothelial growth factor.

In yet another aspect, the present invention refers to a method for differentiation of pluripotent stem cells into hematopoietic precursor cells, wherein the method is carried out under suspension agitation, the method comprising a. (optionally) providing pluripotent stem cells; b. exposing the cells of step a. to the cell culture medium as defined herein for 24 hours (day 0 to day 1), thereby resulting in T-Brachyury (T-Bra; primitive streak/early mesoderm marker) positive cells; c. exposing the cells of step b. to the cell culture medium as disclosed herein for 24 hours (day 1 to day 2); d. exposing the micro-carrier attached cells of step c. to the cell culture medium as disclosed herein for 48 hours (day 2 to day 4), whereby steps b. to d. induce mesoderm induction; e. removing the cell culture medium, and isolating the resulting KDR+PDGFRα-hematopoietic precursor cells of step d.

In another aspect, the present invention refers to a method for differentiation of pluripotent stem cells into hematopoietic precursor cells, wherein the method is carried out under suspension agitation, the method comprising optionally providing pluripotent stem cells; inducing mesoderm induction in the pluripotent stem cells isolated from step a. according to the method as disclosed herein, thereby resulting in KDR+PDGFRα− hematopoietic precursor cells; inducing hematopoietic induction in the cells isolated from step b, thereby resulting in CD34/CD43/CD45 hematopoietic progenitor cells; inducing erythroblast expansion in the cells isolated from step c, thereby resulting in CD235a+CD71+ erythroblast cells; inducing erythroblast maturation in the cells isolated from step d, thereby resulting in CD235a+ DRAQ5-ve enucleated erythroblast cells; removing the cell culture medium, and isolating the resulting CD235a+ DRAQ5-ve enucleated erythroblast cells of step e.

In a further aspect, the present invention refers to a kit comprising micro-carriers and the cell culture media as disclosed herein.

BRIEF DESCRIPTION OF THE DRAWINGS

The invention will be better understood with reference to the detailed description when considered in conjunction with the non-limiting examples and the accompanying drawings, in which:

FIG. 24 shows images and column graphs depicting the results of Donor 5 O-neg human induced pluripotent stem cell-microcarrier (hiPSC-MC) agitation culture: Cumulative fold-expansion from day 0 to day 56 for selected conditions (identified from DoE multifactorial study). All data are mean±SEM, n=3. Concentrations of cytokines and small-molecules for the respective conditions used on Day 1 or 2 of differentiation are shown in the table below. Red blood cell pellet at day 34 of experiment for conditions 7 and 18 are shown.

FIG. 25 shows the results of mean expansion of hematopoietic precursors in blast growth medium for 2 weeks of 9 different human pluripotent stem cell (hPSC) lines. (A) shows column graph of the 9 different human pluripotent stem cell (hPSC) lines which were initially cultured on microcarriers (MC) under agitation condition (D5, D9, D11, D12, X13, BR2, BR7, IMR90, hES-3) and differentiated with different concentrations of CHIR99021 (5, 10 and 15 μM). (B) shows a table showing the percentage (%) of CD235a+ve erythroid cells and fetal hemoglobin (HbF) expressing cells as well as corresponding cumulative fold expansion on day 42 of differentiation for the 9 different lines. Cell lines denoted with "^" failed to expand during the erythroblast expansion stage.

(B) shows a column graph of the percentage of Annexin V positive (apoptotic) cells evaluated weekly by flow cytometry. *p<0.05, ***p<0.001.

Figure 34:
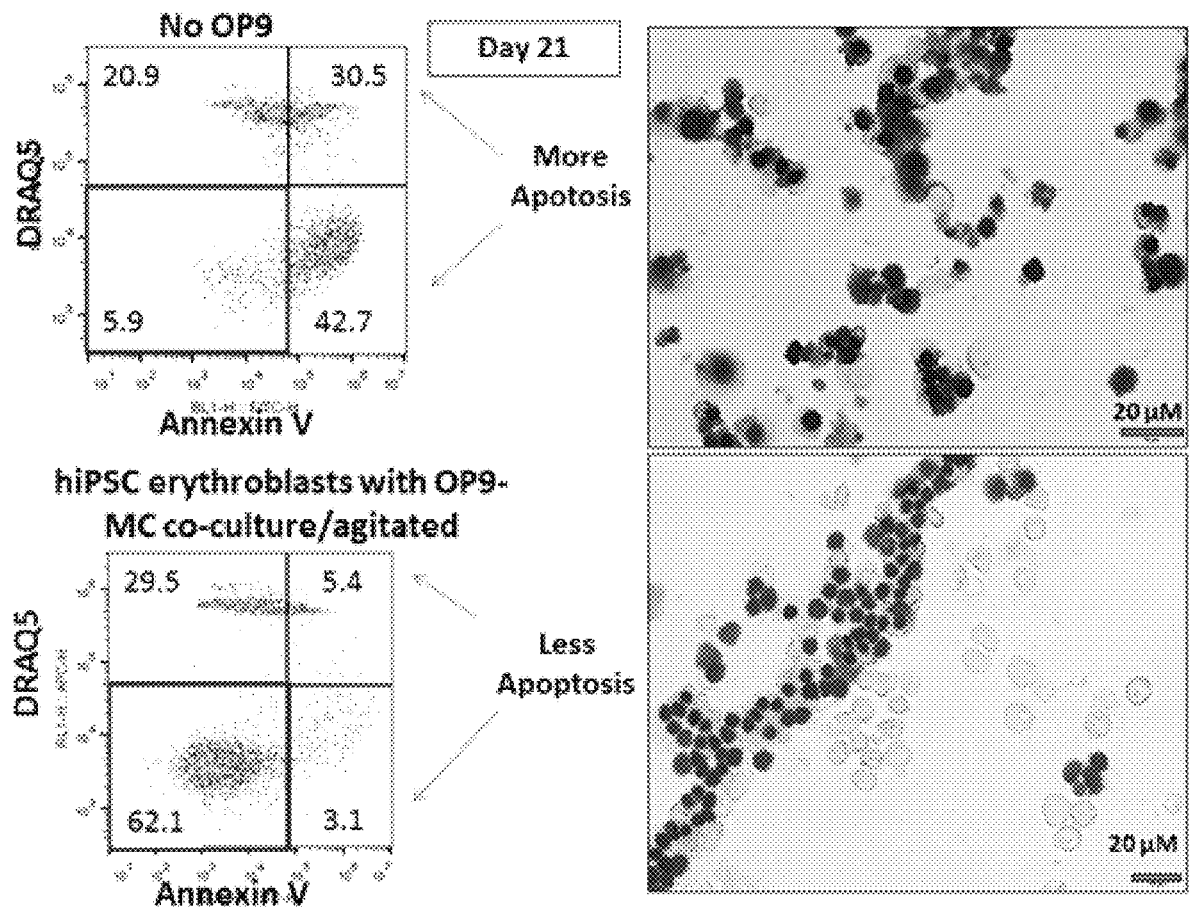

FIG. 34 shows data resulting from the evaluation of human induced pluripotent stem cell (hiPSC) erythroblasts enucleation. Top-left: Flow cytometry evaluation of hiPSC erythroblasts (no OP9 co-culture) with Annexin V and DRAQ5 shows significant apoptotic cells (Annexin V+). Top-right: Giemsa staining of human induced pluripotent stem cell (hiPSC) erythroblasts matured for 3 weeks without any co-culture. Bottom left: Flow cytometry evaluation of hiPSC erythroblasts (with OP9-microcarrier co-culture) with Annexin V and DRAQ5 shows significant percentage of non-apoptotic enucleated cells (Annexin V⁻ DRAQ5⁻). Boxes demarcate cell population that are enucleated and non-apoptotic. Bottom-right: Giemsa staining of hiPSC erythroblasts matured for 3 weeks with co-culture of OP9-MC aggregates shows significantly more enucleated cells.

Figure 35:
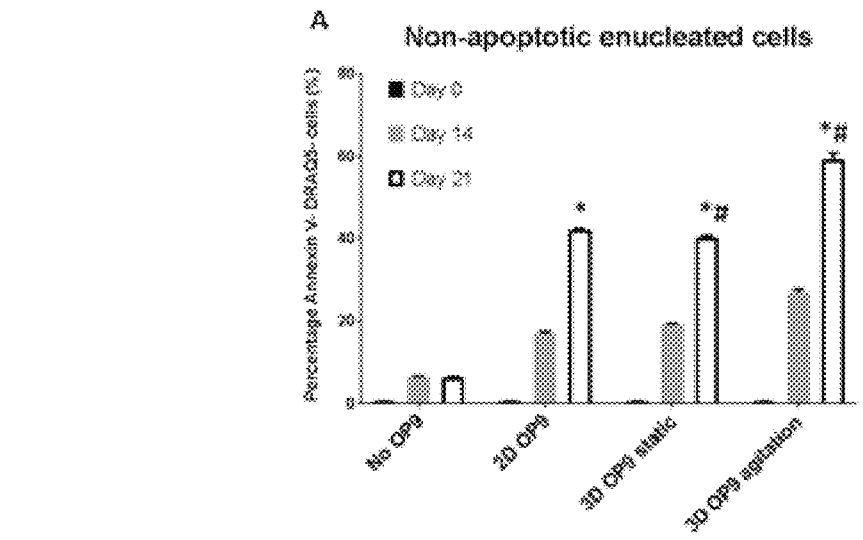
Figure 35:
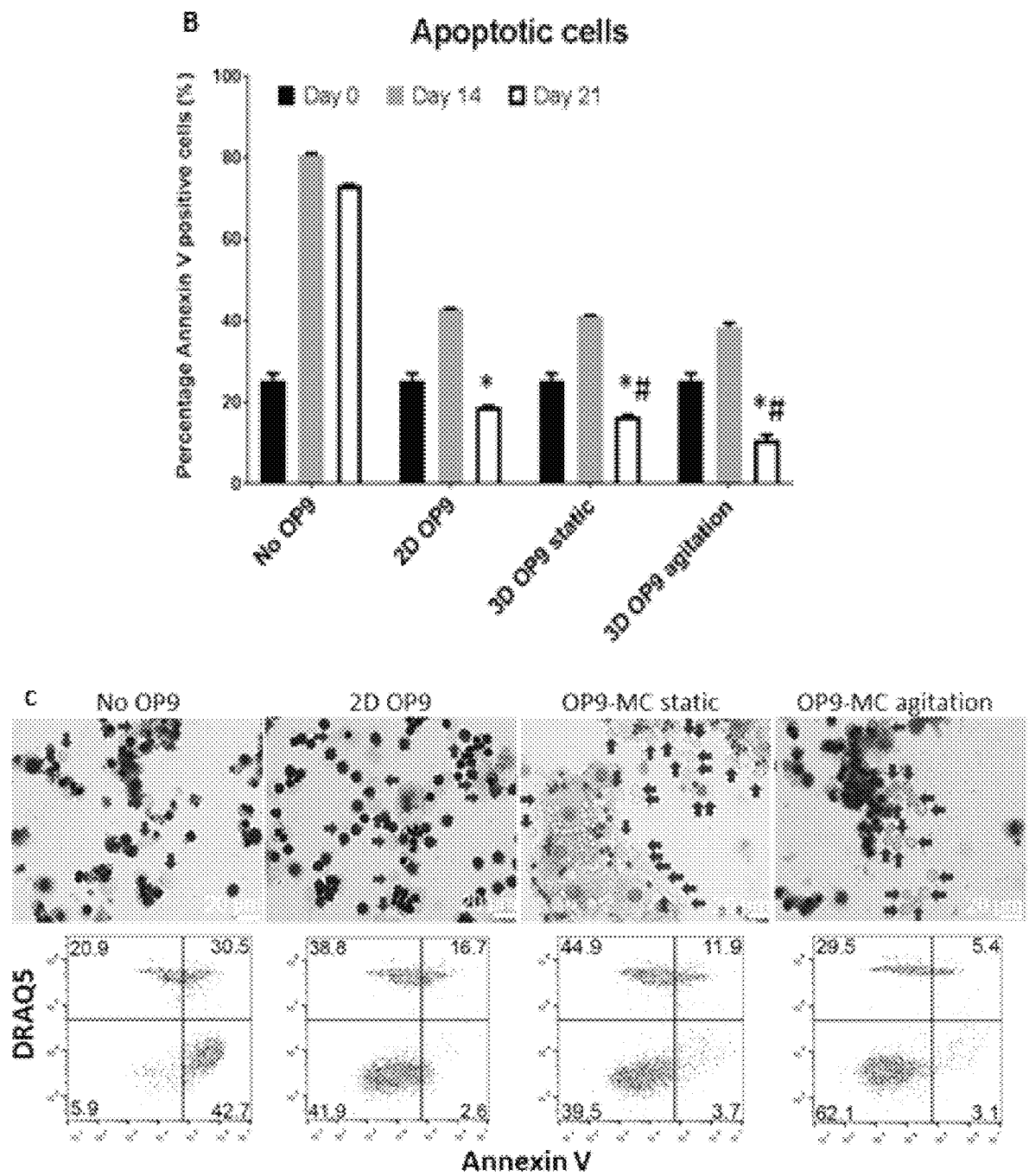

FIG. 35 shows data from the optimization of human induced pluripotent stem cell (hiPSC) erythroblasts enucleation under different conditions. HiPSC erythroblasts were terminally matured for 3 weeks under the following conditions: No OP9 co-culture, 2D (monolayer) OP9 co-culture, 3D OP9 (0P9-microcarrier (MC) aggregates) co-culture under static condition and 3D OP9 co-culture under agitation condition (75 rpm). (A) shows the percentage of Annexin V negative DRAQ5– (non-apoptotic enucleated) red blood cells. (B) shows the percentage of Annexin V positive (apoptotic) cells evaluated weekly by flow cytometry. *p-values as compared to no OP9 co-culture, #p-values as compared to 2D OP9 co-culture. (C) shows images of Giemsa staining of hiPSC erythroblasts matured for 3 weeks without any co-culture (No OP9), with monolayer OP9 co-culture (2D OP9), with 3D OP9-MC co-culture under static condition (0P9-MC static) and 3D OP9-MC co-culture under agitation condition (0P9-MC agitation). Representative flow cytometry plots for Annexin V and DRAQ5 are shown below.

Figure 36:
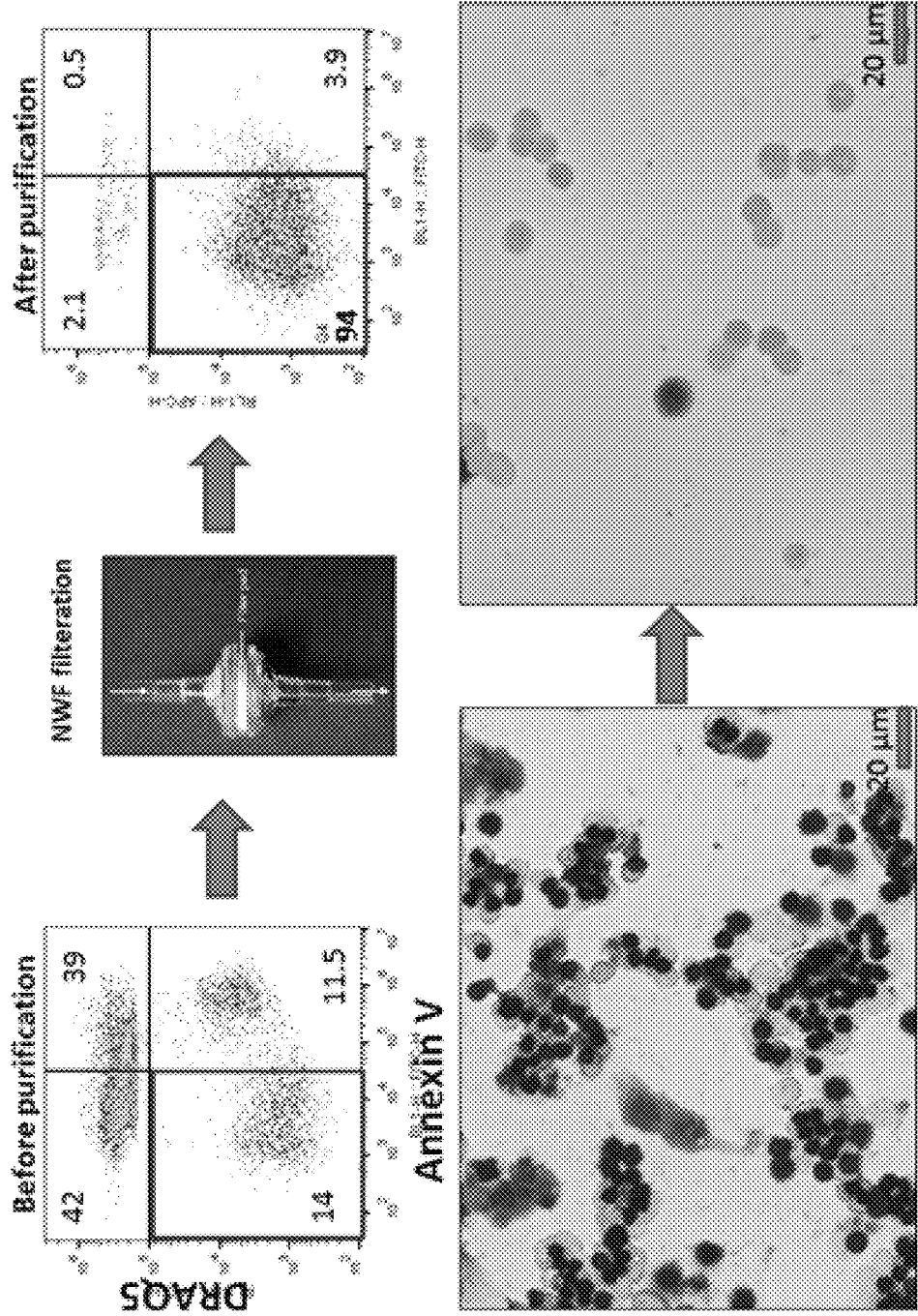

FIG. 36 shows the results of enrichment of enucleated red blood cells with non-woven fabric (NWF) filtration. (Top) Flow cytometry plots of Annexin V and DRAQ5 for human induced pluripotent stem cell (hiPSC) erythroblasts before and after enrichment by passing through NWF filters. The box demarcates non-apoptotic enucleated red blood cells. (Bottom) Corresponding Giemsa staining of cells before and after enrichment are shown below.

Figure 37:
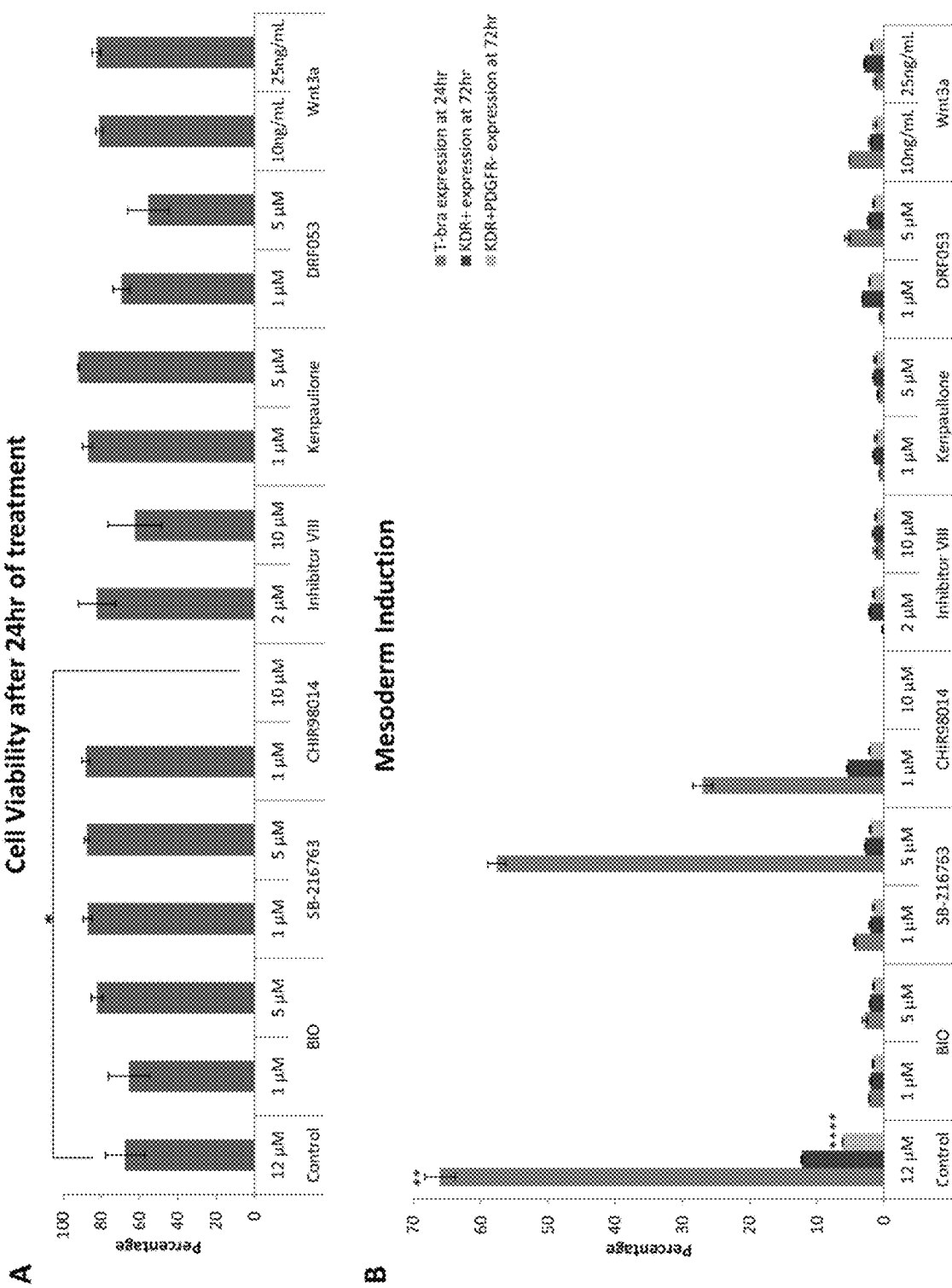

FIG. 37 shows column graphs depicting the results of screening of various Wnt Pathway Activators effective for mesoderm induction. (A) is a column graph showing two different concentrations of seven Wnt pathway activators (BIO, SB-216763, CHIR98014, Inhibitor VIII, Kenpaullone, DRF053 dihydrochloride and Wnt3a). which were selected from literature reviews and screened with CHIR99021 as a control for the disclosed hematopoietic differentiation protocol. The viability of the X13 induced pluripotent stem cells (iPSCs) on microcarriers were tabulated accordingly 24 hours post treatment of the various Wnt pathway modulators. There were no significant differences between the cell viabilities of X13 treated with the various compounds (p>0.05) except at 10 µM of CHIR98014 (p=0.02) where significantly reduced viability was observed. (B) is a column graph showing the percentage of mesogerm induction. To investigate the potency of the Wnt pathway modulators for mesoderm induction, the percentage of T-bra (T-brachyury) expressing cells at 24 hours and KDR+ PDGFRα– (Kinase insert domain receptor; Platelet-derived growth factor receptor) cell populations at 72 hours were analysed using flow cytometry. T-bra expression for all conditions were found to be significantly lower when compared to control (p<0.05) after 24 hours. At 72 hours, KDR+PDGFRα– population for control remained significantly highest when compared to other Wnt pathway modulators (highest p-value being $1.6 \times 10^{-5}$). Two inhibitors (SB-216763 at 5 µM and CHIR98014 at 1 µM) were able to induce higher T-bra expression, compared to other Wnt pathway modulators.

Figure 38:
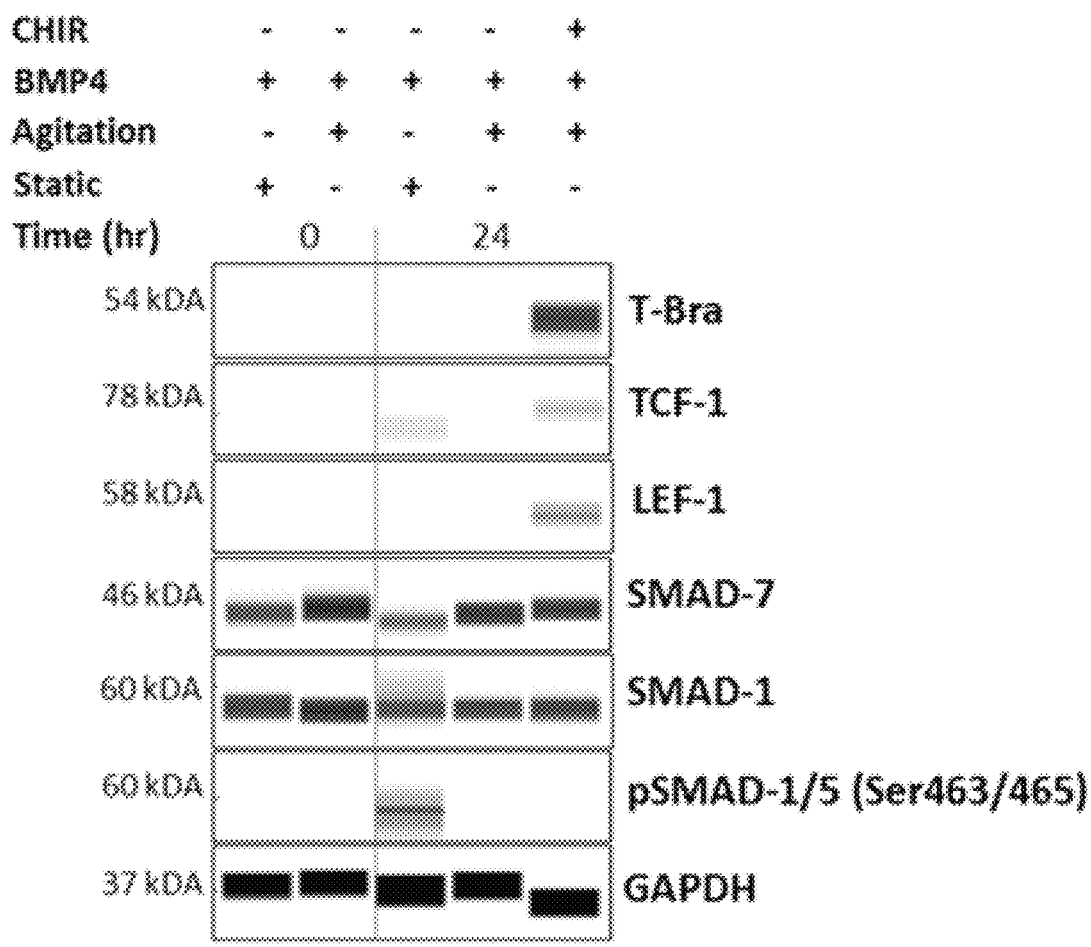
Figure 38:
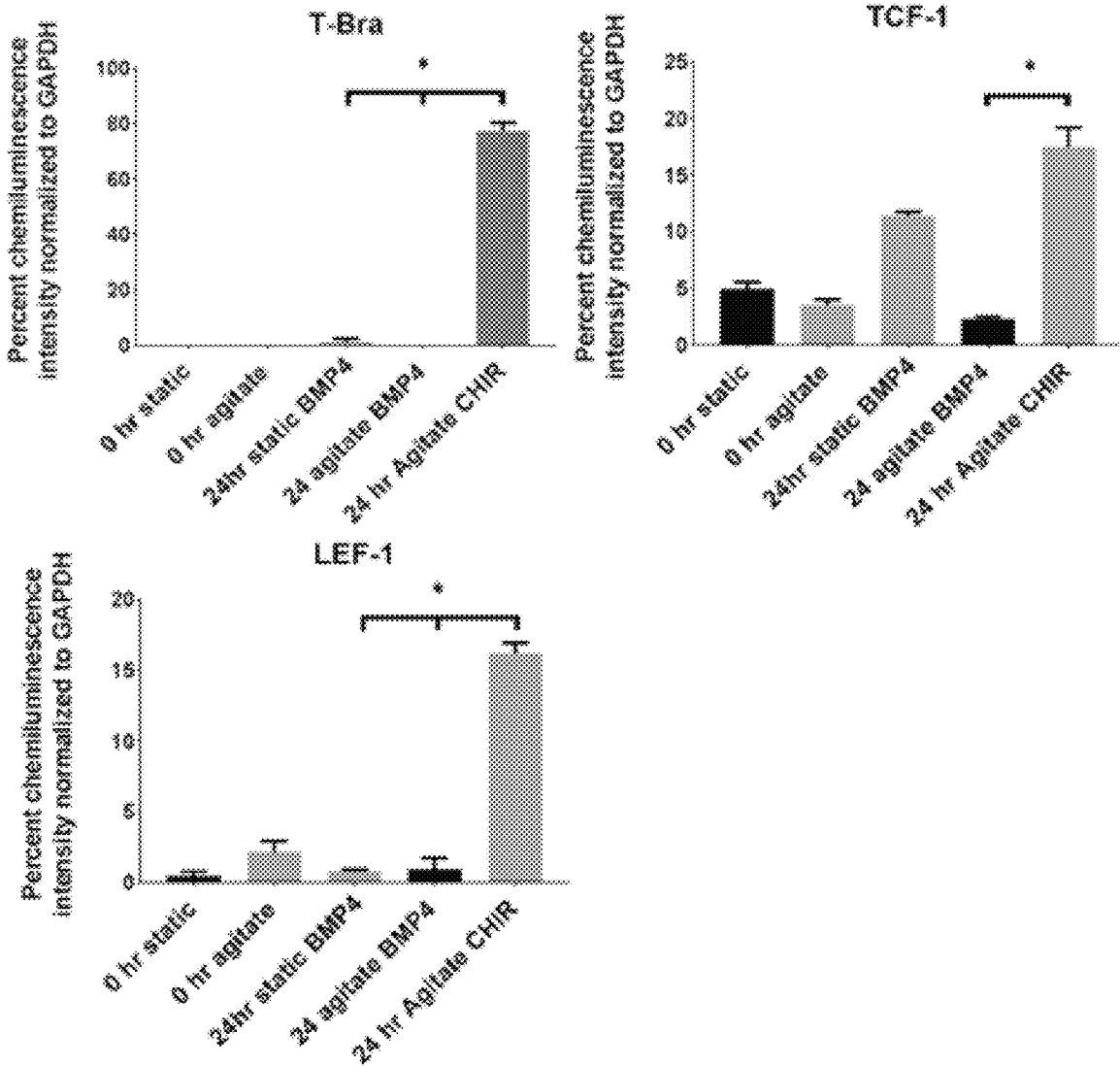
Figure 38:
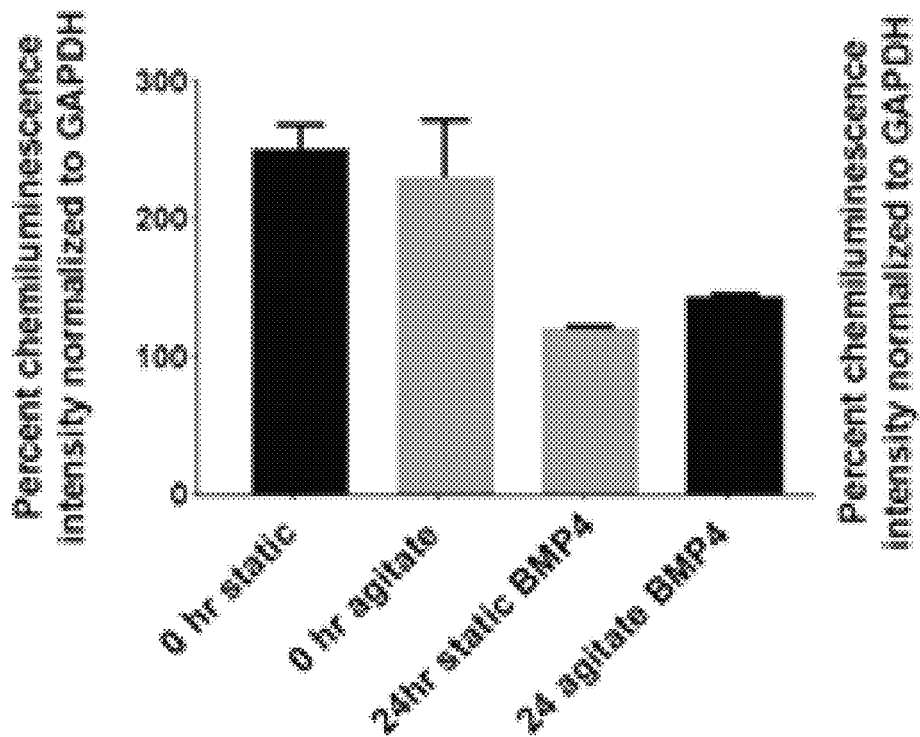
Figure 38:
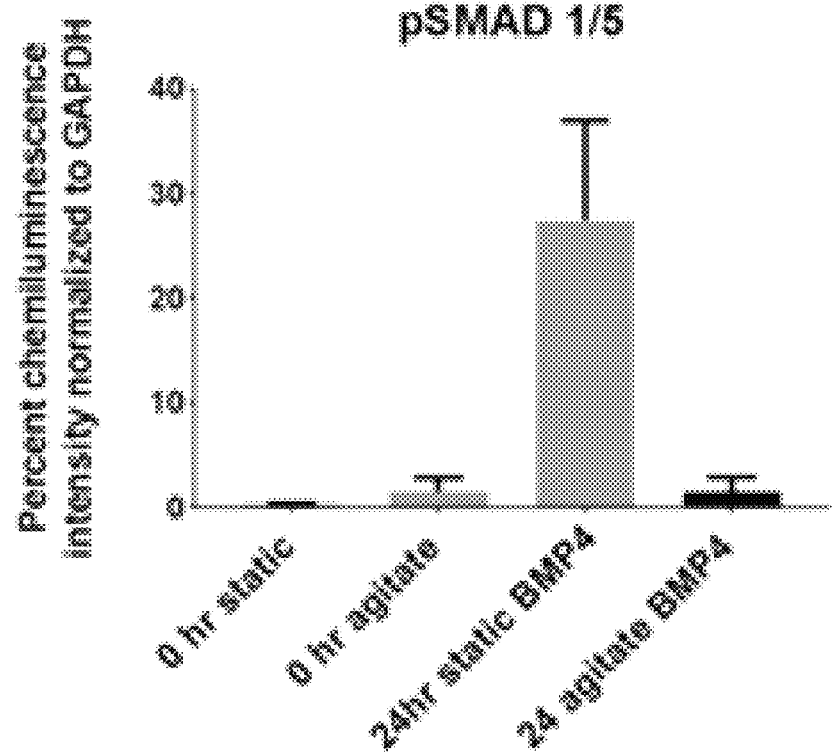
Figure 38C:
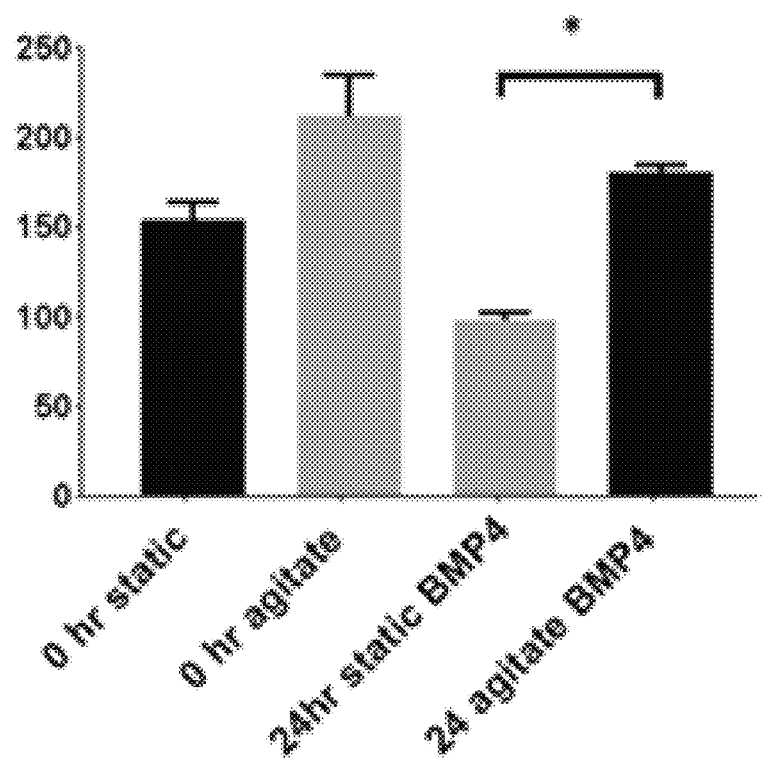

FIG. 38 shows images and the results of capillary Western Blot analysis of hES-3 microcarrier aggregates derived from static or agitated cultures and differentiated with BMP4-based or CHIR-based protocol. Day 7 hES-3-MC aggregates from static or agitation conditions were subjected to differentiation using BMP4 protocol (50 ng/ml BMP4) or optimized CHIR-based protocol (30 ng/ml BMP4, 40 ng/ml Activin A and 15 µM CHIR). Cell lysates before start of differentiation (0 hours) and 24 hours after onset of differentiation were analysed for proteins involved in Wnt/β-catenin signalling (T-BRA, TCF-1 and LEF-1) and BMP4 signalling (SMAD7, SMAD1 and phospho SMAD1/5) using an automated Capillary Western Blot system (Peggy Sue). All samples including GAPDH as a protein loading control were run in parallel. (A) is an image showing digitalized chemiluminescence signals represented as band intensities. Corresponding molecular weight of detected proteins are indicated. Vertical blue line demarcates region of digitalized gels that were merged together. Graphical representation of chemiluminescence intensity of proteins (expressed as a percentage of GAPDH expression) involved in (B) Wnt/β-catenin signalling and (C) BMP4 signalling. Data are mean±SEM, n=2,* p<0.05.

Figure 39:
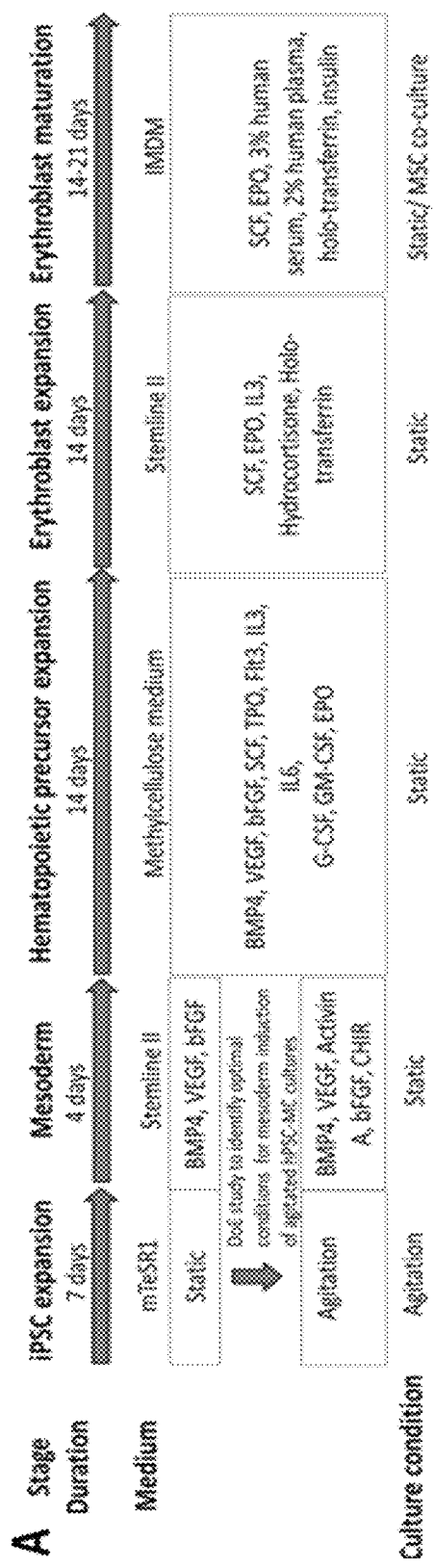
Figure 39:
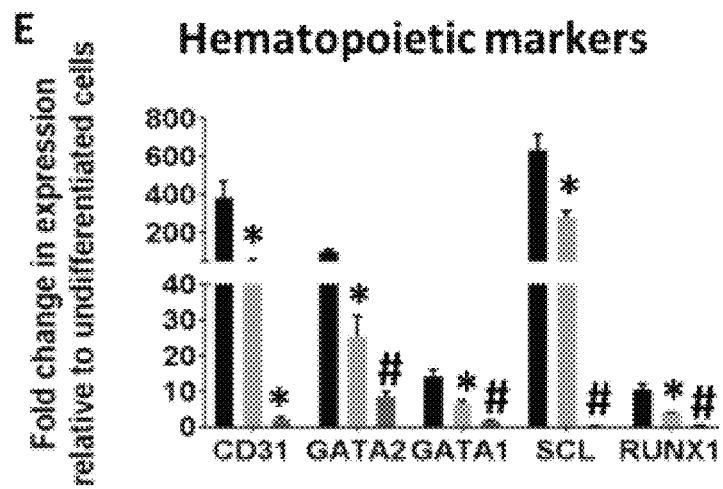
Figure 39:
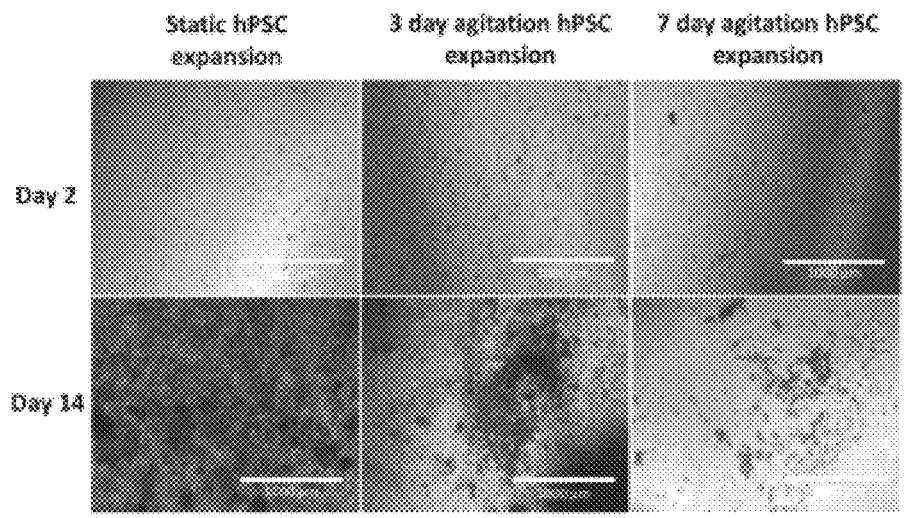
Figure 39:
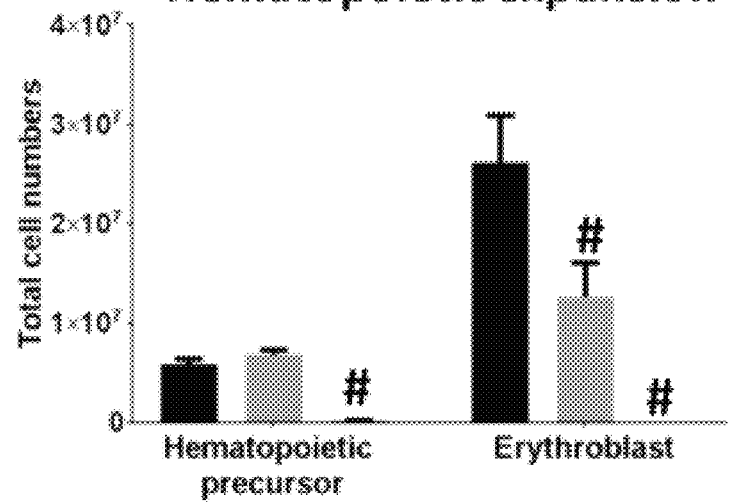

FIG. 39 shows results of the expansion of human pluripotent stem cells (hPSC) in agitated microcarrier (MC) cultures result in reduced BPM4-based hematopoietic differentiation as compared to non-agitated static cultures. (A) shows a schematic of the entire differentiation process starting from human pluripotent stem cell (hPSC) expansion on microcarriers (MCs; under static/agitation) to differentiation and expansion of hematopoietic precursors and erythroblasts followed by terminal maturation. All subsequent steps were performed under static conditions. (B) shows images of hES-3 microcarrier aggregates following 7 days of static or 3 and 7 days of agitated culture. Column graphs summarising results of flow cytometry evaluation of (C) pluripotency markers (3 or 7 days post hPSC expansion), (D) T-Bra (48 hrs post differentiation) and KDR (4 days post differentiation) expression in hES-3-MC aggregates initially expanded under static (static hPSC expansion) or agitated (3 or 7 days agitated hPSC expansion) condition during the pluripotent expansion stage are shown. *P<0.05; #P<0.001 as compared to static human pluripotent stem cell (hPSC) expansion conditions. (E) shows column graphs depicting real-time RT-PCR data showing mean fold change in expression (relative to undifferentiated hES-3) of early hematopoietic specification markers (CD31, GATA2, GATA1, SCL, RUNX1) from hES-3-microcarrier aggregates differentiated for 4 days. *P<0.05; #P<0.001 as compared to static human pluripotent stem cell (hPSC) expansion conditions. (F) shows images of hematopoietic precursors on day 2 and day 14 post expansion in methylcellulose-based medium. Scale bar=1000 micron. (G) shows a column graph representing total counts of hematopoietic precursors (day 14 post expansion in BGM medium following initial seeding of $1 \times 10^5$ cells) and erythroblasts (Day 14 post seeding in erythroblast expansion medium) differentiated from hES-3-microcarrier aggregates derived from static and 3 or 7 days agitation cultures (#P<0.001 as compared to static hPSC expansion condition). (H) is a table summarizing flow cytometry expression (%) of CD235a+CD71+, total CD235a+ and fetal hemoglobin (HbF) expressing cells and total yield of viable cells 28 days post differentiation of hES3-MC aggregates. Corresponding P-values for comparison between static and agitation cultures as well as images of erythroblast cell pellets at termination of experiment (day 28) are shown. All data are mean±SEM, n=3.

Figure 40:
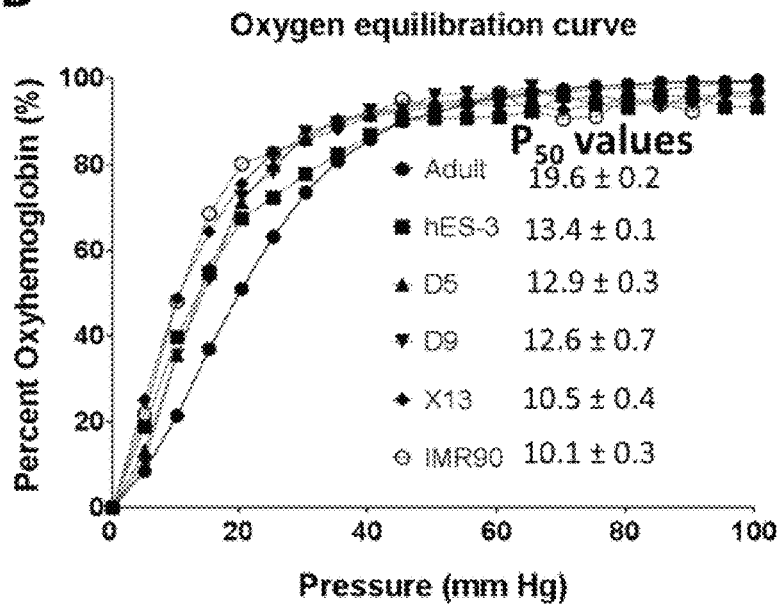
Figure 40:
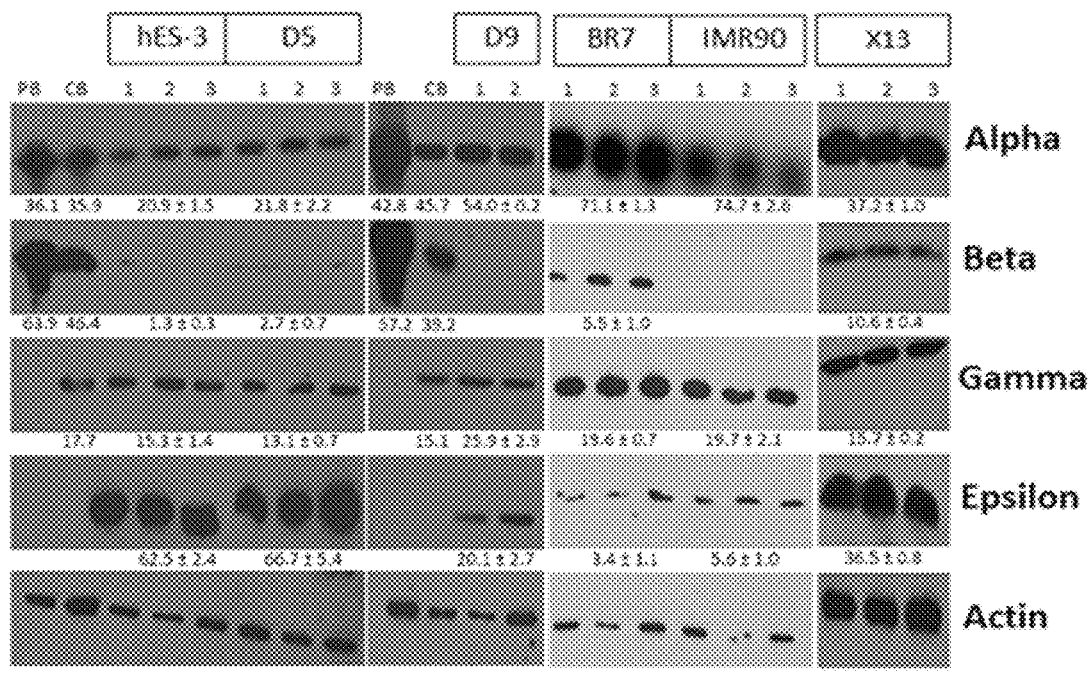
Figure 40:
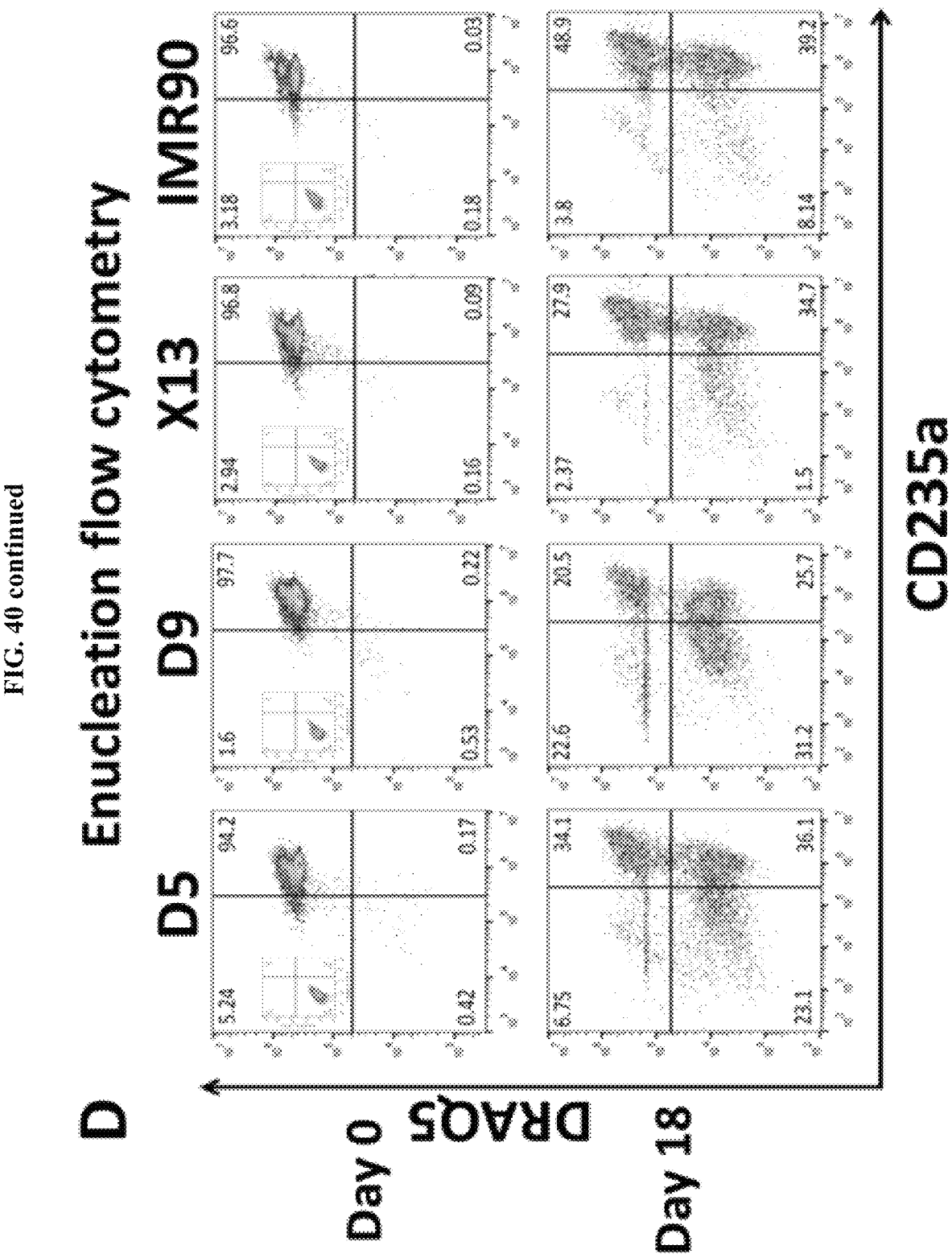
Figure 40:
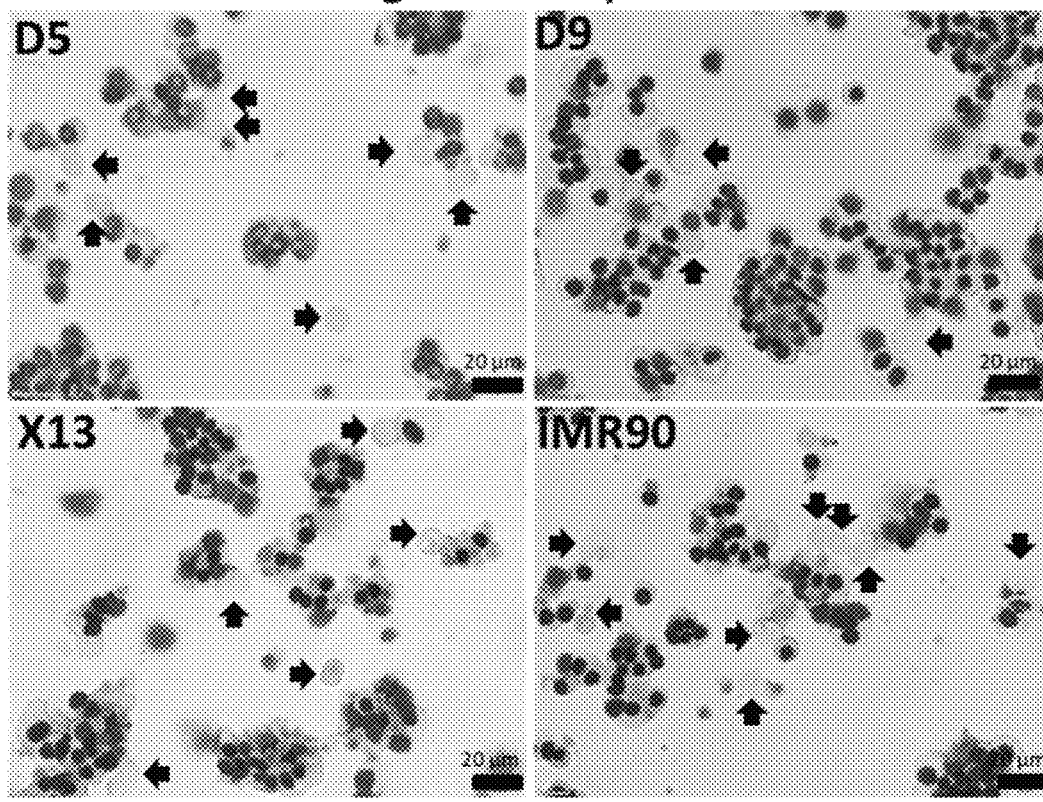
Figure 40:
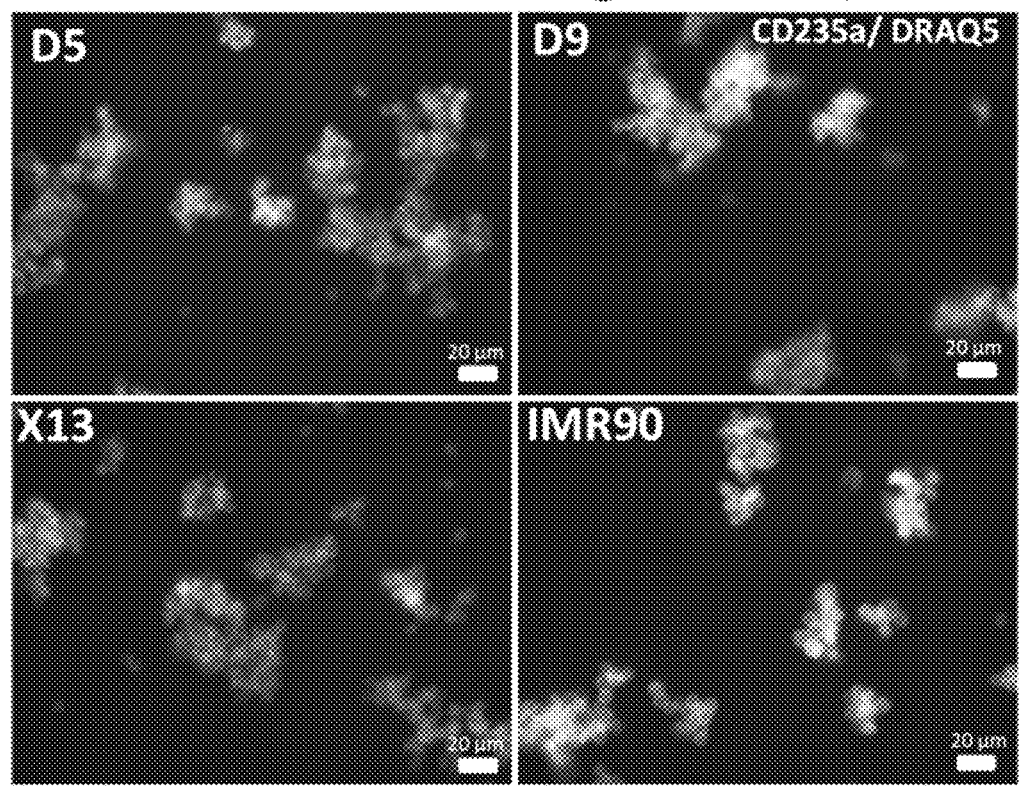

FIG. 40 shows results of the functional characterization and terminal maturation of hPSC derived erythroblasts. (A) shows a table summarizing P50 values (hemox analysis), percentage of hemoglobin subtypes relative to total hemoglobin (based on densitometric measurements of immunoblots) and percentage of enucleated cells (CD235a+ DRAQ5-) following 18 days of MSC co-culture. NA=Not available; NIL=Not expressed. (B) shows oxygen equilibrium curves [percent oxyhemoglobin vs. oxygen pressure (mm Hg)] of adult RBCs (•), hES-3 differentiated erythroblasts (■) and hiPSC differentiated erythroblasts D5 (▲), D9 (∇), X13 (◆) and IMR90 (o). Corresponding p50 values (mean±SD, n=2) are presented. (C) shows Western Blots of cell lysates from peripheral blood (PB), cord-blood (CB) and erythroblasts differentiated from X13, D5, D9, BR7, IMR90 and hES-3 (day 35 post differentiation), which were immunoblotted with antibodies specific to alpha, beta, gamma, epsilon human hemoglobin subtypes, and the house-keeping control human β-actin. White lines demarcate regions of gel images that were merged together. Densitometric measurement of immunoblot bands was done using ImageJ software. Based on densitometric measurements, the percentage of hemoglobin (relative to total hemoglobin expressed) after normalization with actin loading control are shown (mean±SEM). (D) shows the results of flow cytometry evaluation of CD235a and DRAQ5 expression of hiPSC derived erythroblasts cultured in expansion medium (Day 0) or co-cultured with human mesenchymal stem cells (MSCs) for 18 days under terminal maturation conditions (Day 18). Erythroblasts stained with isotype antibodies served as controls (shown inset of Day 0 FACS plots). (E) shows images of Giemsa staining of human induced pluripotent stem cell (hiPSC) differentiated erythroblasts following 18 days of maturation on mesenchymal stem cell (MSC) co-culture. Arrows indicate enucleated erythrocytes. (F) shows images of terminally matured human induced pluripotent stem cell (hiPSC) differentiated human erythroblasts were stained with anti-human CD235a-FITC antibody and DRAQ5. Merged fluorescence images of CD235a and DRAQ5 are shown. Enucleated red blood cells can be identified in the merged image as CD235a positive cells lacking nuclear staining. Scale bar=20 micron.

DETAILED DESCRIPTION OF THE PRESENT INVENTION

The O-negative rhesus factor D negative (O-neg) blood, the universal donor blood type, is considered a limited and valuable source of red blood cells (RBCs) for emergency transfusion applications. Anticipated supply shortages in the future due to an aging population and risks from emerging viruses and pathogens have driven initiatives to develop alternate and ready sources of universal donor blood. The potential of using O-neg hiPSCs as starting materials for generating universal donor red blood cells has been a long withstanding idea and has recently been demonstrated. Unlimited proliferation potential of hiPSCs coupled with their potential to differentiate into hematopoietic lineages4 have made these cells appealing as limitless source of cells for generating universal red blood cells. It has been postulated that as few as 10 hiPSC clones with rare blood phenotypes could be sufficient to cover the necessary blood types for 99% of the population with recurrent transfusion needs. With recent advances in the generation and banking of high quality GMP-grade hiPSCs, large-scale derivation of clinical grade universal RBCs appears to be the next major impending step forward.

Several approaches have been proposed for generation of red blood cells from hiPSC and these can be broadly categorized as monolayer or embryoid body (EB) mediated differentiation. Majority of differentiation studies have relied on the use of hiPSCs expanded on planar 2-dimensional (2D) surfaces, which though feasible for small-scale studies, become limiting when the need for scaling up is required. Embryoid body-mediated differentiation approaches developed with xeno-free and defined conditions may be more feasible for future clinical development. However, conventional approaches for embryoid body generation such as by forced aggregation have not yet been successfully demonstrated on large-scale in suspension culture. Thus, further improvements are still needed to make embryoid body (EB)-differentiation processes suitable for up-scaling.

Culture of hiPSC as 3-dimensional (3D)-aggregates or on defined extracellular matrix (ECM)-coated microcarriers (MCs) are possible means for scaling up hPSC expansion in suspension culture. Beyond hPSC expansion, scaling up of the embryoid body stage would require means to generate embryoid bodies of consistent size and quality. In the present disclosure, it is shown that continuous agitation of hPSC-MC aggregates during the pluripotent expansion stage was initially shown to have a negative impact on the expression of primitive-streak/mesoderm markers T-bra and KDR and subsequent hematopoietic differentiation when used with the conventional BMP4-based differentiation protocol. To overcome this limitation, a multifactorial design approach was used to identify factors that could improve generation of KDR positive cells from agitated hPSC-MC cultures. It is shown that transient activation of Wnt/β-Catenin signalling using CHIR-99021 in combination with BMP4 and Activin A significantly improved mesoderm induction, hematopoietic and erythroblast differentiation from agitated hPSC-MC cultures. In one example, shown herein is the erythroid differentiation from several O-negative human induced pluripotent stem cell lines and up-to 60,000 fold-expansion from hematopoietic precursors to erythroblast within 50 days. O-negative erythroblast mainly expressed fetal hemoglobin and could be enucleated following co-culture with primary human mesenchymal stromal cells. The developed MC-suspension culture approach has potential for scaling up the expansion and mesoderm stages of differentiation of human pluripotent stem cells and, can be further developed for large scale differentiation of red blood cells.

An microcarrier (MC)-based suspension culture platform has been developed herein, that can be used in an integrated scale-up of human pluripotent stem cell expansion and embryoid bodies stage of differentiation and demonstrated that human pluripotent stem cell-microcarrier (hPSC-MC) aggregate cultures can be differentiated into hematopoietic precursors and erythroblast when differentiated with a BMP4-based protocol.

Here, the inventors show that continuous agitation of human pluripotent stem cell-microcarrier (hPSC-MC) aggregates during the pluripotent cell expansion stage impedes the expression of primitive streak/mesoderm marker, T-bra and hematopoietic mesoderm marker, KDR, as well as subsequent hematopoietic precursor and erythroblast differentiation compared to cultures derived from static condition, when differentiated with the BMP4-based protocol. Without being bound by theory, it is thought that shear stress induced by agitation during the expansion stage may be responsible for reduced mesoderm induction. Using a multifactorial Design of Experiment (DoE) approach, combinations of factors were screened for their ability to improve hematopoietic mesoderm induction of hPSC-MC-aggregate cultures derived from continuous agitation during the pluripotent expansion stage. The combination of, for example, CHIR-99021 (CHIR), a selective inhibitor of glycogen synthase kinase 3-beta (GSK-3β) and a potent activator of canonical Wnt/β-Catenin signalling, with BMP4 and Activin A, activators of the transforming growth factor beta (TGF-β) superfamily signalling pathway, were identified to significantly improve development of KDR+ cells and subsequent hematopoietic precursor and erythroblast differentiation of hPSC-MC aggregate cultures.

Dosage and the timing of exposure to the GSK3-inhibitor, such as CHIR for example, are critical in promoting early mesoderm induction and subsequent hematopoietic differentiation. Using the optimized component dose, for example for CHIR, efficient erythroid differentiation of several O-neg human induced pluripotent stem cell lines was is demonstrated. The microcarrier platform enabling the identification of O-neg human induced pluripotent stem cell (hiPSC) lines that expanded well on microcarriers, a criterion essential for future scale-up in suspension culture bioreactors, as well as those having good hematopoietic differentiation potential. These are the first steps for up-stream process development towards the development of large-scale processes for generating universal red blood cells.

The inventors had previously reported successful erythroid differentiation of hES-3 (a hES line)-microcarrier aggregates that were initially expanded under agitation condition using a BMP4-based differentiation protocol. However, repeated attempts to differentiate the same line showed significantly better erythroid differentiation when microcarrier-aggregates were expanded in static condition, compared to agitation condition (0.25-7.3×10$^7$ vs 0.004-4.2×10$^7$ erythroid cells starting from 2×10$^5$ hematopoietic precursors, respectively) when using a BMP4-based differentiation protocol for both conditions. Attempts to differentiate multiple O-neg hiPSC lines initially expanded under agitation condition also resulted in highly variable and poor erythroid differentiation (data not shown). Without being bound by theory, these observations appeared to indicate that build-up of inhibitory signals due to agitation induced shear-stress could have negatively impacted differentiation. It was thought that under the above mentioned conditions and beyond a certain threshold of these inhibitory signals, agitated HES-3 MC aggregates fail to differentiate.

Figure 1:
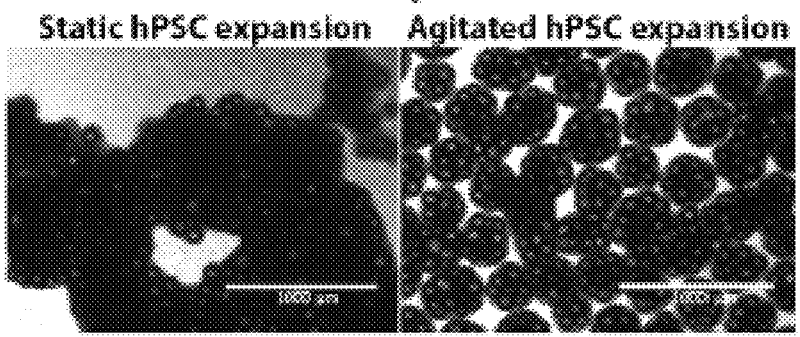
FIG. 1 shows the results of the expansion of human pluripotent stem cells (hPSC) in agitated microcarrier (MC) cultures result in reduced BPM4-based hematopoietic differentiation as compared to non-agitated static cultures. (A) shows images of hES-3 MC aggregates following 7 days of static or agitated culture. The results of flow cytometry evaluation of (B) pluripotency markers (7 days post hPSC expansion), (C) T-bra (48 hours post differentiation) and KDR (4 days post differentiation) expression in hES-3-MC aggregates initially expanded under static (static hPSC expansion) or agitated (agitated hPSC expansion) condition during the pluripotent expansion stage are shown. (D) shows real-time RT-PCR data showing mean fold-change in expression (relative to undifferentiated hES-3) of early hematopoietic specification markers (CD31, GATA2, GATA1, SCL, RUNX1) from hES-3-MC aggregates (derived from static or agitated hPSC expansion) differentiated for 4 days. (E) shows images of hematopoietic precursors (derived from static/agitated hPSC expansion) on day 2 and day 14 post expansion in methylcellulose-based medium. Scale bar=1000 micron. (F) is a table summarizing total counts of hematopoietic precursors per well (day 14 post expansion in Blast growth medium (BGM) medium following initial seeding of $1\times10^5$ cells), erythroblast per well of a 6-well plate (day 28 post differentiation) obtained from hES-3-MC aggregates (derived from static or agitation hPSC expansion) and corresponding flow cytometry expression (%) of CD235a$^+$ cells and fetal hemoglobin (HbF) expressing cells (day 28 post differentiation) as well as images of erythroblast cell pellets after day 28. All data are mean±SEM, n=3, p-values compares cells derived from static or agitation hPSC expansion.
Figure 1:
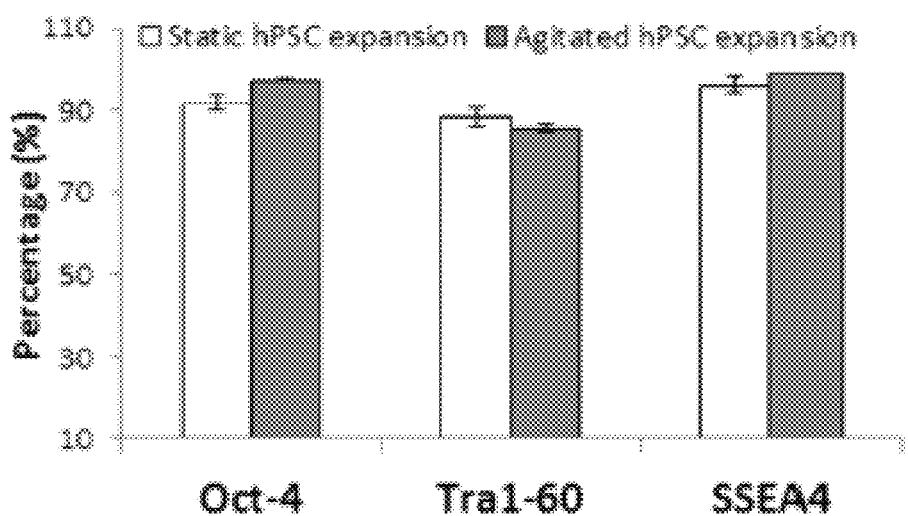
Figure 1:
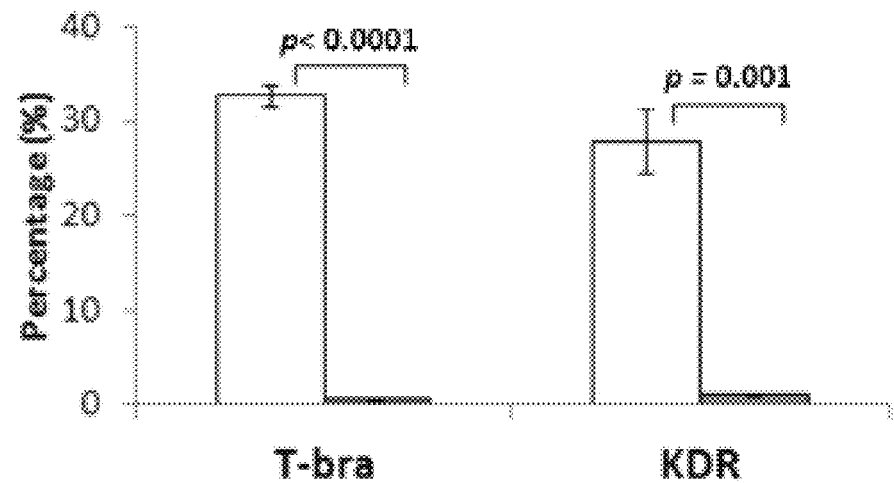
Figure 1:
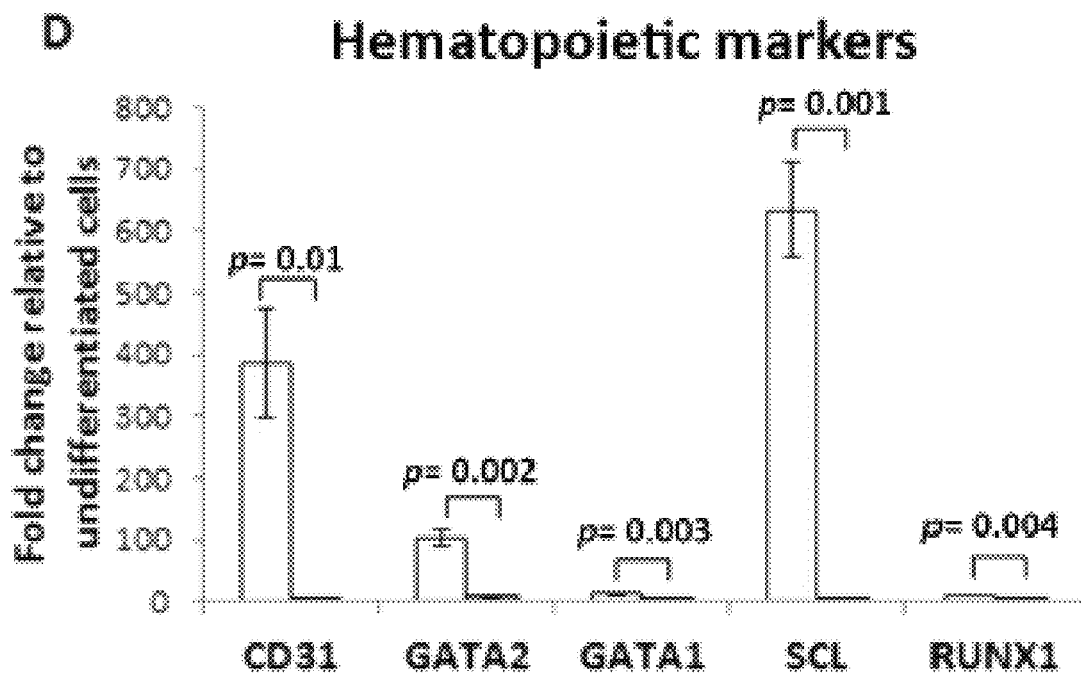
Figure 1:
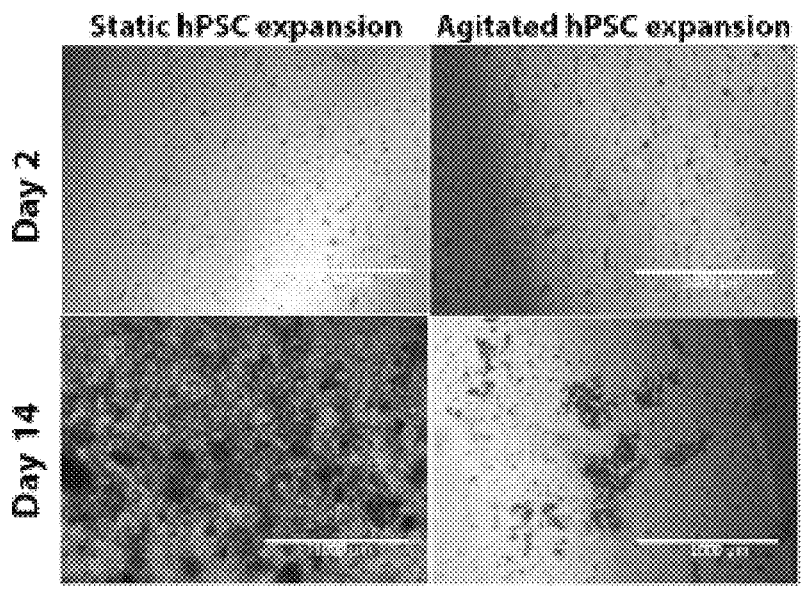
Figure 10:
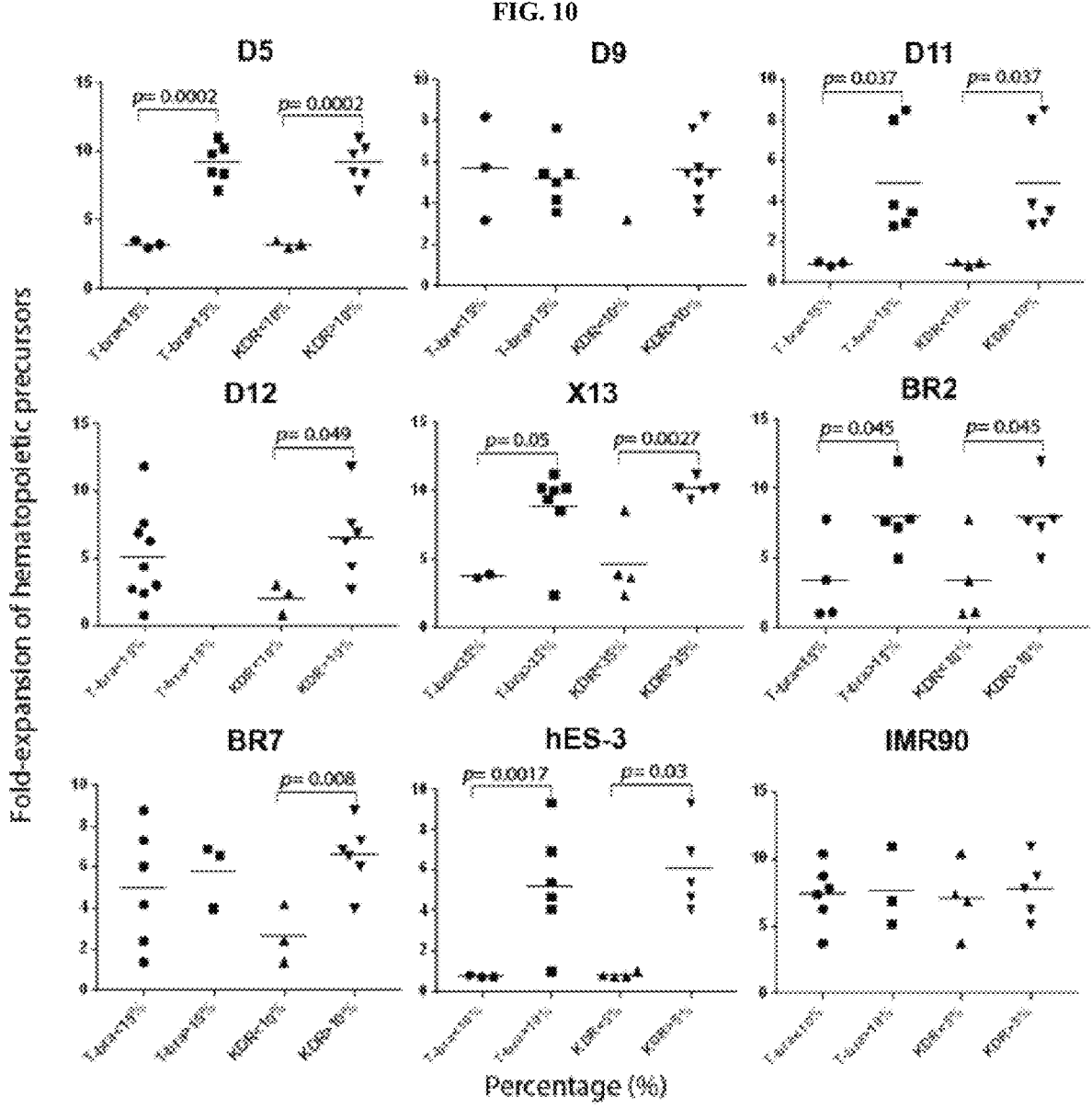
FIG. 10 shows box plot results of a correlation analysis between KDR and T-bra levels and hematopoietic precursor fold-expansion. Day 7 human pluripotent stem cell-microcarrier (hPSC-MC) aggregate cultures of 9 different human pluripotent stem cell lines (hPSCs) differentiated using optimized condition and 3 different CHIR-99021 doses (5, 10 and 15 μM) were evaluated by flow cytometry for T-bra (day 2 post differentiation) and KDR (day 4 post differentiation) expression. Differentiated cells were expanded as hematopoietic precursors for 14 days in methylcellulose medium and fold-expansion was determined. For each cell-line tested, T-bra expressing cells were grouped as <15% T-bra+ or >15% T-bra+ and KDR expressing cells were grouped as <10% KDR+ or >10% KDR+ and the corresponding fold-expansion of hematopoietic precursors were plotted. Note that hES-3 and IMR90 were segregated as T-bra<10%/T-bra>10% and KDR<5%/KDR>5% while X13 was segregated as T-bra<35%/T-bra>35% and KDR<35%/KDR>35%.

BMP4-Based Differentiation of HPSC-MC Aggregates Derived from Agitated Cultures Show Reduced Hematopoietic Differentiation To test the hypothesis that agitation condition may be a major factor for variable differentiation, hES-3 that was initially expanded under either static (static human pluripotent stem cell (hPSC) expansion) or agitation (agitated human pluripotent stem cell expansion) condition for 7 days were differentiated under static condition using a BMP4-based differentiation protocol. Both cultures demonstrated similar expression of pluripotency markers (FIG. 1B) despite the fact that cells grew on microcarriers as a large cluster in static cultures and as even aggregates (approximately 400 μm in diameter) in agitation cultures (FIG. 1A). However, following onset of differentiation, significant differences were observed in the expression of the primitive streak/mesoderm marker, T-bra [Day 2 T-bra: 32.6±1.2% and 0.50±0.02% in static vs agitated hPSC expansion cultures (p<0.0001)] and hematopoietic mesoderm marker, KDR [Day 4 KDR: 27.9±3.3% and 1.1±0.12% in static vs agitated hPSC expanded cultures (p=0.001)] (FIG. 10). Up-regulation of key hematopoietic markers indicative of hematopoietic differentiation was significantly impeded in agitated hPSC expansion group. RT-PCR analysis showed significant increase in expression of CD31 (an early hematoendothelial marker), GATA2, GATA1, SCL/Tal-1 and RUNX1, 4 days post differentiation for static hPSC expansion group but not agitated hPSC expansion group (FIG. 1D). The effects of continuous agitation of hPSC-MC aggregates were most apparent in the subsequent differentiation stages (FIGS. 1D and E) where in the agitated hPSC expansion group after 2 weeks of differentiation no hematopoietic precursors expansion were observed (total hematopoietic precursors per well: 1.39×10$^5$±2.18×10$^4$) while in the static hPSC expansion group, significant expansion was noted (total hematopoietic precursors per well: 5.77× 10$^6$±6.30×10$^5$, p=0.0009). Like-wise, subsequent generation of erythroblast was also severely impaired in cultures derived from agitated as compared to static hPSC expansion group (total erythroblast per well: 4.11±2.4×10$^4$ vs 26.2±4.7×10$^6$, respectively, p=0.005; total CD235a population: 0.51±0.1% vs 51.8±2.0%, p<0.0001) (FIG. 1E). These findings initially appeared to demonstrate that continuous agitation of hES-3-MC aggregates during the pluripotent expansion stage negatively impacts the following differentiation process at the early generation of KDR+ cells as well as the later erythroid stage.

Conventional mesoderm differentiation protocols rely on the use of human pluripotent stem cell (hPSC) aggregates/embryoid bodies (EBs) that are derived under static condition. As such, the media used for induction of mesoderm differentiation for human pluripotent stem cells derived under static condition may be sub-optimal for human pluripotent stem cells derived under agitation condition. Given that agitation conditions are important when scaling up the differentiation process in stirred tank bioreactors, it was sought to develop a media formulation that would allow for efficient mesoderm differentiation and subsequent erythroid differentiation of hPSC-MC aggregates derived under agitation condition. This is the basis for performing Design of Experiment multifactorial study to improve the initial mesoderm induction medium for differentiation of hPSC-MC aggregates derived under agitation condition. Evaluation of multifactorial conditions identified that the inclusion of optimal concentration of CHIR99021 for the first 24 hours of differentiation was critical for efficient hematopoietic-fated mesoderm induction for hPSC-MC aggregates initially derived under agitation condition.

Increased expression of KDR at the early differentiation stage has previously been shown to correlate with increased hematopoietic differentiation at later stages. Thus, Design of Experiment (DoE) multifactorial analysis was performed to identify initial mesodermal differentiation conditions that could improve generation of KDR+ cells from hES-3-MC aggregates expanded in agitated conditions.

Figure 2:
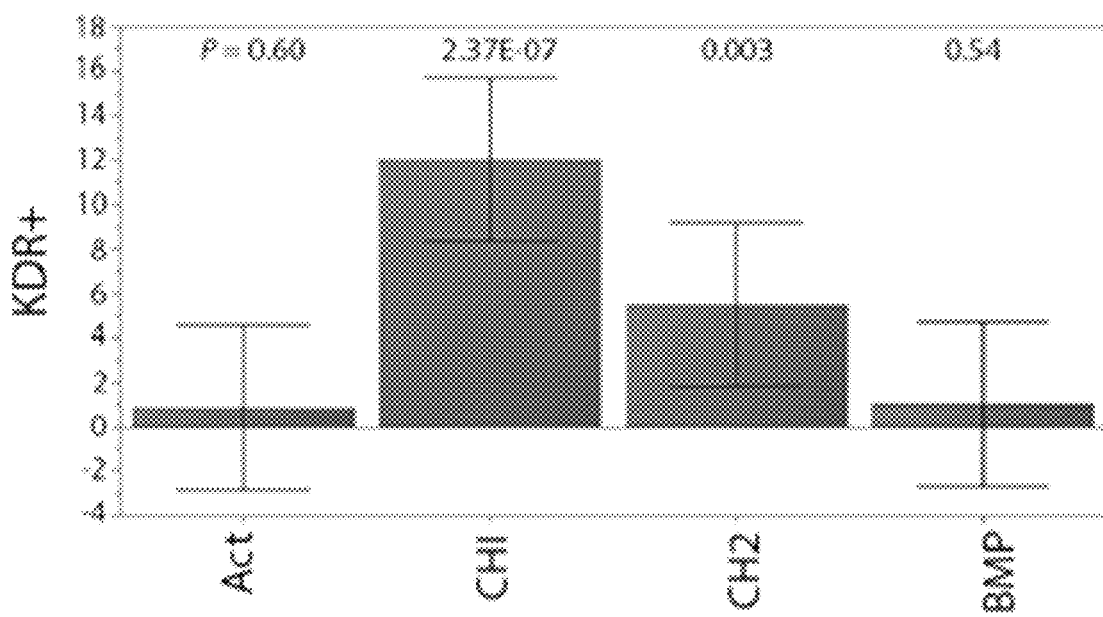
FIG. 2 shows results of a multifactorial Design of Experiment (DoE) analysis, which identified CHIR-99021 as a significant factor for improved hematopoietic mesoderm induction and hematopoietic precursor generation from hPSC-MC cultures initially expanded under agitation condition. (A) is a table showing the different Design of Experiment (DoE) conditions with varying concentrations of Activin A (ng/ml), CHIR-99021 (µM) maintained for 24 hours, CHIR-99021 (µM) from 24 to 48 hours and BMP4 (ng/ml) added at start of experiment and the corresponding percent KDR+ cells on day 4 post differentiation as determined by flow cytometry and total hematopoietic precursor cells per well following 14 day expansion in Blast growth medium (BGM) following initial seeding of $1\times10^5$ cells. (B) is a column graph in which CHIR-99021 (maintained for 24 hrs only) was identified as a significant factor for achieving higher % KDR+ cells on day 4 of differentiation (P=2.3E-07) and (C) greater hematopoietic precursor expansion (P=1.01 E-05). Act=Activin; CHI=CHIR-99021 for 24 hours, CH2=CHIR-99021 from 24 to 48 hours; BMP=BMP4. Significant P-values are indicated in the chart. (D) shows the correlation between high (>15%) and low (<5%) KDR expression on day 4 of differentiation and the corresponding total number of hematopoietic precursors per well derived following 14 days of culture in Blast growth medium (BGM).
Figure 2:
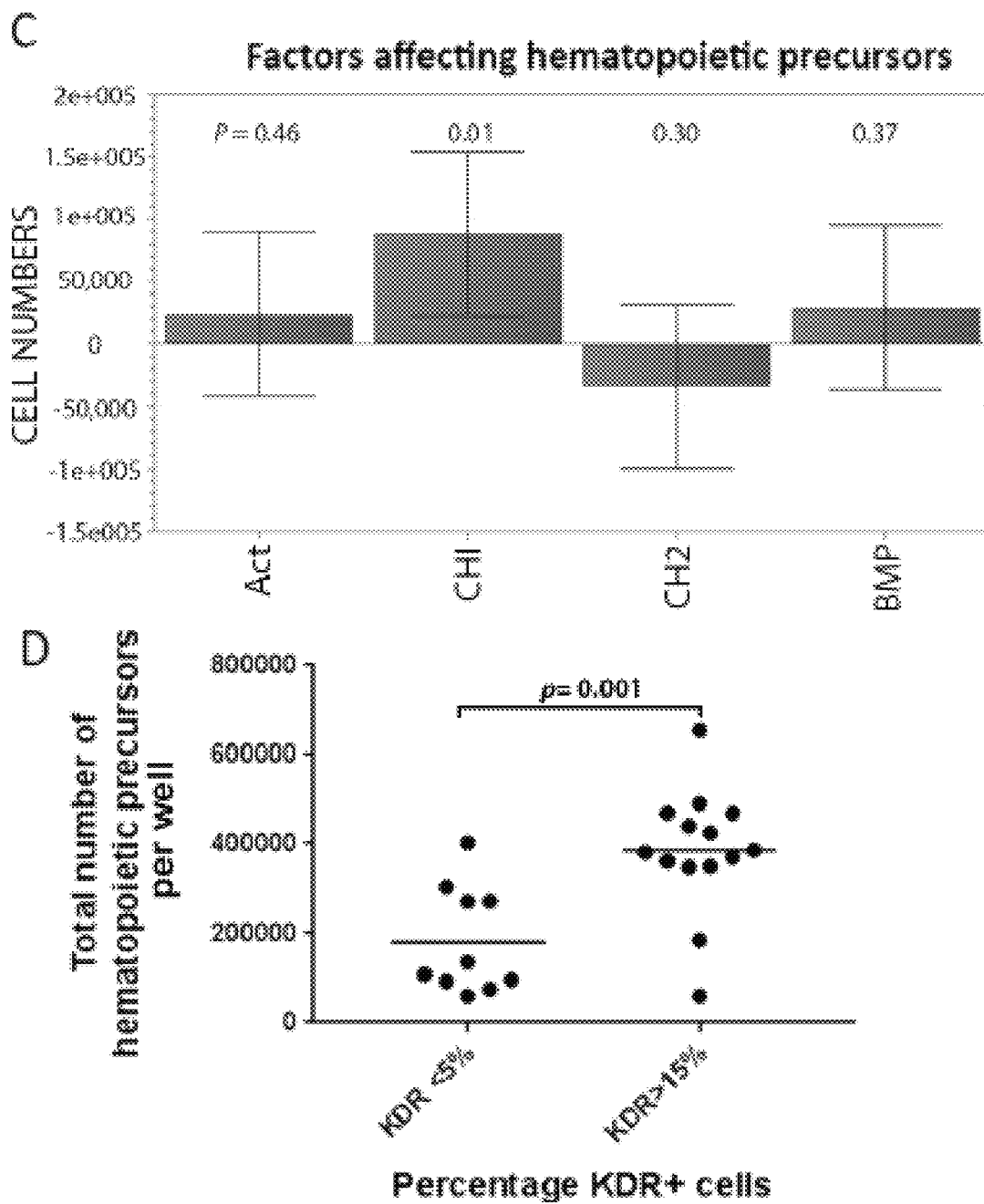

Different doses (and/or duration of exposure) of cytokines and small-molecules with known roles in inducing mesoderm and hematopoietic differentiation were evaluated using the MODDE® software for differentiation of hES-3 MC aggregate cultures initially derived under agitation. The DoE was designed to investigate effects of BMP4 (10-50 ng/ml), Activin A (0 to 80 ng/ml), CHIR (0-15 μM at 0 to 48 hours after start of mesoderm induction). These variables generated 29 culture conditions (FIG. 2A), which were tested for their effects on percent of KDR+ cells (4 days post initiation of differentiation) and the following stage of hematopoietic precursors generation (2 weeks of culture in Blast growth medium (BGM)). BMP4 levels (10 to 50 ng/ml) and Activin A levels (0-80 ng/ml) did not significantly alter KDR+ cells or hematopoietic precursor generation. However, exposure of CHIR for 0 to 24 hours resulted in significant increase in percentage of KDR+ cells (P=2.37E-07; FIG. 2B) as well as for generation of hematopoietic precursor cells (P=1.01E-05) (FIG. 2C).

Consistent with earlier observations, treatment of BMP4 alone (condition 1) resulted in very low KDR+ cells (0.44%) and as did treatment with Activin A in combination with BMP4 (condition 2: 1.07%), whereas combinations of CHIR, Activin A and BMP4 (condition 4) resulted in increased KDR+ cells (18.5%). It is important to note that cultures which express higher initial percent KDR+ cell population resulted in higher number of hematopoietic precursors [(Total hematopoietic precursors/well: $3.85 \times 10^5 \pm 3.72 \times 10^4$ vs $1.82 \times 10^5 \pm 3.79 \times 10^4$ for high (>15%) and low(<5%) KDR+ cell populations, respectively; p=0.001] (FIG. 2D).

Figure 6:
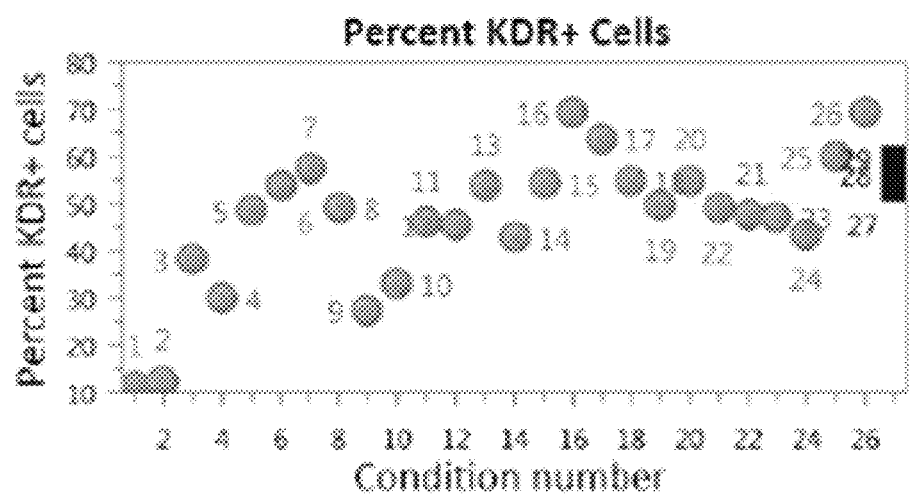
FIG. 6 shows the results of Design of experiments (DoE) multi-factorial analysis, which identifies CHIR-99021 as a significant factor for increased KDR expression following differentiation of O-negative hiPSC-MC aggregates initially expanded under continuous agitation condition. (A) shows a table listing the concentrations of Activin A (ng/ml), CHIR-99021 (μM) maintained for 24 hours, CHIR-99021 (μM) at 48 hours and BMP4 (ng/ml) added at start of experiment for the multifactorial conditions generated by MODDE® software and the corresponding KDR levels (%) determined by flow cytometry on day 4 post differentiation. (B) Plot of KDR levels (%) for respective conditions tested (day 4 post differentiation). Conditions 27, 28 and 29 are triplicates of the same condition tested. (C) shows the identification of CHIR-99021 (maintained for 24 hours only) as a significant factor (P=0.0005) for achieving higher KDR levels on day 4 of differentiation, as identified using MODDE software. Act=Activin A; CHI=CHIR-99021 for 24 hr, CH2=CHIR-99021 from 24-48 hr; BMP=BMP4. Computed P-values are indicated below the chart. (D) shows a computational summary of model statistics generated by MODDE software showing probability scores of R2=0.56, 02=0.24, model validity>0.3 and reproducibility score>0.9.
Figure 6:
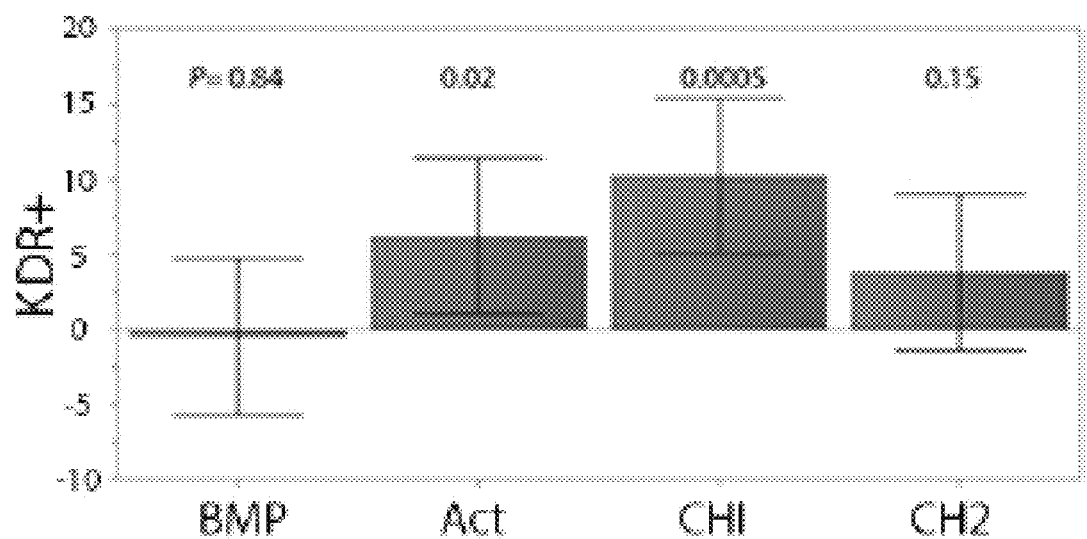
Figure 6:
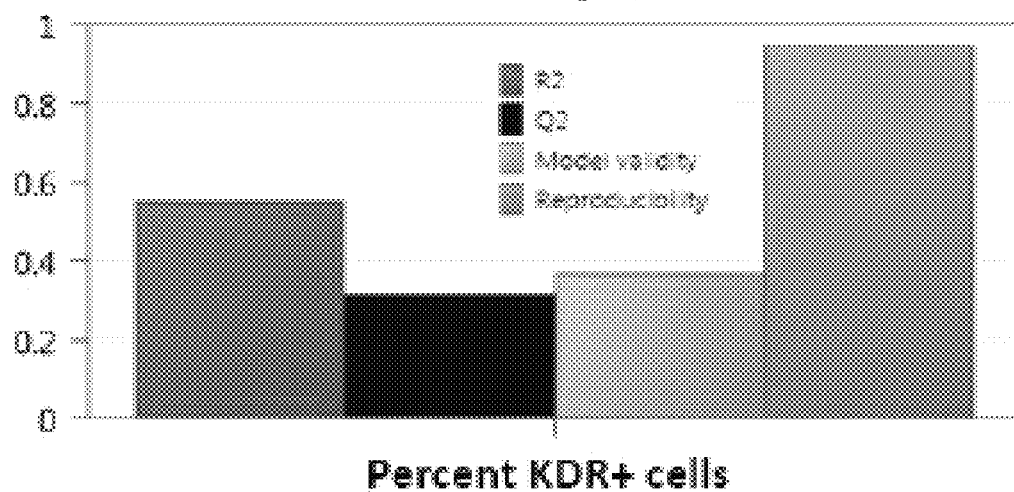

These findings were also confirmed using an O-neg hiPSC line (D5) expanded in agitated microcarrier cultures (FIG. 6). DoE analysis of the O-neg human induced pluripotent stem cells showed that Activin A (P=0.02) and CHIR exposure for 24 hours (P=0.0005) were significant factors for increased KDR+ cells 4 days post differentiation (FIG. 6C). In summary, from the Design of experiment analysis, it was established that a BMP4 dose of 10 to 50 ng/ml, Activin A dose of 25 to 50 ng/ml and exposure of CHIR for 24 hours at a dose of 6 to 12 μM would be efficient for the generation of KDR+ cells.

Validation of the Effect of CHIR on Hematopoietic Mesoderm Induction, Hematopoietic Precursor and Erythroblast Generation from Pluripotent Cells Expanded in Agitated Microcarrier Culture In order to validate the effect of CHIR on efficiency of hematopoietic differentiation of pluripotent cells expanded in agitated microcarrier culture, differentiation of D5 O-neg hiPSC line (initially expanded on microcarriers under agitation condition) was evaluated using either a BMP4/Activin A protocol (non-CHIR mediated) or CHIR mediated protocol (Table 1; established from Design of Experiment conditions from FIG. 6). The BMP4/Activin A protocol resulted in very little primitive streak/mesoderm induction, as reflected by very low percentage of T-bra+ cells (6.66-8.36%) 48 hours post induction and low hematopoietic mesoderm induction (5.3-13.84% of KDR+ cells) 96 hours post induction (Table 1). These conditions also resulted in very low induction of the hematopoietic transcription factors SCL and RUNX1 and had little or no hematopoietic precursor expansion following 2 weeks of culture in Blast growth medium (BGM) and subsequently failed to expand as erythroblast (Table 1).

Table 1—Comparison of CHIR and non-CHIR mediated differentiation of pluripotent cells expanded in agitated microcarrier culture, from mesoderm induction to erythroblast expansion. O-neg hiPSC-MC aggregates (D5 hiPSC), initially expanded under agitation condition, were differentiated using CHIR and non-CHIR-mediated differentiation protocols identified by selected DoE conditions. For each condition tested, percentage of cells expressing T-bra and KDR was determined by flow cytometry at the indicated time points. Mean-fold change in expression of early hematopoietic specification markers (CD31, SCL and RUNX1) relative to undifferentiated cells was determined 4 days post differentiation by real-time RT-PCR. Corresponding fold-expansion of hematopoietic precursors after 14 days in Blast growth medium (BGM) and cumulative fold-expansion of erythroblast on day 34 are reported. P-values as compared to condition #7 are shown in parenthesis.

TABLE 1

| Condition number | Condition | Primitive streak/Mesoderm | | | Hematopoietic mesoderm |
|---|---|---|---|---|---|
| | | % T-Bra$_{24\ hr}$ | % T-Bra$_{48\ hr}$ | % T-Bra$_{96\ hr}$ | % KDR$_{96\ hr}$ |
| BMP4/Activin protocol | | | | | |
| 1 | 10 ng/ml BMP4; | 4.0 | 7.75 | 5.36 | 5.33 ± 2.18 (0.015) |
| 2 | 50 ng/ml BMP4 | 3.37 | 8.36 | 4.56 | 13.84 ± 3.92 (0.36) |
| 4 | 50 ng/ml BMP4; 50 ng/ml Activin A | 2.38 | 6.66 | 2.11 | 7.36 ± 1.54 (0.017) |
| CHIR-99021 protocol | | | | | |
| 7 | 10 ng/ml BMP4; 50 ng/ml Activin A; 12 μM CHIR$_{24\ hr}$ | 14.0 | 52.6 | 1.45 | 18.6 ± 2.42 |
| 16 | 50 ng/ml BMP4; 50 ng/ml Activin A; 12 μM CHIR$_{24\ hr}$; 12 μM CHIR$_{48\ hr}$ | 24.3 | 44.9 | 2.63 | 28.2 ± 2.65 (0.06) |
| 18 | 50 ng/ml BMP4; 25 ng/ml Activin A; 6 μM CHIR$_{24\ hr}$; 6 μM CHIR$_{48\ hr}$ | 53.3 | 89.6 | 1.19 | 29.4 ± 2.72 (0.04) |

TABLE 1-continued

| Condition number | Condition | Fold-change in expression of early hematopoietic markers | | | Fold-expansion of hematopoietic precursors | Fold-expansion of erythroblast |
|---|---|---|---|---|---|---|
| | | CD31 | SCL | RUNX1 | Day 14 | Day 34 |
| BMP4/Activin protocol | | | | | | |
| 1 | 10 ng/ml BMP4; | 34.2 ± 19.3 (0.009) | 4.96 ± 4.2 (0.03) | 6.10 ± 4.2 (0.002) | 0.56 ± 0.1 (<0.0001) | Failed to expand |
| 2 | 50 ng/ml BMP4 | 29.2 ± 6.6 (0.009) | 11.3 ± 2.9 (0.03) | 3.84 ± 0.8 (0.001) | 0.56 ± 0.06 (<0.0001) | Failed to expand |
| 4 | 50 ng/ml BMP4; 50 ng/ml Activin A | 15.4 ± 0.6 (0.008) | 36.0 ± 5.7 (0.03) | 5.92 ± 0.1 (0.001) | 0.60 ± 0.09 (<0.0001) | Failed to expand |
| CHIR-99021 protocol | | | | | | |
| 7 | 10 ng/ml BMP4; 50 ng/ml Activin A; 12 µM CHIR$_{24\ hr}$ | 863.4 ± 77 | 556.8 ± 94.5 | 378.8 ± 14.1 | 7.57 ± 0.28 | 284.4 ± 9.24 |
| 16 | 50 ng/ml BMP4; 50 ng/ml Activin A; 12 µM CHIR$_{24\ hr}$; 12 µM CHIR$_{48\ hr}$ | 926.3 ± 218 (0.81) | 112.5 ± 37.5 (0.048) | 72.4 ± 28.0 (0.001) | 0.57 ± 0.05 (<0.0001) | Failed to expand |
| 18 | 50 ng/ml BMP4; 25 ng/ml Activin A; 6 µM CHIR$_{24\ hr}$; 6 µM CHIR$_{48\ hr}$ | 704 ± 67 (0.26) | 321.4 ± 0.1 (0.13) | 122.4 ± 5.0 (0.003) | 5.23 ± 0.53 (0.017) | 95.79 ± 1.19 (<0.0001) |

Figure 3:
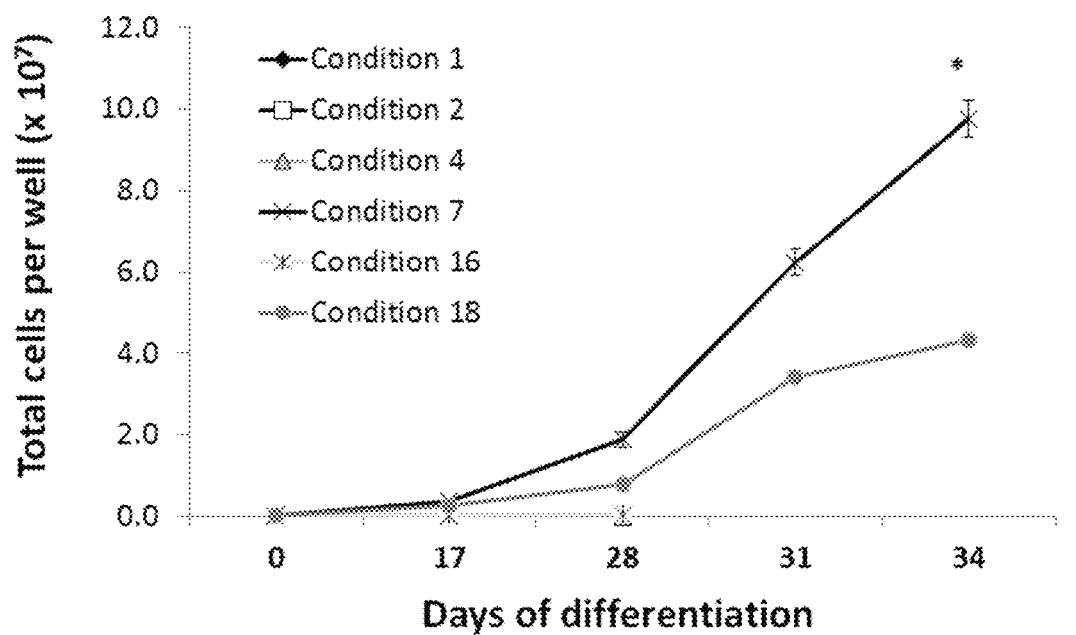
FIG. 3 shows the results of erythroid differentiation of an O-negative hiPSC line initially expanded on microcarriers (MC) under agitation condition using selected DoE conditions. (A) shows a line graph depicting the total cell expansion from day 0 to day 34 for selected conditions: Day 0-4 (mesoderm induction of hPSC-MC aggregates), day 4-17 (hematopoietic precursor expansion in Blast growth medium (BGM)), day 17-34 (erythroblast expansion in suspension culture) (*p<0.05 compared to condition #7). All data are mean±SEM, n=3. (B) is a table summarizing total viable cell counts per well (of a 6-well plate) and flow cytometry expression (%) of erythroblast surface markers (CD235a and CD71) and HbF on day 34 of experiment for erythroblast derived using conditions #7 and #18. Corresponding red blood cell pellets from conditions #7 and #18 on day 34 of experiment. Corresponding p-values for comparison between condition #7 and #18 are reported. All data are mean±SEM, n=3.
Figure 3:
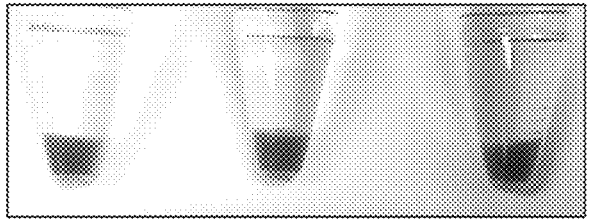
Figure 3:
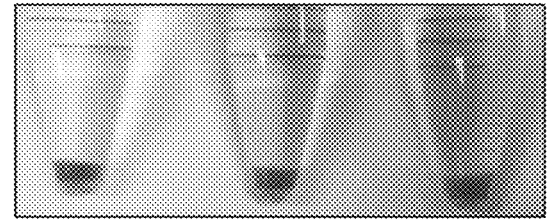

On the other hand, modulation of Wnt/β-Catenin signalling with CHIR-based protocol resulted in high primitive streak/mesoderm induction (46.9-89.6% T-bra+ cells on day 2) and high hematopoietic mesoderm induction (18.63-29.43% KDR+ cells on day 4). Consistent with improved mesoderm and hematopoietic precursor induction with addition of CHIR, higher fold-induction of CD31, SCL/Tal-1 (regulator of hematopoiesis) and RUNX1 (regulator of hematopoiesis) was noted by RT-PCR analysis 4 days post differentiation and improved hematopoietic precursor expansion 17 days post differentiation (Table 1). Condition #16 which had high concentration of CHIR exposure for 48 hours had lower induction of SCL (p=0.048 vs condition #7) and RUNX1 (p=0.01 vs condition #7) and poor hematopoietic precursor expansion (p<0.001 vs condition #7) and subsequently failed to differentiate into erythroblast (Table 1). Subsequently, only condition #7 and #18 resulted in significant erythroid differentiation and expansion (Day 34 fold-expansion: 284.4±9.2 vs 95.79±1.2, respectively; Table 1 and FIG. 3). Among these, condition #7 resulted in significantly higher number of erythroblast than condition #18 [9.77×10$^7$ as compared to 4.31×10$^7$ cells, 34 days post differentiation, p=0.0003) (FIG. 3A). Moreover, erythroblast population differentiated from condition #7 also had higher percentage of erythroid cells and fetal hemoglobin (HbF) expression as compared to the population derived from condition #18 (FIG. 3B). Erythroblast successfully differentiated from conditions #7 and #18 were visibly hemoglobinized by day 34 of differentiation (FIG. 3B). Given the higher erythroblast fold-expansion and purity of erythroid cells achieved with condition #7, all subsequent experiments were performed according to condition #7 (50 ng/ml Activin A, 12 µM of CHIR for 24 hours, 10 ng/ml of BMP4). Erythroblast differentiated using condition #7 could achieve a cumulative fold-expansion of 62343±15070 (as compared to initial seeding of 2×10$^5$ hematopoietic precursors on day 0) by day 56 of continuous culture by re-seeding at a density of 2.5×10$^5$ cells/ml in fresh culture medium whenever cell densities exceeded 2×10$^6$ cells/ml.

Figure 4:
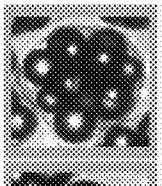
FIG. 4 shows the effect of CHIR dose on hematopoietic differentiation of 9 human pluripotent stem cell (hPSC) lines expanded in agitated-microcarrier (MC) cultures. (A) shows the results of the expansion of 9 different human pluripotent stem cell lines in agitated-microcarrier culture for 7 days. Table shows: cell-microcarrier aggregate image, cell fold expansion, pluripotency (Oct-4, Tra1-60 and SSEA4 expression), karyotype and average aggregate size. NA=Not available. Effect of CHIR dose (µM) on (B) the percentage of T-bra+ cells (as determined by flow cytometry) 48 hours post differentiation and (C) percentage of KDR+PDGFRα− cells (as determined by flow cytometry) 96 hours post differentiation of 9 different human pluripotent stem cell-microcarrier lines are shown. Effect of CHIR dose (µM) on (D) the mean fold-expansion of hematopoietic precursors 14 days post differentiation and (E) percentage of CD43+ cells in the derived hematopoietic precursor population following differentiation of 9 different hPSC-MC lines. (F) Cumulative fold-expansion of total viable cell numbers was determined following differentiation of different hPSC lines (*p<0.05 cumulative fold-expansion of each line (except D11, D12 and BR2) on day 42 as compared to X13). All data are mean±SEM, n=3. (G) Corresponding red blood cell pellets from the different human pluripotent stem cell lines on day 35 of experiment.
Figure 4:
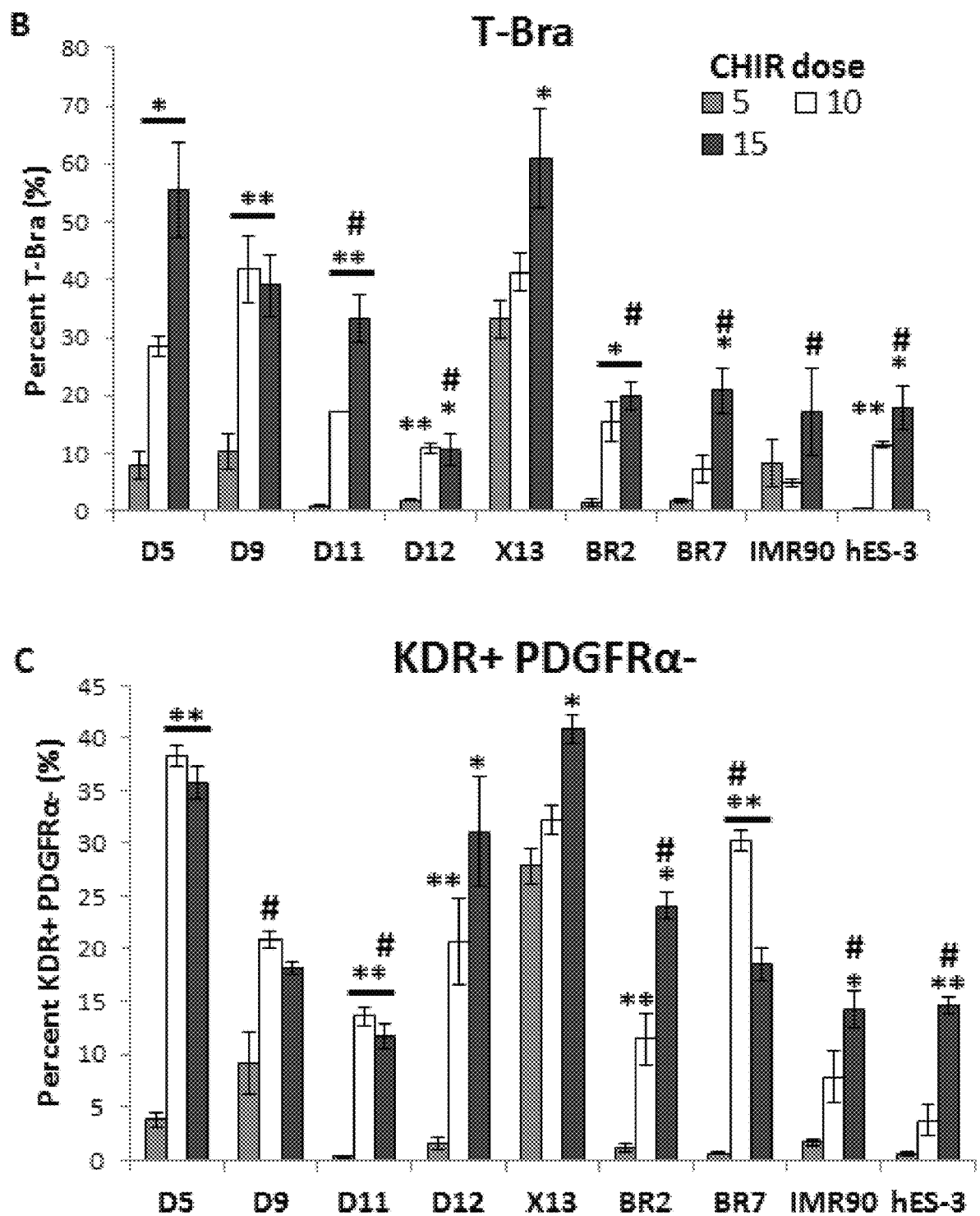
Figure 4:
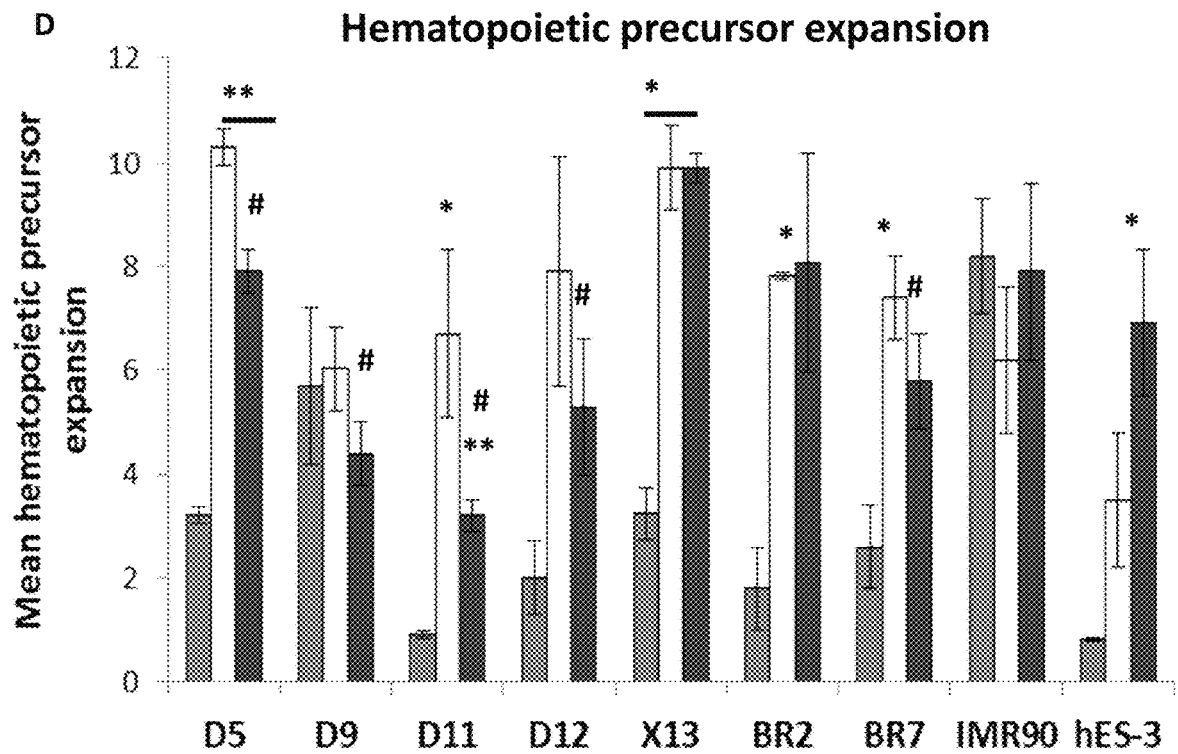
Figure 4:
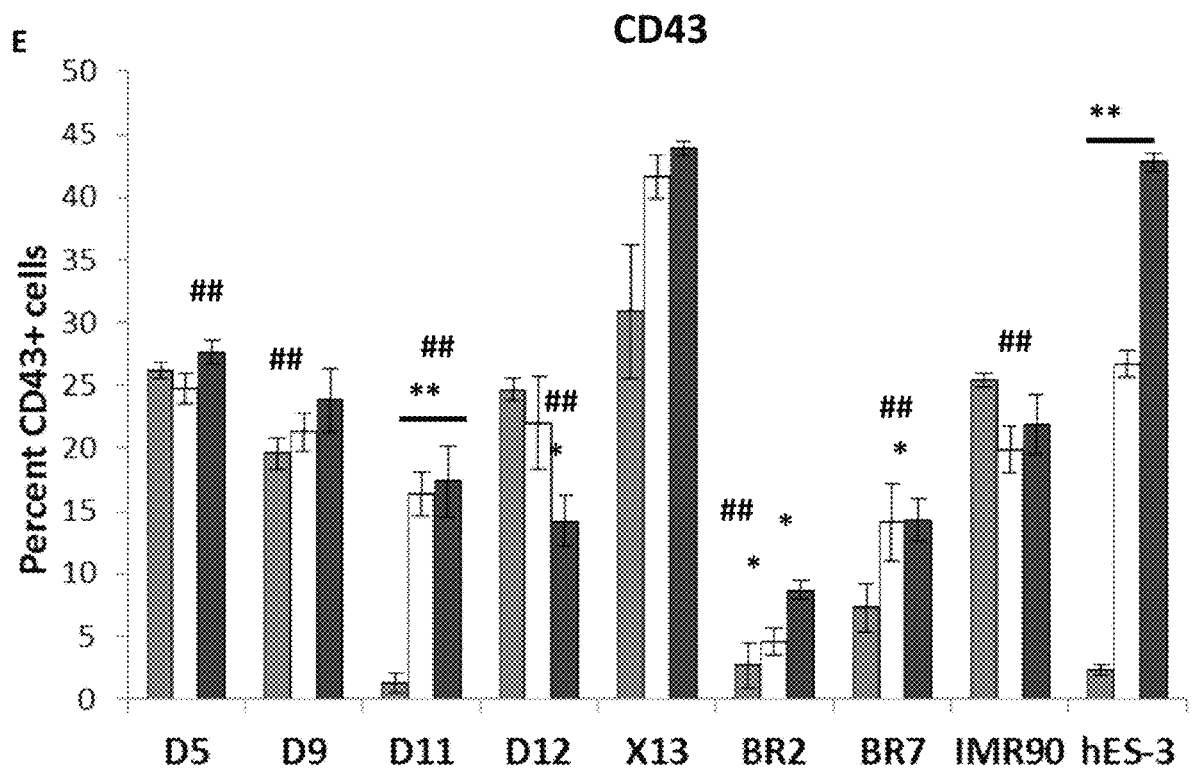
Figure 4:
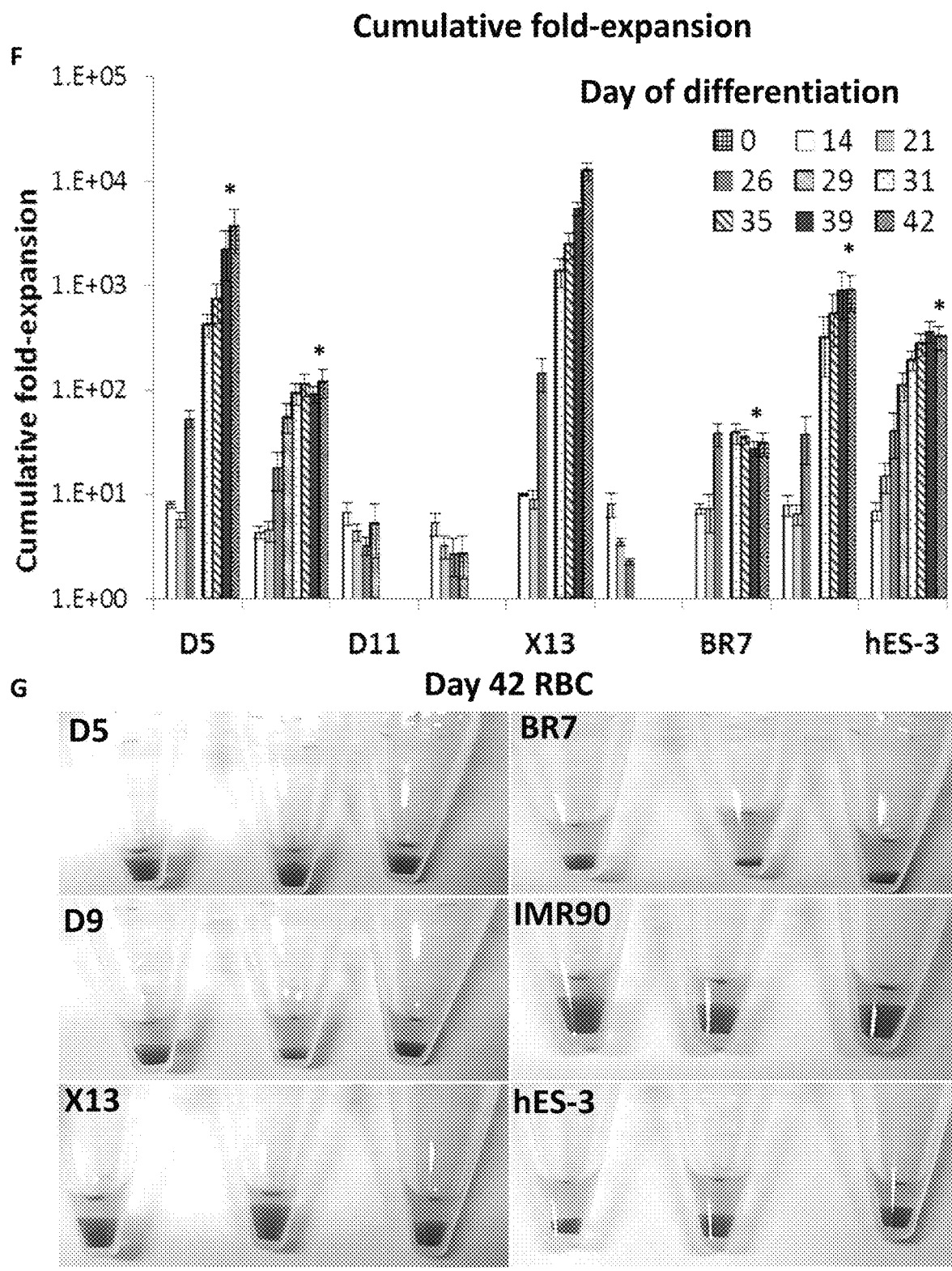
Figure 7:
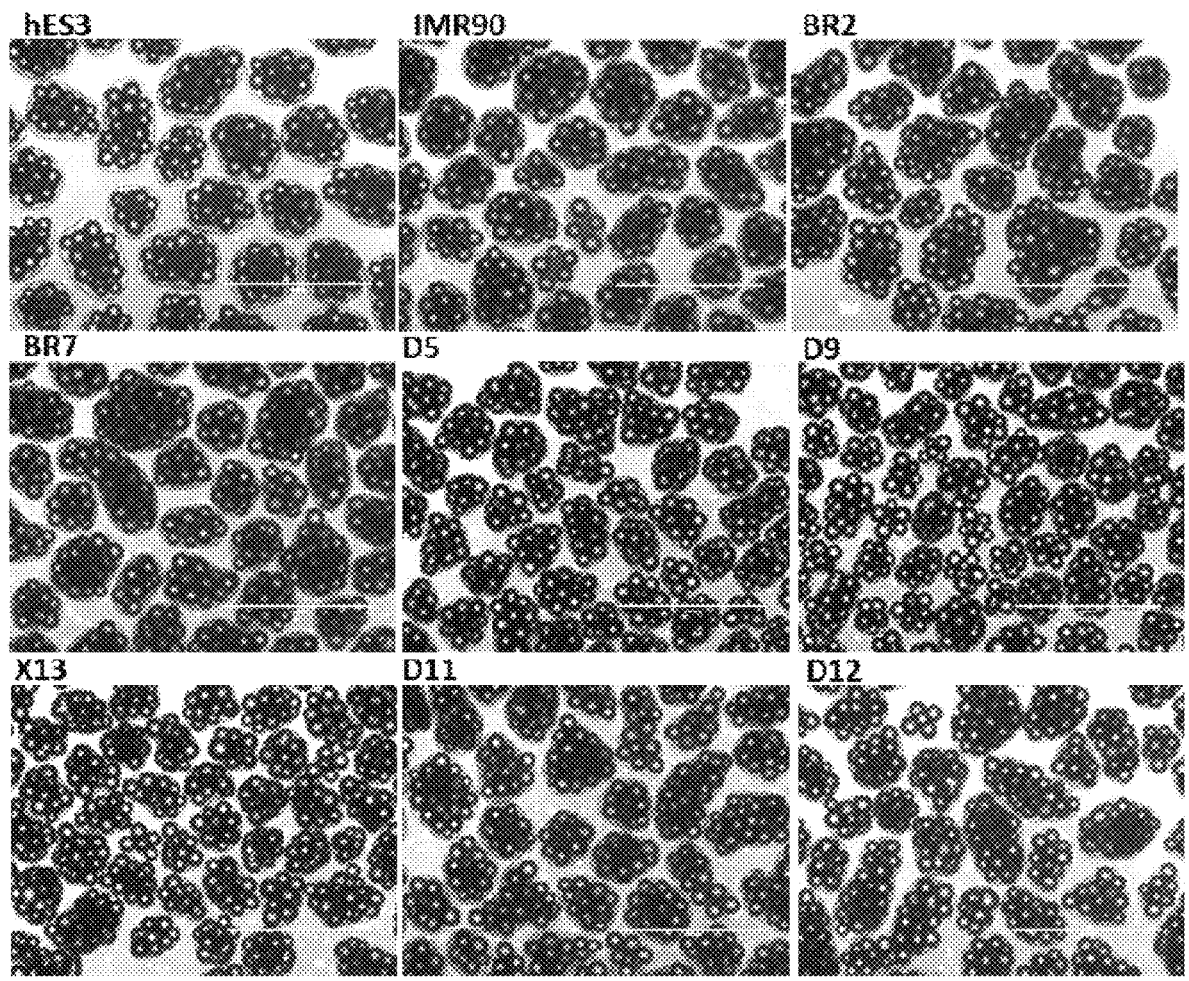
FIG. 7 shows images of microcarrier aggregate cultures of different hPSC lines. Day 7 images of 9 different hPSC lines expanded on iPSC-Spheres™ under continuous agitation. Scale-bar=1000 micron.
Figure 8:
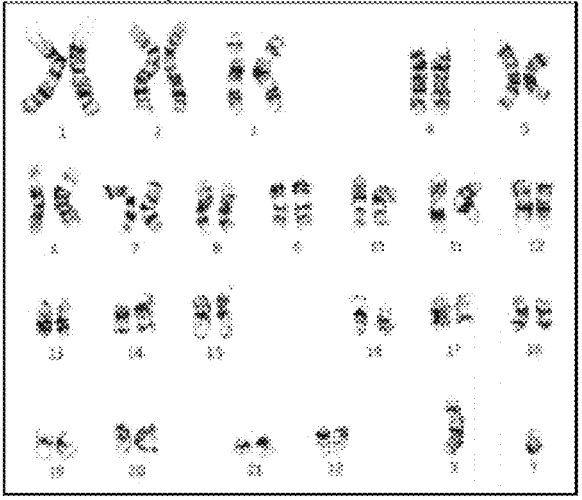
FIG. 8 shows the results of G-banded karyotype analysis of different hPSC lines. Representative images of G-banded karyotypes of different hPSC lines (D5, D9, D11, D12, X13, hES-3, BR2 and BR7) used in this experiment. No gross karyotypic abnormalities were detected in counts of 20 G-banded metaphases for each line.
Figure 8:
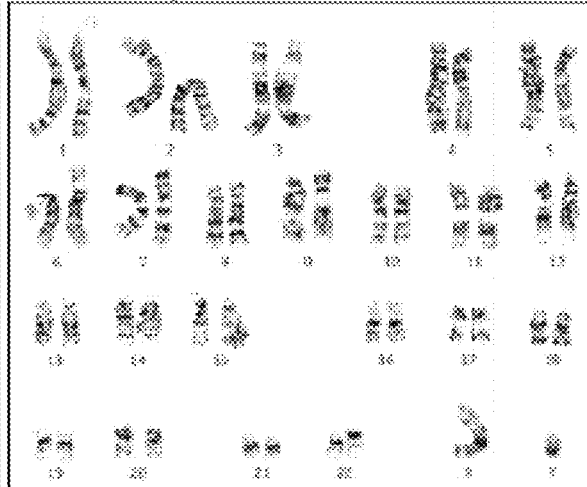
Figure 8:
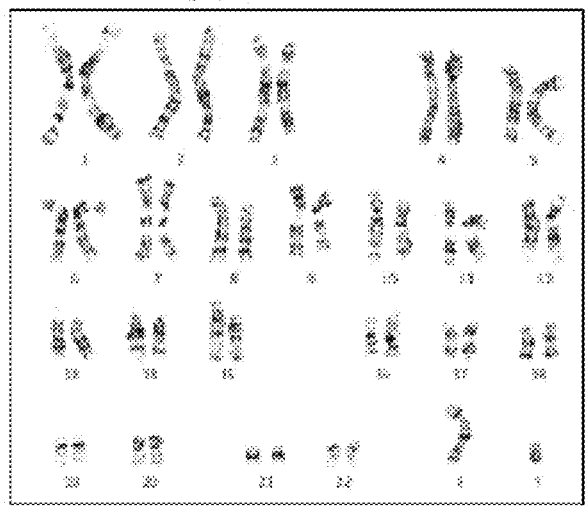
Figure 8:
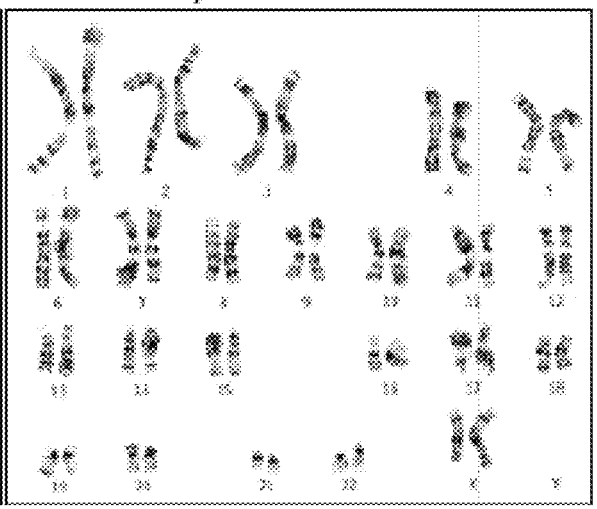
Figure 8:
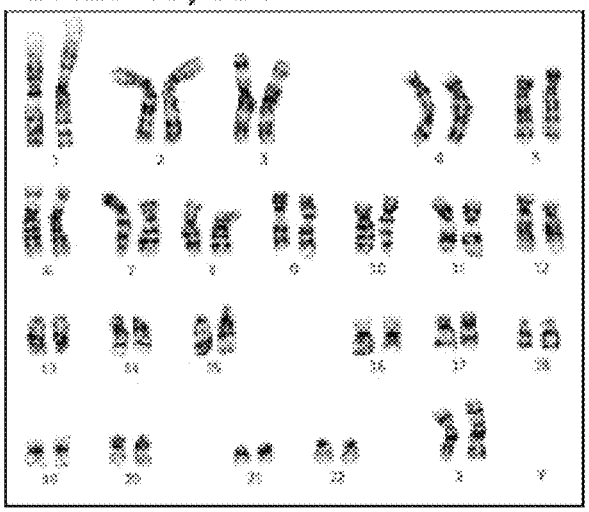
Figure 8:
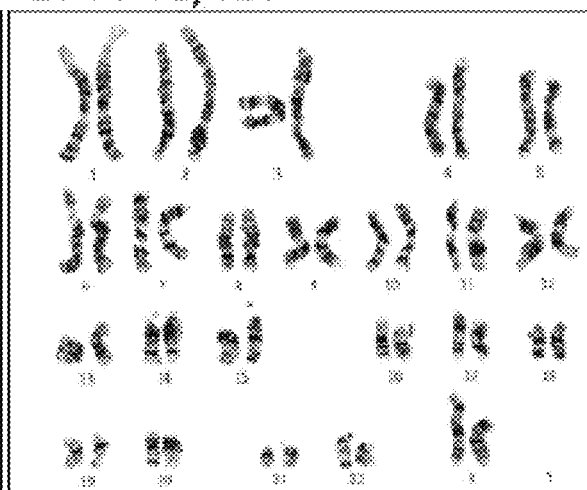
Figure 8:
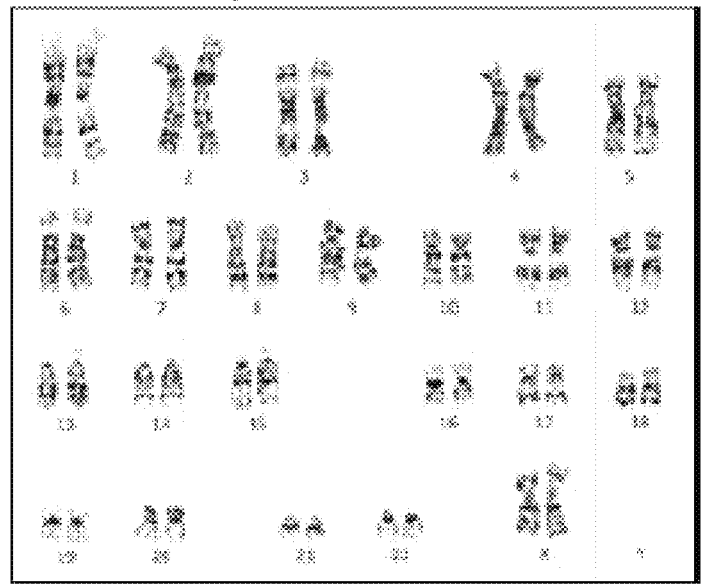
Figure 8:
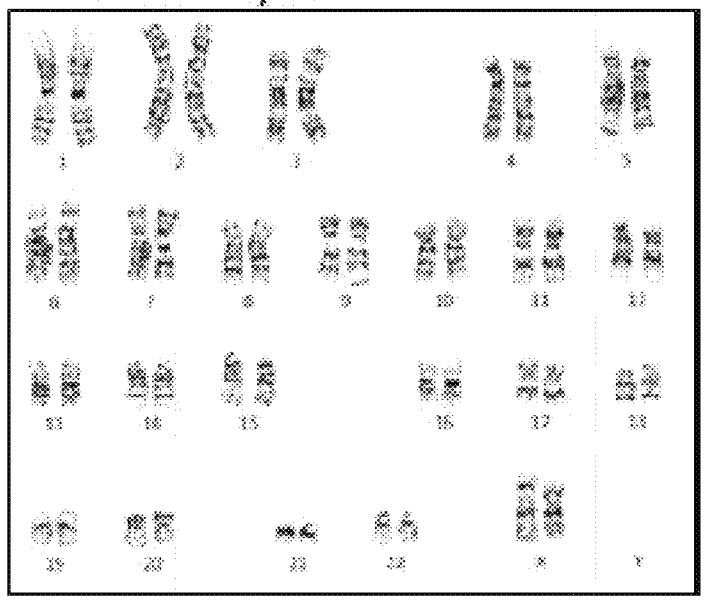

Optimization of CHIR Dose Results in Improved Erythroid Differentiation of Different Human Pluripotent Stem Cell Lines Expanded in Agitated Microcarrier Culture Following successful differentiation of a single O-negative (O-neg) human induced pluripotent stem cell-microcarrier (hiPSC-MC) line (initially expanded under continuous agitation) into erythroid lineage, with transient exposure to 12 µM of CHIR, differentiation of seven (7) different O-neg hiPSC lines (BR2, BR7, D5, D9, D11, D12, X13), one (1) commercial hiPSC line (IMR90), and a hESC line (hES-3) were tested. All the hPSC lines were successfully expanded on microcarriers under continuous agitation for 7 days (FIG. 7) achieving fold expansion of 5.3 to 12.5 fold, with mean aggregate diameters ranging from 255 to 510 µm (FIG. 4A). Expression of the pluripotency marker Oct-4 ranged from 72.9 to 94.6%, Tra1-60 ranged from 84.8 to 93.5% and SSEA4 ranged from 97.2 to 99.7% (FIG. 4A). G-banding karyotype analysis were performed on 8 of the human pluripotent lines used herein and all of them were found to be karyotypically normal (FIG. 8).

Human pluripotent stem cell-microcarrier (HPSC-MC) aggregates generated from different hPSC lines were differentiated using 3 different CHIR doses (5, 10 and 15 µM for 24 hours) and were evaluated for T-bra (day 2) and KDR+ PDGFRβ− (day 4) expression by flow cytometry, induction of key hematopoietic transcription factors by RT-PCR (day 4), hematopoietic precursor expansion (day 14) and erythroblast expansion (day 42).

For all of the lines tested, 15 µM CHIR resulted in significantly higher (p<0.05) T-Bra+ cells (D5: 55.6±8.26%; D9: 39±5.37%; D11: 33.4±4.10%; D12: 10.6±2.78%; X13: 60.9±8.55%; BR2: 20.1±2.4%; BR7: 20.8±3.8%; IMR90: 17.22±7.4%: hES-3: 18±3.82%) as compared to 5 µM CHIR (FIG. 4B).

Figure 9:
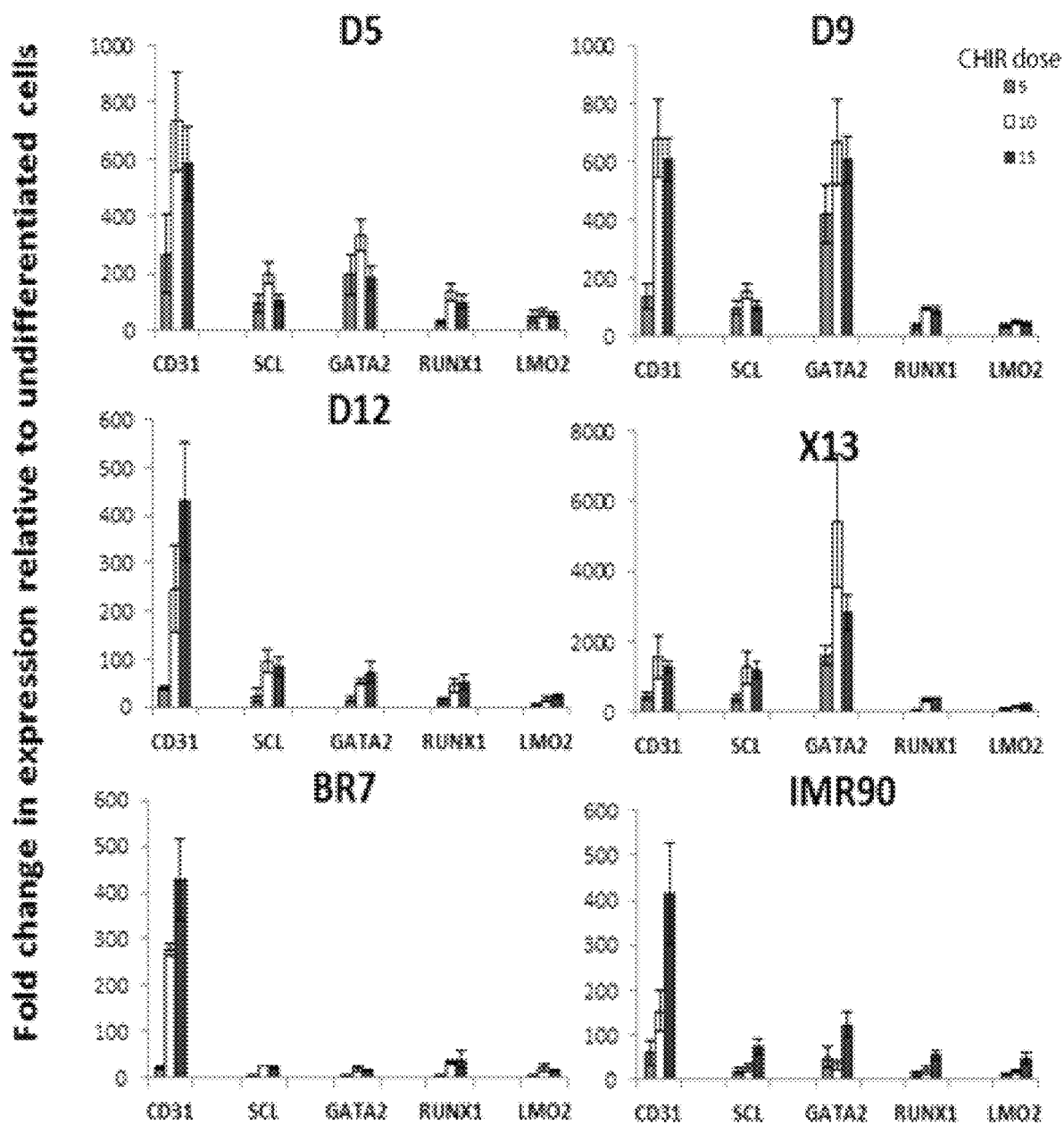
FIG. 9 shows column graphs depicting the results of real-time RT-PCR analysis for expression of hematopoietic specification markers. Continuous agitation hPSC-MC aggregate cultures from 9 different lines (D5, D9, D11, D12, X13, BR2, BR7, IMR90 and hES-3) were differentiated using optimized conditions and CHIR-99021 dose of 5, 10 and 15 μM (legend). Day 4 samples were evaluated by RT-PCR for expression levels of CD31, SCL, GATA2, RUNX1 and LMO2. Fold-change in expression relative to undifferentiated cells (Day 7 hPSC-MC aggregates before differentiation) are reported. Data are mean±SEM, n=3.

Expression of KDR+PDGFRβ− cells, indicative of hematovascular progenitors mirrored the trend of T-bra+ cells. 15 μM CHIR resulted in significantly higher (p<0.05) KDR+ PDGFRβ-cells (D5: 35.77±1.53%; D9: 18.07±0.6%; D11: 11.74±1.16%; D12: 31.13±5.17%; X13: 40.8±1.34%; BR2: 24.07±1.34%; BR7: 18.6±1.57%; IMR90: 14.2±1.69%: hES-3: 14.6±0.81%) as compared to 5 μM CHIR (FIG. 4C). Hematopoietic induction of differentiated cells evaluated by RT-PCR for expression of CD31 and key hematopoietic transcription factors SCL, GATA2, RUNX1 and LMO2 on day 4 post differentiation showed higher fold-up-regulation with increasing dose of CHIR in most of the lines tested (FIG. 9). Amongst the different hiPSC lines tested, X13 had the highest up-regulation in expression of CD31, SCL, GATA2, RUNX1 and LMO2 (FIG. 9).

With the exception of D9 and IMR90, which had hematopoietic precursor expansion even at 5 μM CHIR dose, all other human pluripotent stem cell lines had significantly increased (p<0.05) fold-expansion of hematopoietic precursors at day 14 post differentiation when induced with 15 μM CHIR dose (D5: 7.99±0.82; D11: 3.2±0.33; D12: 5.26±1.32; X13: 9.93±0.28; BR2: 8.07±2.06; BR7: 5.81±0.92; hES-3: 6.97±1.35) as compared to 5 μM CHIR (FIG. 4D). Differentiated cells expanded 14 days post differentiation expressed CD43, indicative of hematopoietic precursors (FIG. 4E). For 7 of the 9 lines tested (D5, D11, D12, X13, BR2, BR7 and hES-3) a higher initial KDR+ cell population (KDR>10%) on day 4 resulted in significantly increased hematopoietic precursor expansion 2 weeks later (FIG. 10), while 5 of 9 lines tested (D5, D11, X13, BR2, hES-3) had a positive correlation between higher T-bra+ cells on day 2 of differentiation and increased hematopoietic precursor expansion (FIG. 10). Thus in one example, the concentration of CHIR present is 15 μM.

differentiated into erythroblast, whereas 3 lines (D11, D12, BR2) failed to differentiate into erythroid cells (FIG. 4F). X13 had maximal cumulative fold-expansion of 12605±2126 which was significantly higher than the other lines tested [cumulative fold-expansion: D5; 3712±1651 (p=0.03), D9; 121.2±36.89 (p=0.0042), IMR90; 918.1±342.4 (p=0.0056), hES-3; 324±83.97 (p=0.0045) and BR7; 31.48±7.7 (p=0.0041)] (FIG. 4F; Table 2). For the best performing line, X13, 7607±1016 CD235a+ erythroid cells could be derived per hPSC seeded (Table 2). Differentiated erythroblast with visibly hemoglobinized red pellet (FIG. 4G) had expression of CD235a and high levels of HbF (Table 2).

Table 2—Hematopoietic differentiation of nine human pluripotent stem cell (hPSC) lines, from expansion in agitated microcarrier culture to erythroblast expansion—This table summarises the different stages of differentiation; hPSC expansion, mesoderm induction, hematopoietic precursor and erythroblast expansion of multiple hPSC-MC aggregate lines differentiated with optimal dose of CHIR-99021. Fold-expansion of hPSC-MC aggregates following 7 days of agitated culture, hematopoietic precursors following 14 days of culture in methylcellulose medium and erythroblast expansion following 24 days in expansion medium are reported. Flow cytometric evaluation of % T-bra+ cells on day 2 and % KDR+ cells on day 4 during mesoderm induction, % CD43+ cells during hematopoietic precursor expansion, % CD235a+ cells and fetal hemoglobin expression during erythroblast expansion stage are summarised. Total erythroid cells per hPSC seeded on day 42 was calculated as number of embryoid bodies derived on day 4 per hPSC seeded*erythroblast fold expansion*percent CD235a+ erythroblast.

TABLE 2

| Stage | hPSC expansion 7 days in mTESR1 (agitation) | Mesoderm induction 4 days in Stemline II medium (static) | | Hematopoietic precursor expansion 14 days in methyl cellulose medium (static) | | Erythroblast expansion | | | Total erythroid cells per hPSC |
|---|---|---|---|---|---|---|---|---|---|
| | | | | | | 24 days in erythroblast expansion medium (static) | | | |
| Process Cell line | Fold-expansion | % T-Bra | % KDR+ PDGFRα− | Fold-expansion | % CD43 | Fold-expansion | % CD235a+ | Hemoglobin expression | seeded (day 42) |
| D5 | 7.7 ± 0.9 | 55.6 ± 8.3 | 35.8 ± 1.5 | 7.9 ± 0.4 | 27.7 ± 0.9 | 3712 ± 1651 | 74.6 ± 6.8 | 99.2 ± 0.1 | 2308 ± 601 |
| D9 | 8.0 ± 0.5 | 41.8 ± 5.8 | 20.9 ± 0.8 | 6.0 ± 0.8 | 21.3 ± 1.5 | 121 ± 37 | 57.5 ± 4.6 | 97.8 ± 0.3 | 63 ± 21 |
| D11 | 7.8 ± 1.4 | 33.4 ± 4.1 | 11.7 ± 1.2 | 3.2 ± 0.3 | 17.4 ± 2.8 | NA | NA | NA | NA |
| D12 | 6.0 ± 0.4 | 10.9 ± 0.9 | 20.7 ± 4.1 | 7.9 ± 2.2 | 22 ± 3.7 | NA | NA | NA | NA |
| X13 | 5.3 ± 0.8 | 60.9 ± 8.6 | 40.8 ± 1.3 | 9.9 ± 0.3 | 43.9 ± 0.5 | 12605 ± 2126 | 67.4 ± 3.8 | 96.9 ± 1.4 | 7607 ± 1016 |
| BR2 | 6.0 ± 0.7 | 20.1 ± 2.4 | 24.1 ± 1.3 | 8.1 ± 2.1 | 8.7 ± 0.7 | NA | NA | NA | NA |
| BR7 | 9.6 ± 0.9 | 20.8 ± 3.8 | 18.6 ± 1.6 | 5.8 ± 0.9 | 14.3 ± 1.7 | 31.5 ± 7.7 | 33.8 ± 3.6 | 95.5 ± 1.5 | 12 ± 3 |
| IMR90 | 12.5 ± 0.9 | 17.2 ± 7.4 | 14.2 ± 1.7 | 7.9 ± 1.7 | 21.9 ± 2.4 | 918.1 ± 342 | 75.9 ± 1.8 | 98.1 ± 0.5 | 1300 ± 570 |
| hES-3 | 10.1 ± 1.1 | 18 ± 3.8 | 14.6 ± 0.8 | 6.9 ± 1.4 | 42.8 ± 0.7 | 324 ± 84 | 78.5 ± 3.0 | 99.3 ± 0.1 | 244 ± 68 |

Figure 5:
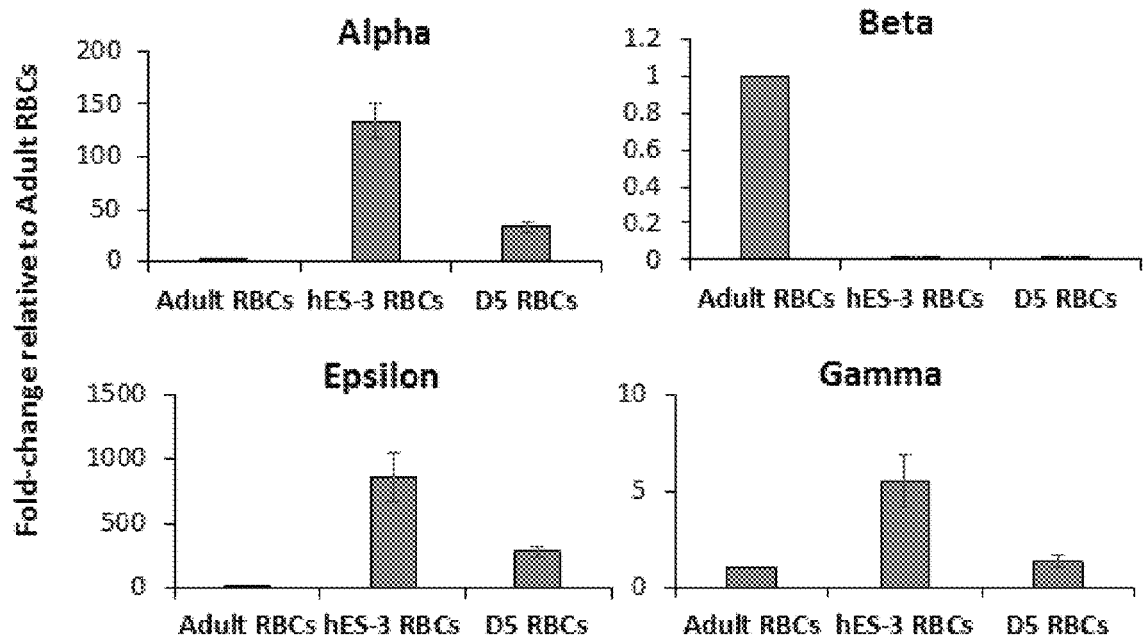
FIG. 5 shows results of the functional characterization and terminal maturation of 0-neg hiPSC derived erythroblast. (A) shows the results of real-time RT-PCR evaluation of hemoglobin subtypes of adult peripheral blood red blood cells (adult RBCs), hES-3 derived erythroblast (hES-3 RBCs) and O-neg hiPSC derived erythroblast (D5 red blood cells). Data is represented as mean fold-change in expression relative to adult red blood cells±SEM, n=3. (B) shows results of immunoblot detection of hemoglobin subtypes and beta-actin from cell lysates of adult peripheral blood red blood cells (PB), cord blood red blood cells (CB) and triplicate testing of hES-3 derived erythroblast and O-neg human induced pluripotent stem cell (hiPSC) derived erythroblast (D5). White lines demarcate regions of gel images that were merged together. (C) shows line graphs depicting oxygen equilibrium curves [percent oxyhemoglobin vs oxygen pressure (mm Hg)] of adult red blood cells (♦), hES-3 differentiated erythroblast (□) and triplicate samples of D5 erythroblast (1-▲, 2-□, 3-o). Corresponding p50 values (mean±SD, n=2) and p-values as compared to adult red blood cells are presented. (D) shows the results of the flow cytometry evaluation of CD235a and DRAQ5 expression of O-neg hiPSC derived erythroblast cultured in expansion medium (Expansion) or co-cultured with human fetal mesechyml stem cells (MSC) for 19 days under terminal maturation conditions (Enucleation replicate 1-3). Erythroblast stained with isotype antibodies served as controls. (E) shows images of terminally matured O-neg erythroblast stained with anti-human CD235a-FITC antibody and DRAQ5. Representative Brightfield image, fluorescence image of CD235a, DRAQ5 and merged fluorescence image of CD235a and DRAQ5 are shown. Enucleated cells can be identified in the merged image as CD235a positive cells lacking nuclear staining (zoomed in view shown below). Scale bar=20 micron. (F) shows a Giemsa staining of O-neg erythroblast before (day 0) and during maturation (days 4-19). Black arrows indicate enucleated erythrocytes. Scale-bar=20 micron.
Figure 5:
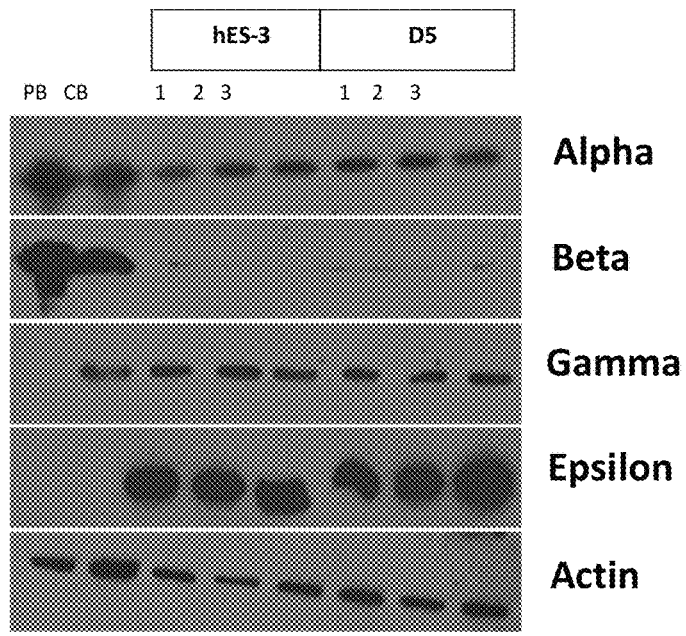
Figure 5:
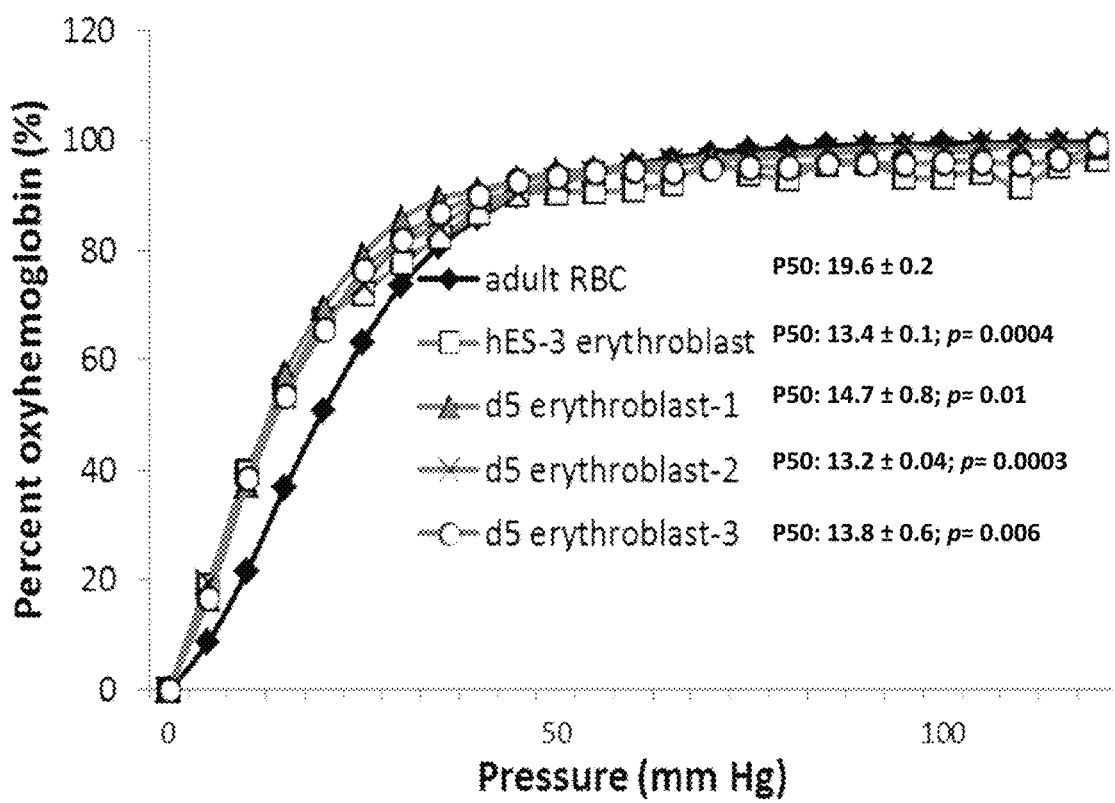
Figure 5:
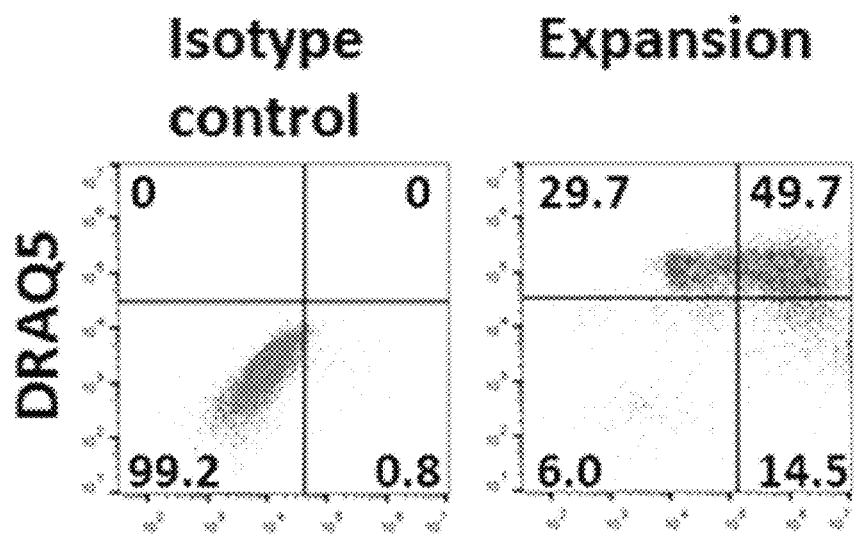
Figure 5:
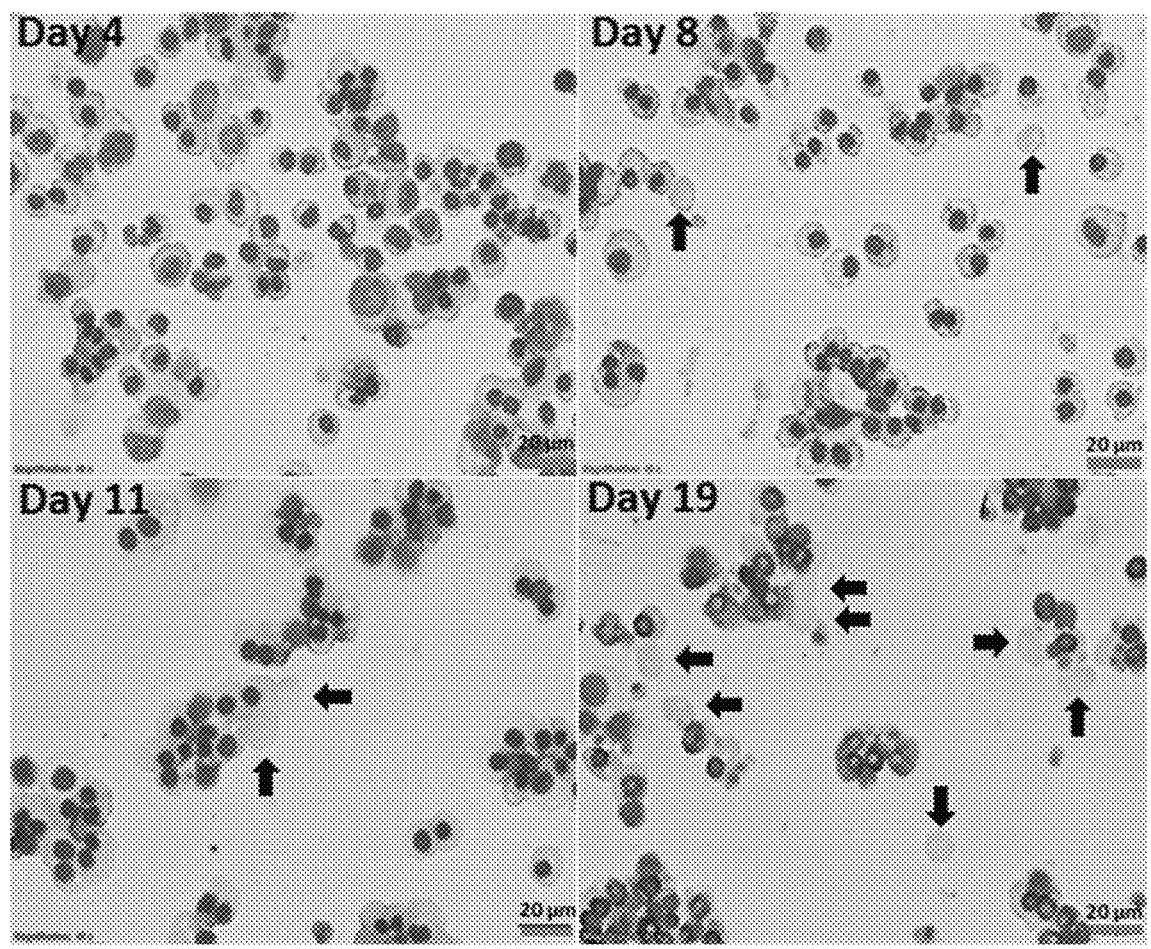
Figure 11:
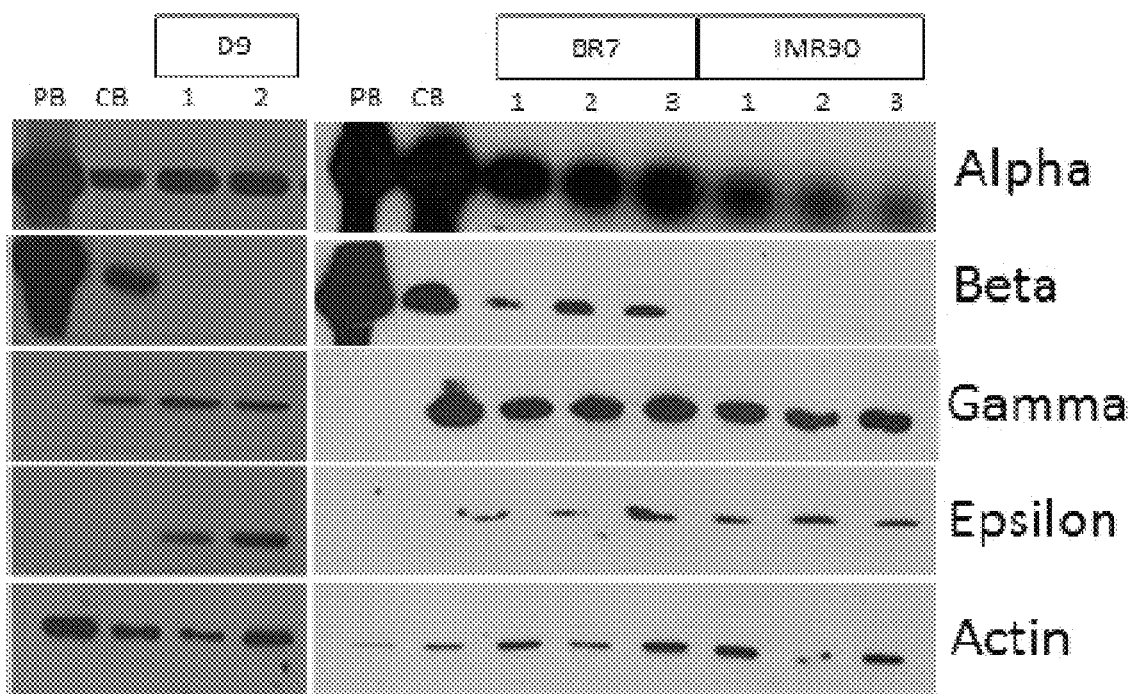
FIG. 11 shows immunoblots illustrating the results of detection of different hemoglobin subtypes in differentiated erythroblast. Cell lysates from erythroblast differentiated from D9, BR7 and IMR90 (day 35 post differentiation) were immunoblotted with antibodies specific to alpha, beta, gamma, epsilon human hemoglobin subtypes and the housekeeping control human β-actin. Cell lysates from peripheral blood (PB) and cord-blood (CB) derived erythroblast were run as controls. White lines demarcate regions of gel images that were merged together.
Figure 12:
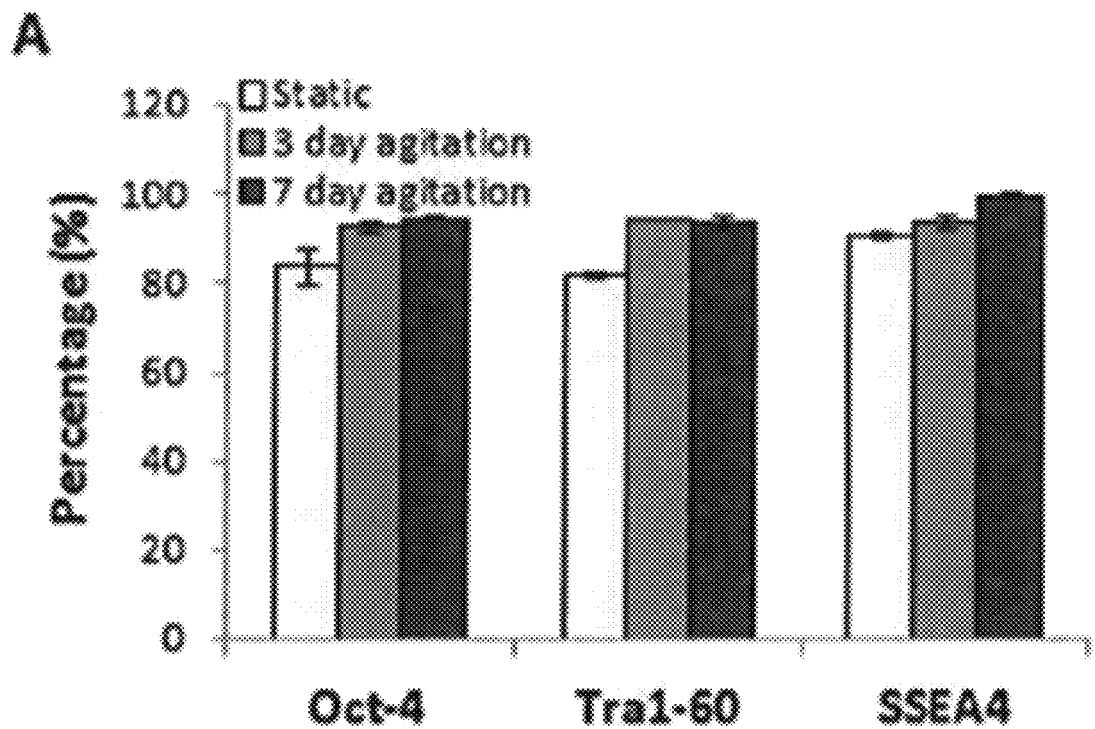
FIG. 12 shows data depicting that continuous agitation microcarrier aggregates have reduced differentiation when differentiated with BMP4 protocol. (A) shows column graphs depicting the results of flow cytometry analysis of pluripotency markers (Oct-4, Tra1-60, SSEA-4) for hES-3 aggregates cultured on microcarriers initially expanded under static condition for 7 days, or agitated condition (3 or 7 days agitated human pluripotent stem cell (hPSC) expansion) during the pluripotent expansion stage. (B) shows column graphs depicting the results of flow cytometry analysis of T-bra (48 hours post differentiation) and KDR (4 days post differentiation) from differentiated hES-3 cells initially cultured on microcarriers under static condition, 3 day agitation or 7 day agitation (*p<0.05, #p<0.001 as compared to static hPSC expansion condition). (C) shows a column graph depicting real-time RT-PCR data showing mean fold change in expression (relative to undifferentiated hES-3) of early hematopoietic specification markers (CD31, GATA2, GATA1, SCL, RUNX1), as characterization for hematopoietic specification, from hES-microcarrier aggregates (initially derived from static culture, 3 day agitation or 7 day agitation cultures) differentiated for 4 days (* p<0.05; #p<0.001 compared to static hPSC expansion conditions). Data are represented as mean fold-change in expression relative to undifferentiated hES-3, n=3. (D) shows images of hES-3 microcarrier aggregates. Day 0 images of hES-3 microcarrier aggregates are presented, following 7 days of static or 3 and 7 days of agitated culture. Images of hematopoietic precursors on day 2 and day 14 post expansion in methylcellulose-based medium. (E) shows a column graph of the total counts of hematopoietic precursors (day 14 post expansion in BGM medium following initial seeding of $1\times10^5$ cells) and erythroblasts (Day 14 post seeding in erythroblast expansion medium) differentiated from hES-3-microcarrier (MC) aggregates derived from static and 3 or 7 days agitation cultures (#P<0.001 as compared to static hPSC expansion condition). (F) shows images of erythroblast cell pellets at termination of experiment (day 28).
Figure 12:
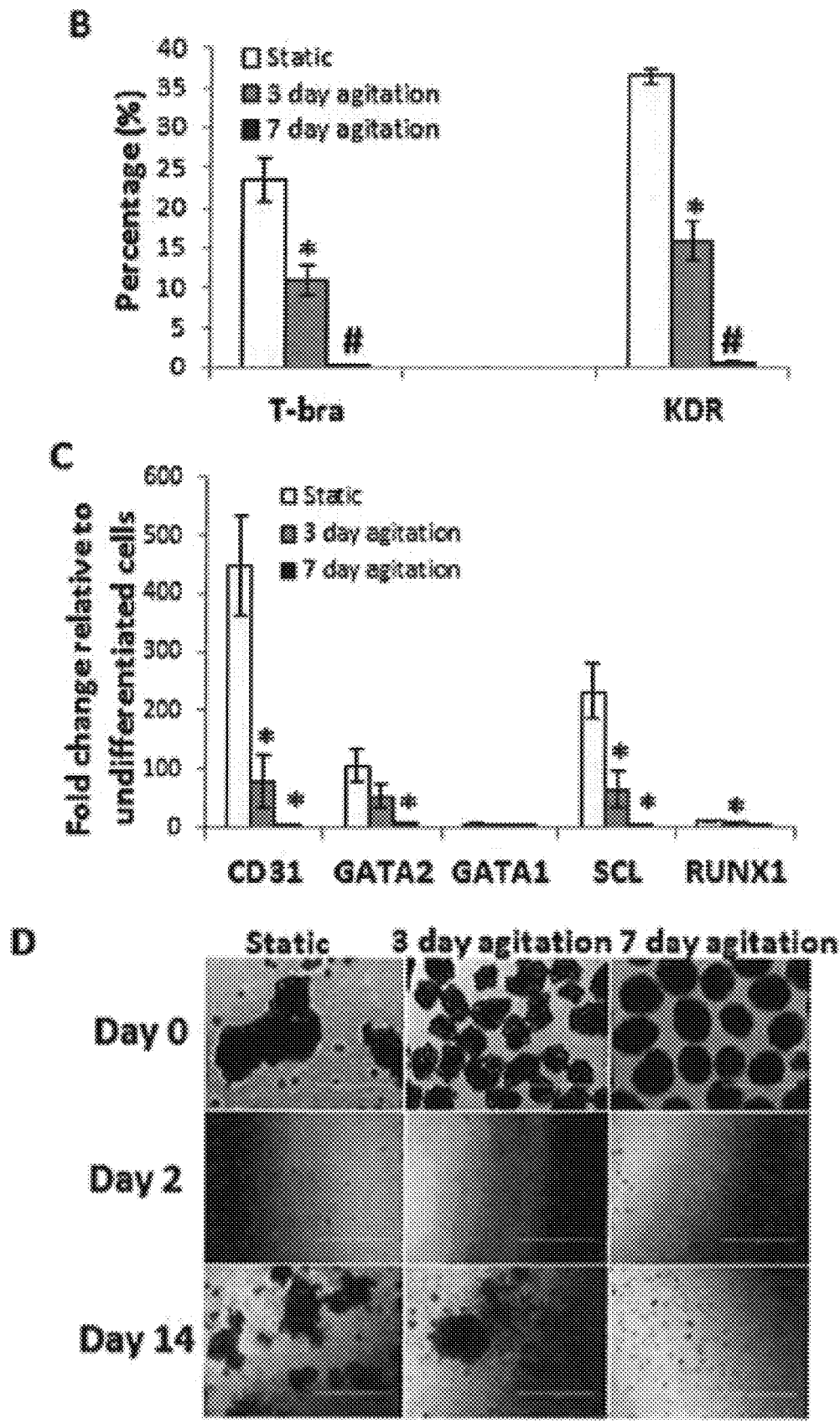
Figure 12:
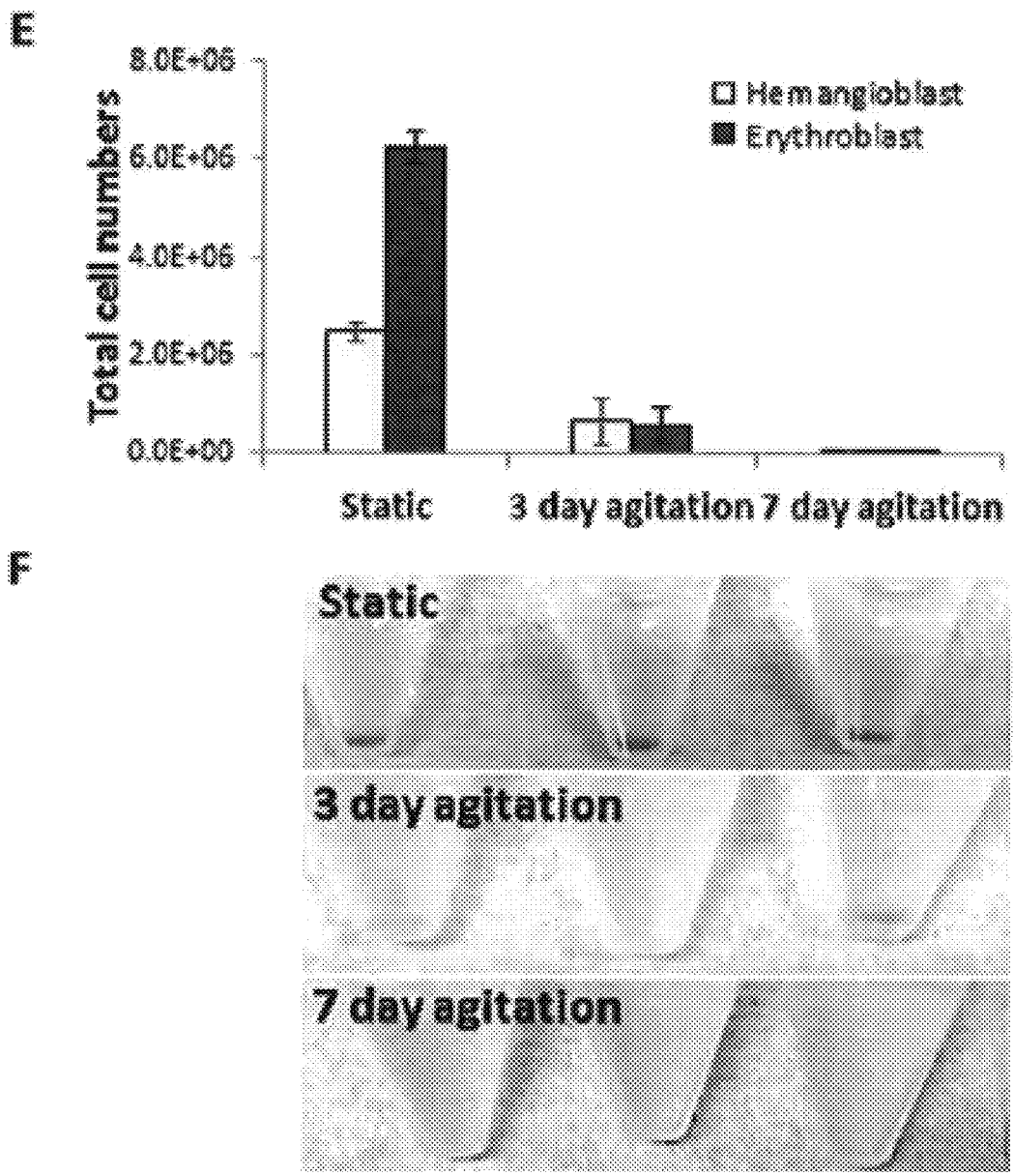
Figure 13:
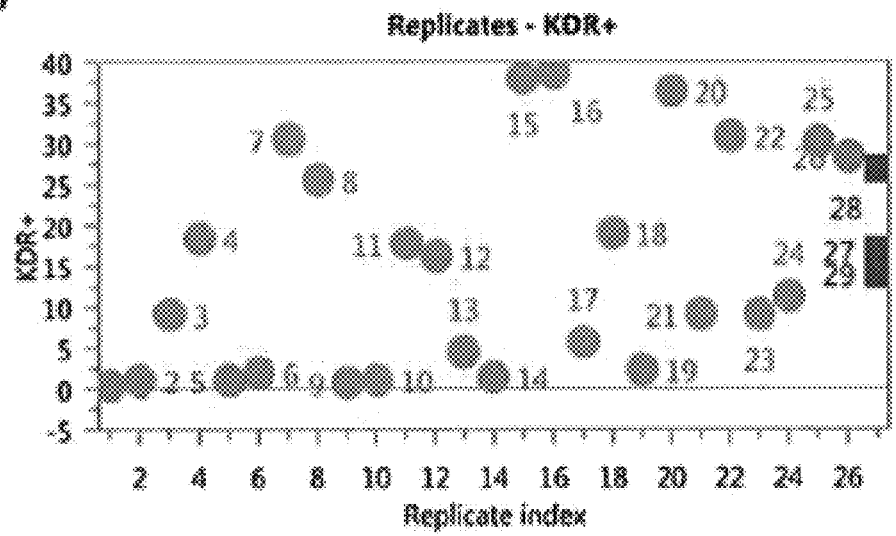
FIG. 13 shows the results of Design of Experiments (DoE) analysis, which identifies CHIR99021 as a significant factor for increased KDR expression in differentiation of hES-3 microcarrier aggregate cultures expanded under continuous agitation. (A) Table showing concentrations of Activin A (ng/ml), CHIR99021 (μM) maintained for 24 hours, CHIR99021 (μM) at 48 hours, SB-431542 (μM) added on day 3 and BMP4 (ng/ml) added at start of experiment for the multifactorial conditions generated by MODDE software and the corresponding KDR levels (%) determined by flow cytometry on day 4 post differentiation. (B) shows a scatter plot of KDR (%) levels for respective conditions tested (day 4 post differentiation). (C) shows data of the MODDE software in which CHIR (maintained for 24 hrs only) was identified as a significant factor for achieving higher KDR levels on day 4 of differentiation. Act=Activin; CHI=CHIR for 24 hours, CH2=CHIR from 24-48 hours; SB=SB-431542; BMP=BMP4; CHI*CH2=interaction between CHI and CH2. (D) shows a computational summary of model statistics generated by MODDE software showing probability scores for R2 (shows model fit; >0.5 suggests model of significant fit), Q2 (shows an estimate of the future prediction precision, Q2>0.1 for significant model and >0.5 for good model), model validity (is a test of diverse model problems, <0.25 indicates statistically significant model problems) and reproducibility (is the variation of the replicates compared to overall variability, >0.5 is warranted).
Figure 13:
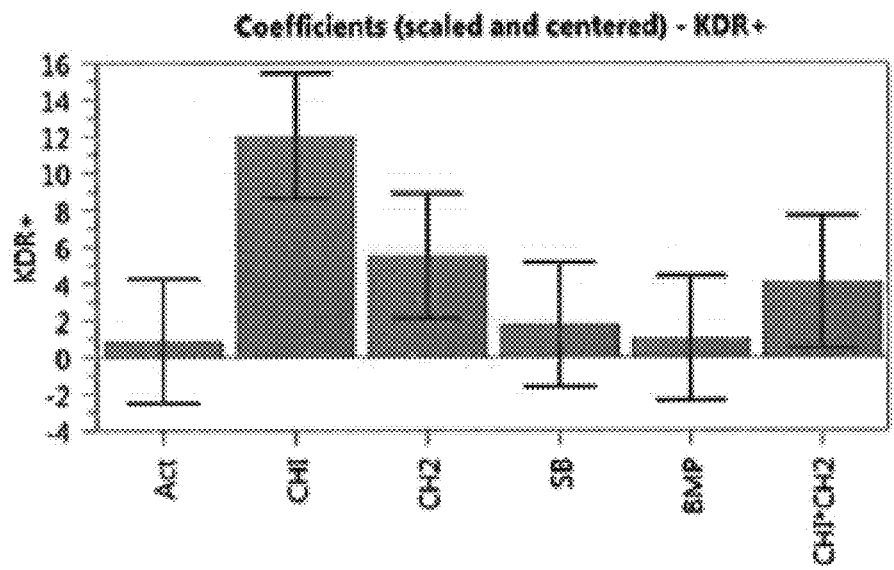
Figure 13:
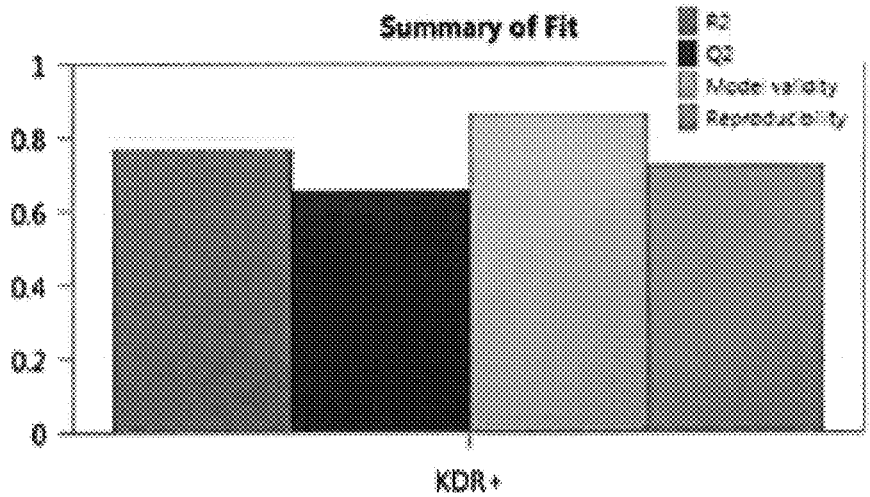
Figure 14:
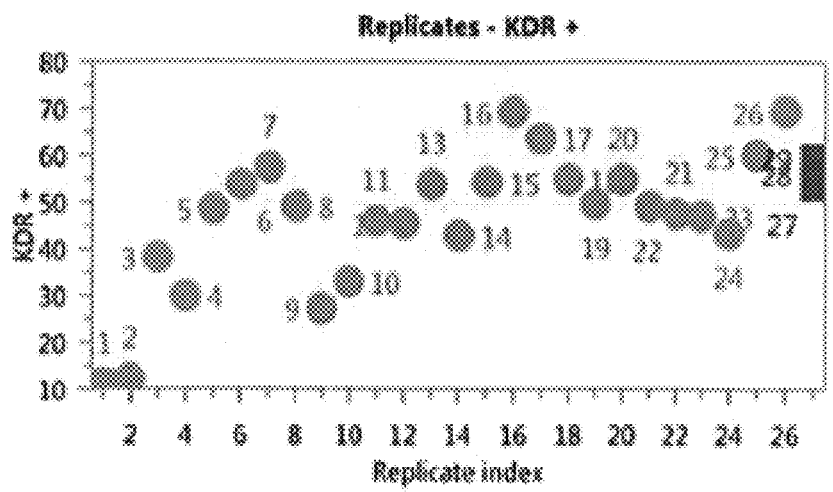
FIG. 14 provides further data, showing that Design of experiments multi-factorial analysis identified CHIR99021 as a significant factor for increased KDR expression in differentiation of O-negative human induced pluripotent stem cell (hiPSC) microcarrier aggregate culture expanded under continuous agitation. (A) shows a table of the concentrations of Activin A (ng/ml), CHIR99021 (µM) maintained for 24 hours, CHIR99021 (µM) at 48 hours, SB-431542 (µM) added on day 3 and BMP4 (ng/ml) added at start of experiment for the multifactorial conditions generated by MODDE software and the corresponding KDR levels (%) determined by flow cytometry on day 4 post differentiation. (B) shows a scatter plot of KDR (%) levels for respective conditions tested (day 4 post differentiation). (C) shows that the MODDE software identified CHIR (maintained for 24 hrs only) as a significant factor for achieving higher KDR levels on day 4 of differentiation. Act=Activin A; CHI=CHIR for 24 hours, CH2=CHIR from 24-48 hours; SB=SB-431542; BMP=BMP4; CHI*CH2=interaction between CHI and CH2. (D) shows the results of computational summary of model statistics generated by MODDE software showing probability scores for R2 (shows model fit; >0.5 suggests model of significant fit), Q2 (shows an estimate of the future prediction precision, Q2>0.1 for significant model and >0.5 for good model), model validity (is a test of diverse model problems, <0.25 indicates statistically significant model problems) and reproducibility (is the variation of the replicates compared to overall variability, >0.5 is warranted).
Figure 14:
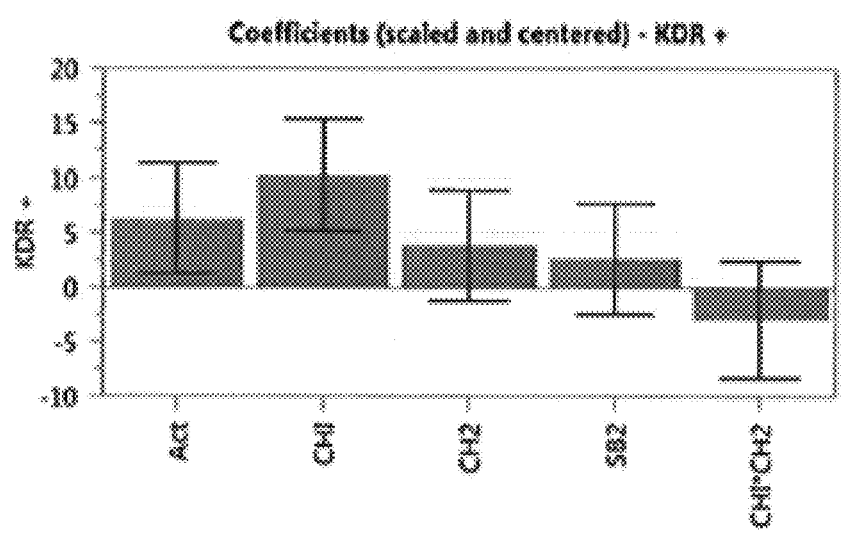
Figure 14:
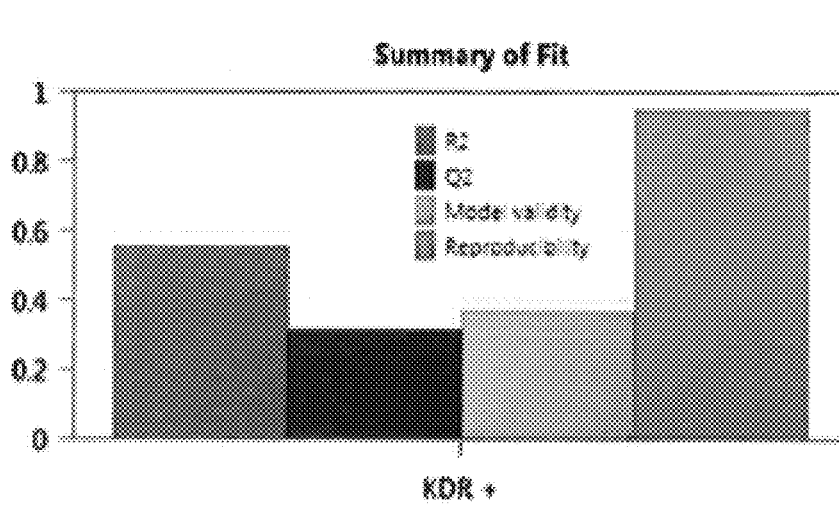
Figure 15:
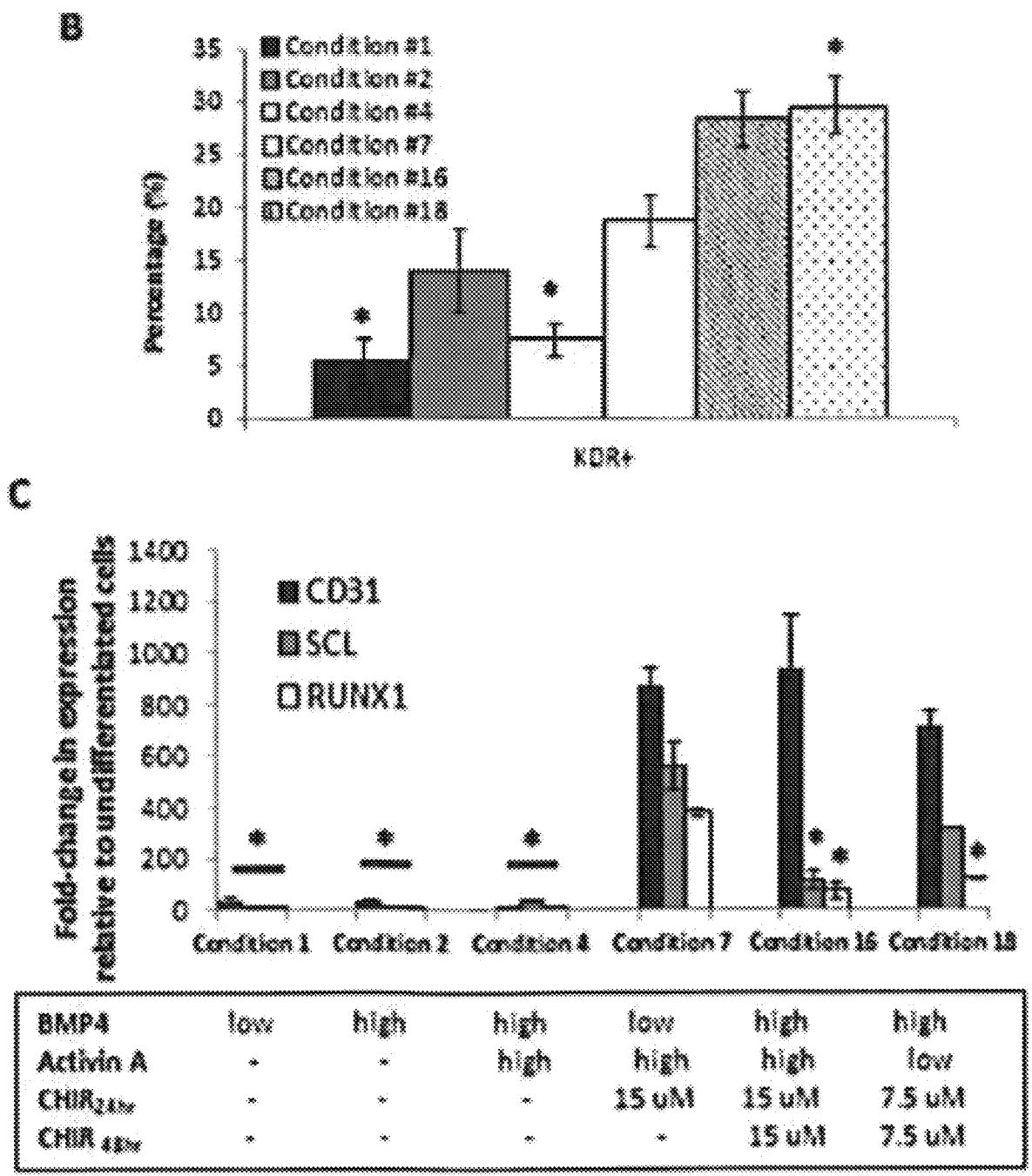
FIG. 15 shows results indicating that modulation of BMP4, Activin A and Wnt signalling significantly improves mesoderm induction, hemangioblast expansion and erythroblast differentiation of O-negative hiPSC microcarrier aggregate culture expanded under continuous agitation. (A) is a table showing selected conditions (generated by MODDE software) that were tested and their corresponding T-bra levels (%) determined by flow cytometry at the indicated time points. (B) shows a column graph depicting the flow cytometry levels of KDR (%) determined 4 days post differentiation for selected conditions tested. (C) is a column graph showing the results of real-time RT-PCR characterization of selected conditions for hematopoietic specification (CD31, SCL, RUNX1) 4 days post differentiation (*$p<0.05$ as compared to condition 7). Data are represented as mean fold-change in expression relative to undifferentiated cells, n=3. (D) presents images of hemangioblast expansion 4 days, 10 days and 17 days post expansion in methylcellulose medium for selected conditions tested. Corresponding fold-expansion of hemangioblast (Day 17 as compared to initially seeding) and fold-upregulation of CD31, SCL and RUNX1 markers of microcarrier aggregates (day 4 as compared to day 0) are reported. (E) shows a line graph depicting the total cell expansion from day 0 to day 34 for selected conditions. Day 0-4 (mesoderm induction of microcarrier aggregates), day 4-17 (hemangioblast expansion in methylcellulose), day 17¬34 (erythroblast expansion in suspension culture).
Figure 15:
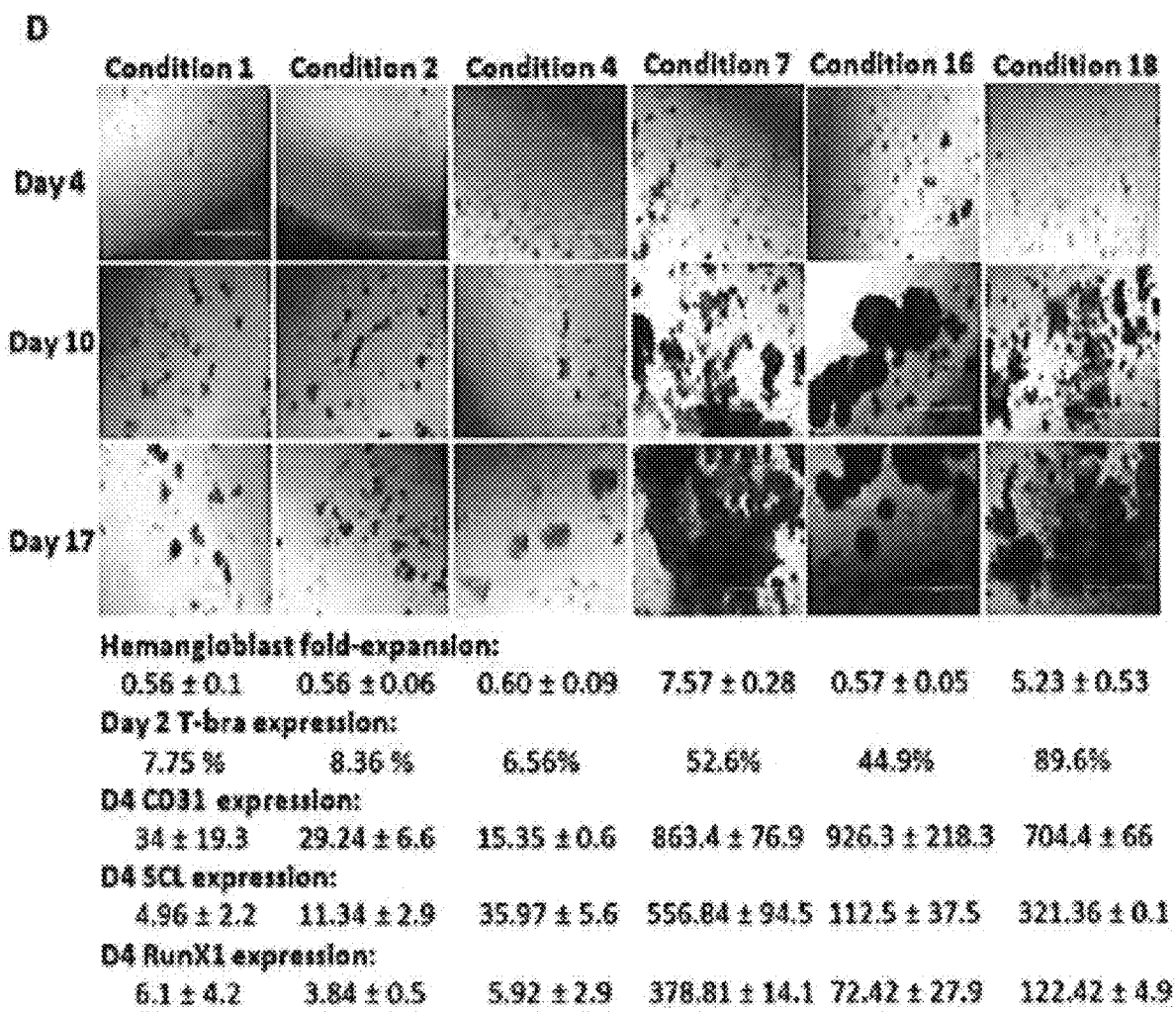
Figure 15:
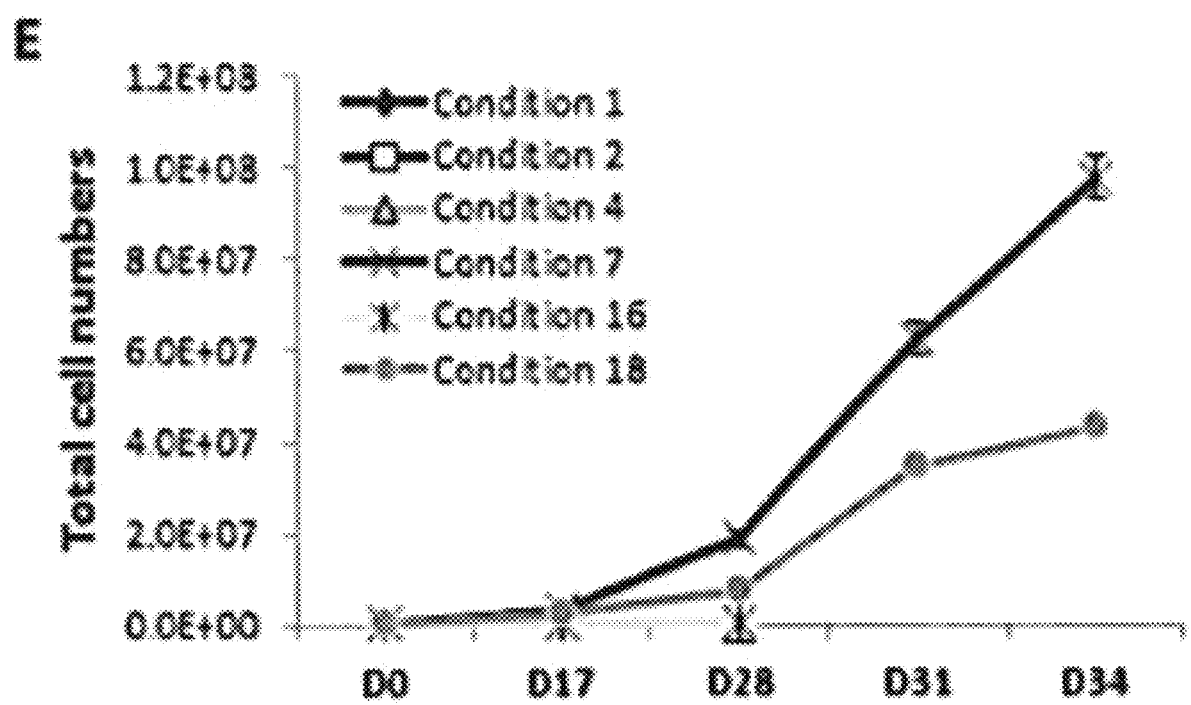
Figure 16:
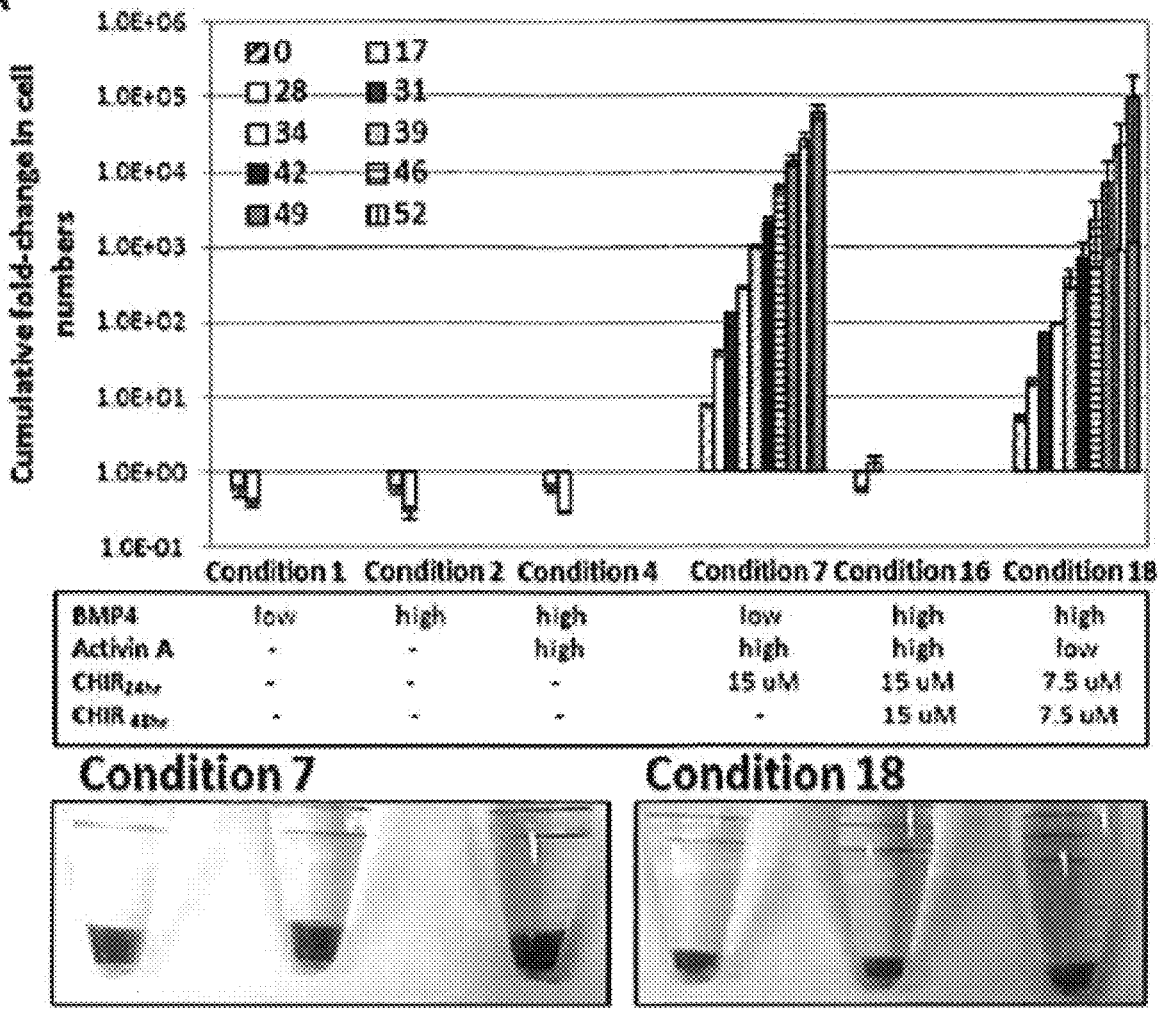
FIG. 16 shows the results of an evaluation of O-negative erythroblasts derived from optimized differentiation condition. (A) shows a column graph, in which cumulative fold-expansion in total viable cell numbers was determined for O-negative donor iPSC (Donor #5) differentiated using the different conditions (during mesoderm induction stage). Corresponding red blood cell pellets from conditions 7 and 18 on day 34 of experiment. (B) shows a table summarizing flow cytometry expression (%) of erythroblast surface markers (CD235a and CD71), fetal hemoglobin (HbF) and total viable cell yield on day 34 of experiment for erythroblast derived using conditions 7 and 18. Corresponding p-values for comparison between condition 7 and 18 are reported. (C) is a table summarizing expression profiles of hemoglobin subtypes (embryonic; epsilon chain, fetal; gamma chain and adult; beta chain) of adult red blood cells, hES-3 derived erythroblast and O-negative hiPSC derived erythroblast as determined by RT-PCR. (D) shows data from the flow cytometry evaluation of CD235a and DRAQ5 expression of O-negative induced pluripotent stem cells (iPSC) derived erythroblast cultured in expansion medium (Expansion) or 2 and 3 weeks post culture in terminal maturation conditions (E nucleation 1-3). Erythroblast stained with isotype antibodies served as isotype controls. Graphical representation of percent enucleation (average percentage of CD235+ and DRAQ5-erythroblast, data are mean±SEM, n=3). (E) shows images of erythroblast cultured under terminal maturation conditions for 3 weeks were stained with anti-human CD235a-FITC antibody and DRAQ5. Representative Brightfield image, fluorescence image of CD235a (FITC channel), DRAQ5 (CY5 channel) and merged fluorescence image of CD235a and DRAQ5 are shown. White arrows indicate enucleated (DRAQ5-) CD235a+ RBCs. Yellow asterisk indicate late-stage erythroblast undergoing enucleation. Original magnification X40.
Figure 16:
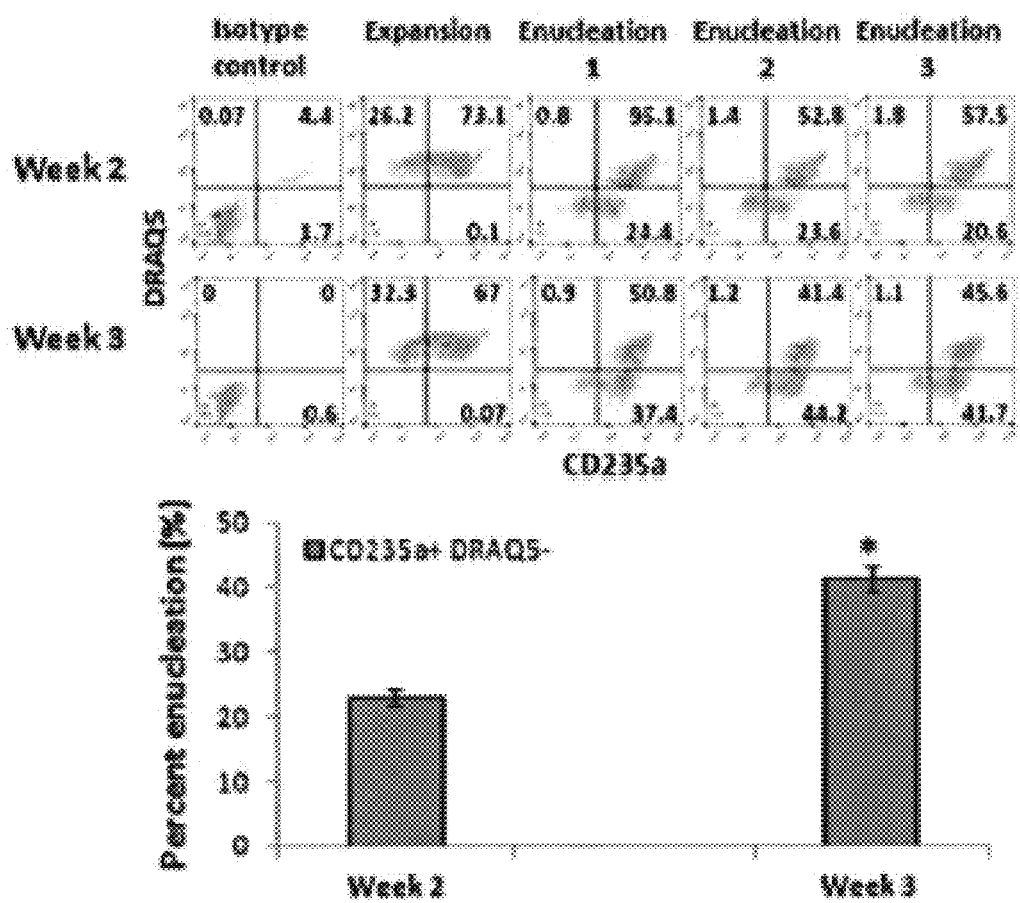
Figure 16:
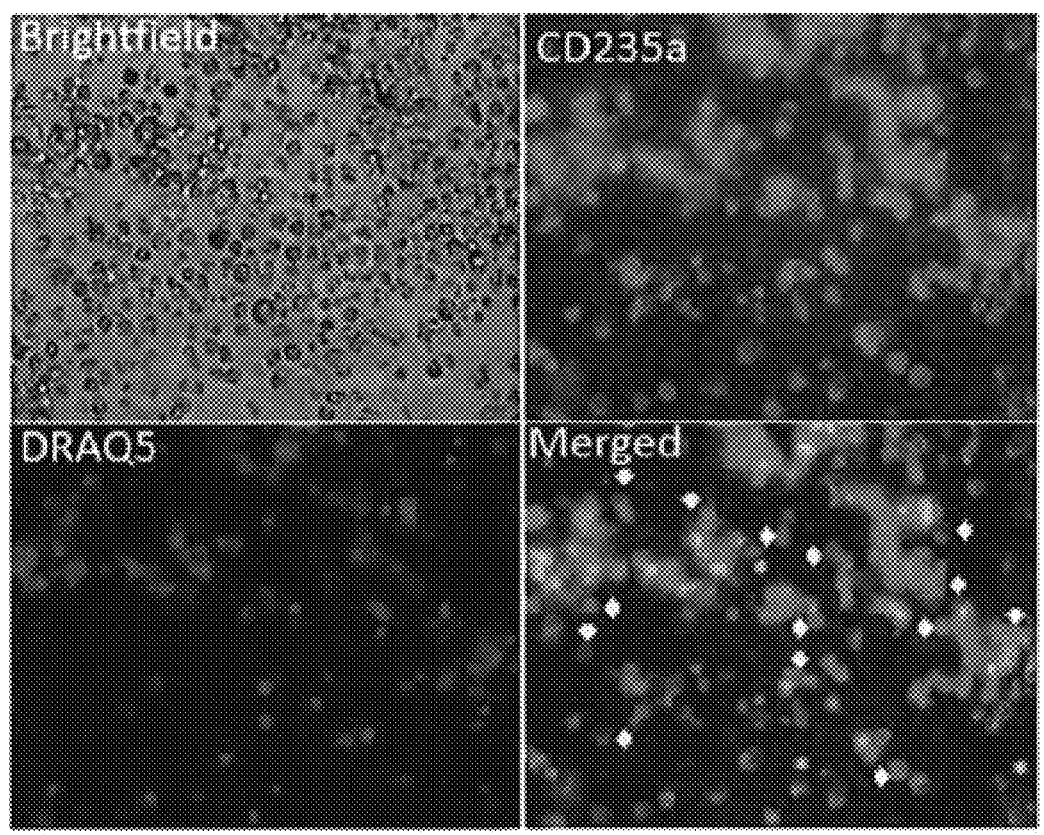
Figure 17:
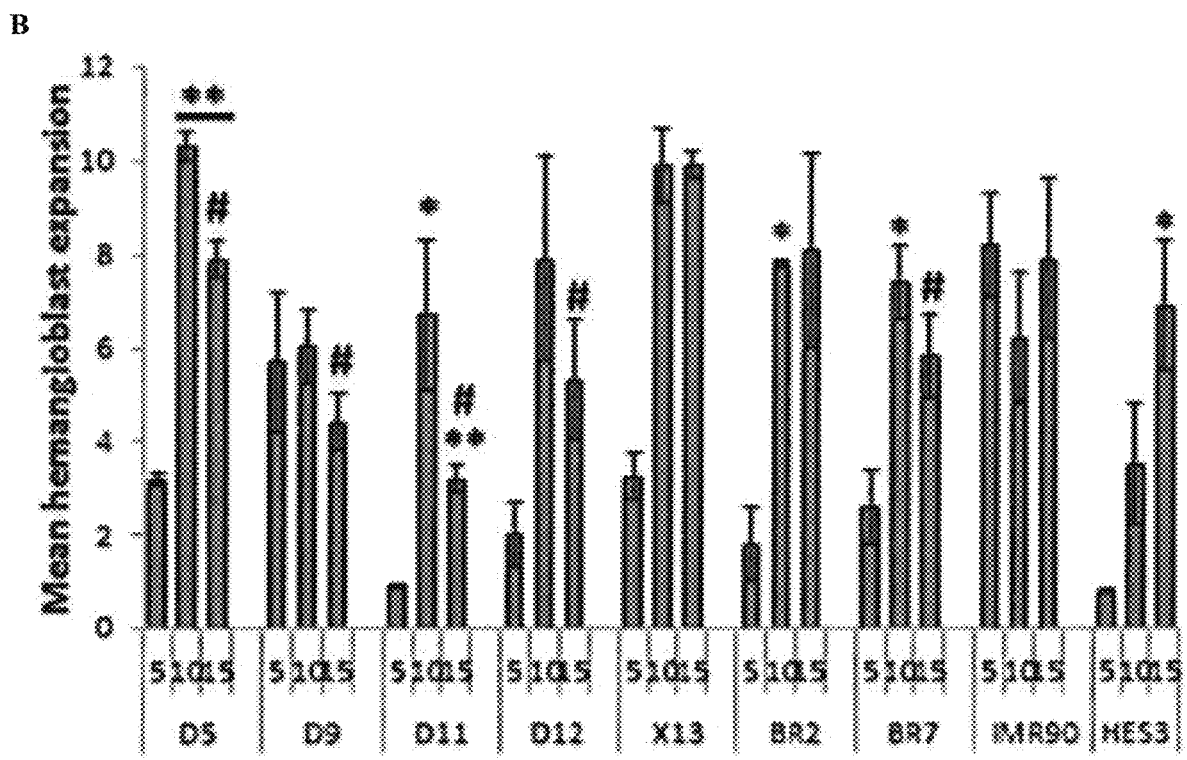
FIG. 17 shows data depicting the differentiation of different hPSC microcarrier aggregate cultures initially expanded under continuous agitation (one human embryonic stem cell line, one commercial hiPSC line, seven O-negative hiPSC lines). (A) is a table summarizing nine different hPSC microcarrier aggregate lines expanded under continuous agitation for 7 days. Pluripotency levels (%) of Oct-4, Tra1-60 and SSEA4 were determined by flow cytometry. Selected lines were karyotyped by G-banding and found to have no abnormal clones. Mean fold-expansion and aggregate diameters (micron) of microcarrier aggregates following 7 day continuous agitation cultures are reported. IGF-2 mRNA levels (relative to hES-3) of undifferentiated hPSC microcarrier aggregates were determined by RT-PCR. (B) shows the effect of CHIR99021 dose (µM) on the mean fold-expansion of hemangioblast 14 days post differentiation of different hPSC microcarrier aggregate cultures (*$p<0,05$, **$p<0.01$ as compared to 5 pM CHIR99021 dose for each line; #$p<0.05$ for comparison of 15 pM CHIR99021 dose of each line to 15 pM CHIR99021 dose of X13). (C) shows column graphs representing the effect of CHIR99021 dose (µM) on the percentage of CD43+ cells in hemangioblast population derived 14 days post differentiation of different hPSC microcarrier aggregate cultures (*$p<0.05$, **$p<0.01$ as compared to 5 pM CHIR99021 dose for each line; #p<0.001 for comparison of indicated CHIR99021 dose of each line to 15 pM CHIR99021 dose of X13).
Figure 17:
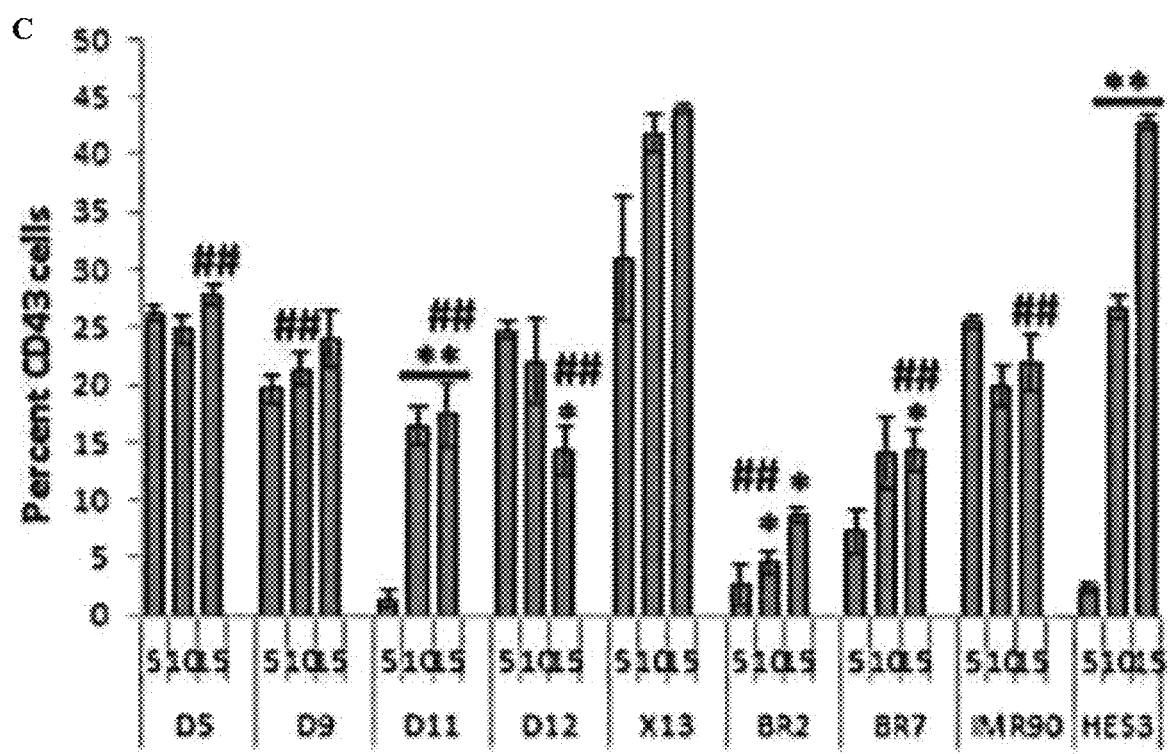
Figure 18:
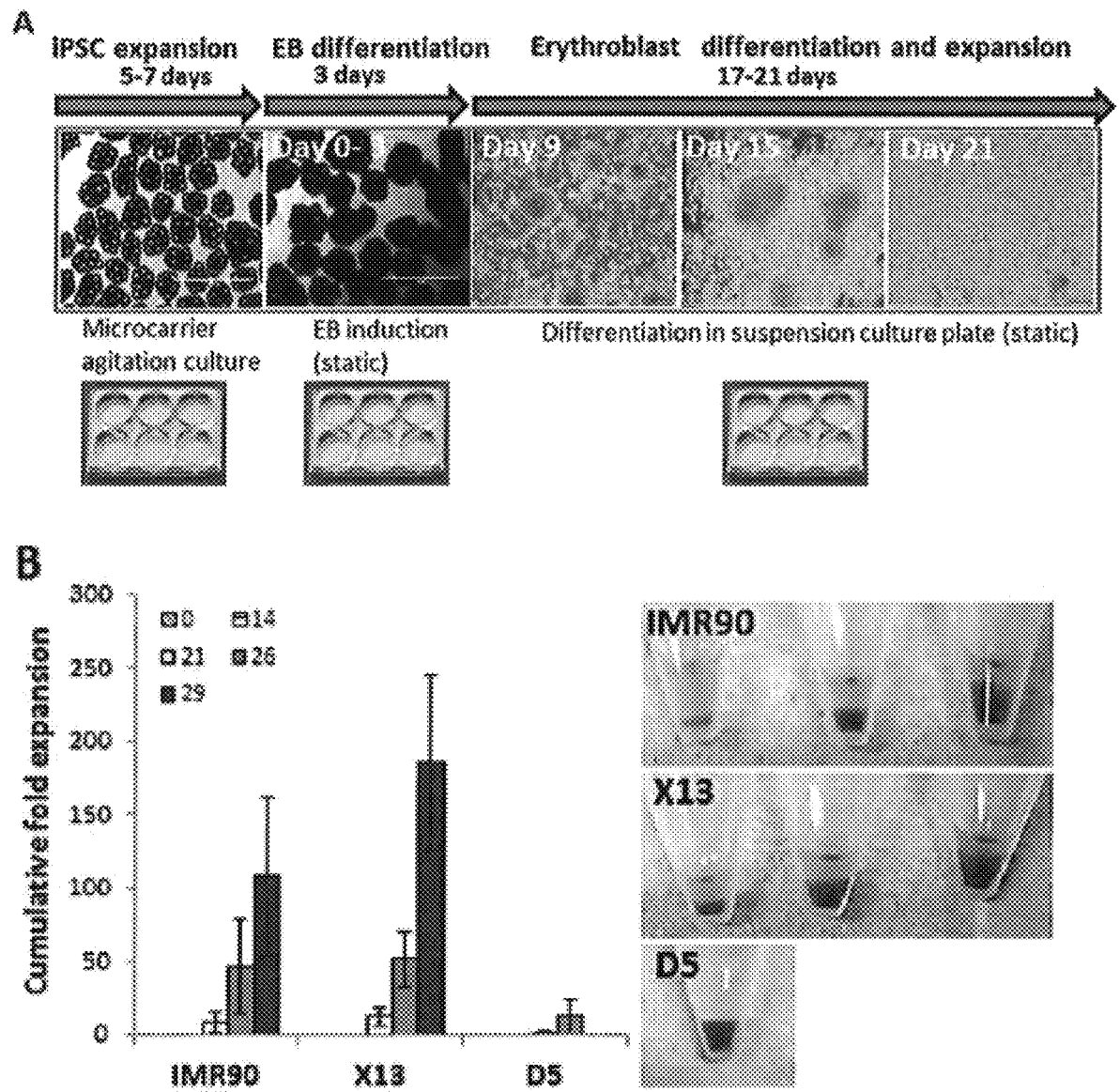
FIG. 18 shows the results of suspension culture differentiation of microcarrier human pluripotent stem cell (hPSC) aggregates derived from continuous agitation culture. (A) is a schematic of suspension culture differentiation of human pluripotent stem cell microcarrier aggregate cultures. Human induced pluripotent stem cell (hiPSC) microcarrier aggregate cultures continuously agitated for 5-7 days in ultra-low attachment 6 well plates were differentiated as embryoid bodies (EB) for 3 days under static condition, detached from microcarriers and further differentiated as single cell suspension cultures (static condition) for 17-21 days. (B) is a column graph showing cumulative fold-expansion of total viable cell numbers was determined following differentiation of the indicated human pluripotent stem cell lines. Corresponding red blood cell pellets from the different human pluripotent stem cell lines on day 29 of experiment. (C) is a table summarizing flow cytometry expression (%) of erythroblast surface markers (CD235a), fetal hemoglobin (HbF) and cumulative fold-expansion in viable cell numbers on day 29 of experiment for erythroblast derived from different hPSC lines.
Figures 18, 19:
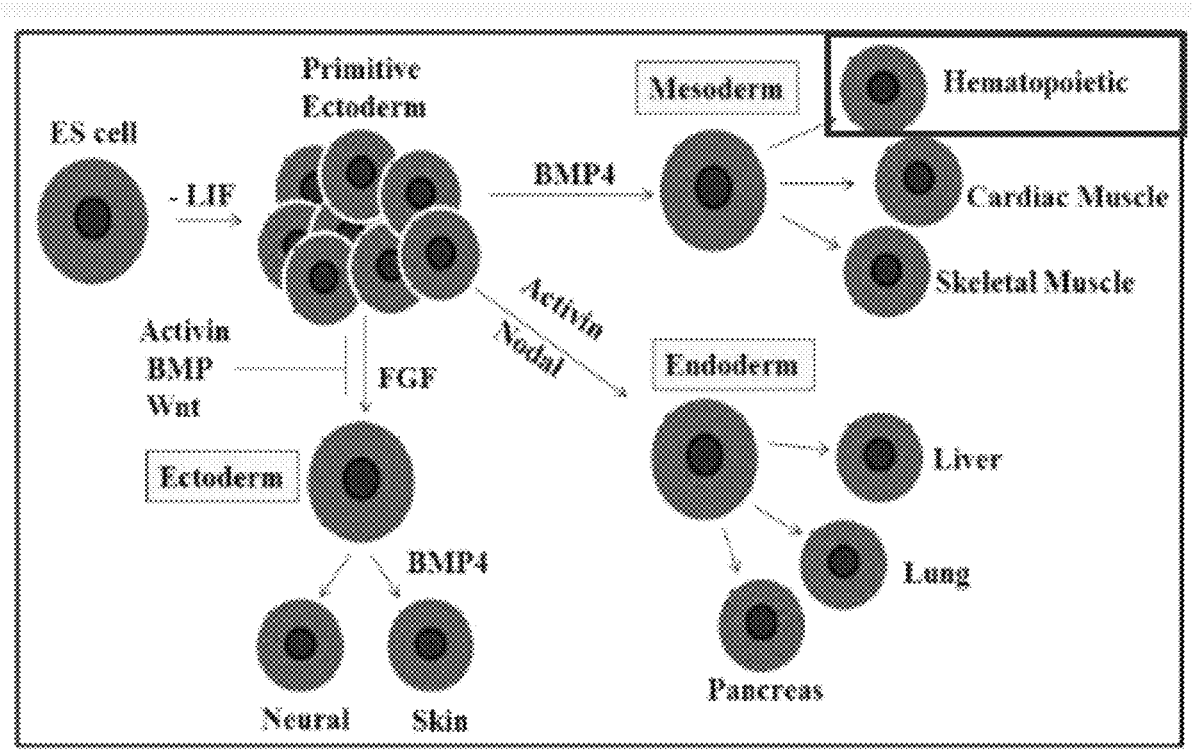
FIG. 19 shows a schematic of the differentiation potential of human embryonic stem (ES) cells/induced pluripotent stem cells (iPSC) towards ectoderm, endoderm and mesoderm lineages. Image taken from Zacharoula Konsoula MATER METHODS 2013; 3:166.
Figure 20:
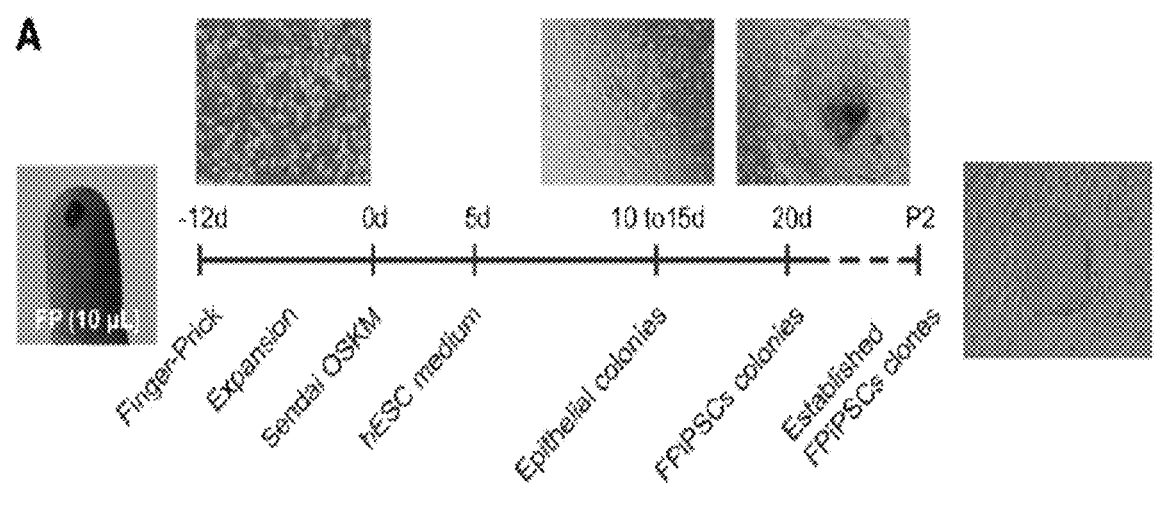
FIG. 20 shows information pertaining to red blood cell types and the derivation of red blood cells from finger-prick blood. (A) Schematic showing the derivation of human induced pluripotent stem cells (iPSCs) from finger-prick blood. Erythroblasts from 10 μl of finger prick blood were expanded in vitro for 12 days and transduced with Sendai virus expressing OCT4, KLF4, SOX4, c-MYC (OKSM). hiPSC can be derived within 3 weeks of transduction. Image taken from *Tan HK Stem Cells Trans Med* 2014, 3:586-598. (B) Schematic showing ABO blood grouping, antigen expression on the red blood cell surface and antibodies in plasma. Group O blood lack A and B antigens on their surface and therefore can serve universal donors.
Figure 21:
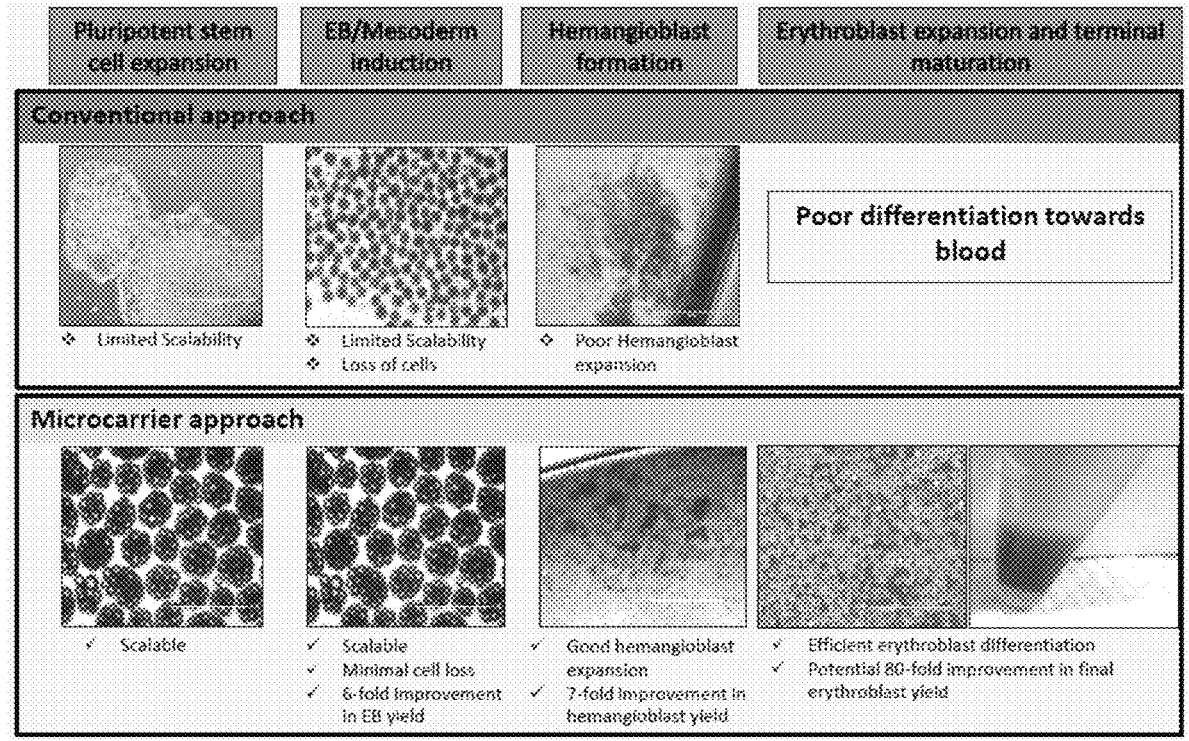
FIG. 21 shows a schematic of red blood cell (RBC) differentiation using the conventional embryoid body (EB) method and microcarrier-EB method. Image taken from Sivalingam et al., Tissue Eng Part C Methods. 2016 August; 22(8):765-80. Differentiation process involves pluripotent stem cell expansion, embryoid body (EB)/mesoderm induction, hemangioblast formation and erythroblast expansion and terminal maturation. In the conventional approach, hiPSCs are cultured as monolayer culture on Geltrex-coated dishes, while in the microcarrier approach, hiPSCs are cultured as agitated suspension culture on recombinant human LN-521-coated Solohill microcarriers with mTeSR medium for 7 days. Mesoderm induction by conventional method involves embryoid body formation by single cell seeding onto AggreWell 800 plates, followed by mechanical harvesting and transfer of embryoid bodies to suspension culture, whereas the microcarrier method simply involves switching microcarrier clusters from growth medium to mesoderm induction medium. Hemangioblast expansion stage involves growth in methylcellulose-based medium with cytokines for a period of 12-17 days. Embryoid bodies from conventional method are dissociated by enzymatic treatment to derive single cells for hemangioblast seeding, while embryoid bodies formed from microcarrier method can simply be dissociated by gentle pipetting. Erythroid expansion and terminal maturation stages are common to both methods and involve suspension culture of erythroid progenitors for up to 14 days in hematopoietic expansion medium followed by induction of terminal maturation by coculture on human mesenchymal stem cell (MSC) feeder layers for a further 14-21 days. Image shows red cell pellet characteristic of hemoglobinized red blood cells derived from the respective stages of differentiation. Cells differentiated by conventional method failed to expand during erythroblast expansion and terminal maturation stages.
Figure 22:
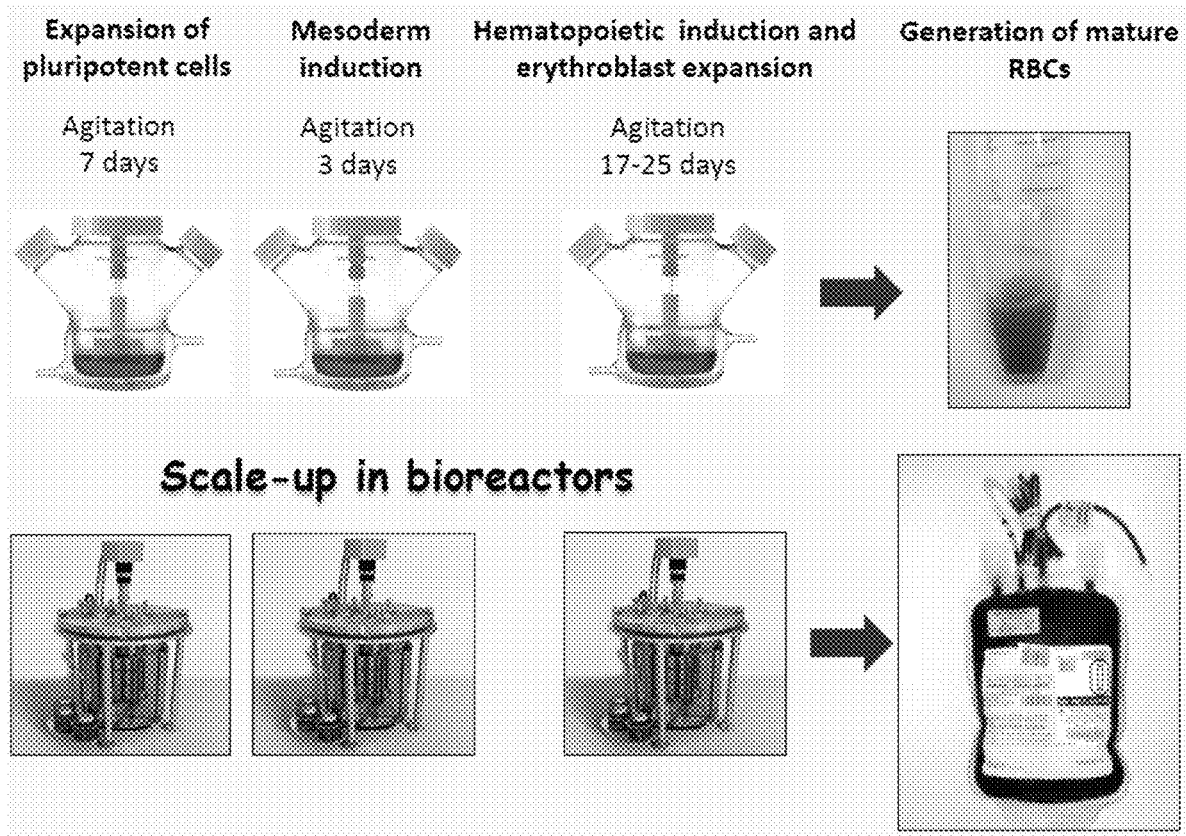
FIG. 22 shows a schematic depicting an example of the suspension agitation differentiation protocol as disclosed herein in spinner flasks to derive small quantities of red blood cells, and the potential to scale-up each stage of differentiation (expansion of pluripotent cells, mesoderm induction and hematopoietic induction and erythroblasts expansion) in controlled stirred-tank bioreactors to derive sufficient numbers of red blood cells for obtaining transfusable units of red blood cells.

Hematopoietic precursors expanded in blast growth medium from day 0 to day 14 were seeded in erythroblast expansion medium to induce erythroblast differentiation. Cells were continually expanded up to day 42 post differentiation and cumulative fold-expansion was calculated. Six of 9 lines (D5, D9, X13, BR7, IMR90, hES-3) successfully Terminal maturation and functional characterization of differentiated erythroblast from an O-Negative hiPSC O-neg erythroblasts (D5) were terminally matured by co-culture with primary human MSCs and functional characterization was performed on differentiated erythroblast. RT-PCR evaluation of the expression of hemoglobin subtypes showed that O-neg erythroblast (D5 red blood cells) had expression of alpha (33.13±5.16 fold-increase, p=0.0034), gamma (1.31±0.33 fold-increase), epsilon (279±43.89 fold-increase, p=0.0032) but very little beta (0.009±0.001 fold-increase, p<0.0001) hemoglobin expression as compared to adult erythroblast. Like-wise comparison of hES-3 derived erythroblast to adult erythroblast showed higher alpha, gamma and epsilon but lower beta hemoglobin (FIG. 5A). Immunoblot analysis confirmed the expression of alpha, gamma and epsilon hemoglobin with very little or no beta hemoglobin expression in hES-3 and D5 differentiated erythroblast (FIG. 5B) as well as in other hPSC lines (FIG. 11). Intriguingly, erythroblast differentiated from BR7 also showed expression of beta hemoglobin subtype (FIG. 11). Analysis of oxygen equilibrium curves of three (3) O-neg erythroblast lines differentiated from donor 5 human induced pluripotent stem cells (hiPSC) showed comparable oxygen binding affinity (D5 erythroblast-1: p50–14.7±0.8; D5 erythroblast-2: p50–13.2±0.04; D5 erythroblast-3: p50–13.8±0.6) which was significantly different (p<0.01) from adult red blood cells (p50–19.6±0.2) but similar to erythroblast derived from a human ES line (hES-3: p50–13.4±0.1) which was previously shown to be similar to cord-blood red blood cells (FIG. 5C). O-neg erythroblasts were terminally matured by co-culturing with primary human MSCs in maturation medium for a period of 19 days. Flow cytometric analysis showed that 39.0±1.0% of erythroblast were CD235a+ and DRAQ5 (cell permeable nuclear dye) negative, indicating enucleated erythroid cells (FIG. 5D). This was further corroborated by immunofluorescence staining of terminally matured erythroblast which showed CD235a+ erythrocytes lacking nuclear staining (FIG. 5E) and by Giemsa staining of cells which showed greater proportion of enucleated erythrocytes (FIG. 5F) with longer duration of maturation.

Discussion

Several variations of embryoid body (EB)-based differentiation approaches have been put forth for differentiating hPSCs towards erythroid cells but thus far, none have shown the feasibility for scale-up. Human pluripotent stem cell-microcarrier (hPSC-MC) aggregate cultures have previously been successfully scaled up in spinner culture platforms and bioreactors for cardiac progenitor cell differentiation. There is therefore potential use for human pluripotent stem cell-microcarrier (hPSC-MC) aggregates for developing large scale-erythroid differentiation processes as well.

One of the requisite for volumetric scale-up of human pluripotent stem cell-microcarrier (hPSC-MC) aggregate suspension culture is the need for continuous agitation as a means to maintain efficient oxygen and mass transfer as well as to keep cells in suspension. However, the inventors have observed that hPSC-MC aggregates expanded under continuous agitation during pluripotent expansion stage had reduced potential for mesoderm and hematopoietic differentiation even though their pluripotency levels were relatively unaffected. The earliest stages of mesoderm induction involve the expression of the primitive streak marker, T-bra, a conserved T-box transcription factor implicated in early gastrulation. Subsequently, KDR+ hematopoietic mesodermal cells responsive to VEGF signalling emerge and differentiate into hematopoietic progenitor cells. Agitation of hPSC-MC aggregates was shown to result in severely reduced expression of T-bra and KDR, as well as reduced induction of key transcription factors, such as SCL33, 38, GATA239 and RUNX134, which have been implicated in early hematopoietic induction. Consequentially, erythroid differentiation was severely reduced, if not completely abolished when these cells were differentiated with a BMP4-based protocol. Without being bound by theory, it was thought that the build-up of differentiation inhibitory signals due to agitation induced shear-stress could contribute to the poor differentiation observed with human pluripotent stem cell-microcarrier (hPSC-MC) aggregates derived from agitation cultures.

Negative effects of agitation during the pluripotent expansion stage and during cardiac differentiation have previously been reported. It has been thought that shear stress could induce expression of SMAD-7 which are known to have inhibitory effects on SMAD, components of the TGF-β signalling pathway induced by BMP4 during the initial stages of mesodermal differentiation. Thus, inhibition of BMP4 signalling in agitated cultures could be a likely reason for poor mesoderm induction and differentiation. However, given that it had been previously shown with differentiation from continuously agitated hES-3-microcarrier aggregates, it was thought that there could be a threshold effect for tolerating inhibitory signals induced by agitation shear stress, beyond which, agitated microcarrier aggregates fail to differentiate. Effects of continued passaging and/or batch-to-batch heterogeneity of the hES-3 line could also account for differences in tolerating agitation induced shear stress and variable differentiation outcomes.

Given that T-bra and KDR development were negatively affected in agitation hPSC expansion cultures, it was hypothesised that initial mesodermal differentiation conditions that could improve T-bra and KDR expression may improve the outcome of hematopoietic differentiation. Indeed, previous studies have correlated higher percentage of KDR+ cells with increased hematopoietic precursor generation. The Design of Experiment screen performed established that a transient exposure of CHIR during the first 24 hours of differentiation was a significant factor for increasing KDR+ cells on day 4 of differentiation (from hPSC-MC aggregates initially expanded under agitation condition). CHIR-99021, activates the canonical Wnt/β-catenin signalling pathway and has been shown to induce primitive streak/mesoderm development of human pluripotent stem cells (hPSCs) for cardiomyocyte and hematopoietic differentiation. T-bra, one of the direct target genes of Wnt signalling pathway was significantly up-regulated following transient exposure to CHIR in human pluripotent stem cell-microcarrier (hPSC-MC) aggregates derived from agitated cultures, but was clearly not induced when differentiated with the BMP4-based protocol. T-bra has been reported to directly interact with the downstream effector of BMP4 signalling, SMAD1 for proper mesodermal differentiation. Furthermore, in BMP4 treated cells, T-bra expression has been shown to be necessary for activation of genes such as KDR and LMO2 which are necessary for hematopoiesis. Thus, activation of Wnt/β-catenin signalling could have bypassed the inhibitory effects sustained with BMP4-mediated signalling by directly activating T-bra expression and allowing subsequent development of KDR+ mesodermal cells which underwent hematopoietic specification and eventual erythroid differentiation. As shown herein, it was possible to correlate initial generation of higher percentage of KDR+ cells with significantly improved hematopoietic precursor generation via differentiation of multiple hPSC lines.

In the data shown herein, efficient differentiation of O-neg hiPSC into mature red blood cells is shown. Differences in the efficiency of differentiation between the different O-neg hiPSC lines may be attributed to inherent genetic or epigenetic differences among the different donor samples. With the best performing line, an up to 60,000-fold expansion in cell numbers was shown within 56 days in culture. This translates to starting with $2 \times 10^7$ hematopoietic precursors to derive $1 \times 10^{12}$ red blood cells (RBCs; equivalent to 1 unit of red blood cells).

Several improvements have been considered that would be required before the method disclosed herein can be translated into a routine method for generating red blood cells (RBCs). Firstly, in order to scale-up in bioreactors, the process has to be modified so that the initial stage of hematopoietic precursor differentiation and expansion can be performed in liquid suspension culture, rather than in semi-solid blast growth medium. Secondly, the entire process of pluripotent expansion stage, mesoderm induction stage and hematopoietic expansion stage would need to be demonstrated under agitation conditions, to simulate conditions in a stirred tank bioreactor. Thirdly, methods for culture intensification have to be developed so that high cell densities in the range of $1 \times 10^8$ cells/ml can routinely be achieved. This would ensure that one unit of blood can be generated in a 10 L bioreactor, with a more practical and cost-effective media usage. Fourthly, the issue of fetal hemoglobin (HbF) expression has to be addressed as the oxygen binding affinity of fetal hemoglobin expressing red blood cells (RBCs) appear to resemble cord blood red blood cells, rather than adult red blood cells. Expression of KLF-1 and BCL11A have been proposed as means to induce hemoglobin switching from fetal to adult. Beta hemoglobin protein expression was observed in erythroblast differentiated from one of the human induced pluripotent stem cell (hiPSC) lines that had been tested (BR7), which warrants further investigation as to whether maintenance of epigenetic memory may play a role in activation of the beta hemoglobin promoter. Lastly, the low efficiency of enucleation with human induced pluripotent stem cell (hiPSC) differentiated erythroblast needs to be improved. As presently presented, it is shown that the erythroblast have the potential to enucleate given the right signals, in this case, with co-culture of primary human mesenchymal stem cells (MSCs). Moving forward, scale-up of the process requires the development of enucleation protocols with defined medium formulation.

In conclusion, through up-stream process optimization, an optimized protocol is provided herein that can allow efficient erythroid differentiation of O-neg hiPSC-MC aggregates initially expanded under continuous agitation. This serves as a method that allows further development of processes that can translate to suspension culture bioreactors for large-scale generation of universal red blood cells (RBCs).

Development of a Scalable Agitation Suspension Culture Differentiation Platform for Generating Erythroid Cells from O-Negative Human Induced Pluripotent Stem Cells It had been previously shown that six of nine human pluripotent stem cells (hPSCs) expanded on defined extracellular matrix (ECM)-coated microcarriers under agitation suspension culture can be efficiently differentiated into erythroid cells by using an optimized protocol consisting of BMP4, Activin A and CHIR for initial mesoderm induction. However, aside from expansion of hiPSC under suspension agitation condition, all the other remaining stages had been performed under static condition. Moreover, the initial expansion of hematopoietic precursors from hematopoietic fated mesodermal cells was performed in a semi-solid methylcellulose based medium, which would be challenging for volumetric scale-up of the process.

In order to address the limitations of the lack of scalability of the methylcellulose-based expansion protocol, a differentiation process was developed, as disclosed herein, that can proceed from hiPSC expansion stage all the way to erythroid expansion stage in an agitation suspension culture format, so as to allow for volumetric scale-up of the entire process, and to make these cultures amenable for scale-up to controlled bioreactors. An optimized mesoderm induction condition for microcarrier expanded hiPSCs and modified the process for hematopoietic induction conditions were combined to allow for agitation suspension culture differentiation and expansion of erythroblast.

Thus, in one example, there is disclosed a method of differentiation of pluripotent stem cells into hematopoietic precursor cells, wherein the method is carried out under suspension agitation, and wherein a GSK-3-inhibitor or a Wnt pathway activator is added during a stage of mesoderm induction. In another example, the method of differentiation of pluripotent stem cells into hematopoietic precursor cells comprises the following stages of optionally a pluripotent stem cell expansion stage; the mesoderm induction stage; a hematopoietic induction stage; an erythroblast induction stage; and an erythroblast maturation stage. In yet another example, the method of differentiation of pluripotent stem cells into hematopoietic precursor cells comprises the following stages of the mesoderm induction stage; a hematopoietic induction stage; an erythroblast induction stage; and an erythroblast maturation stage.

As used herein, the term "pluripotent stem cells" refers to a stem cell that has the potential to differentiate into any of the three germ layers: endoderm (interior stomach lining, gastrointestinal tract, the lungs), mesoderm (muscle, bone, blood, urogenital), or ectoderm (epidermal tissues and nervous system). Having said that, cell pluripotency is a continuum, ranging from the completely pluripotent cell that can form every cell of the embryo proper, for example embryonic stem cells and induced pluripotent stem cells, to the incompletely or partially pluripotent cell that can form cells of all three germ layers but that may not exhibit all the characteristics of completely pluripotent cells. Pluripotent stem cells can be cells which naturally possess pluripotency, or can be cells which have been chemically or methodically made to be pluripotent (induced pluripotency). In one example, the pluripotent stem cells are induced pluripotent stem cells. In another example, the pluripotent stem cells are human pluripotent stem cells. In yet another example, the pluripotent stem cells are not isolated using methods that involve the destruction of embryos.

In one example, the pluripotent stem cells are attached to microcarriers.

A person skilled in the art would be readily able to determine at which stage a cell is based on methods known in the art, for example, but not limited to, the use of stage specific cell surface-expressed markers, the presence or absence of specific cell types, the secretion of developmental factors and the like. For example, hematopoietic precursor cells are KDR+PDGFRα− hematopoietic precursors cells.

Thus, in another example, the mesoderm induction stage results in the induction of mesoderm formation in pluripotent stem cells from the pluripotent stem cell expansion stage, resulting in KDR$^+$PDGFRα− hematopoietic precursor cells. In another example, the hematopoietic induction stage results in an expansion of hematopoietic precursor cells from the mesoderm induction stage, resulting in CD34/

CD43/CD45 hematopoietic progenitor cells. Such an expansion can be, for example, an expansion of 10 to 100-fold. In yet another example, he erythroblast expansion stage results in an expansion of hematopoietic progenitor cells from the hematopoietic induction stage, resulting in CD235a$^+$CD71$^+$ erythroblast cells. Such an expansion can be, for example, an expansion of 50 to 1000-fold. In one example, the erythroblast maturation stage results in terminal maturation and enucleation of mature CD235a$^+$ erythroblast cells from the erythroblast expansion stage, resulting in enucleated CD235a$^+$ erythroblast cells. In a further example, the enucleated CD235a$^+$ erythroblast cells are identified by staining selected from, but not limited to, DRAQ5 (DRAQ5-ve), Hoechst 33342, SYTO16 and combinations thereof. In some examples, the staining is DRAQ5 (DRAQ5-ve).

As used herein, the pluripotent cells are typically expanded from $2\times10^5$ cells/ml to $2\times10^6$ to $3\times10^6$ cells/ml. Typically, pluripotent cell densities are kept to below $4\times10^6$ cells/ml and microcarrier-aggregate size between 250 to 700 μm in diameter. A higher cell concentration during expansion might result in build of inhibitory levels of lactate/ammonia which might cause cells to lose pluripotency. Aggregate sizes greater than 700 μm in diameter might result in nutrient limitation to cells in the inner regions of the cluster due to reduced diffusion. During start of mesoderm differentiation (when the GSK3-inhibitor is added in; for example CHIR) cells are seeded at $2\times10^5$ cells/ml to $1\times10^6$ cells/ml.

In one example, for example during the pluripotent stem cell expansion stage, pluripotent stem cells are expanded to a concentration of between $1.5\times10^5$ to $4\times10^6$ cells/ml. In another example, the pluripotent stem cells are expanded to a concentration of between $1.5\times10^5$ to $4\times10^6$ cells/ml, between $2\times10^5$ to $1\times10^6$ cells/ml, between $5\times10^5$ to $1.5\times10^6$ cells/ml, between $1.75\times10^6$ to $3\times10^6$ cells/ml between $2\times10^6$ to $3\times10^6$ cells/ml, or about $2\times10^5$ cells/ml, about $5\times10^5$ cells/ml, about $8\times10^5$ cells/ml, about $1\times10^6$ cells/ml, about $1.5\times10^6$ cells/ml, about $2.0\times10^6$ cells/ml, about $2.1\times10^6$ cells/ml, about $2.2\times10^6$ cells/ml, about $2.3\times10^6$ cells/ml, about $2.4\times10^6$ cells/ml, about $2.5\times10^6$ cells/ml, about $2.6\times10^6$ cells/ml, about $2.75\times10^6$ cells/ml, about $2.8\times10^6$ cells/ml, about $2.9\times10^6$ cells/ml, or about $3\times10^6$ cells/ml.

In another example, culturing at the pluripotent stem cell expansion stage is performed for 5 to 8 days, or for 5, 6, 7, 8 days.

In yet another example, culturing at the mesoderm induction stage is performed for 3 to 4 days.

In a further example, culturing at the hematopoietic induction stage is performed for 7 to 12 days, 7 to 9 days, 8 to 10 days, 9 to 11 days or 10 to 12 days, or for 7, 8, 9, 10, 11, or 12 days.

In yet another example, culturing at the erythroblast induction stage is performed for 10 to 18 days, 10 to 13 days, 12 to 16 days, 13 to 17 days, 14 to 18 days, or 11, 12, 13, 14, 15, 16, 17 or 18 days.

In another example, culturing at the erythroblast maturation stage is performed for 7 to 21 days, 7 to 14 days, 13 to 21 days, or 8, 9, 10, 11, 12, 13, 14, 15, 16, 17, 18, 19, 21, or 21 days.

Thus, based on the time lines disclosed herein, a method as disclosed herein can take between 46 to 50 days, 48 to 54 days, 50 to 55 days, 51 to 57 days, or 52 to 58 days to derive enucleated human induced pluripotent stem cell (hiPSC) derived erythroblasts starting from expansion of the hiPSC on microcarriers to the final enucleated. In another example, the method disclosed herein can take up to 45, 46, 47, 48, 49, 50, 51, 52, 53, 54, 55, 56, 57 or 58 days. In yet another example, the method disclosed herein can take up to a minimum of 48 days to a maximum of 56 days to derive enucleated human induced pluripotent stem cell (hiPSC) derived erythroblasts starting from expansion of the hiPSC on microcarriers to the final enucleated red blood cells.

Figure 27:
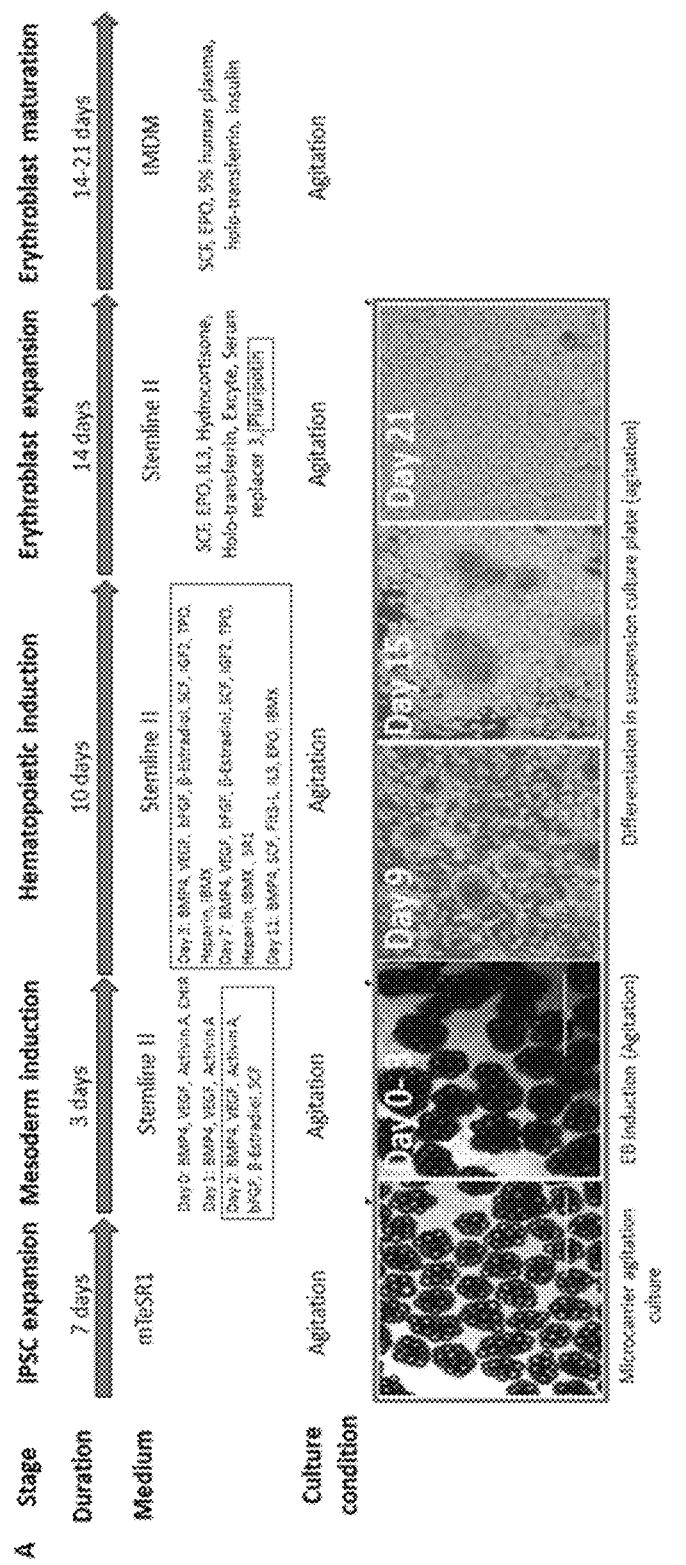
FIG. 27 Continuous agitation suspension culture differentiation of O-neg hiPSCs in 6-well ultra-low attachment (ULA) plates. (A) is a schematic of suspension culture continuous agitation differentiation process from hiPSC to erythroblast stage. Boxes demarcate the protocols from Olivier et al. Human induced pluripotent stem cells (hiPSC) were cultured on Laminin-521 coated Solohill microcarriers for 7 days before being used for differentiation in 6-well ultra-low attachment plates. Single cell derived from day 3 hPSC-MC aggregates expand and differentiate into erythroblast from days 9 to 21. (B) show data indicating the cumulative fold-expansion of total viable cell numbers was determined following differentiation of 2 different O-neg hiPSC lines (D12 and D5) and corresponding hemoglobinized cell pellets are shown. (C) is a table summarising flow cytometric characterisation of differentiated cells from day 35 of differentiation. Percentage of erythroid specific markers CD235a, CD71, CD36 and fetal/adult hemoglobin expression as well as markers for myelomonocytic cells (CD14, CD15) and hematopoietic stem cells (CD133, CXCR4) are shown together with cumulative fold-expansion on Day 35.
Figure 27:
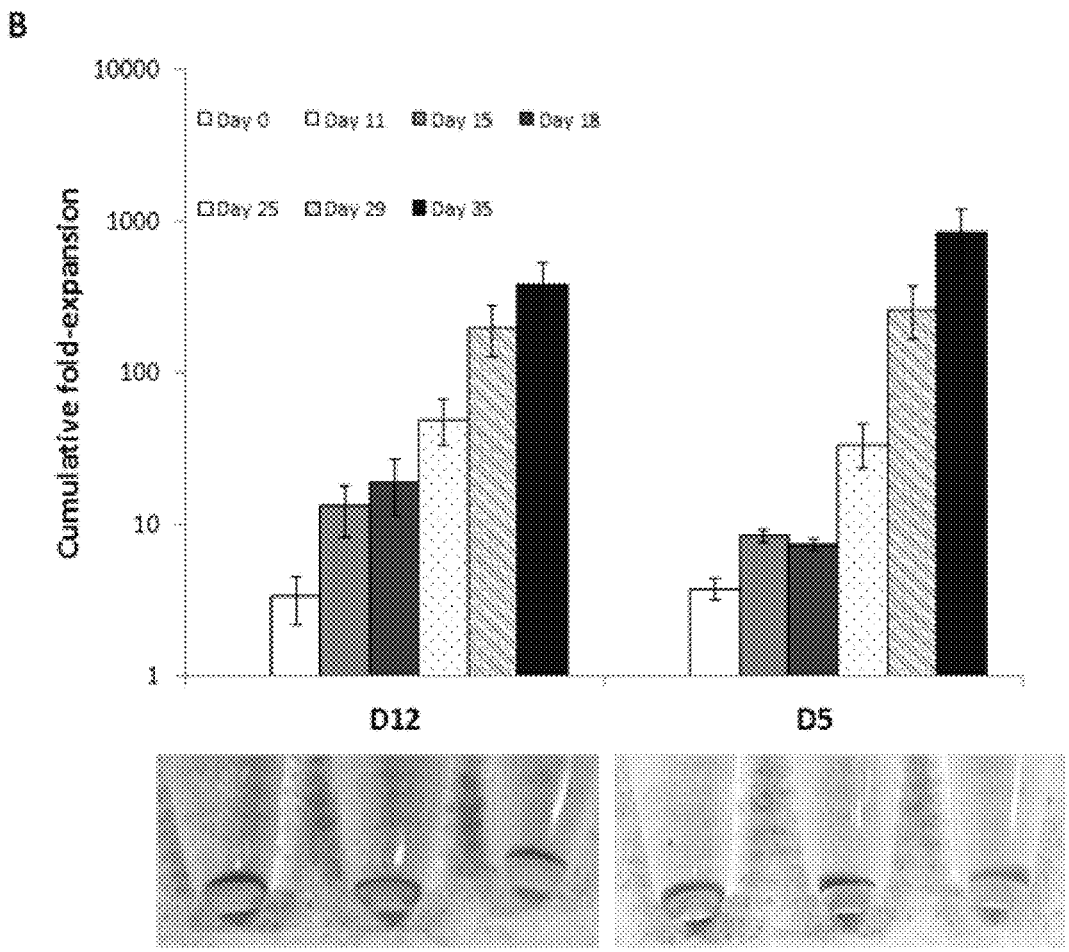

O-neg hiPSCs initially expanded on laminin-521 coated Solohill microcarriers under agitation suspension condition in 6-well ultra-low attachment (ULA) plates were induced into mesoderm stage by switching from human pluripotent stem cell expansion medium to an in-house, optimized mesoderm induction medium, in the same 6 well ultra-low attachment plates under agitation condition. After 3 days of hematopoietic-fated mesoderm induction, single cells derived from microcarrier aggregate cultures were seeded at low density in agitation suspension culture for a further 10 days using conditions as previously described. On day 14, hematopoietic cells were cultured in a previously described erythroblast expansion medium under agitation suspension condition for a further 14 days to allow for erythroblast expansion. It is shown that the entire process of O-neg human induced pluripotent stem cell expansion to mesoderm induction, hematopoietic induction and erythroblast expansion can be performed in suspension culture under agitation condition (FIG. 27).

Figure 28:
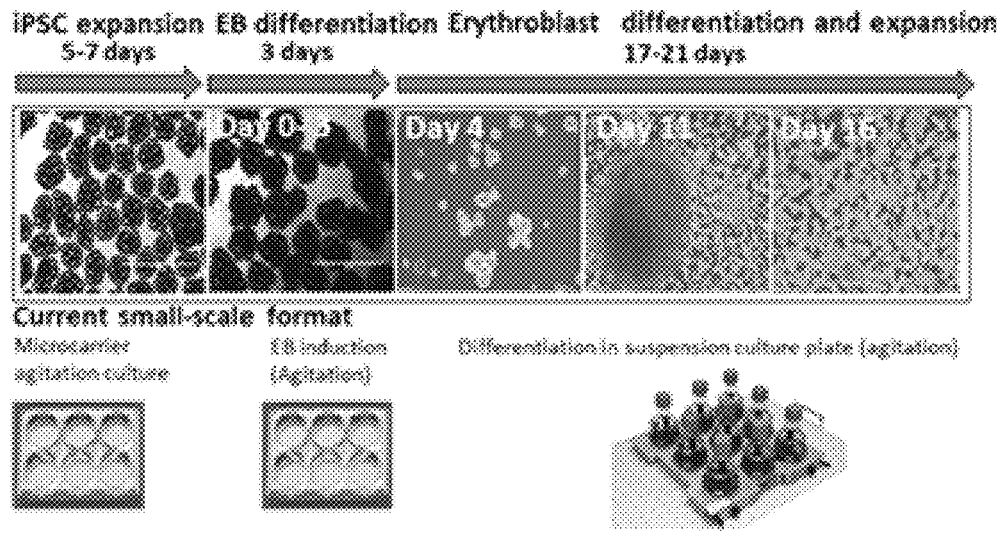
FIG. 28 shows results of continuous agitation suspension culture differentiation of 0-neg human induced pluripotent stem cells (hiPSCs) in shake-flasks. (A) is a schematic showing images of hPSC-MC aggregates expanded and differentiated in 6-well ultra-low attachment plates under continuous agitation. Single cell derived from day 3 human pluripotent stem cell-microcarrier (hPSC-MC) aggregates were expanded and differentiated into erythroblast in shake-flasks. (B) shows the results of cumulative fold-expansion of total viable cell numbers was determined following differentiation of 8 different human induced pluripotent stem cell lines (D12, D9, BR7 and X13 are O-neg human induced pluripotent stem cells). (C) shows images of pellets. All 8 different human induced pluripotent stem cell lines could differentiate into hemoglobinized erythroblasts. (D) shows line graphs representing cell density and viability, which was monitored during erythroblast expansion from days 18 to 26. For human induced pluripotent stem cell line D9, at cell density of $1\times10^7$ cells/ml (1e7 cells/nil), a drop in viability and total cell numbers was noted from day 23 to day 26. Complete media change for human induced pluripotent stem cell line X13 at day 23 and day 24 (as indicated by arrows) allowed for cell densities of greater than $1.2\times10^7$ cells/ml (1.2e7 cells/nil). (E) shows a table summarising remaining glucose levels and accumulated lactate and ammonia levels on day 23 of culture (and day 26 of culture for X13).
Figure 28:
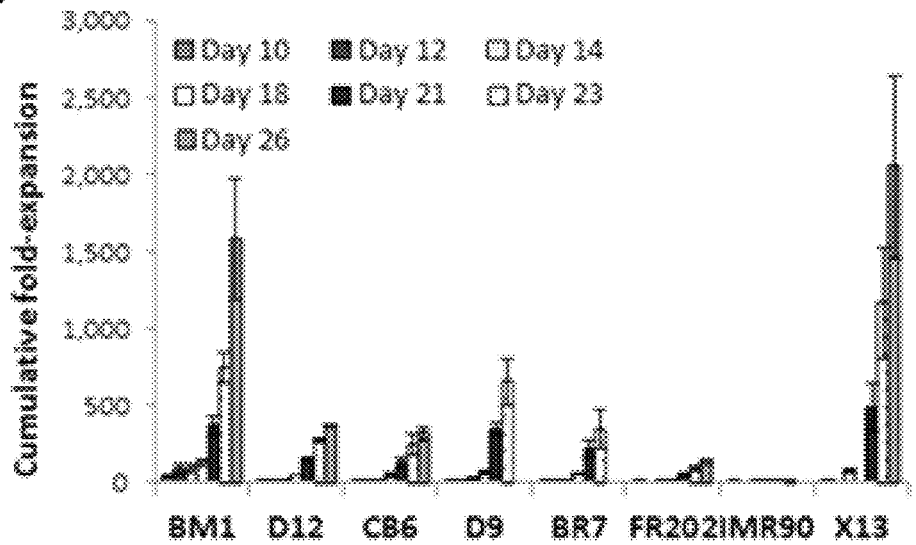
Figure 28:
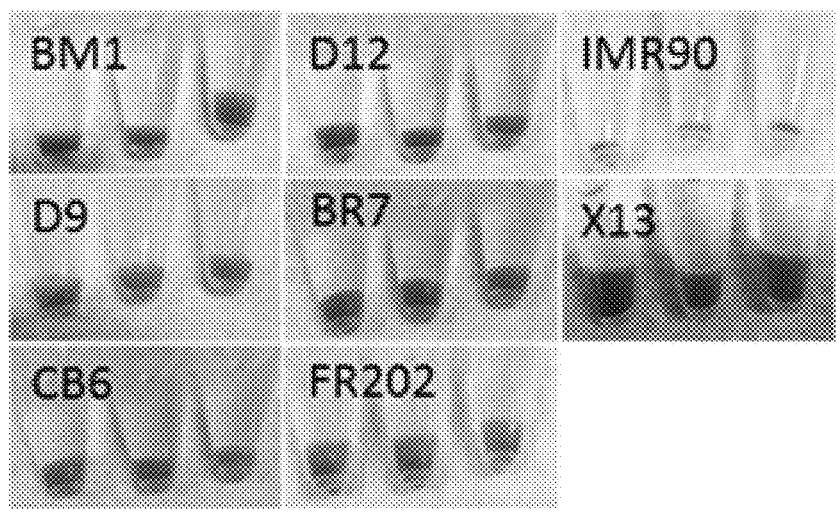
Figure 28:
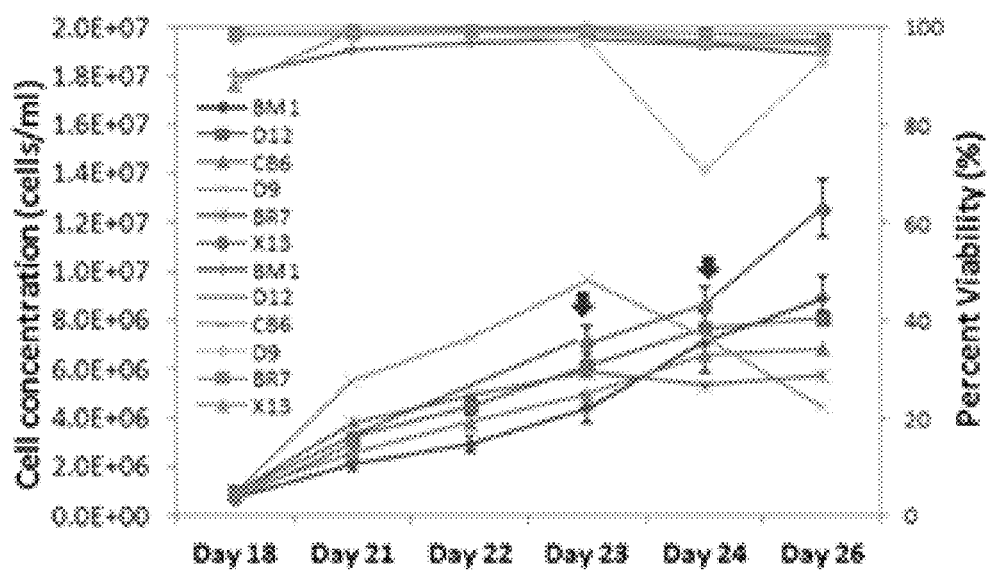

In order to demonstrate the scaling up the process, single cells derived following mesoderm induction stage were seeded in ultra-low attachment shake-flasks in 10 ml volume under continuous agitation condition (FIG. 28). Using multiple human induced pluripotent stem cell lines, the feasibility to achieve high density erythroid cell cultures by frequent media change was shown. Here, it is shown that the build-up of lactate and ammonia in culture should be kept below 2 g/L and 4 mM, in order to maintain high cell viabilities and allow for continued expansion of erythroblast. For the best differentiated line, X13, an over 1000-fold expansion from initial seeding of single cells to differentiated erythroblast was achieved. Complete media exchange to ensure the prevention of inhibitory levels of lactate and ammonia allowed attainment of cell densities of greater than $1\times10^7$ cells/ml (1e7 cells/nil), among the highest reported for in vitro red blood cell culture.

In one example, the method comprises use of a cell culture media during the mesoderm induction stage, the cell culture media comprising a bone morphogenic protein, GSK3-inhibitor, or a Wnt pathway activator, Activin A, and a vascular endothelial growth factor. In another example, the culture medium as disclosed herein is for use in agitation suspension culture.

Also disclosed herein is a cell culture media for differentiation of pluripotent stem cells into hematopoietic precursor cells, thereby generating hematopoietic precursor cells from pluripotent stem cells using microcarrier embryoid bodies (EB) or pluripotent stem cells, the cell culture media comprising a bone morphogenic protein, Activin A, and a vascular endothelial growth factor.

In yet another example, there is described a cell culture media for differentiation of pluripotent stem cells into hematopoietic precursor cells, thereby generating hematopoietic precursor cells from pluripotent stem cells using microcarrier embryoid bodies (EB), the cell culture media comprising a bone morphogenic protein, a GSK-3 kinase inhibitor, wherein the inhibitor is selected from the group consisting of CHIR99021, (2'Z,3'E)-6-Bromoindirubin-3'-oxime (Bio; CAS 667463-62-9), Kenpaullone (CAS 142273-20-9), GSK-3beta Inhibitor XII (TWS119; CAS 601514-19-6), Bio-Acetoxime (CAS 667463-85-6), CHIR-98014, SB216763 (CAS 280744-09-4), GSK-3beta Inhibitor VIII (CAS 487021-52-3) and combinations thereof, or a Wnt pathway activator, Activin A, and a vascular endothelial growth factor.

Also disclosed herein is a cell culture media for differentiation of pluripotent stem cells into hematopoietic precursor cells, thereby generating hematopoietic precursor cells from pluripotent stem cells using microcarrier embryoid bodies (EB) or pluripotent stem cells, the cell culture media comprising a bone morphogenic protein, Activin A, bFGF (basic fibroblast growth factor) or variant thereof, a hormone, a cytokine, and a vascular endothelial growth factor.

As used herein, the term "GSK-3-inhibitor" refers to a compound or a group of compounds, capable of inhibiting glycogen synthase kinase 3 (GSK-3; either fully or partially). Glycogen synthase kinase 3 is a serine/threonine protein kinase that mediates the addition of phosphate molecules onto serine and threonine amino acid residues. Phosphorylation of a protein by GSK-3 usually inhibits the activity of its downstream target. GSK-3 has been shown to be integrally tied to pathways of cell proliferation and apoptosis. For example, GSK-3 has been shown to phosphorylate beta-catenin, resulting in beta-catenin being targeted for degradation. GSK-3 is therefore a part of the canonical beta-catenin/Wnt pathway, which signals the cell to divide and proliferate. GSK-3 also participates in a number of apoptotic signalling pathways by phosphorylating transcription factors that regulate apoptosis. GSK-3 can promote apoptosis by both activating pro-apoptotic factors, such as p53, for example, and inactivating survival-promoting factors through phosphorylation.

In one example, the GSK3-inhibitor is, but is not limited to, valproic acid sodium salt, staurosporine, KT 5720 (CAS 108068-98-0), GSK-3 Inhibitor IX (CAS 667463-62-9), Ro 31-8220 (CAS 138489-18-6), SB-216763 (CAS 280744-09-4), CID 755673 (CAS 521937-07-5), Kenpaullone (CAS 142273-20-9), lithium chloride, GSK-3beta Inhibitor XII (TWS119; CAS 601514-19-6), GSK-3 Inhibitor XVI (CAS252917-06-9), 10Z-Hymenialdisine (CAS 82005-12-7), Indirubin (CAS 479-41-4), CHIR-98014 (CAS 252935-94-7), GSK-3beta Inhibitor VI (CAS 62673-69-2), Manzamine A (CAS 104196-68-1), Indirubin-3prime-monoxime (CAS 160807-49-8), GSK-3 Inhibitor X (CAS 740641-15-0), GSK-3 Inhibitor XV, SB-415286 (CAS 264218-23-7), 1-Azakenpaullone (CAS 676596-65-9), TWS 119 ditrifluoroacetate (CAS 601514-19-6), 5-Iodo-indirubin-3'-monoxime, GSK-3beta Inhibitor I (CAS 327036-89-5), 9-Cyanopaullone, Indirubin-5-sulfonic acid sodium salt, GSK-3beta inhibitor VII (CAS 99-73-0), Cdk1/5 inhibitor (CAS 40254-90-8), Hymenidin (CAS 107019-95-4), bisindolylmaleimide X hydrochloride (CAS 131848-97-0), 3F8 (CAS 159109-11-2), isogranulatimide (CAS 244148-46-7), CR8, (R)-isomer (CAS 294646-77-8) L-779,450 (CAS 303727-31-3), indirubin-3prime-monoxime-5-sulphonic acid (CAS 331467-05-1), GSK-3 Inhibitor II (CAS 478482-75-6), GSK-3beta Inhibitor VIII (CAS 487021-52-3), Aloisine A (CAS 496864-16-5), GSK-3beta Inhibitor XI (CAS 626604-39-5), GSK-3 Inhibitor IX (CAS 710323-61-8), Alsterpaullone, 2-Cyanoethyl (CAS 852529-97-0), TCS 2002 (CAS 1005201-24-0), TCS 21311 (CAS 1260181-14-3), A 1070722 (CAS 1384424-80-9), Ro-31-8220 (CAS 138489-18-6), Enzastaurin (CAS 138489-18-6), MeBIO (CAS 667463-95-8), Cdk2/9 Inhibitor (CAS 507487-89-0), Cdk1/2 Inhibitor III (CAS 443798-55-8), PHA 767491 hydrochloride (CAS 845714-00-3), AR-AO 14418-d3, Indole-3-acetamide (CAS 879-37-8), Hymenialdisine Analogue 1 (CAS 693222-51-4), CHIR-99021 (also known as 6-[[2-[[4-(2,4-Dichlorophenyl)-5-(5-methyl-1H-imidazol-2-yl)-2-pyrimidinyl]amino]ethyl] amino]-3-pyridinecarbonitrile and CT99021; CAS 252917-06-9), CHIR-98014 (CAS 556813-39-9), (2'Z,3'E)-6-Bromoindirubin-3'-oxime (Bio; CAS 667463-62-9), Bio-Acetoxime (CAS 667463-85-6), SB216763 (CAS 280744-09-4), and combinations thereof.

In another example, the GSK3-inhibitor is, but is not limited to, CHIR-99021, (2'Z,3'E)-6-Bromoindirubin-3'-oxime (Bio; CAS 667463-62-9), Kenpaullone (CAS 142273-20-9), GSK-3beta Inhibitor XII (TWS119; CAS 601514-19-6), Bio-Acetoxime (CAS 667463-85-6), CHIR-98014, SB216763 (CAS 280744-09-4), GSK-3beta Inhibitor VIII (CAS 487021-52-3), and combinations thereof. In yet another example, the GSK3-inhibitor is CHIR-99021 or a derivative thereof.

In yet another example, the GSK3-inhibitor is, but is not limited to, CHIR-99021, (2'Z,3'E)-6-Bromoindirubin-3'-oxime (Bio; CAS 667463-62-9), SB216763 (CAS 280744-09-4), CHIR-98014 (556813-39-9), GSK-3beta Inhibitor VIII (CAS 487021-52-3), Kenpaullone (CAS 142273-20-9), DRF053 (also known as 2-[[9-(1-Methylethyl)-6-[[3-(2-pyridinyl)phenyl]amino]-9H-purin-2-yl]amino]-1-butanol hydrochloride hydrate), Wnt3a and combinations thereof. In a further example, the GSK3-inhibitor is, but is not limited to, CHIR-99021, SB216763, CHIR-98014, DRF053, Wnt3a, and combinations thereof. In one example, the GSK3-inhibitor is, but is not limited to, CHIR-99021, SB216763, CHIR-98014, and combinations thereof.

In one example, the GSK3-inhibitor is present in a concentration of between 0.001 µM to 15 µM, between 1 µM to 5 µM, between 4 µM to 10 µM, between 8 µM to 14 µM, between 10 µM to 14 µM, between 0.5 µM to 2 µM, between 1.45 µM to 3.75 µM, between 3.4 µM to 5 µM, between 5.3 µM to 7.5 µM, between 7.4 µM to 8.8 µM, between 8.6 µM to 9.9 µM, between 9.8 µM to 10.8 µM, between 10.7 µM to 11.5 µM, between 11.4 µM to 12.8 µM, between 12.6 µM to 13.5 µM, between 13.4 µM to 14.5 µM, between 14.1 µM to 15 µM, about 11 µM, about 12 µM, about 13 µM about 14 µM, or about 14.5 µM.

CHIR is a factor that has been shown to improve hematopoietic mesoderm induction and precursor generation from human pluripotent stem cell-microcarrier (hPSC-MC) cultures expanded in agitation condition. The structure of CHIR-99021, as an example of compounds of this group, is shown below.

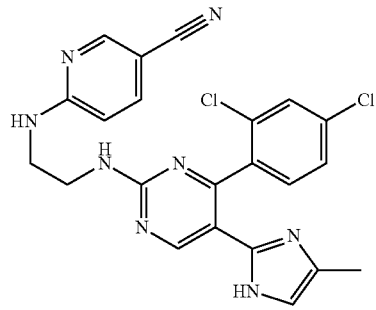 [SMILES: Cc1c[nH]c(-c2cnc(NCCNc3ccc(C#N)cn3)nc2-c2ccc(Cl)cc2Cl)n1]

As used herein, the term "derivative" or "variant" refers to is a compound that is derived from a similar compound by a chemical reaction. A derivative may also be known as a structural and/or functional analogue of the original compound.

For example, a derivative of CHIR-99021 is, but is not limited to, CHIR-98014:

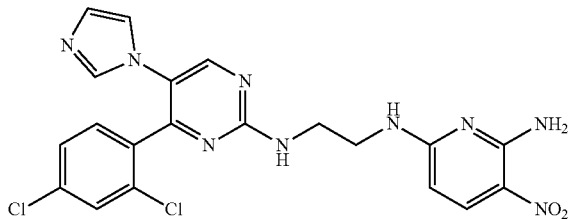 [SMILES: Nc1nc(NCCNc2ncc(-n3ccnc3)c(-c3ccc(Cl)cc3Cl)n2)ccc1[N+](=O)[O-]]

One example of a GSK3-inhibitor is, but is not limited to, CHIR.

The term "Wnt pathway activator" refers to compounds which activate the Wnt signalling pathway. The Wnt gene family consists of structurally related genes that encode secreted signalling proteins. These proteins have been implicated in for example, but not limited to, oncogenesis, adipogenesis and in several other developmental processes, including regulation of cell fate and patterning during embryogenesis. One example of such a protein is Wnt3a.

Wnt signalling was first identified for its role in carcinogenesis, rather than for its (later elucidated) role in embryonic development. The embryonic processes it controls include body axis patterning, cell fate specification, cell proliferation and cell migration. These processes are necessary for proper formation of important tissues including bone, heart and muscle. Its role in embryonic development was discovered when genetic mutations in Wnt pathway proteins produced abnormal fruit fly embryos. Wnt signalling also controls tissue regeneration in adult bone marrow, skin and intestine. It was later found that the genes responsible for these abnormalities also influenced breast cancer development in mice.

In one example, the Wnt pathway activator is present in a concentration of between 0.5 µM to 20 µM, between 1 µM to 15 µM, between 0.5 µM to 5 µM, between 4 µM to 11 µM, between 8 µM to 15 µM, between 10 µM to 16 µM, between 17 µM to 20 µM, about 1 µM, about 1.5 µM, about 2 µM, about 2.5 µM, about 3 µM, about 3.5 µM, about 4 µM, about 4.5 µM, about 5 µM, about 5.5 µM, about 6 µM, about 6.5 µM, about 7 µM, about 7.5 µM, about 7 µM, about 7.5 µM, about 8 µM, about 8.5 µM, about 9 µM, about 9.5 µM, about 10 µM, about 10.5 µM, about 11 µM, about 11.5 µM, about 12 µM, about 12.5 µM, about 13 µM, about 13.5 µM, about 14 µM, about 14.5 µM, about 15 µM, about 15.5 µM, about 16 µM, about 16.5 µM, about 17 µM, about 17.5 µM, about 18 µM, about 18.5 µM, about 19 µM, about 19.5 µM, or about 20 µM. An example of a Wnt pathway activator is, but is not limited to, IQ-1 and Wnt3a.

In yet another example, the Wnt pathway activator, for example Wnt3a, is present in a concentration of between 1 ng/ml to 150 ng/ml, between 10 ng/ml to 100 ng/ml, between 1 ng/ml to 50 ng/ml, between 45 ng/ml to 75 ng/ml, between 60 ng/ml to 110 ng/ml, between 115 ng/ml to 150 ng/ml, about 10 ng/ml, about 15 ng/ml, about 20 ng/ml, about 25 ng/ml, about 30 ng/ml, about 35 ng/ml, about 40 ng/ml, about 45 ng/ml, about 50 ng/ml, about 55 ng/ml, about 60 ng/ml, about 65 ng/ml, about 70 ng/ml, about 75 ng/ml, about 80 ng/ml, about 85 ng/ml, about 90 ng/ml, about 95 ng/ml, about 100 ng/ml, about 105 ng/ml, about 110 ng/ml, about 115 ng/ml, about 120 ng/ml, about 125 ng/ml, about 130 ng/ml, about 140 ng/ml, about 145 ng/ml, or about 150 ng/ml.

As used herein, the term "bone morphogenetic protein" (BMP) refers to a group of growth factors also known to have functions similar to cytokines and metabologens. These proteins were originally discovered by their ability to induce the formation of bone and cartilage. Today, bone morphogenetic proteins are considered to constitute a group of morphogenetic signals, orchestrating tissue architecture throughout the body. The important functioning of bone morphogenetic protein signals in physiology is emphasized by the multitude of roles for dysregulated BMP signalling in pathological processes. Cancerous disease often involves misregulation of the BMP signalling system.

Bone morphogenetic proteins interact with specific receptors on the cell surface, also known as bone morphogenetic protein receptors (BMPRs). Signal transduction through bone morphogenetic protein receptors results in mobilisation of members of the SMAD family of proteins. The signalling pathways involving BMPs, BMPRs and SMADs are important in the development of the heart, central nervous system, and cartilage, as well as post-natal bone development. Bone morphogenetic proteins also have an important role during embryonic development on the embryonic patterning and early skeletal formation. As such, disruption of BMP signalling can affect the body plan of the developing embryo. For example, BMP4 and its inhibitors noggin and chordin help regulate polarity of the embryo (that is, the so-called back to front patterning). Specifically BMP-4 and its inhibitors play a major role in neurulation and the development of the neural plate. BMP-4 signals ectoderm cells to develop into skin cells, but the secretion of inhibitors by the underlying mesoderm blocks the action of BMP-4 to allow the ectoderm to continue on its normal course of neural cell development. BMP4 is usually found in early embryonic development in the ventral marginal zone and in the eye, heart blood and otic vesicle.

In an example, the bone morphogenic protein is present in a concentration of between 5 ng/ml to 50 ng/ml, between 10 ng/ml to 20 g/ml, between 18 ng/ml to 27 ng/ml, between 26 ng/ml to 36 g/ml, between 35 ng/ml to 45 g/ml, about 9 ng/ml, about 10 ng/ml, about 11 ng/ml, about 19 ng/ml, about 20 ng/ml, about 21 ng/ml, about 28 ng/ml, about 29 ng/ml, about 30 ng/ml, about 48 ng/ml, about 50 ng/ml, or about 51 ng/ml. One example of a bone morphogenic protein is, but is not limited to, BMP4. Thus, in another example, BMP4 is present in a concentration of between 5 ng/ml to 50 ng/ml, between 10 ng/ml to 20 g/ml, between 18 ng/ml to 27 ng/ml, between 26 ng/ml to 36 ng/ml, between 35 ng/ml to 45 g/ml, about 9 ng/ml, about 10 ng/ml, about 11 ng/ml, about 19 ng/ml, about 20 ng/ml, about 21 ng/ml, about 28 ng/ml, about 29 ng/ml, about 30 ng/ml, about 48 ng/ml, about 50 ng/ml, or about 51 ng/ml.

As used herein, the term "vascular endothelial growth factor (VEGF)" refers to a signal protein produced by cells that stimulates the formation of blood vessels. In other words, VEGF is a sub-family of growth factors, the platelet-derived growth factor family of cystine-knot growth factors. These growth factors are important signalling proteins involved in both vasculogenesis (which is the de novo formation of the embryonic circulatory system) and angiogenesis (which is the growth of blood vessels from pre-existing vasculature).

In one example, the vascular endothelial growth factor is present in a concentration of between 35 ng/ml to 55 ng/ml, between 37 ng/ml to 47 ng/ml, between 44 ng/ml to 51 ng/ml, between 50.5 ng/ml to 52 ng/ml, between 51.9 ng/ml to 53 ng/ml, between 53.5 ng/ml to 54 ng/ml, about 40 ng/ml, about 45 ng/ml, about 48 ng/ml, about 49 ng/ml, about 50 ng/ml or about 51 ng/ml.

One example of a vascular endothelial growth factor is, but is not limited to, $VEGF_{165}$. In such an example, $VEGF_{165}$ is present in a concentration of between 20 ng/ml to 35 ng/ml, between 32 to 38 ng/ml, between 35 ng/ml to 55 ng/ml, between 37 ng/ml to 47 ng/ml, between 44 ng/ml to 51 ng/ml, between 48 ng/ml to 51 ng/ml, between 50.5 ng/ml to 52 ng/ml, between 51.9 ng/ml to 53 ng/ml, between 53.5 ng/ml to 54 ng/ml, about 29 ng/ml, about 30 ng/ml, about 35 ng/ml, about 38 ng/ml, about 40 ng/ml, about 45 ng/ml, about 48 ng/ml, about 49 ng/ml, about 50 ng/ml or about 51 ng/ml.

As used herein, the term "Activin A" refers to a dimeric protein complex, which enhances FSH biosynthesis and secretion, and participates in the regulation of the menstrual cycle. Many other functions have been found to be exerted by activin, including roles in cell proliferation, differentiation, apoptosis, metabolism, homeostasis, immune response, wound repair, and endocrine function. The types of Activin which have been identified are Activin A, Activin B, and Activin AB, whereby Activin A comprises two beta-A ($\beta_A$) subunits. As with other members of the superfamily, Activins interact with two types of cell surface transmembrane receptors (Types I and II), which have intrinsic serine/threonine kinase activities in their cytoplasmic domains, which are Activin type 1 receptors (for example, ACVR1, ACVR1B, ACVR1C) and Activin type 2 receptors (for example, ACVR2A, and ACVR2B). Activin binds to the Type II receptor and initiates a cascade reaction that leads to the recruitment, phosphorylation, and activation of Type I Activin receptor. This then interacts with and then phosphorylates SMAD2 and SMAD3, two of the cytoplasmic SMAD proteins. Smad3 then translocates to the nucleus and interacts with SMAD4 through multimerisation, resulting in their modulation as transcription factor complexes responsible for the expression of a large variety of genes.

In one example, Activin A is present in a concentration of between 0.001 ng/ml to 50 ng/ml, between 0.5 ng/ml to 10 ng/ml, between 8 ng/ml to 18 ng/ml, between 17 ng/ml to 27 ng/ml, between 26 ng/ml to 36 ng/ml, between 35 ng/ml to 46 ng/ml, between 44 ng/ml to 49 ng/ml, about 38 ng/ml, about 39 ng/ml, about 40 ng/ml, about 41 ng/ml, about 42 ng/ml, or about 43 ng/ml. In another example, Activin A is present in a concentration of between 0.1 ng/ml to 10 ng/ml, between 0.5 ng/ml to 8 ng/ml, between 2.5 ng/ml to 6 ng/ml, between 3 ng/ml to 7 ng/ml, between 4 ng/ml to 8 ng/ml, between 3 ng/ml to 9 ng/ml, about 3 ng/ml, about 4 ng/ml, about 4.25 ng/ml, about 4.5 ng/ml, about 4.75 ng/ml, about 5 ng/ml, about 5.25 ng/ml or about 5.5 ng/ml.

As used herein, the term "hormone" refers to any member of a class of signalling molecules produced by glands in multicellular organisms that are transported by the circulatory system to target distant organs to regulate physiology and behaviour. Hormones comprise compounds with diverse chemical structures, which can be mainly categorised into three classes: eicosanoids, steroids, and amino acid/protein derivatives (which include, but are not limited to, amines, peptides, and proteins).

In one example, the hormone is present in a concentration of between 0.05 ng/ml to 2 ng/ml, between 0.1 ng/ml to 1.5 ng/ml, between 0.25 ng/ml to 1 ng/ml, between 0.2 ng/ml to 0.8 ng/ml, between 0.4 ng/ml to 0.6 ng/ml, between 0.3 ng/ml to 1 ng/ml, about 0.38 ng/ml, about 0.39 ng/ml, about 0.40 ng/ml, about 0.41 ng/ml, about 0.42 ng/ml about 0.43 ng/ml about 0.44 ng/ml about 0.45 ng/ml about 0.46 ng/ml about 0.47 ng/ml about 0.48 ng/ml, about 0.49 ng/ml about 0.50 ng/ml, or about 0.51 ng/ml.

In another example, the hormone is beta-estradiol. Thus, in such an example, beta-estradiol is present in a concentration of between 0.05 ng/ml to 2 ng/ml, between 0.1 ng/ml to 1.5 ng/ml, between 0.25 ng/ml to 1 ng/ml, between 0.2 ng/ml to 0.8 ng/ml, between 0.4 ng/ml to 0.6 g/ml, between 0.3 ng/ml to 1 ng/ml, about 0.38 ng/ml, about 0.39 ng/ml, about 0.40 ng/ml, about 0.41 ng/ml, about 0.42 ng/ml about 0.43 ng/ml about 0.44 ng/ml about 0.45 ng/ml about 0.46 ng/ml about 0.47 ng/ml about 0.48 ng/ml, about 0.49 ng/ml about 0.50 ng/ml, or about 0.51 ng/ml.

As used herein, the term "basic fibroblast growth factor" refers to a growth factor and signalling protein encoded by the FGF2 gene. Basic fibroblast growth factor (bFGF, also known as FGF2) is known to possess broad mitogenic and cell survival activities, and is involved in a variety of biological processes, including embryonic development, cell growth, morphogenesis, tissue repair, tumour growth and invasion. Basic fibroblast growth factor is also known as a component of human embryonic stem cell culture medium; it is one of the growth factors deemed necessary for the cells to remain in an undifferentiated state. It has been demonstrated to induce gremlin expression, which in turn is known to inhibit the induction of differentiation by bone morphogenetic proteins. Basic fibroblast growth factor, in conjunction with, for example, BMP4, have been shown to promote differentiation of stem cells to mesodermal lineages.

In one example, basic fibroblast growth factor (bFGF) or variant thereof is present in a concentration of between 2 ng/ml to 15 ng/ml, between 5 ng/ml to 14 g/ml, between 8 ng/ml to 11 ng/ml, between 6 ng/ml to 10 g/ml, about 5 ng/ml, about 6 ng/ml, about 7 ng/ml, about 8 ng/ml, about 9 ng/ml, about 9.5 ng/ml, about 10 ng/ml, about 10.25 ng/ml, about 10.5 ng/ml, about 11 ng/ml, about 12 ng/ml, or about 13 ng/ml. In another example, basic fibroblast growth factor (bFGF) or variant thereof is a heat-stable chimeric variant of bFGF or a stable chimeric fibroblast growth factor (FGF).

As used herein, the term "cytokine" refers to a broad and loose category of small proteins (~5-20 kDa) important in cell signalling. They are released by cells and affect the behaviour of other cells, and sometimes the releasing cell itself. Cytokines include chemokines, interferons, interleukins, lymphokines, tumour necrosis factor but generally not hormones or growth factors. Cytokines are produced by broad range of cells, including immune cells like macrophages, B-lymphocytes, T-lymphocytes and mast cells, as well as endothelial cells, fibroblasts, and various stromal cells. A given cytokine may be produced by more than one type of cell. Cytokines modulate the balance between humoral and cell-based immune responses, and also regulate the maturation, growth, and responsiveness of particular cell populations. Some cytokines enhance or inhibit the action of other cytokines in complex ways and are different from hormones, which are also important cell signalling molecules, in that hormones circulate in much lower concentrations and hormones tend to be made by specific kinds of cells.

In one example, the cytokine is present in a concentration of between 5 ng/ml to 50 ng/ml, between 10 ng/ml to 20 g/ml, between 18 ng/ml to 27 ng/ml, between 26 ng/ml to 36 g/ml, between 35 ng/ml to 45 g/ml, about 9 ng/ml, about 10 ng/ml, about 11 ng/ml, about 19 ng/ml, about 20 ng/ml, about 21 ng/ml, about 28 ng/ml, about 29 ng/ml, about 30 ng/ml, about 48 ng/ml, about 50 ng/ml, or about 51 ng/ml.

In another example, the cytokine is stem cell factor (SCF). In such an example, the stem cell factor (SCF) is present in a concentration of between 5 ng/ml to 50 ng/ml, between 10 ng/ml to 20 g/ml, between 18 ng/ml to 27 ng/ml, between 26 ng/ml to 36 g/ml, between 35 ng/ml to 45 g/ml, about 9 ng/ml, about 10 ng/ml, about 11 ng/ml, about 19 ng/ml, about 20 ng/ml, about 21 ng/ml, about 28 ng/ml, about 29 ng/ml, about 30 ng/ml, about 48 ng/ml, about 50 ng/ml, or about 51 ng/ml.

In a further example, the cell culture media comprises BMP4, Activin A, CHIR99021 and $VEGF_{165}$. In another example, BMP4 is present in a concentration of between 26 to 36 ng/ml, Activin A is present in a concentration of between 35 to 46 ng/ml, CHIR-99021 is present in a concentration of between 8 μM to 14 μM, and $VEGF_{165}$ is present in a concentration of between 48 ng/ml to 51 ng/ml. In yet another example, BMP4 is present in a concentration of about 30 ng/ml, Activin A is present in a concentration of about 40 ng/ml, CHIR99021 is present in a concentration of about 12 μM, and $VEGF_{165}$ is present in a concentration of about 50 ng/ml.

In one example, the method as disclosed herein requires the use of a cell culture medium as disclosed herein, the cell culture media comprises BMP4, Activin A, CHIR99021 and $VEGF_{165}$. In one example, BMP4 is present in a concentration of between 26 to 36 ng/ml, Activin A is present in a concentration of between 35 to 46 ng/ml, CHIR-99021 is present in a concentration of between 8 μM to 14 μM, and $VEGF_{165}$ is present in a concentration of between 48 ng/ml to 51 ng/ml.

In a further example, the cell culture media comprises BMP4, Activin A, and $VEGF_{165}$. In such an example, BMP4 is present in a concentration of between 26 ng/ml to 36 ng/ml, Activin A is present in a concentration of between 35 to 46 ng/ml, and $VEGF_{165}$ is present in a concentration of between 48 ng/ml to 51 ng/ml. In another example, BMP4 is present in a concentration of about 30 ng/ml, Activin A is present in a concentration of about 40 ng/ml, and $VEGF_{165}$ is present in a concentration of about 50 ng/ml.

In another example, the cell culture media comprises BMP4, Activin A, bFGF, beta-estradiol, stem cell factor (SCF) and $VEGF_{165}$. In one example, BMP4 is present in a concentration of between 18 ng/ml to 27 ng/ml, Activin A is present in a concentration of between 3 ng/ml to 7 ng/ml, the bFGF is present in a concentration of between 5 ng/ml to 14 g/ml, the beta-estradiol is present in a concentration of between 0.2 ng/ml to 0.8 ng/ml, the SCF is present in a concentration of between 26 ng/ml to 36 g/ml, and $VEGF_{165}$ is present in a concentration of between 32 to 38 ng/ml. In another such an example, BMP4 is present in a concentration of about 20 ng/ml, Activin A is present in a concentration of about 5 ng/ml, the bFGF is present in a concentration of about 10 ng/ml, the beta-estradiol is present in a concentration of about 0.4 ng/ml, the stem cell factor (SCF) is present in a concentration of about 20 ng/ml, and $VEGF_{165}$ is present in a concentration of about 30 ng/ml.

Thus, also disclosed herein is a method for differentiation of pluripotent stem cells into hematopoietic precursor cells, wherein the method is carried out under suspension agitation, the method comprising a. optionally providing pluripotent stem cells; b. exposing the cells of step a. to the cell culture medium as described herein for 24 hours (day 0 to day 1), thereby resulting in T-Brachyury (T-Bra; primitive streak/early mesoderm marker) positive cells; c. exposing the cells of step b. to the cell culture medium as described herein for 24 hours (day 1 to day 2); d. exposing the micro-carrier attached cells of step c. to the cell culture medium as described herein for 48 hours (day 2 to day 4), whereby steps b. to d. induce mesoderm induction; e. removing the cell culture medium, and isolating the resulting $KDR^+PDGFR\alpha$-hematopoietic precursor cells of step d.

In another example, the method for differentiation of pluripotent stem cells into hematopoietic precursor cells, wherein the method is carried out under suspension agitation, the method comprises a. exposing pluripotent stem cells to the cell culture medium as defined herein for 24 hours (day 0 to day 1), thereby resulting in T-Brachyury (T-Bra; primitive streak/early mesoderm marker) positive cells; b. exposing the cells of step a. to the cell culture medium disclosed herein for 24 hours (day 1 to day 2); c. exposing the micro-carrier attached cells of step b. to the cell culture medium as disclosed herein for 48 hours (day 2 to day 4), whereby steps a. to b. induce mesoderm induction; d. removing the cell culture medium, and isolating the resulting KDR+PDGFRα-hematopoietic precursor cells of step c.

In another example, there is disclosed a method for differentiation of pluripotent stem cells into hematopoietic precursor cells, wherein the method is carried out under suspension agitation, the method comprising a. optionally providing pluripotent stem cells; inducing mesoderm induction in the pluripotent stem cells isolated from step a. according to the method disclosed herein, thereby resulting in $KDR^+PDGFR\alpha-$ hematopoietic precursor cells; inducing hematopoietic induction in the cells isolated from step b, thereby resulting in CD34/CD43/CD45 hematopoietic progenitor cells; inducing erythroblast expansion in the cells isolated from step c. as disclosed herein, thereby resulting in CD235a+CD71+ erythroblast cells; inducing erythroblast maturation in the cells isolated from step d. as disclosed herein, thereby resulting in CD235a+ DRAQ5-ve enucleated erythroblast cells; removing the cell culture medium, and isolating the resulting CD235a+ DRAQ5-ve enucleated erythroblast cells of step e.

In yet another example, there is disclosed a method for differentiation of pluripotent stem cells into hematopoietic precursor cells, wherein the method is carried out under suspension agitation, the method comprising a. inducing mesoderm induction in pluripotent stem cells isolated from a cell culture subjected to suspension agitation thereby resulting in KDR+PDGFRα− hematopoietic precursor cells; b. inducing hematopoietic induction in the cells isolated from step a, thereby resulting in CD34/CD43/CD45 hematopoietic progenitor cells; c. inducing erythroblast expansion in the cells isolated from step b, thereby resulting in CD235a+CD71+ erythroblast cells; d. inducing erythroblast maturation in the cells isolated from step c, thereby resulting in CD235a+ DRAQ5-ve enucleated erythroblast cells; e. removing the cell culture medium, and isolating the resulting CD235a+ DRAQ5-ve enucleated erythroblast cells of step d.

Figure 29:
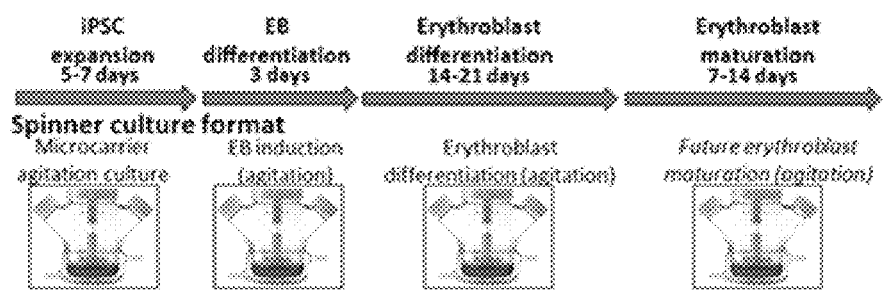
FIG. 29 shows the results of continuous agitation suspension culture differentiation of a single O-neg hiPSC line (X13) in spinner flasks. (A) is a schematic showing expansion and differentiation of hiPSC line in spinner flasks under continuous agitation. (B) shows result of flow cytometric characterisation of pluripotent markers Oct-4, Nanog, Tra1-60 and SSEA4 after 7 days of expansion in spinner flasks and expression of mesoderm markers T-Bra and KDR on day 1 and day 3 of mesoderm differentiation. (C) show column graphs depicting results of flow cytometric characterisation of CD34 and CD43 markers on days 7 to 16 during hematopoietic induction stage. (D) is a line graph showing the cumulative fold-expansion of total viable cell numbers during pluripotent expansion, mesoderm induction, hematopoietic induction and erythroid expansion. (E) is an image of hemoglobinized red cell pellets in 15 ml falcon tubes on day 27 of differentiation. (F) is a table summarising maximal cell concentration, total cells derived, media usage, lactate and ammonia production and glucose consumption of day 27 of differentiation. (G) is an image showin Giemsa staining of differentiated cells from day 27 of differentiation. Arrows indicate spontaneously enucleated red blood cells.
Figure 29:
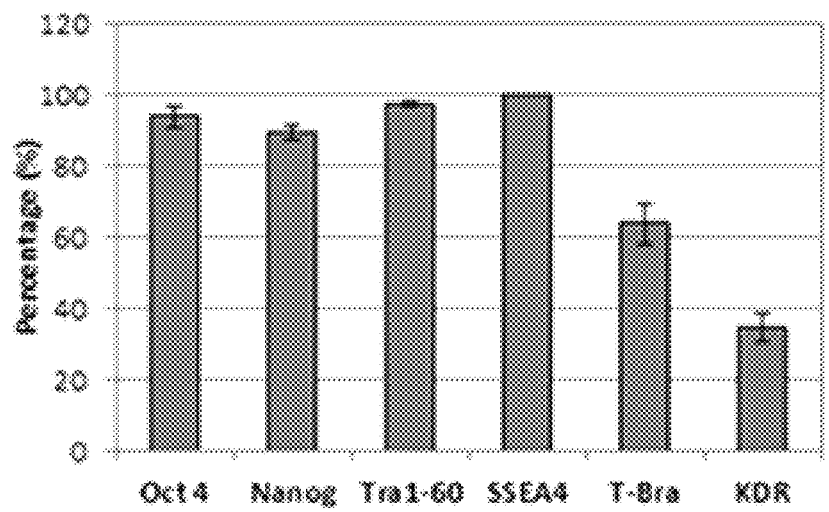
Figure 29:
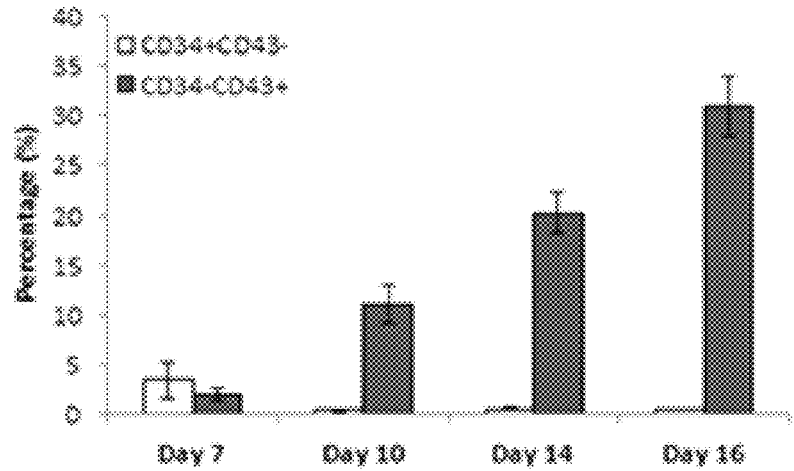
Figure 29:
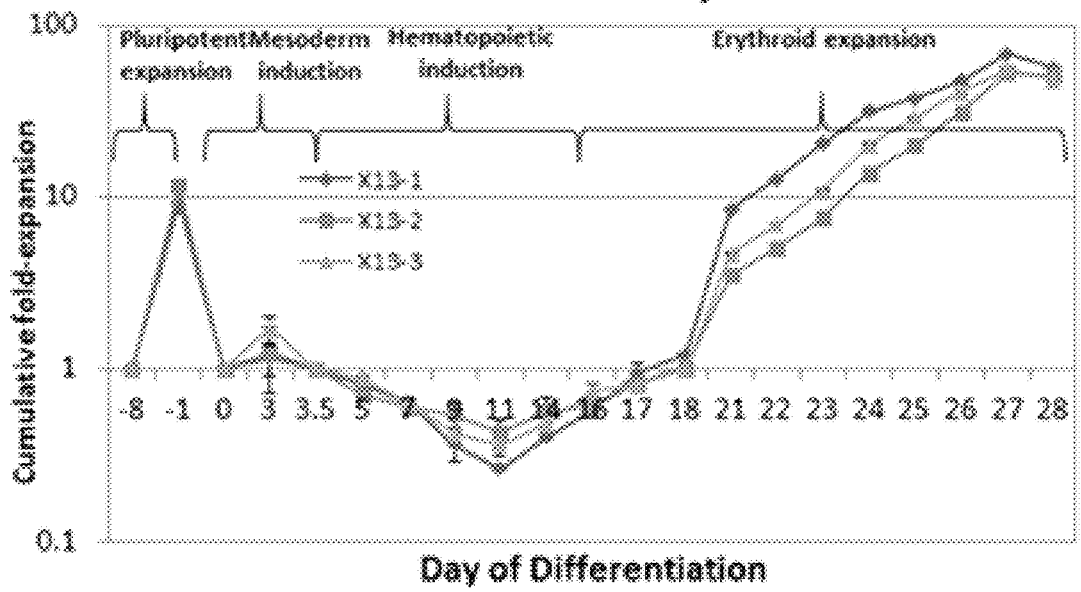
Figure 29:
Figure 29:
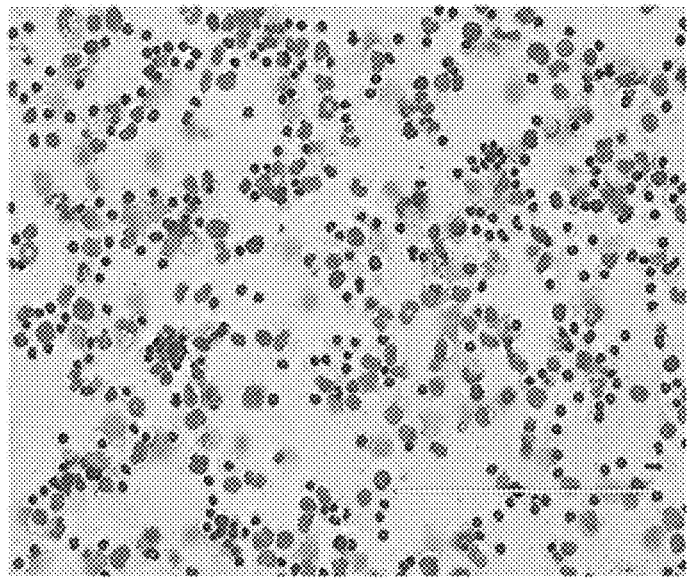
Figure 30:
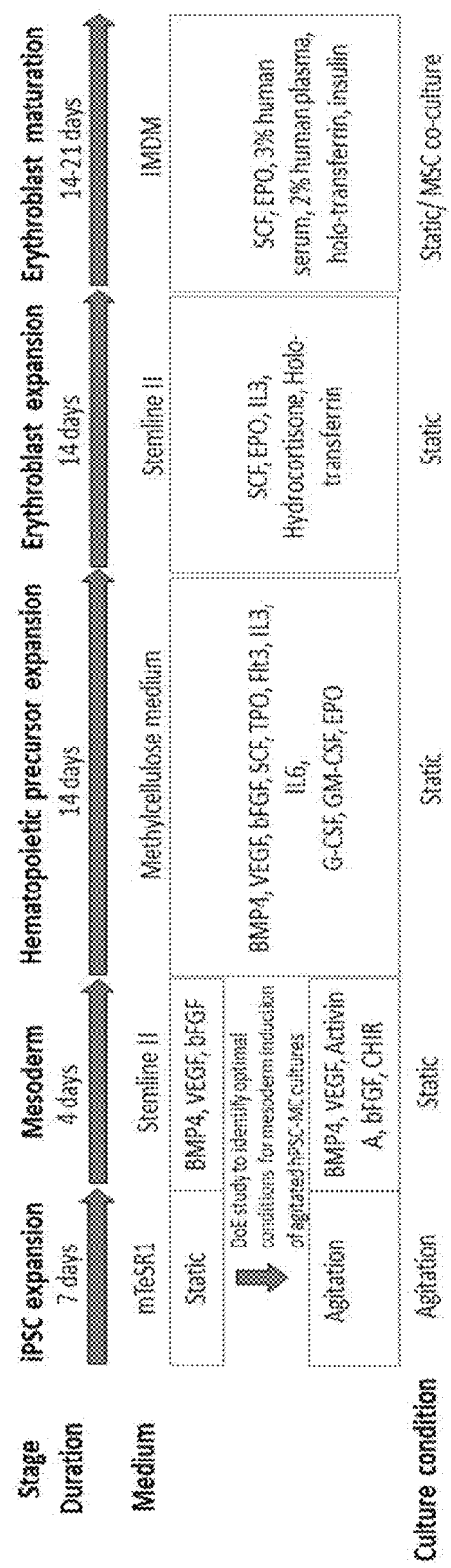
FIG. 30 shows a schematic timeline representing one embodiment of the method disclosed herein. Design of Experiment (DoE) study was performed to identify conditions for optimal mesoderm induction of agitated human pluripotent stem cell-microcarrier (hPSC-MC) cultures. For mesoderm induction, static cultures were differentiated using BMP4, VEGF and bFGF whereas agitated cultures were differentiated with BMP4, VEGFA, bFGF±Activin A, CHIR99021 during the mesoderm stages. Hematopoietic precursor expansion, erythroblast expansion and maturation were all performed under static condition with medium as detailed in for each section in the figure.
Figure 31:
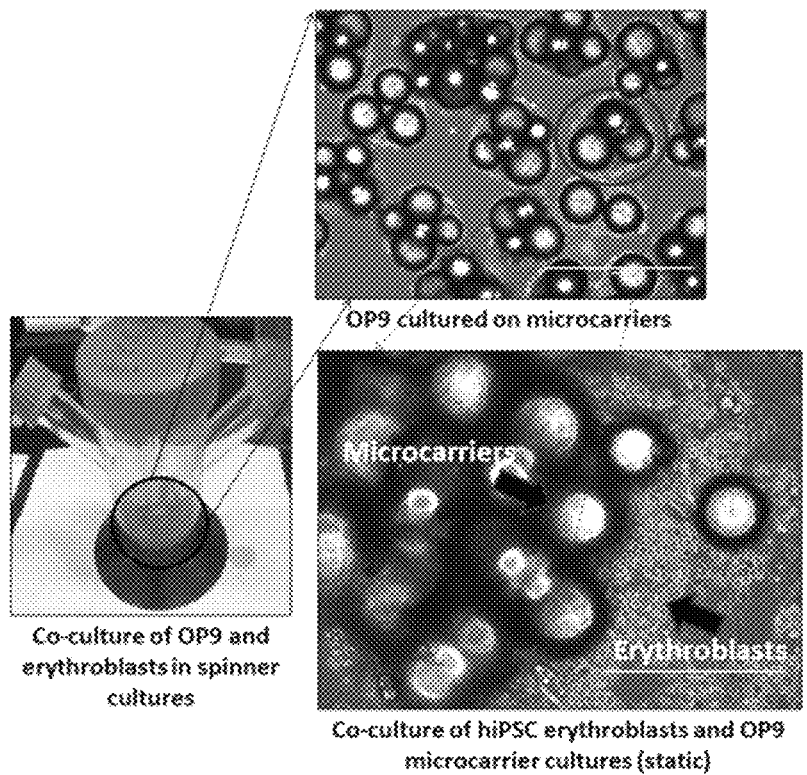
FIG. 31 shows a schematic of suspension agitation co-culture of erythroblasts and OP9 cells on microcarriers in spinner flasks.
Figure 32:
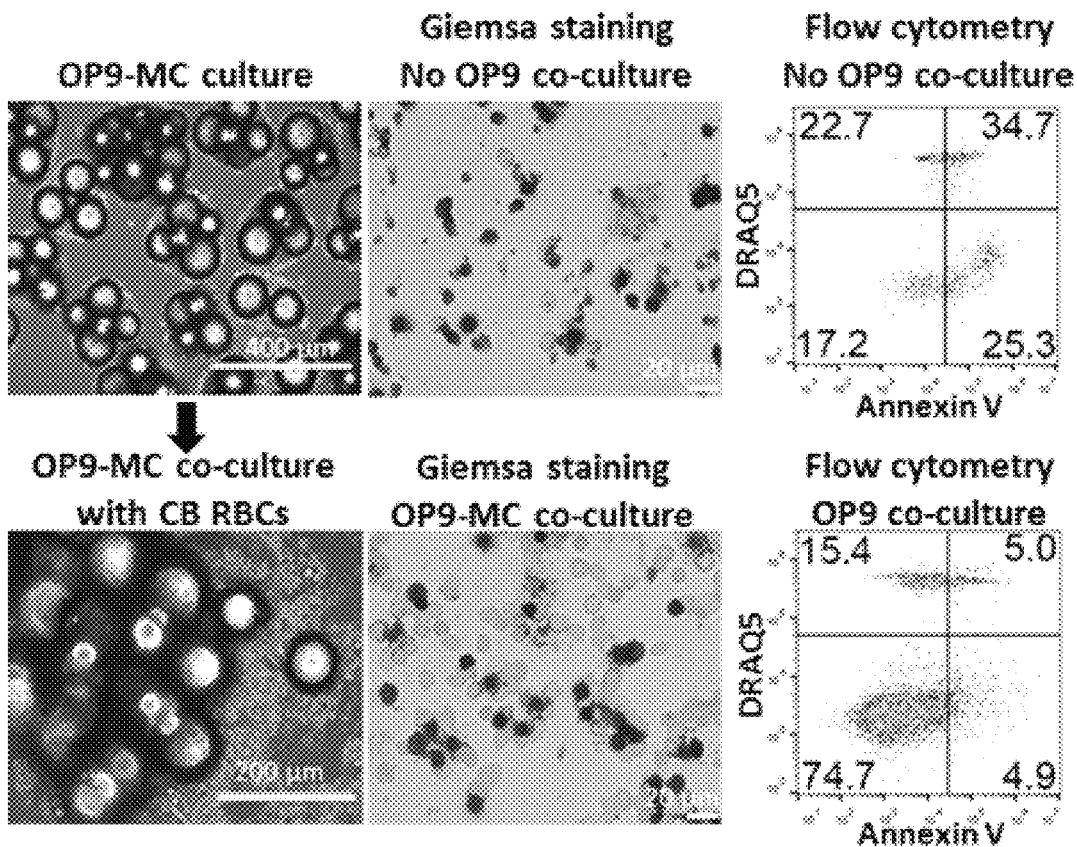
FIG. 32 shows the results of the evaluation of cord blood (CB) erythroblasts enucleation. Top-left: Low magnification bright-field images of OP9-microcarrier (MC) aggregates. Top-center: Giemsa staining of cord blood erythroblasts matured for 3 weeks without any co-culture. Top-right: Flow cytometry evaluation of cord blood erythroblasts (no OP9 co-culture) with Annexin V and DRAQ5 shows significant apoptotic cells (annexin V+). Bottom left: Co-culture of OP9-microcarrier aggregates with cord blood erythroblasts under static condition. Bottom-center: Giemsa staining of cord blood erythroblasts after 3 weeks of co-culture with OP9-microcarrier aggregates. Bottom-right: Flow cytometry evaluation of cord blood erythroblasts (with OP9-microcarrier co-culture) with Annexin V and DRAQ5 shows significant non-apoptotic enucleated cells (Annexin $V^-$ DRAQ5$^-$).
Figure 33:
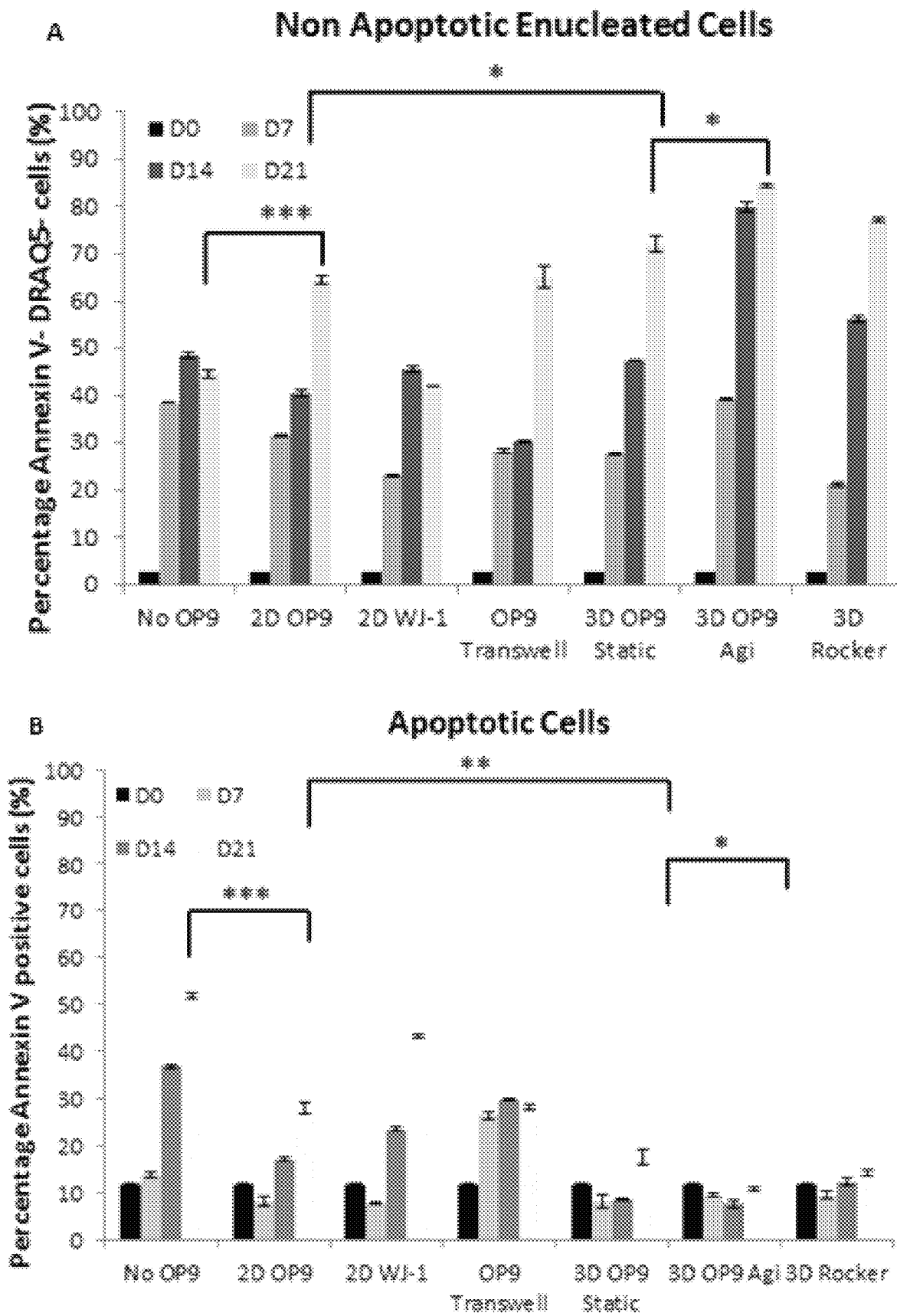
FIG. 33 shows column graphs depicting the optimization of cord blood (CB) erythroblasts enucleation under different conditions. Cord blood erythroblasts were terminally matured for 3 weeks under the following conditions: No OP9 co-culture, 2D (monolayer) OP9 co-culture, 2D Warton's Jelly derived human MSCs (WJ1) co-culture, OP9 monolayer co-culture in 0.4 µm transwell plates, 3D OP9 (0P9-MC aggregates) co-culture under static condition, 3D OP9 co-culture under agitation condition (75 rpm) and 3D OP9 co-culture in rocking platform (50 rpm). (A) shows a column graph depicting the percentage of Annexin V negative DRAQ5− (non-apoptotic enucleated) red blood cells.

In order to have a platform similar to stirred tank bioreactors, the entire expansion and differentiation of human induced pluripotent stem cells was performed in 125 ml spinner flasks (FIG. 29). Human induced pluripotent stem cell-microcarrier (HiPSCs-MC) cultures were expanded in spinner flasks under continuous agitation for 7 days in mTeSR1 medium. hiPSC-MC aggregates were differentiated into hematopoietic fated mesoderm by medium exchange in the same spinner flasks for a further 3 days. Single cells derived from human induced pluripotent stem cell-microcarrier (HiPSCs-MC) aggregates were next seeded back into the same spinner and subjected to 10 days of hematopoietic induction under agitation condition with periodic media changes. Erythroblast expansion under continuous agitation was achieved by changing to erythroblast expansion medium and culturing for a further 14 days with periodic media changes. By day 30, it was possible to achieve a 1000-fold expansion in cell numbers (data not shown). In a separate experiment, it was shown that it is possible to achieve high cell density in the spinner flasks by complete media change while monitoring and keeping lactate and ammonia levels below their inhibitory levels. It was shown that in 50 ml culture volumes, a very high cell density of $1.7 \times 10^7$ cells/ml (1.7e7 cells/nil) and total cell numbers of $8.5 \times 10^8$ cells (8.5e8 cells) can be achieved. By day 30, differentiated cells were >73% CD235a erythroid cells and showed mainly foetal hemoglobin (HbF; >85%) expression with some level of detectable hemoglobin A (HbA; 16%). Following maturation in the same spinner flasks under agitation condition, 5% to 10% of enucleated red blood cells could be observed. The oxygen binding profiles of differentiated red blood cells were left-shifted compared to adult red blood cells, indicating higher affinity to oxygen consistent with expression of high levels of foetal hemoglobin (HbF).

In one example, the method is performed in a cell culture vessel selected from the group consisting of multi-welled ultra-low attachment cell culture vessels (for example, 6-well plates), roller bottles, bioreactors such as stirred-tank bioreactors, wave bioreactors, shake flasks, and spinner flasks.

Also disclosed herein is a kit comprising micro-carriers and one or more of the cell culture media as disclosed herein. The components as disclosed herein can be provided in any storage-stable formulation or state. For example, the cell culture media are provided as concentrated solutions, along with an appropriate basal medium for dilution. In another example, the concentrated solutions are 20×, 50× or 100× concentrated solutions. In yet another example, the cell culture media are provided as frozen (ready-to-use) solutions. Any components of the cell culture media can also be provided separately from the basal media. Components of the cell culture media may also be provided as lyophilised substances.

Improved Enucleation Efficiency of Cord Blood and hiPSC Derived Erythroblasts in a Scalable Agitation Suspension Culture Platform This section describes a method for deriving high percentage of non-apoptotic enucleated red blood cells from human induced pluripotent stem cell (hiPSC) differentiated erythroblasts and cord blood-derived (CB) erythroblasts. The enucleation efficiency of cord blood-derived erythroblasts (<40% enucleated red blood cells) and hiPSC erythroblasts (<10% enucleated red blood cells) is generally very low when performed using conventional approaches described in the literature, that is the culture of erythroblasts in medium containing 10-15% of human serum/plasma (in addition to EPO, insulin, holo-transferrin). A method has been tested, whereby cord blood-derived/hiPSC erythroblasts are co-cultured with an OP9 murine stromal cell-line (ATCC:CR-2749) cultured on microcarriers under continuous agitation. It is shown that in such a suspension agitation co-culture system, the percentage of non-apoptotic (Annexin V negative) enucleated erythroblasts (DRAQ5 negative) was increased from 6.3±0.3% (conventional method) to 59.3±1.5% for hiPSC erythroblasts and 44.6±0.8% (conventional method) to 84.5±0.5% for cord blood-derived differentiated erythroblasts. When cells were terminally matured as in the conventional approach, a very high percentage of apoptotic cells were detected. Co-culture of OP9 was found to significantly reduce the proportion of apoptotic cells. Without being bound by theory, experimental data shows that this anti-apoptotic effect of OP9 may be due to paracrine effect, rather than from cell-cell contact. Furthermore, it is shown that including agitation into the process of co-culture with OP9 significantly improved the enucleation efficiency.

It has been shown that co-culture of cord blood-derived/ hiPSC erythroblasts on monolayer cultures of OP9 and/or other stromal cell-lines, such as MS-5, can significantly improve enucleation. However, because of surface area limitations associated with monolayer cultures, this approach has limitations in terms of scaling up the process to derive large numbers of enucleated red blood cells. On the other hand, the approach of culturing the OP9 on microcarriers, as disclosed herein, allows for the development of a potentially scalable agitation suspension culture platform for deriving enucleated red blood cells. Thus far, there has been no other description of a suspension co-culture of OP9 or other mesenchymal stem cells (MSCs) with erythroblasts for development of scalable platform for increasing enucleation efficiency.

Erythroid Differentiation of Multiple Human Pluripotent Stem Cell Lines in Microcarrier Culture by Modulation of Wnt/β-Catenin Signalling Differentiation of O-negative Rhesus factor D negative (O-neg) human induced pluripotent stem cells (hiPSCs) can generate universal donor red blood cells (RBCs) that may find use in transfusion applications. Among the approaches described for red blood cell generation, embryoid body (EB)-mediated differentiation approaches developed with xeno-free and defined conditions appear to be most feasible for future clinical development. However, conventional approaches for embryoid body generation, such as by forced aggregation, have not yet been successfully demonstrated on large-scale in suspension culture. Culture of hiPSC as 3-dimensional (3D)-aggregates or on defined extracellular matrix (ECM)-coated microcarriers (MCs) are possible means for up-scaling human pluripotent stem cells (hPSC) and embryoid body expansion in suspension culture. It had previously been shown that hPSC-MC aggregates could be differentiated into hematopoietic precursors and erythroblasts when differentiated with a BMP4-based protocol. However, repeated attempts to differentiate multiple hPSC lines initially expanded under continuous agitation condition demonstrated variability in erythroid differentiation. Without being bound by theory, it had been hypothesized that agitation shear stress could induce expression of SMAD7, which is known to have inhibitory effects on phosphorylation of SMAD 1, 5 and 8, all of which are components of the TGF-β signalling pathway activated by BMP4 during the initial stages of mesodermal differentiation. Thus, inhibition of BMP4 signalling in agitated cultures could be a possible reason for poor mesoderm induction and variability in differentiation outcomes. An optimized protocol for erythroid differentiation of human pluripotent stem cell-microcarrier (hPSC-MC) aggregates initially expanded under agitation is shown herein, which serves as basis or a process for large-scale generation of universal red blood cells.

Figure 26:
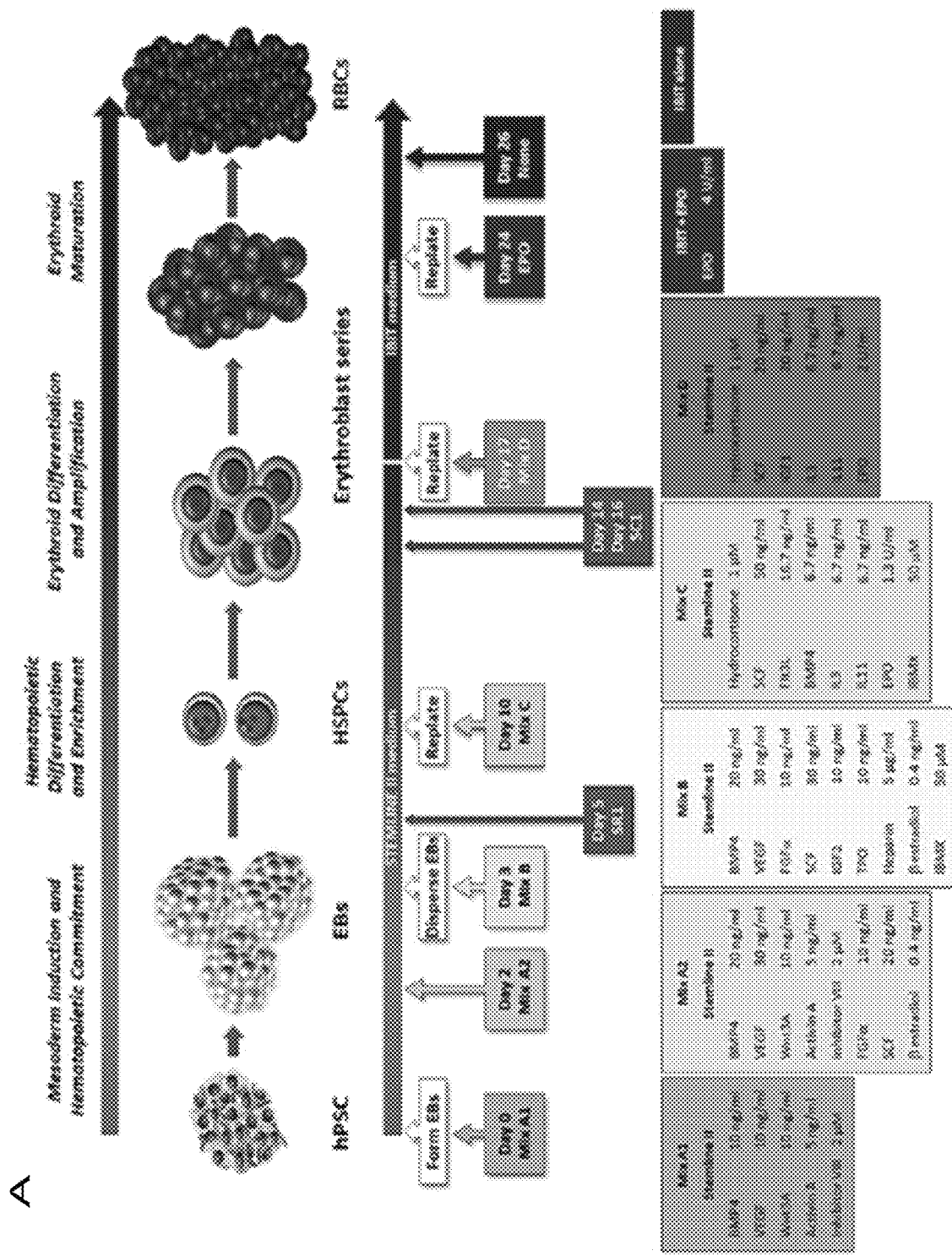
FIG. 26 shows two schematics. (A) is a schematic taken from Olivier et al. (Stem Cell Trans Med; 2016; 5: 1-12) illustrating a differentiation protocol for deriving erythroid cells as disclosed in the art. This schematic represents feeder-free and serum-free erythroid differentiation of hPSCs augmented by the addition of small molecules. Abbreviations used: BMP, bone morphogenic protein; EBs, embryoid bodies; EPO, erythropoietin; FGF, fibroblast growth factor; Flt3L, Flt3-ligand; hPSC, human pluripotent stem cells; HSPCs, hematopoietic stem and progenitor cells; IBIT, IMDM+bovine serum albumin, insulin, transferrin; IBMX, isobutylmethyl xanthine; IGF, insulin-like growth factor; IL, interleukin; RBCs, red blood cells; SCF, stem cell factor; TPO, thrombopoietin; VEGF, vascular endothelial growth factor 165. (B) is a schematic for direct comparison between the method disclosed herein and that of the prior art. The differences between the method as disclosed in the prior art and the presently claimed methods are, for example, that the method disclosed herein uses microcarrier culture of human induced pluripotent stem cells (hiPSCs) and microcarrier-hiPSCs as embryoid bodies (EBs) for mesoderm induction. Furthermore, all the steps of the method as disclosed herein are performed in suspension culture under continuous agitation. In addition, the conditions for Day 0 and Day 1 for mesoderm induction, erythroblast expansion medium, maturation medium conditions as disclosed herein are different from those as described by Olivier et al.

The method disclosed herein differs from that shown in the art, as illustrated in FIG. 26. FIG. 26B is a schematic for direct comparison between the method disclosed herein and that of the prior art (Olivier et al; 2016). The differences between the method as disclosed in the prior art and the presently claimed methods are, but not limited to, for example that the method disclosed herein uses microcarrier culture of human induced pluripotent stem cells (hiPSCs) and microcarrier-hiPSCs as embryoid bodies (EBs) for mesoderm induction. In another example, all the steps of the method disclosed herein are performed in suspension culture under continuous agitation. In another example of the difference between the presently claimed method and that of the prior art, the conditions for Day 0 and Day 1 for mesoderm induction, erythroblast expansion medium, maturation medium conditions as disclosed herein are different from those as described by the prior art.

FIG. 39A summarizes the experimental study performed to evaluate effects of agitation on mesoderm induction and subsequent erythroid differentiation. By comparing human pluripotent stem cell-microcarrier (hPSC-MC) aggregates derived from static, 3-days or 7-days agitation condition during the human pluripotent stem cell (hPSC) expansion stage (FIG. 39B) of an human embryonic stem cell (hESC) line, hES-3, which maintained pluripotency (FIG. 39C), it was shown that continuous agitation for 7 days using a BMP4-based protocol impedes the expression of the primitive streak/mesoderm marker, T-Bra9 and hematopoietic mesoderm marker, KDR10 (FIG. 39D), as well as subsequent hematopoietic precursors (FIG. 39E-G) and erythroblasts differentiation (FIG. 39G-H) compared to cultures derived from static condition when differentiated with the BMP4-based protocol. In line with the hypothesis outlined above, agitation cultures showed increased levels of inhibitory SMAD7 compared to static cultures. BMP4 signalling was adversely affected in agitation cultures, with phosphorylation of SMAD1/5 evident only in static cultures (FIGS. 38A and C).

In order to improve the poor differentiation outcome from agitation culture, a multifactorial Design of Experiment (DoE) approach was utilised to screen for combination of factors that could improve hematopoietic mesoderm induction of hPSC-MC-aggregate cultures derived from continuous agitation of hES-3 (FIG. 2B,C and Table 3) and an O-neg hiPSC line, D5 (FIG. 6).

TABLE 3

Multifactorial DoE analysis identifies CHIR-99021 as a significant factor for improved hematopoietic mesoderm induction and hematopoietic differentiation; hES-3-MC agitation culture: Table showing the different DoE conditions with varying concentrations of Activin A (ng/ml), CHIR-99021 (µM) maintained for 24 hours, CHIR-99021 (µM) from 24-48 hours and BMP4 (ng/ml) added at start of experiment and the corresponding percent KDR+ cells on day 4 post differentiation as determined by flow cytometry and total hematopoietic precursors per well following 14 days of expansion in BGM following initial seeding of $1 \times 10^5$ cells.

| | Dose and duration of factors evaluated | | | | Response outcome | |
|---|---|---|---|---|---|---|
| Condition | Activin A (ng/ml) | $CHIR^{24\ hr}$ (µM) | $CHIR_{48\ hr}$ (µM) | BMP4 (ng/ml) | % KDR+ cells | Total number of hematopoietic precursors |
| 1 | 0 | 0 | 0 | 50 | 0.44 | 136000 |
| 2 | 80 | 0 | 0 | 10 | 1.07 | 271500 |
| 3 | 0 | 15 | 0 | 10 | 9.19 | 401500 |
| 4 | 80 | 15 | 0 | 50 | 18.5 | 469000 |
| 5 | 0 | 0 | 15 | 10 | 1.18 | 271000 |
| 6 | 80 | 0 | 15 | 50 | 2.06 | 403000 |
| 7 | 0 | 15 | 15 | 50 | 30.7 | 185500 |
| 8 | 80 | 15 | 15 | 10 | 25.6 | 370500 |
| 9 | 0 | 0 | 0 | 10 | 0.6 | 96500 |
| 10 | 80 | 0 | 0 | 50 | 0.97 | 92500 |
| 11 | 0 | 15 | 0 | 50 | 17.7 | 655000 |
| 12 | 80 | 15 | 0 | 10 | 16.3 | 348000 |
| 13 | 0 | 0 | 15 | 50 | 4.57 | 75500 |
| 14 | 80 | 0 | 15 | 10 | 1.38 | 108500 |
| 15 | 0 | 15 | 15 | 10 | 38 | 60000 |
| 16 | 80 | 15 | 15 | 50 | 38.7 | 381000 |
| 17 | 0 | 7.5 | 7.5 | 30 | 5.61 | 498000 |
| 18 | 80 | 7.5 | 7.5 | 30 | 19.2 | 362000 |
| 19 | 40 | 0 | 7.5 | 30 | 2.42 | 304500 |
| 20 | 40 | 15 | 7.5 | 30 | 36.6 | 469500 |
| 21 | 40 | 7.5 | 0 | 30 | 9.25 | 344500 |
| 22 | 40 | 7.5 | 15 | 30 | 30.8 | 350500 |
| 23 | 40 | 7.5 | 7.5 | 30 | 9.24 | 450500 |
| 24 | 40 | 7.5 | 7.5 | 30 | 11.4 | 388000 |
| 25 | 40 | 7.5 | 7.5 | 10 | 30.1 | 440500 |
| 26 | 40 | 7.5 | 7.5 | 50 | 28.3 | 491000 |
| 27 | 40 | 7.5 | 7.5 | 30 | 16.9 | 425000 |
| 28 | 40 | 7.5 | 7.5 | 30 | 26.7 | 385500 |
| 29 | 40 | 7.5 | 7.5 | 30 | 14 | 368500 |

Figure 23:
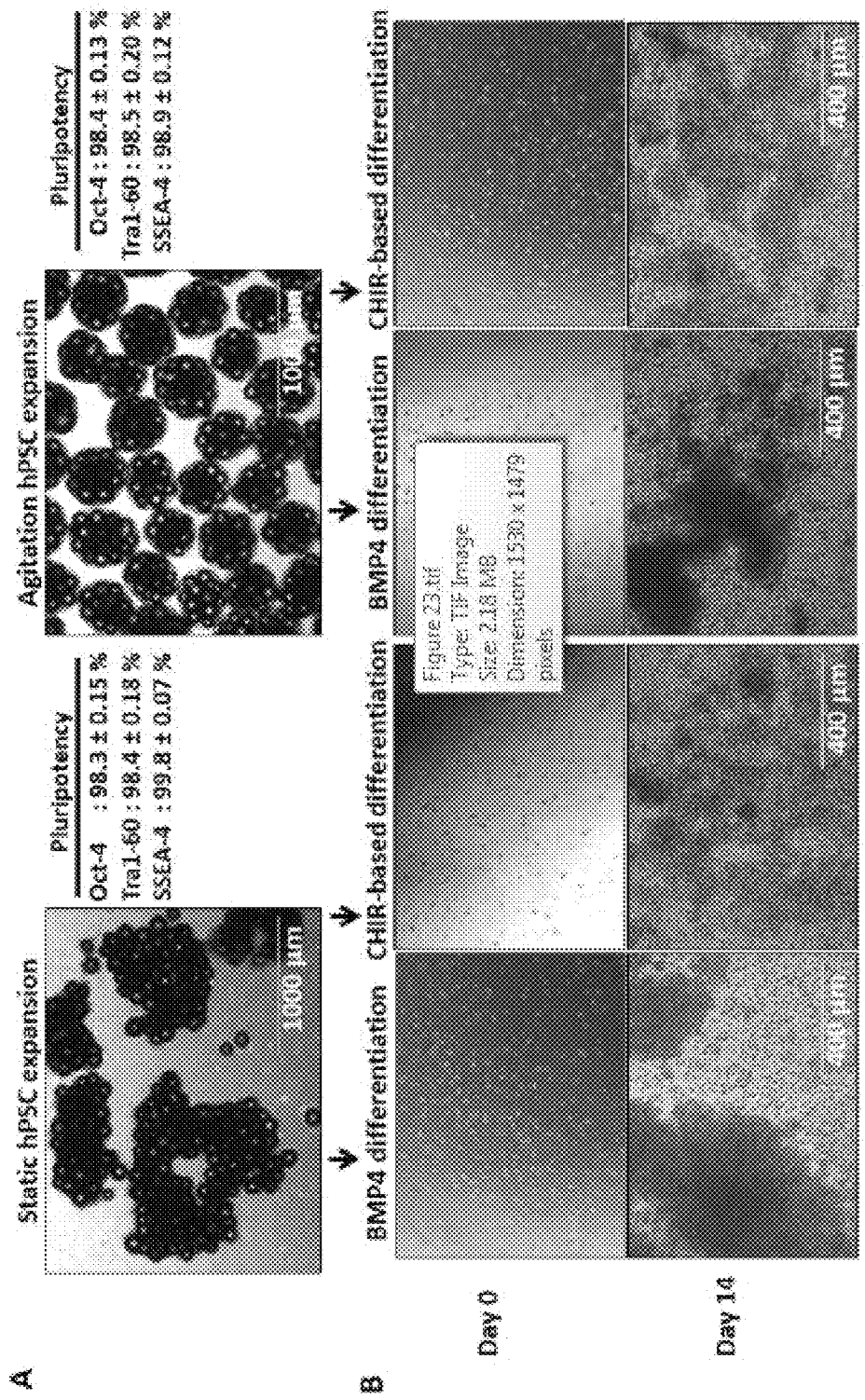
FIG. 23 shows the differentiation of hES-3 MC aggregates from static and agitation conditions using BMP4 or CHIR-based protocol. (A) shows micrograph images of hES3-microcarrier aggregates expanded under static or agitation conditions for 7 days, which were then evaluated for pluripotency by flow cytometry and differentiated using (B) shows images of cells subjected to BMP4-based or CHIR-based differentiation protocol and expanded in BGM for 14 days to derive hematopoietic precursors. (C) shows a column graph depicting the total counts of hematopoietic precursors (day 14 post expansion in BGM medium following initial seeding of $3 \times 10^5$ cells) and erythroblasts (day 12 post seeding in erythroblast expansion medium). *p<0.05 for comparison of BMP4-agitation group vs all other groups. (D) shows images of red blood cell (RBC) pellets on day 32 of differentiation and erythroid output per human pluripotent stem cell seeded. P<0.05 for comparison of BMP4-agitation group vs all other groups. Data are mean±SEM, n=3.
Figure 23:
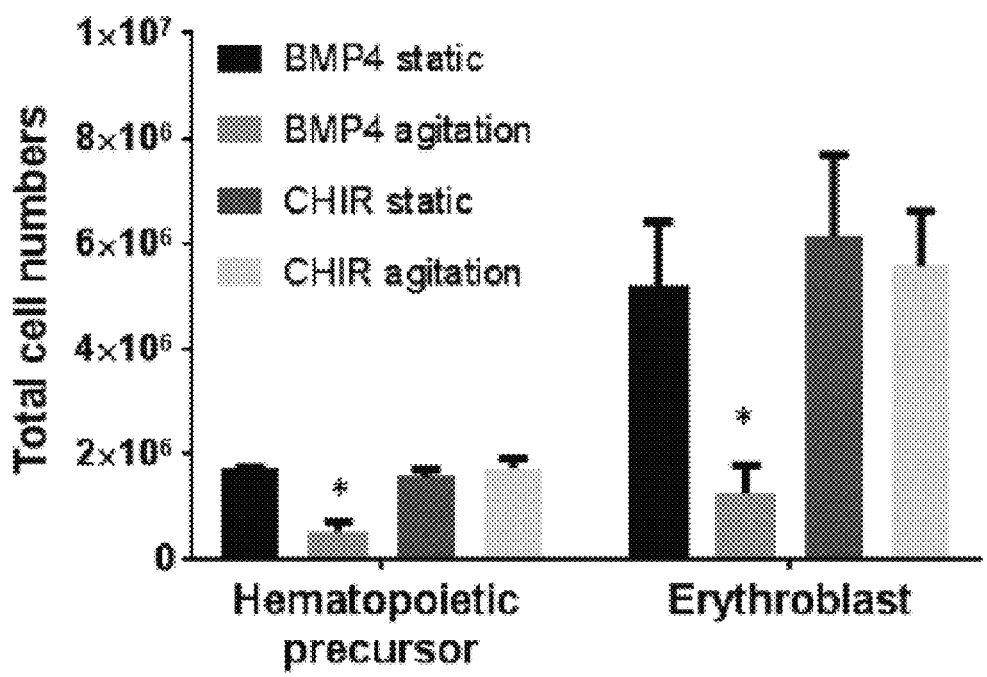
Figure 23:
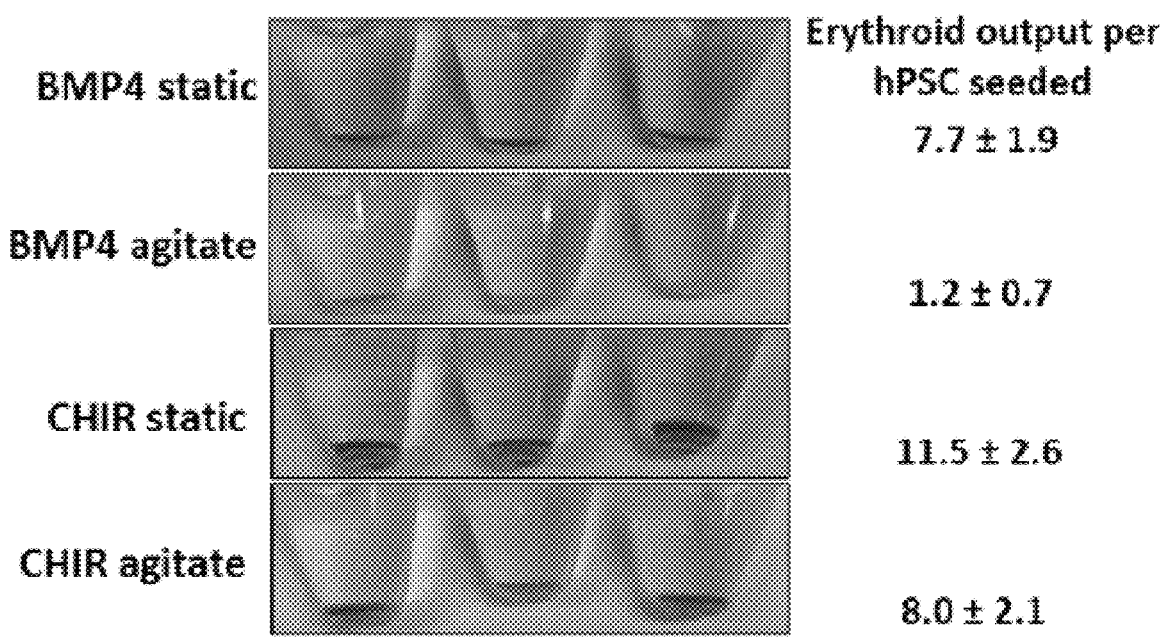

The DoE study identified CHIR-99021 (CHIR), a selective inhibitor of glycogen synthase kinase 3-beta (GSK-3β) and an activator of canonical Wnt/β-Catenin signalling, as the most significant factor for improved development of KDR+ cells (FIG. 2B and FIG. 6C) and subsequent generation of hematopoietic precursors (FIG. 2C, D), when used in combination with BMP4 and Activin A. It was further possible to correlate higher initial percent KDR+ cell population with higher total number of hematopoietic precursors generated (P=0.001) (FIG. 2D). CHIR-99021 has been shown to induce primitive streak/mesoderm development of human pluripotent stem cells (hPSCs) for cardiomyocyte and hematopoietic differentiation. Components of the Wnt/β-catenin signalling pathway, such as TCF-1 and LEF-1, as well as direct target of Wnt signalling such as T-BRA, were detected as early as 24 hours upon induction with CHIR (FIGS. 38A and B). The CHIR-based protocol as disclosed herein resulted in similar erythroblasts output per human pluripotent stem cell seeded (P>0.05) following differentiation of hES-3 microcarrier aggregates derived from static (11.5±2.6) or agitation (8.0±2.1) condition, whereas for BMP4-based differentiation, efficient expansion was observed only with static (7.7±1.9) and not agitation (1.2±0.7) condition (P<0.05) (FIG. 23). In order to validate the effect of CHIR on improved erythroid differentiation of human pluripotent stem cells expanded in agitated microcarrier culture, 29 conditions from a DoE study (FIG. 6A) were evaluated using D5 (a human induced pluripotent stem cell line). Six conditions were then chosen for the detailed study; conditions 1, 2 and 4 were based on BMP4/Activin A protocols, while conditions 7, 16 and 18 were CHIR-mediated protocols (Table 1). The BMP4/Activin A protocol resulted in very little primitive streak/mesoderm induction (T-Bra+ cells: 6.66-8.36%) 48 hours post induction and low hematopoietic mesoderm induction (5.33-13.8% of KDR+ cells) 96 hours post induction (Table 1). These conditions also resulted in very low induction of the hematopoietic transcription factors SCL and RUNX1 and had little or no expansion of hematopoietic precursors following 2 weeks of culture in methylcellulose-based blast growth medium (BGM) and subsequently failed to expand as erythroblasts (Table 1). On the other hand, the CHIR-based protocol resulted in high primitive streak/mesoderm induction (44.9-89.6% T-Bra+ cells on day 2), high hematopoietic mesoderm induction (18.6-29.4% KDR+ cells on day 4), higher fold-induction of CD31, SCL/Tal-1 and RUNX1 (known as master regulators of hematopoiesis) and improved expansion of hematopoietic precursors 14 days post differentiation (Table 1). Among the CHIR-based conditions tested, condition #7 (12 mM CHIR for 24 hours) and #18 (6 mM CHIR for 48 hours) resulted in erythroid differentiation and expansion (Day 34 fold-expansion: 284.4±9.2 vs. 95.8±1.2, respectively) (Table 1) with condition #7 showing significantly higher number of erythroblasts than condition #18 ($1.42\times10^8$ compared to $4.31\times10^7$ cells, 34 days post differentiation, P=0.0003) (FIG. 3A). Erythroblasts differentiated using condition #7 achieved a cumulative fold-expansion of 62343±15070 by day 56 of culture.

Having optimized conditions for erythroid differentiation of human pluripotent stem cell-microcarrier (hPSC-MC) aggregates derived from agitation condition, differentiation of 7 karyotypically normal O-neg hiPSC lines (BR2, BR7, D5, D9, D11, D12, X13), 1 commercial hiPSC line (IMR90) and a hESC line (hES-3) were tested. Human pluripotent stem cell lines were expanded on microcarriers for 7 days under agitation condition maintained pluripotency and achieved 5.3 to 12.5-fold expansion, with mean aggregate diameters ranging from 255 to 510 mm (FIG. 4A). HPSC-MC aggregates generated from different hPSC lines were differentiated using 3 different CHIR doses (5, 10 and 15 mM for 24 hours). For all of the lines tested, 15 mM CHIR resulted in significantly higher (P<0.05) T-Bra+ cells compared to 5 mM CHIR (FIG. 4B). Expression of KDR+ PDGFRα− cells, indicative of hematovascular progenitors, mirrored the trend of T-Bra+ cells, with 15 mM CHIR showing significantly higher (P<0.05) KDR+PDGFRα− cells as compared to 5 mM CHIR (FIG. 4C). Hematopoietic induction of differentiated cells evaluated by RT-PCR for expression of CD31 and hematopoietic transcription factors SCL, GATA2, RUNX1 and LMO2 (day 4 post differentiation) showed higher fold up-regulation with increasing dose of CHIR in most of the lines tested (FIG. 9). With the exception of D9 and IMR90, all other hPSC lines had significantly increased (P<0.05) fold-expansion of hematopoietic precursors at day 14 post differentiation when induced with 15 mM CHIR dose as compared to 5 mM CHIR (FIG. 4D). Following erythroid differentiation, X13 achieved a cumulative fold-expansion of 12605±2126 which was significantly higher than all other lines tested (FIG. 4F). Six of 9 lines (D5, D9, X13, BR7, IMR90, hES-3) successfully differentiated into erythroblasts (FIG. 4G) and had expression of CD235a and high levels of HbF (Table 2). For the best performing line, X13, 7607±1016 CD235a+ erythroid cells could be derived per human pluripotent stem cell seeded (Table 2). Immunoblot evaluation of hemoglobin subtypes showed that majority of human pluripotent stem cell-differentiated erythroblasts had expression of alpha, gamma and epsilon with very little beta-hemoglobin, compared to adult erythroblasts (FIGS. 40A and C).

It was further noted that erythroblasts differentiated from BR7 and X13 also showed some expression of beta-hemoglobin subtype (FIG. 40). Oxygen equilibrium curves of human pluripotent stem cell-differentiated erythroblasts indicated higher oxygen binding affinity (P50 values ranging from 10.1 to 13.4) compared to adult RBCs (P50−19.6±0.2) (FIGS. 40A and B). Following 18-day co-culture with primary human mesenchymal stem cells (MSCs), 28-40.6% of erythroblasts were CD235a+ and DRAQ5 (cell permeable nuclear dye) negative, indicating enucleated erythroid cells (FIGS. 40A and D). This was further corroborated by Giemsa staining of cells (FIG. 40E) and immunofluorescence staining of terminally matured erythroblasts which showed CD235a+ erythrocytes lacking nuclear staining (FIG. 40F).

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

As used in this application, the singular form "a," "an," and "the" include plural references unless the context clearly dictates otherwise. For example, the term "a genetic marker" includes a plurality of genetic markers, including mixtures and combinations thereof.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Monolayer Pluripotent Cell Culture

O-neg human induced pluripotent stem cell (hiPSC) lines (D5, D9, D11, D12, X13, BR2, BR7) were reprogrammed from CD71+ erythroblast, derived from finger-prick blood of consented human donors (with approval from the ethics committee of the National University of Singapore), using Sendai viral transduction of the four (4) reprogramming factors.

In summary, a total of 10 ml of finger-tip capillary blood was collected in a sterile laboratory setting. The samples were lysed in 2 ml of 1× red blood cell (RBC) lysis buffer (eBioscience) for 10 minutes before spinning at 250 g for 5 minutes. The lysis buffer was aspirated immediately after the centrifugation. Purified cells were re-suspended with 500 ml of cell expansion medium and seeded into one well of a 24-well tissue culture plate. Finger-prick (FP) blood-cell expansion medium containing StemSpan Serum-Free Expansion Medium (StemCell Technologies) was supplemented with 1× penicillin/streptomycin (pen/strep) (Gibco), 1× L-glutamine (Gibco), 1× nonessential amino acids (Gibco), 50 mg/ml L-ascorbic acid (Sigma-Aldrich), 50 ng/ml stem cell factor (Peprotech), 10 ng/ml, interleukin-3 (Peprotech), 40 ng/ml insulin-like growth factor-1 (Peprotech), 2 U/ml erythropoietin (R&D Systems), and 1 mM dexamethasone (Sigma-Aldrich), with or without 10 ng/ml interleukin-6 (Peprotech). The medium was changed every day by carefully pipetting out half of the medium and replacing it with fresh medium. Twelve to 16 days later, when the cell population reached 20,000-30,000 cells, they were transduced with Sendai virus.

A total of 20,000-30,000 cells were transduced by OCT4, SOX2, KLF4, and c-MYC Sendai virus (CytoTune-iPS Reprogramming Kit; Life Technologies) with each factor at a multiplicity of infection of 10 (approximately 5 ml of each factor). The transduction was terminated after 24 hours by replacing with fresh cell expansion medium. At day 3, cells were transferred to four or five wells of irradiated CF1-mouse embryonic fibroblasts (MEFs; seeded at density of 200,000 per well) in six-well tissue culture plates and cultured with a 1:1 ratio of expansion medium and human embryonic stem cell (hESC) medium (Dulbecco's modified Eagle's medium [DMEM]/F12 supplemented with 20% Knockout Serum Replacement, 100 mM Minimum Essential Medium with nonessential amino acid solution, 100 mM β-mercaptoethanol, 1× penicillin/streptomycin, 1× L-glutamine, and 10 ng/ml basic fibroblast factor).

Two days later, the medium was changed to hESC medium with daily medium changes. From day 14, reprogramming continued with MEF-conditioned hESC medium and mTeSR1 in a 1:1 ratio. The volume of medium used for six-well culture was 2 ml per well. Once human induced pluripotent stem cell (hiPSC) colonies resembling human embryonic stem cells (hESCs) in morphology emerged, the colonies were mechanically picked and re-plated onto MEFs for expansion.

The human embryonic stem cell line, hES-3, and the induced pluripotent stem cell (iPSC) line, IMR90-iPSC, were obtained. All human pluripotent stem cell (hPSC) lines were cultured using mTeSR™1 medium (STEMCELL™ Technologies, USA). G-banding karyotype analysis was performed on selected lines as detailed herein.

Microcarrier Pluripotent Cell Culture

Briefly, one million single cell human pluripotent stem cells derived from monolayer cultures following enzymatic treatment with Accutase (ThermoFisher Scientific, USA) were seeded into each well of 6-well ultra-low attachment (ULA) plate (Corning, USA) containing 5 ml of mTeSR1 medium, 10 μM ROCK inhibitor Y27632 (STEMCELLTechnologies) and extracellular matrix-coated polystyrene microcarriers, iPS-Spheres (Brilliant Research, Singapore), and cultured according to manufacturer's instructions. Human pluripotent stem cell-microcarrier (HPSC-MC) aggregates were either cultured under continuous agitation in an agitated platform at 110 rpm or under static conditions for 7 days with daily medium changes, before use in experiments.

Hematopoietic Mesoderm Induction of hPSC-MC Aggregates Using BMP4 Protocol

Mesoderm induction of hPSC-MC aggregates using BMP4 based protocol has previously been described. One million HPSC-MC aggregates were cultured in Stemline II hematopoietic stem cell expansion medium (Sigma-Aldrich, USA) containing 50 ng/ml of BMP4 and 50 ng/ml of $VEGF_{165}$ under static condition. 48 hours later, half the medium was removed and replaced with Stemline II medium containing 50 ng/ml of BMP4, 50 ng/ml of VEGF165 and 20 ng/ml of bFGF (all cytokines from STEM- CELL Technologies). HPSC-MC aggregates were cultured for a further 48 hours before being used for hematopoietic precursors differentiation.

Multifactorial Evaluation of Hematopoietic Mesoderm Induction and Hematopoietic Precursor Generation Using Design of Experiments Design of experiments (DoE) using a resolution IV Fractional Factorial Design was performed using the MODDE software (Sartorius Stedim Biotech, Germany) to evaluate initial BMP4, Activin A and CHIR-99021, doses and duration of exposure for their effects on the following response factors: induction of KDR+ cells 4 days post mesoderm induction or total hematopoietic precursor cells generated 2 weeks post differentiation.

Hematopoietic Mesoderm Induction Using CHIR Mediated Optimized Protocol

Analysis of Design of experiments (DoE) outcomes and evaluation of selected conditions generated by the MODDE® software allowed the development of an optimized protocol for hematopoietic mesoderm induction of human pluripotent stem cell-microcarrier (hPSC-MC) aggregates initially expanded under continuous agitation. Approximately 2 to 4 million hPSC-MC aggregates in 3 ml of Stemline® II medium were differentiated as follows: day 1; 30 ng/ml of BMP4, 50 ng/ml VEGF$_{165}$, 12 µM CHIR-99021 (Selleck Chemicals, USA), 50 ng/ml Activin A, day 2; 30 ng/ml of BMP4, 50 ng/ml VEGF165, 50 ng/ml Activin A, day 3: 30 ng/ml of BMP4, 50 ng/ml VEGF165 and 20 ng/ml bFGF. Four days post-differentiation, single cells derived by TryPLE™ Express (ThermoFisher Scientific) treatment and strained through 40 µm cell strainers (Greiner Bio-one, Germany) were used for hematopoietic precursor and erythroblast expansion and erythroblast terminal maturation as detailed herein. Hematopoietic and erythroblast differentiation were monitored by flow cytometry, quantitative real-time PCR, immunoblotting and microscopic imaging. Oxygen binding affinity of differentiated erythroblast was determined using a Hemox Analyzer (TCS Scientific Corp, USA).

Hematopoietic Mesoderm Induction of hPSC-MC Aggregates Using BMP4 Protocol

One million HPSC-MC aggregates were cultured in Stemline II hematopoietic stem cell expansion medium (Sigma-Aldrich, USA) containing 50 ng/ml of BMP4 and 50 ng/ml of VEGF$_{165}$. 48 hours later, half the medium was removed and replaced with Stemline II medium containing 50 ng/ml of BMP4, 50 ng/ml of VEGF165 and 20 ng/ml of bFGF (all cytokines from STEMCELL. Technologies). HPSC-MC aggregates were cultured for a further 48 hours before being used for hematopoietic precursor expansion.

Hematopoietic Precursor Expansion in Methylcellulose Medium

HPSC-MC aggregates were dissociated into single cells by treatment with TrypLE. Express (ThermoFisher Scientific) for 5 minutes at 37° C., passed through 40 µm cell strainer (Greiner Bio-one), centrifuged at 1300 rpm for 3 minutes to pellet cells, and rinsed once with phosphate buffered saline (PBS) before re-suspension in Stemline II medium. Two hundred thousand cells in 100 µl of Stemline II medium were transferred to a 6-well ultra-low attachment plate and cultured with Blast growth medium (BGM) for 2 weeks in static conditions as detailed herein.

Erythroblast Differentiation and Expansion

Hematopoietic precursors were mixed with equal volume of Stemline II medium containing 50 ng/ml of SCF (STEMCELL. Technologies) and 3 U/ml EPO (Peprotech, USA), for an additional 7 days. Subsequently, cells were diluted 10-fold with PBS and pelleted by centrifugation at 3000 rpm for 10 minutes. Erythroblast cells were seeded at a concentration of $2.5 \times 10^5$ cells/ml in 3 ml of Stemline II media containing 1× Serum Replacement 3 (Sigma-Aldrich), 0.3% v/v Ex-CYTE growth enhancement media supplement (Merck, USA), 100 ng/ml SCF, 3 U/ml EPO, 1 µM hydrocortisone (Sigma-Aldrich), 200 µg/ml holo-transferrin (MP Biomedicals) and 1× penicillin-streptomycin (ThermoFisher Scientific) in 6-well ultra-low attachment plates under static condition. Cells were re-suspended in fresh media every 4 days and reseeded at $2.5 \times 10^5$ cells/m=1 when cell concentrations exceeded $2 \times 10^6$ cells/ml. Cumulative fold-expansion was calculated by multiplying fold-expansion achieved between passaging of cells over the course of experiment(s).

Multifactorial Evaluation of Hematopoietic Mesoderm Induction and Hematopoietic Precursor Generation Using Design of Experiments (MODDE Software)

Design of experiments (DoE) using a resolution IV Fractional Factorial Design was performed using the MODDE software (Sartorius Stedim Biotech, Germany) to evaluate initial BMP4, Activin A and CHIR-99021, doses and duration of exposure for their effects on the following response factors: induction of KDR+ cells 4 days post mesoderm induction or total hematopoietic precursors generated 2 weeks post differentiation. MODDE software generates different experimental conditions with different combinations of the factors being tested and allowed to identify if a single factor or 2-factor interactions had a statistically meaningful effect (positive or negative) on the response factors. Computed model with R2 scores>0.5 indicate a model of significant fit, Q2 scores>0.1 indicate a significant model while Q2>0.5 indicate a good model for estimation of future prediction precision, model validity score of <0.25 indicate statistically significant model problems and reproducibility (the variation of the replicates compared to overall variability) should be greater than 0.5.

Human pluripotent stem cell-microcarrier (HPSC-MC) aggregates (derived from 7 day continuous agitation conditions), equivalent to $5 \times 10^5$ cells, were seeded and differentiated in 24-well ultra-low attachment plates with Stemline II medium using multi-factorial conditions as detailed in FIG. 2A and FIG. 6A, as well as in Table 3. The following factors/doses and durations were tested: BMP4 for 4 days (10 to 50 ng/ml), Activin A for first 48 hours (0 to 80 ng/ml), CHIR-99021 for first 24 hours (0 to 15 µM) and CHIR-99021 from 24 hours to 48 hours (0 to 15 µM). Concentration of VEGF165 was maintained at 50 ng/ml for the 4 days of differentiation while 20 ng/ml of bFGF was added on day 2 and maintained until day 4 of differentiation. Analysis of Design of Experiment (DoE) outcomes and evaluation of selected conditions generated by the MODDE software allowed the development of an optimized protocol for hematopoietic mesoderm induction of hPSC-MC aggregates initially expanded under continuous agitation. Approximately 2 to 4 million hPSC-MC aggregates in 3 ml of Stemline II medium were differentiated as follows: day 1: 30 ng/ml of BMP4, 50 ng/ml VEGF165, 10-15 μM CHIR-99021 (Selleck Chemicals, USA), 50 ng/ml Activin A; day 2: 30 ng/ml of BMP4, 50 ng/ml VEGF$_{165}$, 50 ng/ml Activin A; day 3: 30 ng/ml of BMP4, 50 ng/ml VEGF$_{165}$ and 20 ng/ml bFGF.

Following 4 days of differentiation, single cells were derived from microcarrier aggregates by treatment with TrypLE. Express and passed through 40 μm strainer to separate the cells from microcarriers. Differentiated cells were fixed in 4% paraformaldehyde for 30 minutes at room temperature, centrifuged and rinsed once with PBS before storage at 4° C. in PBS containing 1% BSA (Sigma-Aldrich) for flow cytometry analysis of KDR. For hematopoietic precursor generation, $1 \times 10^5$ single cells from each experimental condition were seeded into each well of a 12-well ultra-low attachment plate in Blast growth medium (BGM) as detailed above. Hematopoietic cultures were allowed to expand for 2 weeks before total number of expanded cells was enumerated using Nucleocounter NC-3000 (Chemometec). Cells were then fixed for flow cytometric analysis of CD31 and CD43. Fold-expansion was calculated as total number of cells derived after 2 weeks as compared to initial seeding of $1 \times 10^5$ cells.

Erythroblast Terminal Maturation

Terminal maturation and enucleation was induced by co-culturing erythroblasts with primary human mesenchymal stem cells (MSCs) for a period of 3 weeks. Mesenchymal stem cells, initially cultured in Alpha-Minimum Essential Media (α-MEM; ThermoFisher Scientific) supplemented with 10% FCS (Life Technologies), were seeded onto a 6-well plate at $1 \times 10^5$ cells per well. Erythroblasts resuspended at $1 \times 10^6$ cells/ml in enucleation medium comprising of Iscove's Modified Dulbecco's medium (IMDM; ThermoFisher Scientific) with 8% human serum (Sigma-Aldrich), 1x Lipid mix (Peprotech), 6 U/ml EPO, 50 ng/ml SCF, 1000 μg/ml holo-transferrin and 1x Penicillin-Streptomycin were co-cultured with pre-seeded mesenchymal stem cells. Cells were transferred to freshly seeded mesenchymal stem cells (MSCs; $1 \times 10^5$ cells per well) every week for a period of 2 to 3 weeks with fresh medium change.

RNA Extraction and Quantitative Real-Time Polymerase Chain Reaction (PCR)

Cell samples were lysed in Trizol reagent (ThermoFisher Scientific) and stored at −80° C. until time of RNA extraction. RNA extraction with DNAse treatment was performed using Direct-zol RNA extraction kit (Zymo Research) according to manufacturer's instruction. RNA samples were quantified by OD260 nm measurements using a NanoDrop UV-Vis spectrophotometer (ThermoFisher Scientific).

500 ng of total RNA was used for 1st strand cDNA synthesis using iScript. Advanced cDNA synthesis kit (Bio-Rad, USA). cDNA samples diluted 1:10 in RNAse-free water were used for quantitative real-time PCR using gene-specific primers as detailed in Table 4.

TABLE 4

Gene-specific primers used for real-time PCRT

| Marker | SEQ ID NO: | Forward primer | SEQ ID NO: | Reverse primer |
|---|---|---|---|---|
| CD31 | 1 | 5'-gctgacccttctgctctgtt-3' | 2 | 5'-tgagaggtggtgctgacatc-3' |
| GATA2 | 3 | 5'-atcaagcccaagcgaagact-3' | 4 | 5'-catggtcagtggcctgttaac-3' |
| GATA1 | 5 | 5'-tcactccctgtccccaatag-3' | 6 | 5'-ggagagttccacgaagcttg-3' |
| LMO2 | 7 | 5'-aactgggccggaagctct-3' | 8 | 5'-cttgaaacattccaggtgataca-3' |
| SCL/Tal-1 | 9 | 5'-ggatgccttccctatgttca-3' | 10 | 5'-ggtgtgggaccatcagtaa-3' |
| RunX1 | 11 | 5'-ccgagaacctcgaagacatc-3' | 12 | 5'-gctgaccctcatggctgt-3' |
| hemoglobin subtype alpha | 13 | 5'-cggtcaacttcaagctcctaag-3' | 14 | 5'-ccgcccactcagactttatt-3' |
| hemoglobin subtype gamma | 15 | 5'-tggatcctgagaacttcaag-3' | 16 | 5'-gcagaataaagcctatccttgaaag-3' |
| hemoglobin subtype epsilon | 17 | 5'-aagatgaatgtggaagaggctgg-3' | 18 | 5'-ttagcaaaggcgggcttgag-3' |
| hemoglobin subtype beta | 19 | 5'-acatttgcttctgacacaac-3' | 20 | 5'-acagatccccaaaggact-3' |
| GAPDH | 21 | ctcctcctgttcgac | 22 | accaaatccgttgact |

Relative quantity of early hematopoietic markers was analysed using gene-specific primers as listed in Table 4 above, iTAQ. Universal SYBR green supermix (BioRad)

and Applied Biosystems 7500 FAST Real-time PCR system (ThermoFisher Scientific). GAPDH was used as a housekeeping gene for normalization of sample quantities. Relative change in gene expression was determined using the delta-delta c(t) method.

Immunoblot

Protein samples for analyses were extracted from frozen cell pellets following lysis using 2x Laemmli buffer (Bio-Rad) and quantified using a BCA protein assay kit (ThermoFisher Scientific). 50 µg of cell lysate was loaded into a SDS-PAGE gel and transferred onto a polyvinylidene difluoride (PVDF) membrane (Bio-Rad). The membrane was blocked with 5% skim milk at room temperature for 2 hours, followed by incubation with primary antibodies [1:800 diluted beta-globin (Santa Cruz, SC-21757), 1:400 diluted gamma-globin (Santa Cruz, SC-21756), 1:2000 diluted alpha-globin (Santa Cruz, SC-31110), 1:400 diluted epsilon-globin (Abcam, ab156041) and 1:2000 diluted Actin (Santa Cruz, SC-1615)] at room temperature for 1.5 hours. The blot was subsequently incubated with either horse-radish peroxidase (HRP)-conjugated anti-mouse IgG (Jackson ImmunoResearch), HRP-conjugated anti-rabbit IgG (Jackson ImmunoResearch), or HRP-conjugated anti-goat IgG (Jackson ImmunoResearch) at dilution of 1:10000. Immunocomplexes were detected using SuperSignal West Dura Extended Duration Substrate (Thermo Scientific) and captured onto CLXposure films (Thermo Scientific). Band intensity was measured using ImageJ software (https://imagej.nih.gov/ij/), normalized to the loading control (actin) and reported as a percentage of the total hemoglobin bands.

Capillary Western Blot

Capillary Western blot was performed using a fully automated system, Peggy Sue (Proteinsimple, R&D, USA). Proteins were separated, detected and quantified according to manufacturer's protocol (www.proteinsimple.com) based on size separation (12-230 kDa). Cell lysates were prepared in 1x cell lysis buffer (Cell Signaling Technology) containing 1x phenylmethylsufonyl fluoride (PMSF), 1x phosphatase and 1x protease inhibitors (BioSpes). 1 mg/ml of total protein samples (denatured with DTT and SDS at 95° C.) were separated by capillary electrophoresis, blocked with blocking buffer, probed with primary rabbit monoclonal antibodies [1:100 diluted Brachyury (D2Z3J), TCF1/TCF7 (C63D9), TCF3/TCFF7L1 (D15G11), Lef1 (C12A5), SMAD1 (D59D7), 1:50 diluted pSMAD1/5 Ser 463/465 (41D10), 1:5000 diluted GAPDH (D16H11)] (all from Cell Signaling Technology)[1:50 diluted SMAD7 (Sigma-Aldrich)] followed by horseradish peroxidase conjugated secondary antibody and detected with Luminol/Peroxidase substrate. Identification and quantification of the chemiluminescence signals were performed with Compass software (Proteinsimple), which was used to transform the chemiluminescence signals into western blot images.

Flow Cytometry

Samples for flow cytometry were fixed in 4% paraformaldehyde (eBioscience) for 30 minutes and stored at 4° C. in PBS containing 1% bovine serum albumine (BSA). For pluripotency measurements, samples were incubated with the following dilutions of primary antibodies: 1:100 Oct4 (R&D Systems, USA); 1:50 Tra1-60 (Millipore), 1:100 SSEA4 (BioLegend, USA), for 20 minutes at room temperature (25° C.). Following washing with FACS buffer (PBS+1% BSA), primary antibodies were detected using 1:500 diluted rabbit anti-mouse IgG-FITC conjugate (DAKO). Following washing with FACS buffer and straining thru 40 µm sieves, samples were run on NovoCyte Flow cytometer (ACEA Biosciences Inc., USA) and analysed using FlowJo Software.

For flow cytometric analysis of mesoderm and hematopoietic surface markers, cells were incubated for 15 minutes at room temperature with 1:50 diluted direct-conjugated antibodies. The following human antibodies were used: T-brachyury-FITC (R&D Systems), KDR-PE (Miltenyi Biotec), CD31-PE, CD43-FITC, CD 45-PE, CD71-APC, CD235a-FITC (all from BD Biosciences, USA). The following antibodies were used as isotype-controls: mouse IgG1-FITC and PE (Miltenyi Biotec, Germany), mouse IgG2bk-FITC and mouse IgG2ak-APC (BD Biosciences). For analysis of hemoglobin, cells were permeabilized with PBS containing 1% BSA and 0.1% TritonX-100 and incubated with 1:50 diluted fetal hemoglobin-FITC (ThermoFisher Scientific) or adult hemoglobin-PE antibodies (Santa Cruz Biotechnology, USA).

Detection of enucleated cells was performed by flow cytometry analysis of live cells stained with 1:100 diluted CD235a-FITC and 1:5000 dilution of a cell-permeable nuclear dye, DRAQ-5. (eBioscience).

Immunohistochemistry and Microscope Imaging

Cell samples in 100 µl of PBS were spun onto slides at 500 rpm for 3 minutes using Cytospin 4 cytocentrifuge (Thermofisher Scientific). Cells were fixed in 100% methanol (Sigma-Aldrich) for 5 minutes, rinsed with distilled water and stored at room temperature. Slides were stained with Giemsa stain (Sigma-Aldrich) for 20 minutes, rinsed with PBS (pH 7.2) and allowed to air dry before being mounted with VECTASHIELD HardSet Antifade Mounting medium (VECTOR Laboratories) and cover-slip. Slides were imaged using Axiovert 200M inverted microscope (Zeiss).

Immunofluorescence imaging of terminally matured erythroblast was done using Nikon Eclipse Ti-E florescence microscope (Nikon).

All other cell images were taken using EVOSR Cell imaging system (Thermofisher Scientific). Calculation of human pluripotent stem cell (hPSC)-microcarrier aggregate mean diameter was done using ImageJ software by analysing at least 40 human pluripotent stem cell-microcarrier aggregates per cell line.

Oxygen Equilibration Curve

Hemox analyzer model B equipment (TCS Scientific Corp) was used to generate the oxygen binding and dissociation equilibration curves of hPSC differentiated erythroblast. Approximately $1\times10^7$ erythroblast cells in HEMOX solution (TCS Scientific Corp) was run under oxygen saturation conditions using compressed air followed by deoxygenation conditions using nitrogen gas. p50 values (oxygen pressure which gives 50% oxyhemoglobin saturation levels) were calculated using Hemox Analytical Software. Adult peripheral blood (donor derived) was run as a control. All samples were measured in duplicates.

Karyotype Analysis

Human pluripotent stem cell lines used in this experiment were sent for G-banding karyotype analysis (KKH Women's and Children's Hospital, Department of Pathology and Laboratory Medicine, Singapore) where typically 20 metaphases were evaluated for gross chromosomal abnormalities and aneuploidy.

Statistical Analysis

Statistical analysis was performed using GraphPad Prism 6 (GraphPad Software Inc.). Student's unpaired t-test was used for comparison between two groups with equal variance and the Mann-Whitney test was used when variances were not assumed to be equal. P values smaller than 0.05 (p<0.05) were considered significant.

Protocol for Microcarrier Culture of OP9 Murine Stromal Cell Line.

OP9 cultures (ATCC: CR-2749) were cultured on monolayer cultures in conventional tissue culture flasks with Alpha-MEM medium (Thermofisher) supplemented with 20% FCS (Gibco) and 1× penicillin/streptomycin. Single cells were derived by enzymatic treatment with TrypLE™ for 5 minutes at 37° C. Two hundred thousand cells were seeded into each well of 6-well ultra-low attachment plate (Corning) containing 5 ml of Alpha-MEM 20% FCS medium and 20 mg Solohill® Plastic Plus microcarriers (Pall Corporation). Plates were agitated at 75 rpm in a rocking platform at 37° C., to allow for attachment of cells to microcarriers. OP9-MCs cultures were cultured for 2 days under continuous agitation before being used for co-culture with erythroblasts.

Protocol for Terminal Maturation of hiPSC/CB Erythroblasts with OP9-MC Co-Culture The derivation and culture of human induced pluripotent stem cell (hiPSC) erythroblasts is described in paragraph [0203] of this application.

Human induced pluripotent stem cell erythroblasts were cultured under continuous agitation in spinner culture flasks. Differentiation of cord blood (CB) erythroblasts was performed according to protocol as previously described, except that this was performed in spinner culture flasks under continuous agitation.

In summary, cells were cultured in a modified serum-free medium supplemented with 1% deionized BSA, 120 mg/ml iron-saturated human transferrin, 900 ng/ml ferrous sulphate, 90 ng/ml ferric nitrate and 10 mg/ml insulin (Sigma). The expansion procedure comprised three steps. In the first step (days 0-8), $10^4$cells/ml CD34$^+$ cells were cultured in the presence of $10^{-6}$ M hydrocortisone (Sigma), 100 ng/ml stem cell factor (SCF), 5 ng/ml IL-3 (R&D Systems) and 3 IU/ml erythropoietin (Eprex). On day 4, one volume of cell culture was diluted in four volumes of fresh medium containing hydrocortisone, SCF, IL-3 and erythropoietin. In the second step (3 days), the cells were re-suspended at $5 \times 10^4$, $1 \times 10^5$, $2 \times 10^5$ or $3 \times 10^5$/ml (for cord blood, leukapheresis (LK), bone marrow and peripheral blood cells, respectively) and co-cultured on an adherent stromal layer in fresh medium supplemented with erythropoietin. In the third step (up to 10 days), the cells were cultured on an adherent stromal layer in fresh medium without cytokines.

The cultures were maintained at 37° C. in 5% $CO_2$ in air. The adherent cell layer consisted of either the MS-5 stromal cell line or mesenchymal stromal cells (MSCs) established from whole normal adult bone marrow in RPMI (Invitrogen) supplemented with 10% fetal calf serum. Adherent MSCs were expanded and purified through at least two successive passages.

Erythroblasts were transferred to 6-well ultra-low attachment plates and seeded in maturation medium at a concentration of $2 \times 10^6$cells/ml (5 ml volume) and co-cultured with OP9-MC aggregates obtained from 1 well of a 6 well plate (originally seeded at $2 \times 10^5$ cells/well and cultured for 2 days). Plates were agitated in a rocking platform at 37° C. at 75 rpm. Terminal maturation was performed for 3 weeks with complete medium change done every 3 days of culture. Single cells (derived from straining thru 40 µM sieve) were collected weekly for flow cytometry analysis and Giemsa staining to evaluate enucleation.

Terminal maturation medium formulation: IMDM supplemented with 10% human plasma (iDNA), 1× penicillin/streptomycin, 10 µg/ml human recombinant insulin (Gibco), 500 µg/ml holo-transferrin, 4 U/ml human recombinant EPO (Peprotech), 5% v/v heparin, 1 µM mifepristone.

Protocol for Enrichment of Enucleated Red Blood Cells (RBCs)

Enucleated red blood cells (RBCs) are separated from mixture of live/dead cells and nucleated cells by passing them through non-woven-fabric (NWF) filters (Antoshin, Singapore). Briefly, non-woven-fabric (NWF) filters were rinsed with 10 ml of phosphate buffered saline (PBS). Cells, at a concentration of $10^7$ cells/ml in 10 ml of phosphate buffered saline, were gently passed through the non-woven-fabric filters using a 30 ml syringe at a slow rate, with the filtrate being collected. Non-woven-fabric filters were subsequently rinsed with 10 ml of phosphate buffered saline and collected in the same tube as the filtrate. Filtered cells were spun down at 1500 rpm for 5 minutes at room temperature. Collected red blood cells were re-suspended in Citrate-phosphate-dextrose solution with adenine (Sigma-Aldrich) and stored at 4° C. for further analysis.

Protocol for Evaluation of Enucleated Red Blood Cells (RBCs)

Flow cytometry

Unfixed Single Cells Derived from Straining Cell Suspension Through 40 µm Strainers were suspended in phosphate buffered saline and used for flow cytometry. Briefly, approximately 100,000 cells per well (of a 96-well v-bottom plate) were spun down at 1500 rpm for 3 minutes. Cell pellets were re-suspended in 100 µl of 1× Annexin V Binding buffer (Thermofisher Scientific) with 1:100 dilution of Annexin V-FITC conjugated antibody (E-bioscience) (for evaluation of apoptosis), or with 1:100 dilution of CD235a-FITC conjugated antibody (E-Bioscience) for 20 minutes at 25° C. in the dark. Cells were spun down at 1500 rpm for 3 minutes and thereafter washed with 200 µl of 1× Annexin V binding buffer. Cells were finally re-suspended in 200 µl of 1× binding buffer containing 1:5000 diluted DRAQ5 (E-bioscience). Cell were evaluated on a Novocyte flow cytometer and detected at 488 nm and 647 nm.

Giemsa Staining

Approximately 50,000-100,000 cells were spun down onto a microscope slide using a cytospin centrifuge at 350 g for 5 minutes. Cells were fixed using 100% methanol for 5 minutes and air dried. Fixed cells were stained with Giemsa stain (Sigma) diluted 1:10 with phosphate buffered saline buffer at pH 7.2 (Sigma) for 15 minutes at 25° C. Stained cells were rinsed with phosphate buffered saline buffer at pH7.2 and thereafter visualized/imaged using a brightfield microscope (Zeiss Axiovert).

Protocol for Development of a Scalable Agitation Suspension Culture Differentiation Platform for Generating Erythroid Cells from O-Negative Human Induced Pluripotent Stem Cells (hiPSCs). Hematopoietic Mesoderm Induction of Human Induced Pluripotent Stem Cell-Microcarrier (hiPSC-MC) Aggregates Human induced pluripotent stem cell-microcarrier (hiPSC-MC) aggregates ($1 \times 10^6$ cells/ml, or 1e6 cells/nil) were transferred to mesoderm induction medium (cytokines all from Stemcell Technologies) plus Stemline II Hematopoietic Stem Cell Expansion medium (SL2) in either 6-well ultra-low attachment plates (5 ml) under continuous agitation at 75 rpm or 125 ml spinner flasks (50 ml) under continuous agitation at 36 rpm. Daily medium changes as indicated: Day 0: SL2+30 ng/ml BMP4+50 ng/ml VEGF-165+40 ng/ml Activin A+12-15 µM CHIR-99021; Day 1: SL2+30 ng/ml BMP4+50 ng/ml VEGF-165+40 ng/ml Activin A; Day 2: SL2+20 ng/ml BMP4+30 ng/ml VEGF165+5 ng/ml Activin A+10 ng/ml bFGF+20 ng/ml SCF+0.4 ng/ml β-estradiol. Samples were collected on day 1 and day 3 for flow cytometry analysis of T-brachyury (T-Bra) and KDR/PDGFRα cells, respectively.

Hematopoietic Induction of Cells Derived from Human Induced Pluripotent Stem Cell-Microcarrier (hiPSC-MC) Aggregates On day 3 of differentiation, single cells were derived from hiPSC-MC aggregates following treatment with TrypLE™ Express (ThermoFisher Scientific) at 37° C. for 5 minutes followed by straining through 40 µm cell strainers (Greiner Bio-one, Germany). Cells were seeded at a concentration of $1.25 \times 10^5$ to $2.5 \times 10^5$ cells/ml in hematopoietic induction medium, in either 6-well ultra-low attachment plates (5 ml), 50 ml shake-flasks (10 ml) or 125 ml spinner flasks (50 ml). Complete medium changes (unless otherwise stated) as indicated: Day 3: SL2+20 ng/ml BMP4+30 ng/ml VEGF-165+10 ng/ml bFGF+30 ng/ml SCF+10 ng/ml IGF2+10 ng/ml TPO+5 U/ml Heparin+50 µM IBMX+0.4 ng/ml β-estradiol; Day 5: Top-up 1:6 with SL2+120 ng/ml BMP4+180 ng/ml VEGF-165+60 ng/ml bFGF+180 ng/ml SCF+60 ng/ml IGF2+60 ng/ml TPO+30 U Heparin+300 µM IBMX+2.4 ng/ml β-estradiol; Day 7: SL2+20 ng/ml BMP4+30 ng/ml VEGF+10 ng/ml bFGF+30 ng/ml SCF+10 ng/ml IGF2+10 ng/ml TPO+5 U/ml Heparin+50 µM IBMX+0.4 ng/ml β-estradiol+1 µM Stem Regenin1 (SR1)(StemcellTech). Day 9: Top-up 1:2 with SL2+20 ng/ml BMP4+30 ng/ml VEGF165+10 ng/ml bFGF+30 ng/ml SCF+10 ng/ml IGF2+10 ng/ml TPO+5 U/ml Heparin+50 µM IBMX+0.4 ng/ml β-estradiol.

Erythroid Induction of Cells Derived from hiPSC-MC Aggregates

Cells were seeded at $1.25 \times 10^5$ to $2.5 \times 10^5$ cells/ml in erythroid induction medium in either 6-well ultra-low attachment plates (5 ml), 50 ml shake-flasks (10 ml) or 125 ml spinner flasks (50-100 ml). Complete medium changes (unless otherwise stated) as indicated: Day 11: SL2+6.7 ng/ml BMP4+30 ng/ml SCF+50 µM IBMX+1 µM hydrocortisone (Sigma-Aldrich)+16.7 ng/ml Flt3L+6.7 ng/ml IL3+4 U/ml EPO (Peprotech); Day 13: Top-up 1:6 with SL2+40.2 ng/ml BMP4+180 ng/ml SCF+300 µM IBMX+6 µM hydrocortisone (Sigma-Aldrich)+100.2 ng/ml Flt3L+40.2 ng/ml IL3+24 U/ml EPO+3 µM Pluripotin; Day 15 onwards: SL2+1× serum replacement 3 (Sigma-Aldrich)+0.3% v/v ExCyte reagent (Millipore)+1 µM hydrocortisone+100 ng/ml SCF+4 U/ml EPO+10 ng/ml IL3+0.2 mg/ml holotransferrin (MP Biomedicals)+1× Pencillin and Streptomycin. From day 15 onwards, complete medium change was performed once every 3 days. For high cell density cultures, complete medium change was performed daily when cell densities exceeded $5 \times 10^6$ cells/ml (5e6 cells/nil). For high cumulative fold-expansion, cells were seeded back at $1 \times 10^6$ cells/ml (1e6 cells/nil) whenever cell densities exceeded $5 \times 10^6$ cells/ml (5e6 cells/nil). Cumulative fold-expansion was calculated by multiplying fold-expansion achieved between passaging of cells over the course of experiments performed.

The invention claimed is:

1. A method for differentiation of pluripotent stem cells into hematopoietic precursor cells, wherein the method is carried out under continuous suspension agitation, the method comprising the steps of:
    (a) culturing pluripotent stem cells in a cell culture medium comprising BMP4, CHIR99021, Activin A and $VEGF_{165}$ for 24 hours to produce T-Brachyury (T-Bra) positive cells,
    (b) culturing the cells obtained in step (a) in a cell culture medium comprising BMP4, Activin A and a vascular endothelial growth factor for 24 hours,
    (c) culturing the cells of step (b) in a cell culture medium comprising BMP4, Activin A, bFGF or a variant thereof, a hormone, a cytokine and a vascular endothelial growth factor for 48 hours to produce KDR+ PDGFRα-hematopoietic precursor cells; and
    (d) removing the cell culture medium from step (c) and isolating the KDR+PDGFRα- hematopoietic precursor cells.

2. The method of claim 1, wherein BMP4 is present in a concentration of 26 ng/ml to 36 ng/ml, wherein Activin A is present in a concentration of 35 ng/ml to 46 ng/ml, wherein CHIR99021 is present in a concentration of 8 μM to 14 μM, and wherein $VEGF_{165}$ is present in a concentration of between 48 ng/ml to 51 ng/ml.

3. The method of claim 1, wherein the vascular endothelial growth factor of the cell culture media of step (b) is $VEGF_{165}$.

4. The method of claim 3, wherein BMP4 is present in a concentration of 26 ng/ml to 36 ng/ml, wherein Activin A is present in a concentration of 3 ng/ml to 46 ng/ml, and wherein $VEGF_{165}$ is present in a concentration of 48 ng/ml to 51 ng/ml.

5. The method of claim 1, wherein the hormone is beta-estradiol; and/or wherein the basic fibroblast growth factor (bFGF), or variant thereof, is a heat-stable chimeric variant of bFGF or a stable chimeric fibroblast growth factor (FGF); and/or wherein the cytokine is stem cell factor (SCF); and/or wherein the vascular endothelial growth factor is $VEGF_{165}$.

6. The method of claim 1, wherein the cell culture media of step (c) comprises BMP4, Activin A, bFGF, beta-stradiol, SCF, and $VEGF_{165}$.

7. The method of claim 6, wherein BMP4 is present in a concentration of 18 ng/ml to 27 ng/ml, wherein Activin A is present in a concentration of 3 ng/ml to 7ng/ml, wherein the bFGF is present in a concentration of 5 ng/ml to 14 g/ml, wherein the beta-estradiol is present in a concentration of 0.2 ng/ml to 0.8 ng/ml, wherein the SCF is present in a concentration of 26 ng/ml to 36 g/ml, and wherein VEGF165 is present in a concentration of 32 ng/ml to 38 ng/ml.

8. The method of claim 1, wherein BMP4 is present in a concentration of 26 ng/ml to 36 ng/ml, wherein Activin A is present in a concentration of 3 ng/ml to 46 ng/ml, and wherein $VEGF_{165}$ is present in a concentration of 48 ng/ml to 51 ng/ml.

9. The method of claim 3, wherein BMP4 is present in a concentration of 26 ng/ml to 36 ng/ml, wherein Activin A is present in a concentration of 3 ng/ml to 46 ng/ml, and wherein $VEGF_{165}$ is present in a concentration of 48 ng/ml to 51 ng/ml.

10. The method of claim 5, wherein the cell culture media of step (c) comprises BMP4, Activin A, bFGF, beta-stradiol, SCF, and $VEGF_{165}$.

11. The method of claim 1, wherein BMP4 is present in a concentration of 18 ng/ml to 27 ng/ml, wherein Activin A is present in a concentration of 3 ng/ml to 7 ng/ml, wherein the bFGF is present in a concentration of 5 ng/ml to 14 g/ml, wherein the beta-estradiol is present in a concentration of 0.2 ng/ml to 0.8 ng/ml, wherein the SCF is present in a concentration of 26 ng/ml to 36 g/ml, and wherein VEGF165 is present in a concentration of 32 ng/ml to 38 ng/ml.

12. The method of claim 5, wherein BMP4 is present in a concentration of 18 ng/ml to 27 ng/ml, wherein Activin A is present in a concentration of 3 ng/ml to 7ng/ml, wherein the bFGF is present in a concentration of 5 ng/ml to 14 g/ml, wherein the beta-estradiol is present in a concentration of 0.2 ng/ml to 0.8 ng/ml, wherein the SCF is present in a concentration of 26 ng/ml to 36 g/ml, and wherein VEGF165 is present in a concentration of 32 ng/ml to 38 ng/ml.

\* \* \* \* \*

UNITED STATES PATENT AND TRADEMARK OFFICE
CERTIFICATE OF CORRECTION

PATENT NO. : 12,104,173 B2
APPLICATION NO. : 16/962973
DATED : October 1, 2024
INVENTOR(S) : Jaichandran Sivalingam et al.

Page 1 of 1

It is certified that error appears in the above-identified patent and that said Letters Patent is hereby corrected as shown below:

In the Claims

At Column 63, Line 25, "cells; and" should be -- cells, and --.

At Column 64, Line 10, "beta-stradiol," should be -- beta-estradiol, --.

At Column 64, Line 18, "VEGF165" should be -- $VEGF_{165}$ --.

At Column 64, Line 30, "beta-stradiol," should be -- beta-estradiol, --.

At Column 64, Line 38, "VEGF165" should be -- $VEGF_{165}$ --.

At Column 64, Line 46, "VEGF165" should be -- $VEGF_{165}$ --.

Signed and Sealed this
Eighteenth Day of March, 2025

Coke Morgan Stewart
*Acting Director of the United States Patent and Trademark Office*

SEQUENCE LISTING

<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: CD31 forward primer

<400> SEQUENCE: 1
gctgaccctt ctgctctgtt                                              20

<210> SEQ ID NO 2
<211> LENGTH: 20
<212> TYPE: DNA
<213> ORGANISM: Artificial sequence
<220> FEATURE:
<223> OTHER INFORMATION: CD31 reverse primer

<400> SEQUENCE: 2
tgagaggtgg tgctgacatc                                              20

```
<210> SEQ ID NO 3
<211> LENGTH: 20
<212> TYPE: DNA
<213> ORGANISM: Artificial sequence
<220> FEATURE:
<223> OTHER INFORMATION: GATA2 forward primer

<400> SEQUENCE: 3
atcaagccca agcgaagact                                                    20

<210> SEQ ID NO 4
<211> LENGTH: 21
<212> TYPE: DNA
<213> ORGANISM: Artificial sequence
<220> FEATURE:
<223> OTHER INFORMATION: GATA2 reverse primer

<400> SEQUENCE: 4
catggtcagt ggcctgttaa c                                                  21

<210> SEQ ID NO 5
<211> LENGTH: 20
<212> TYPE: DNA
<213> ORGANISM: Artificial sequence
<220> FEATURE:
<223> OTHER INFORMATION: GATA1 forward primer

<400> SEQUENCE: 5
tcactccctg tccccaatag                                                    20

<210> SEQ ID NO 6
<211> LENGTH: 20
<212> TYPE: DNA
<213> ORGANISM: Artificial sequence
<220> FEATURE:
<223> OTHER INFORMATION: GATA1 reverse primer

<400> SEQUENCE: 6
ggagagttcc acgaagcttg                                                    20

<210> SEQ ID NO 7
<211> LENGTH: 18
<212> TYPE: DNA
<213> ORGANISM: Artificial sequence
<220> FEATURE:
<223> OTHER INFORMATION: LMO2 forward primer

<400> SEQUENCE: 7
aactgggccg gaagctct                                                      18

<210> SEQ ID NO 8
<211> LENGTH: 23
<212> TYPE: DNA
<213> ORGANISM: Artificial sequence
<220> FEATURE:
<223> OTHER INFORMATION: LMO2 reverse primer

<400> SEQUENCE: 8
cttgaaacat tccaggtgat aca                                                23

<210> SEQ ID NO 9
<211> LENGTH: 20
<212> TYPE: DNA
<213> ORGANISM: Artificial sequence
<220> FEATURE:
<223> OTHER INFORMATION: SCL/Tal-1 forward primer
```

```
<400> SEQUENCE: 9
ggatgccttc cctatgttca                                               20

<210> SEQ ID NO 10
<211> LENGTH: 20
<212> TYPE: DNA
<213> ORGANISM: Artificial sequence
<220> FEATURE:
<223> OTHER INFORMATION: SCL/Tal-1 reverse primer

<400> SEQUENCE: 10
ggtgtgggga ccatcagtaa                                               20

<210> SEQ ID NO 11
<211> LENGTH: 20
<212> TYPE: DNA
<213> ORGANISM: Artificial sequence
<220> FEATURE:
<223> OTHER INFORMATION: RunX1 forward primer

<400> SEQUENCE: 11
ccgagaacct cgaagacatc                                               20

<210> SEQ ID NO 12
<211> LENGTH: 18
<212> TYPE: DNA
<213> ORGANISM: Artificial sequence
<220> FEATURE:
<223> OTHER INFORMATION: RunX1 reverse primer

<400> SEQUENCE: 12
gctgaccctc atggctgt                                                 18

<210> SEQ ID NO 13
<211> LENGTH: 22
<212> TYPE: DNA
<213> ORGANISM: Artificial sequence
<220> FEATURE:
<223> OTHER INFORMATION: hemoglobin subtype alpha forward primer

<400> SEQUENCE: 13
cggtcaactt caagctccta ag                                            22

<210> SEQ ID NO 14
<211> LENGTH: 20
<212> TYPE: DNA
<213> ORGANISM: Artificial sequence
<220> FEATURE:
<223> OTHER INFORMATION: hemoglobin subtype alpha reverse primer

<400> SEQUENCE: 14
ccgcccactc agactttatt                                               20

<210> SEQ ID NO 15
<211> LENGTH: 20
<212> TYPE: DNA
<213> ORGANISM: Artificial sequence
<220> FEATURE:
<223> OTHER INFORMATION: hemoglobin subtype gamma forward primer

<400> SEQUENCE: 15
tggatcctga gaacttcaag                                               20

<210> SEQ ID NO 16
```

```
<211> LENGTH: 25
<212> TYPE: DNA
<213> ORGANISM: Artificial sequence
<220> FEATURE:
<223> OTHER INFORMATION: hemoglobin subtype gamma reverse primer

<400> SEQUENCE: 16
gcagaataaa gcctatcctt gaaag                                              25

<210> SEQ ID NO 17
<211> LENGTH: 23
<212> TYPE: DNA
<213> ORGANISM: Artificial sequence
<220> FEATURE:
<223> OTHER INFORMATION: hemoglobin subtype epsilon forward primer

<400> SEQUENCE: 17
aagatgaatg tggaagaggc tgg                                                23

<210> SEQ ID NO 18
<211> LENGTH: 20
<212> TYPE: DNA
<213> ORGANISM: Artificial sequence
<220> FEATURE:
<223> OTHER INFORMATION: hemoglobin subtype epsilon reverse primer

<400> SEQUENCE: 18
ttagcaaagg cgggcttgag                                                    20

<210> SEQ ID NO 19
<211> LENGTH: 20
<212> TYPE: DNA
<213> ORGANISM: Artificial sequence
<220> FEATURE:
<223> OTHER INFORMATION: hemoglobin subtype beta forward primer

<400> SEQUENCE: 19
acatttgctt ctgacacaac                                                    20

<210> SEQ ID NO 20
<211> LENGTH: 18
<212> TYPE: DNA
<213> ORGANISM: Artificial sequence
<220> FEATURE:
<223> OTHER INFORMATION: hemoglobin subtype beta reverse primer

<400> SEQUENCE: 20
acagatcccc aaaggact                                                      18

<210> SEQ ID NO 21
<211> LENGTH: 15
<212> TYPE: DNA
<213> ORGANISM: Artificial sequence
<220> FEATURE:
<223> OTHER INFORMATION: GAPDH forward primer

<400> SEQUENCE: 21
ctcctcctgt tcgac                                                         15

<210> SEQ ID NO 22
<211> LENGTH: 16
<212> TYPE: DNA
<213> ORGANISM: Artificial sequence
<220> FEATURE:
<223> OTHER INFORMATION: GAPDH reverse primer
```

```
<400> SEQUENCE: 22
accaaatccg ttgact                                                           16
```